(12) United States Patent
Ishitsuka et al.

(10) Patent No.: US 12,298,211 B2
(45) Date of Patent: May 13, 2025

(54) DEVICE FOR TISSUE SECTION IMMOBILIZATION AND RETENTION

(71) Applicant: Singular Genomics Systems, Inc., San Diego, CA (US)

(72) Inventors: Yuji Ishitsuka, San Diego, CA (US); Zhenmin Hong, San Diego, CA (US); Eli N. Glezer, Del Mar, CA (US); Hu Cang, San Diego, CA (US); William Dempsey, San Diego, CA (US); Weiqiao Ding, San Diego, CA (US); Jaekyung Koh, San Diego, CA (US); Mohammad Vatankhah Varnosfaderani, San Marcos, CA (US)

(73) Assignee: SINGULAR GENOMICS SYSTEMS, INC., San Diego, CA (US)

( * ) Notice: Subject to any disclaimer, the term of this patent is extended or adjusted under 35 U.S.C. 154(b) by 0 days.

(21) Appl. No.: 18/943,398

(22) Filed: Nov. 11, 2024

(65) Prior Publication Data

US 2025/0067638 A1 Feb. 27, 2025

Related U.S. Application Data

(63) Continuation of application No. 18/623,376, filed on Apr. 1, 2024, now Pat. No. 12,181,388, which is a (Continued)

(51) Int. Cl.
*G01N 1/00* (2006.01)
*A61L 27/28* (2006.01)
(Continued)

(52) U.S. Cl.
CPC .............. *G01N 1/30* (2013.01); *A61L 27/28* (2013.01); *A61L 27/52* (2013.01); *C12Q 1/6841* (2013.01); *C12Q 1/6874* (2013.01); *G01N 1/06* (2013.01); *G01N 1/28* (2013.01); *G01N 1/286* (2013.01); *G01N 1/312* (2013.01); *G01N 1/36* (2013.01);
(Continued)

(58) Field of Classification Search
None
See application file for complete search history.

(56) References Cited

U.S. PATENT DOCUMENTS

| 4,318,846 A | 3/1982 | Khanna et al. |
| 4,808,521 A | 2/1989 | Allen |

(Continued)

FOREIGN PATENT DOCUMENTS

| CA | 2909344 A1 | 10/2014 |
| WO | WO-1989/010977 A1 | 11/1989 |

(Continued)

OTHER PUBLICATIONS

Arce, S. H. et al. (Jul. 24, 2013). "Fast and accurate automated cell boundary determination for fluorescence microscopy," *Scientific Reports* 3(1): Article 2266, pp. 1-6.

(Continued)

*Primary Examiner* — Jyoti Nagpaul
(74) *Attorney, Agent, or Firm* — Mintz, Levin, Cohn, Ferris, Glovsky & Popeo, P.C.

(57) ABSTRACT

Disclosed herein, inter alia, are devices and methods for transfer and analysis of tissue sections using carrier substrates.

19 Claims, 18 Drawing Sheets

Related U.S. Application Data continuation of application No. PCT/US2022/078462, filed on Oct. 20, 2022.

(60) Provisional application No. 63/350,854, filed on Jun. 9, 2022, provisional application No. 63/350,858, filed on Jun. 9, 2022, provisional application No. 63/297,077, filed on Jan. 6, 2022, provisional application No. 63/271,456, filed on Oct. 25, 2021.

(51) Int. Cl.
| | |
|---|---|
| *A61L 27/52* | (2006.01) |
| *C12Q 1/6841* | (2018.01) |
| *C12Q 1/6874* | (2018.01) |
| *G01N 1/06* | (2006.01) |
| *G01N 1/28* | (2006.01) |
| *G01N 1/30* | (2006.01) |
| *G01N 1/31* | (2006.01) |
| *G01N 1/36* | (2006.01) |
| *G01N 23/2251* | (2018.01) |
| *G02B 21/34* | (2006.01) |

(52) U.S. Cl.
CPC ......... *G01N 23/2251* (2013.01); *G02B 21/34* (2013.01); *G01N 2001/2873* (2013.01); *G01N 2001/288* (2013.01); *G01N 2001/315* (2013.01)

(56) References Cited

U.S. PATENT DOCUMENTS

| | | | |
|---|---|---|---|
| 4,814,167 | A | 3/1989 | Wirth et al. |
| 4,816,253 | A | 3/1989 | Likhite |
| 4,829,012 | A | 5/1989 | Cambiaso et al. |
| 5,034,506 | A | 7/1991 | Summerton et al. |
| 5,066,580 | A | 11/1991 | Lee |
| 5,188,934 | A | 2/1993 | Menchen et al. |
| 5,235,033 | A | 8/1993 | Summerton et al. |
| 5,364,612 | A | 11/1994 | Goldenberg |
| 5,366,860 | A | 11/1994 | Bergot et al. |
| 5,597,725 | A | 1/1997 | Suzuki |
| 5,599,675 | A | 2/1997 | Brenner |
| 5,688,648 | A | 11/1997 | Mathies et al. |
| 5,750,341 | A | 5/1998 | Macevicz |
| 5,763,594 | A | 6/1998 | Hiatt et al. |
| 5,800,996 | A | 9/1998 | Lee et al. |
| 5,808,045 | A | 9/1998 | Hiatt et al. |
| 5,847,162 | A | 12/1998 | Lee et al. |
| 5,872,244 | A | 2/1999 | Hiatt et al. |
| 6,210,891 | B1 | 4/2001 | Nyren et al. |
| 6,218,122 | B1 | 4/2001 | Friend et al. |
| 6,232,465 | B1 | 5/2001 | Hiatt et al. |
| 6,258,568 | B1 | 7/2001 | Nyren |
| 6,274,320 | B1 | 8/2001 | Rothberg et al. |
| 6,664,079 | B2 | 12/2003 | Ju et al. |
| 7,057,026 | B2 | 6/2006 | Barnes et al. |
| 7,465,279 | B2 | 12/2008 | Beckman et al. |
| 7,541,444 | B2 | 6/2009 | Milton et al. |
| 8,178,360 | B2 | 5/2012 | Barnes et al. |
| 10,738,072 | B1 | 8/2020 | Graham et al. |
| 11,311,874 | B2 | 4/2022 | Bandara et al. |
| 11,643,679 | B2 | 5/2023 | Glezer et al. |
| 12,006,534 | B2 | 6/2024 | Glezer |
| 12,158,402 | B2 | 12/2024 | Ishitsuka et al. |
| 12,181,388 | B2 | 12/2024 | Ishitsuka et al. |
| 2002/0164656 | A1 | 11/2002 | Hoeffler et al. |
| 2003/0087985 | A1 | 5/2003 | Hubbell et al. |
| 2004/0247777 | A1 | 12/2004 | Ringeisen et al. |
| 2005/0137372 | A1 | 6/2005 | Kulkarni et al. |
| 2005/0154165 | A1 | 7/2005 | Petereit et al. |
| 2005/0288796 | A1 | 12/2005 | Awad et al. |
| 2006/0223122 | A1 | 10/2006 | Fogo et al. |
| 2006/0223197 | A1 | 10/2006 | Vielsack |
| 2006/0234234 | A1 | 10/2006 | Van Dongen et al. |
| 2006/0246453 | A1 | 11/2006 | Kato et al. |
| 2006/0257629 | A1 | 11/2006 | Lendlein et al. |
| 2007/0196492 | A1 | 8/2007 | Ito et al. |
| 2008/0032328 | A1 | 2/2008 | Cline et al. |
| 2008/0160559 | A1 | 7/2008 | Carre et al. |
| 2009/0026082 | A1 | 1/2009 | Rothberg et al. |
| 2009/0127589 | A1 | 5/2009 | Rothberg et al. |
| 2010/0028261 | A1 | 2/2010 | Emelianov et al. |
| 2010/0047924 | A1 | 2/2010 | Webster et al. |
| 2010/0055733 | A1 | 3/2010 | Lutolf et al. |
| 2010/0136114 | A1 | 6/2010 | Mao |
| 2010/0137143 | A1 | 6/2010 | Rothberg et al. |
| 2010/0282617 | A1 | 11/2010 | Rothberg et al. |
| 2011/0021965 | A1 | 1/2011 | Karp et al. |
| 2011/0059865 | A1 | 3/2011 | Smith et al. |
| 2011/0252935 | A1 | 10/2011 | Welsh |
| 2011/0259744 | A1 | 10/2011 | Moyle |
| 2012/0301886 | A1 | 11/2012 | Farrell et al. |
| 2013/0012399 | A1 | 1/2013 | Myers et al. |
| 2013/0035248 | A1 | 2/2013 | Icenhour |
| 2013/0040344 | A1 | 2/2013 | Ju |
| 2013/0040843 | A1 | 2/2013 | Von Töerne et al. |
| 2013/0040847 | A1 | 2/2013 | Thrippleton et al. |
| 2013/0152710 | A1 | 6/2013 | Laugharn, Jr. et al. |
| 2013/0344500 | A1 | 12/2013 | Trautman et al. |
| 2014/0255333 | A1 | 9/2014 | Song et al. |
| 2014/0335511 | A1 | 11/2014 | Glaser et al. |
| 2015/0125952 | A1 | 5/2015 | Kim et al. |
| 2015/0225778 | A1 | 8/2015 | Hindson et al. |
| 2016/0025604 | A1 | 1/2016 | Laugharn et al. |
| 2016/0116384 | A1 | 4/2016 | Chen et al. |
| 2016/0168650 | A1 | 6/2016 | Kallioniemi et al. |
| 2016/0249891 | A1 | 9/2016 | Gardner et al. |
| 2017/0022553 | A1 | 1/2017 | Vijayan et al. |
| 2018/0110500 | A1 | 4/2018 | Palmer et al. |
| 2019/0048404 | A1 | 2/2019 | Dambacher |
| 2019/0185620 | A1 | 6/2019 | Gorman et al. |
| 2019/0355550 | A1 | 11/2019 | Hayworth et al. |
| 2019/0358312 | A1 | 11/2019 | Irvine et al. |
| 2020/0149115 | A1 | 5/2020 | Dobak et al. |
| 2020/0353120 | A1 | 11/2020 | Zhao et al. |
| 2021/0139884 | A1 | 5/2021 | Kellinger et al. |
| 2021/0150707 | A1* | 5/2021 | Weisenfeld ........... G06T 7/0012 |
| 2021/0247316 | A1 | 8/2021 | Bava et al. |
| 2021/0253987 | A1 | 8/2021 | Engler et al. |
| 2022/0098576 | A1 | 3/2022 | Dadhwal |
| 2023/0266209 | A1 | 8/2023 | Koh et al. |
| 2023/0340591 | A1 | 10/2023 | Glezer et al. |
| 2023/0347021 | A1 | 11/2023 | Koh et al. |
| 2023/0374572 | A1 | 11/2023 | Kovacs et al. |
| 2024/0241018 | A1 | 7/2024 | Ishitsuka et al. |
| 2024/0280446 | A1 | 8/2024 | Ishitsuka et al. |

FOREIGN PATENT DOCUMENTS

| | | |
|---|---|---|
| WO | WO-1996/007669 A1 | 3/1996 |
| WO | WO-2004/018497 A2 | 3/2004 |
| WO | WO-2004/018497 A3 | 6/2004 |
| WO | WO-2016/123480 A1 | 8/2016 |
| WO | WO-2016/130559 A1 | 8/2016 |
| WO | WO-2018/148723 A1 | 8/2018 |
| WO | WO-2020/056044 A1 | 3/2020 |
| WO | WO-2021/133845 A1 | 7/2021 |
| WO | WO-2023/076832 A1 | 5/2023 |
| WO | WO-2024/163634 A2 | 8/2024 |

OTHER PUBLICATIONS

Bains, W. et al. (Dec. 7, 1988). "A novel method for nucleic acid sequence determination," *Journal of Theoretical Biology* 135(3): 303-307.

Cai, M. (2019). " Spatial mapping of single cells in human cerebral cortex using DARTFISH: A highly multiplexed method for in situ quantification of targeted RNA transcripts," *UC San Diego Electronic Theses and Dissertations*. ProQuest ID: Cai_ucsd_0033D_18822.

(56) References Cited

OTHER PUBLICATIONS

Carpenter, A. E. et al. (Oct. 31, 2006). "CellProfiler: image analysis software for identifying and quantifying cell phenotypes," *Genome biology* 7(10): R100.
Chen, F. et al. (Jan. 30, 2015, e-published Jan. 15, 2015). "Optical imaging. Expansion microscopy," *Science* 347(6221): 543-548.
Chen, K. H. et al. (Apr. 24, 2015, e-published Apr. 9, 2015). "RNA imaging. Spatially resolved, highly multiplexed RNA profiling in single cells," *Science* 348(6233): aaa6090.
Choi, S. W. et al. (Aug. 5, 2021). "Basic principles of hydrogel-based tissue transformation technologies and their applications," *Cell* 184(16): 4115-4136.
Christian, A. T. et al. (Dec. 4, 2001, e-published Nov. 27, 2001). "Detection of DNA point mutations and mRNA expression levels by rolling circle amplification in individual cells," *PNAS USA* 98(25): 14238-14243.
Chung, K. et al. (May 16, 2013, e-published Apr. 10, 2013). "Structural and molecular interrogation of intact biological systems," *Nature* 497(7449): 332-337.
Dodt, H. U. et al. (Apr. 2007, e-published Mar. 25, 2007) "Ultramicroscopy: three-dimensional visualization of neuronal networks in the whole mouse brain," *Nature methods* 4(4): 331-336.
Drmanac, S. et al. (Jan. 1, 1998). "Accurate sequencing by hybridization for DNA diagnostics and individual genomics," *Nature Biotech* 16(1):54-58.
El-Sagheer, A. H. et al. (Aug. 21, 2012, e-published Mar. 22, 2012). "Click nucleic acid ligation: applications in biology and nanotechnology," *Accounts of chemical research* 45(8): 1258-1267.
Ertürk, A. et al. (Nov. 2012, e-published Oct. 11, 2012). "Three-dimensional imaging of solvent-cleared organs using 3DISCO," *Nature protocols* 7(11): 1983-1995.
Feeney, R. E. et al. (Apr. 1, 1982). "Chemical modification of proteins: An overview," *Advances in Chemistry* Series 182: 3-55.
Fodor, S. P. A. et al. (Feb. 15, 1991). "Light-directed, spatially addressable parallel chemical synthesis," *Science* 251(4995): 767-773.
Galante, R. et al. (Aug. 2018, e-published Dec. 16, 2017). "Sterilization of hydrogels for biomedical applications: A review," *Journal of Biomedical Materials Research Part B: Applied Biomaterials* 106(6): 2472-2492.
Gao, R. W. et al. (Sep. 1, 2018, e-published Sep. 4, 2018). "Determination of tumor margins with surgical specimen mapping using near-infrared fluorescence," *Cancer research* 78(17): 5144-5154.
Gao, X. H. et al. (Mar. 13, 2020). "Comparison of fresh frozen tissue with formalin-fixed paraffin-embedded tissue for mutation analysis using a multi-gene panel in patients with colorectal cancer," *Frontiers in oncology* 10: 310.
Gelali, E. et al. (Apr. 9, 2019). "iFISH is a publically available resource enabling versatile DNA FISH to study genome architecture," *Nature communications* 10: 1-15.
Giannitto, C. et al. (Dec. 8, 2021). "Frozen Section Analysis and Real-Time Magnetic Resonance Imaging of Surgical Specimen Oriented on 3D Printed Tongue Model to Assess Surgical Margins in Oral Tongue Carcinoma: Preliminary Results," *Frontiers in Oncology*, 5049.
Gore, A. et al. (Mar. 3, 2011, e-published Mar. 2, 2011). "Somatic coding mutations in human induced pluripotent stem cells," *Nature* 471(7336): 63-67.
Hama, H. et al. (Oct. 2015, e-published Sep. 14, 2015). "Sca/eS: an optical clearing palette for biological imaging," *Nature neuroscience* 18(10): 1518-1529.
Han, X. et al. (Jun. 2017, e-published May 16, 2017). "Sterilization, hydration-dehydration and tube fabrication of zwitterionic hydrogels," *Biointerphases* 12(2): Article 02C411.
Hohl, D. K. et al. (Aug. 19, 2019, e-published Apr. 29, 2019). "(De)bonding on demand with optically switchable adhesives," *Advanced Optical Materials* 7(16): Article 1900230.
Hughes, A. J. et al. (Jul. 1, 2021). "Tape strips in dermatology research," *British Journal of Dermatology* 185(1): 26-35.

International Search Report and Written Opinion mailed on Mar. 3, 2023, for PCT application PCT/US2022/078462, filed Oct. 20, 2022, 21 pages.
International Search Report and Written Opinion mailed on Sep. 3, 2024, for PCT application PCT/US2024/013802, filed Oct. 20, 2022, 14 pages.
Jing, D. et al. (Aug. 2018, e-published May 29, 2018). "Tissue clearing of both hard and soft tissue organs with the PEGASOS method," *Cell Research* 28(8): 803-818.
Kappler, K. et al. (Aug. 2020, e-published Aug. 5, 2020). "Emergence and significance of carbohydrate-specific antibodies," *Genes & Immunity* 21(4): 224-239.
Kawamoto, T. (2003). "Use of a new adhesive film for the preparation of multi-purpose fresh-frozen sections from hard tissues, whole-animals, insects and plants," *Archives of histology and cytology* 66(2): 123-143.
Klein A. M. et al. (Jul. 25, 2017). "InDrops and Drop-seq technologies for single-cell sequencing," *Lab Chip* 17(15): 2540-2541.
Klingberg, A. et al. (Feb. 2017). "Fully automated evaluation of total glomerular No. and capillary tuft size in nephritic kidneys using lightsheet microscopy," *Journal of the American Society of Nephrology* 28(2): 452-459.
Koucherian, N. E. et al. (Sep. 23, 2022). "Fabrication of multilayer molds by dry film photoresist," *Micromachines* 13(10): 1583.
Lai, H. M. et al. (Mar. 14, 2018). "Next generation histology methods for three-dimensional imaging of fresh and archival human brain tissues," *Nature communications* 9(1): 1066.
Lareau, C. A. et al. (Feb. 13, 2020). "Inference and effects of barcode multiplets in droplet-based single-cell assays," *Nature Communications* 11(1): 866.
Larsson, C. et al. (May 2010, e-published Apr. 11, 2010). "In situ detection and genotyping of individual mRNA molecules," *Nature methods* 7(5): 395-397.
Lee, T-H. et al. (Nov. 22, 2021). "Photoresponsive, switchable, pressure-sensitive adhesives: influence of UV intensity and hydrocarbon chain length of low molecular weight azobenzene compounds," *RSC advances* 11(59): 37392-37402.
Li, J. B. et al. (May 29, 2009). "Genome-wide identification of human RNA editing sites by parallel DNA capturing and sequencing," *Science* 324(5931): 1210-1213.
Li, J. B. et al. (Jun. 12, 2009). "Multiplex padlock targeted sequencing reveals human hypermutable CpG variations," *Genome research* 19(9): 1606-1615.
Li, W. et al. (Aug. 14, 2017). "Multiplex, quantitative cellular analysis in large tissue volumes with clearing-enhanced 3D microscopy (Ce3D)," *PNAS USA* 114(35): E7321-E7330.
Lim, H. L. et al. (Feb. 12, 2014). "Smart hydrogels as functional biomimetic systems," *Biomaterials Science* 2(5): 603-618.
Liu, Z. et al. (Apr. 25, 2022, e-published Mar. 1, 2022). "Switchable Adhesion: On-Demand Bonding and Debonding," *Advanced Science* 9(12): Article 2200264.
Lizardi, P. M. et al. (Jul. 1998). "Mutation detection and single-molecule counting using isothermal rolling-circle amplification," *Nature Genetics* 19(3):225-232.
Mag, M. et al. (Nov. 24, 1992, e-published Mar. 5, 2001). "Synthesis and selective cleavage of an oligodeoxynucleotide containing a bridged non-chiral internucleotide 3'-phosphoramidate linkage," *Tetrahedron Letters* 33(48): 7319-7322.
Manuguerra, I. et al. (May 4, 2018, e-published Apr. 17, 2018). "Gene assembly via one-pot chemical ligation of DNA promoted by DNA nanostructures," *Chemical Communications (Cambridge)* 54(36): 4529-4532.
Mentré, P. (2004). "Interfacial water: a modulator of biological activity," *Journal of Biological Physics and Chemistry* 4: 115-123.
Mirza, S. P. et al. (Mar. 1, 2008). "Methods and approaches for the comprehensive characterization and quantification of cellular proteomes using mass spectrometry," *Physiological genomics* 33(1): 3-11.
Mohamed, M. A. et al. (Nov. 2019, e-published Aug. 12, 2019). "Stimuli-responsive hydrogels for manipulation of cell microenvironment: From chemistry to biofabrication technology," *Progress in polymer science* 98: Article 101147.

(56) References Cited

OTHER PUBLICATIONS

Nilsson, M. et al. (Sep. 30, 1994). "Padlock probes: circularizing oligonucleotides for localized DNA detection," *Science* 265(5181): 2085-2088.
Noggle, S. et al. (Oct. 6, 2011, e-published Oct. 5, 2011). "Human oocytes reprogram somatic cells to a pluripotent state," *Nature* 478(7367): 70-75.
Normand, V. et al. (Dec. 1, 2000, e-published Nov. 16, 2000). "New insight into agarose gel mechanical properties," *Biomacromolecules* 1(4): 730-738.
Odeh, F. et al. (Jan. 1, 2020, e-published Dec. 18, 2019). "Aptamers Chemistry: Chemical Modifications and Conjugation Strategies," *Molecules* 25(1): 3. Basel, Switzerland.
Pan, C. et al. (Oct. 16, 2016, e-published Aug. 22, 2016). "Shrinkage-mediated imaging of entire organs and organisms using uDISCO," *Nature Methods* 13(10): 859-867.
Porreca, G. J. et al. (Nov. 2007, e-published Oct. 14, 2007). "Multiplex amplification of large sets of human exons," *Nature Methods* 4(11): 931-936.
Qi, Y. et al. (Jan. 11, 2019). "FDISCO: Advanced solvent-based clearing method for imaging whole organs," *Science advances* 5(1): Article eaau8355.
Qin, C. et al. (Sep. 5, 2018). "The cutting and floating method for paraffin-embedded tissue for sectioning," *JoVE (Journal of Visualized Experiments)* 139: Article e58288.
Renier, N. et al. (Oct. 30, 2014). "iDISCO: a simple, rapid method to immunolabel large tissue samples for vol. imaging," *Cell* 159(4): 896-910.
Ronaghi, M. et al. (Nov. 1, 1996, e-published May 25, 2002). "Real-time DNA sequencing using detection of pyrophosphate release," *Analytical Biochemistry* 242(1): 84-89.
Ronaghi, M. et al. (Jul. 17, 1998). "A sequencing method based on real-time pyrophosphate," *Science* 281(5375): 363-365.
Ronaghi, M. (Jan. 2001). "Pyrosequencing sheds light on DNA sequencing," *Genome Research* 11(1):3-11.
Ryu, B. et al. (Dec. 1, 2019, e-published Sep. 14, 2019). "Sticker method for preparation of frozen section using adhesive film," *Journal of Neuroscience Methods* 328: 108436.
Sansone, A. (Jun. 2019, e-published May 30, 2019). "Spatial transcriptomics levels up," *Nature Methods* 16(6): 458.
Schwarz, M. K. et al. (May 20, 2015). "Fluorescent-protein stabilization and high-resolution imaging of cleared, intact mouse brains," *PloS one* 10(5): e0124650.
Shan, Q-H. et al. (Mar. 29, 2022). "A method for ultrafast tissue clearing that preserves fluorescence for multimodal and longitudinal brain imaging," *BMC biology* 20: Article 77.
Shendure, J. et al. (Sep. 9, 2005, e-published Aug. 4, 2005). "Accurate multiplex polony sequencing of an evolved bacterial genome," *Science* 309(5741):1728-1732.
Southworth, M. W. et al. (May 28, 1996). "Cloning of thermostable DNA polymerases from hyperthermophilic marine Archaea with emphasis on Thermococcus sp. 9°N-7 and mutations affecting 3'-5' exonuclease activity," *PNAS USA* 93(11):5281-5285.
Susaki, E. A. et al. (Apr. 24, 2014, e-published Apr. 17, 2014). "Whole-brain imaging with single-cell resolution using chemical cocktails and computational analysis," *Cell* 157(3): 726-739.

Tam, I. et al. (May 2021, e-published Nov. 20, 2020). "Skin tape stripping identifies gene transcript signature associated with allergic contact dermatitis," *Contact dermatitis* 84(5): 308-316.
Tanaka, M. (Mar. 17, 2020). "Interplays of Interfacial Forces Modulate Structure and Function of Soft and Biological Matters in Aquatic Environments," *Frontiers in chemistry* 8: 165.
Ticha, P. et al. (Nov. 11, 2020). "A novel cryo-embedding method for in-depth analysis of craniofacial mini pig bone specimens," *Scientific Reports* 10: Article 19510, pp. 1-11.
Tseng, Y-M. et al. (Jun. 23, 2021, e-published Jun. 10, 2021). "Light-Activated Adhesion and Debonding of Underwater Pressure-Sensitive Adhesives," *ACS Applied Materials & Interfaces* 13(24): 29048-29057.
Tsoi, L. C. et al. (Jun. 2022, e-published Nov. 19, 2021). "Noninvasive Tape-Stripping with High-Resolution RNA Profiling Effectively Captures a Preinflammatory State in Nonlesional Psoriatic Skin," *Journal of Investigative Dermatology* 142(6): 1587-1596.
Turbett, G. R. et al. (Oct. 1, 1997). "The use of optimal cutting temperature compound can inhibit amplification by polymerase chain reaction," *Diagnostic molecular pathology: the American journal of surgical pathology, part B* 6.5: 298-303.
Vickovic, S. et al. (Oct. 2019, e-published Sep. 9, 2019). "High-definition spatial transcriptomics for in situ tissue profiling," *Nature Methods* 16(10): 987-990.
Walker, J. W. et al. (Oct. 1, 1998, e-published May 1, 2002). "Photolabile 1-(2-nitrophenyl) ethyl phosphate esters of adenine nucleotide analogs. Synthesis and mechanism of photolysis," *Journal of the American Chemical Society* 110(21): 7170-7177.
Wang, G. et al. (Mar. 19, 2018). "Multiplexed imaging of high-density libraries of RNAs with MERFISH and expansion microscopy," *Scientific Reports* 8(1): 4847.
Wang X. et al. (Jul. 27, 2018, e-published Jun. 21, 2018). "Three-dimensional intact-tissue sequencing of single-cell transcriptional states," *Science* 361(6400): eaat5691.
Yang, B. et al. (Aug. 14, 2014, e-published Jul. 31, 2014). "Single-cell phenotyping within transparent intact tissue through whole-body clearing," *Cell* 158(4): 945-958.
Yang, Y. et al. (Jan. 2021, e-published Mar. 31, 2020). "A modified tape transfer approach for rapidly preparing high-quality cryosections of undecalcified adult rodent bones," *Journal of Orthopaedic Translation* 26: 92-100.
York, A. G. et al. (Nov. 2013, e-published Oct. 6, 2013). "Instant super-resolution imaging in live cells and embryos via analog image processing," *Nature Methods* 10(11):1122-1126.
Zhang, K. et al. (Aug. 2009, e-published Jul. 20, 2009). "Digital RNA allelotyping reveals tissue-specific and allele-specific gene expression in human," *Nature Methods* 6(8): 613-618.
Zhang, M. et al. (Oct. 7, 2021, e-published Oct. 6, 2021). "Spatially resolved cell atlas of the mouse primary motor cortex by MERFISH," *Nature* 598(7879): 137-143.
Zheng, G. X. et al. (Jan. 16, 2017). "Massively parallel digital transcriptional profiling of single cells," *Nature Communications* 8: 14049.
U.S. Appl. No. 18/704,416, Not yet published, Ishitsuka et al.
U.S. Appl. No. 18/943,409, Not yet published, Ishitsuka et al.

\* cited by examiner

DEVICE FOR TISSUE SECTION IMMOBILIZATION AND RETENTION

CROSS-REFERENCES TO RELATED APPLICATIONS

This application is a continuation application of Ser. No. 18/623,376, filed Apr. 1, 2024, which is a continuation of International Application No. PCT/US2022/078462, filed Oct. 20, 2022, and which claims the benefit of U.S. Provisional Application No. 63/271,456, filed Oct. 25, 2021, U.S. Provisional Application No. 63/297,077, filed Jan. 6, 2022, U.S. Provisional Application No. 63/350,858, filed Jun. 9, 2022, and U.S. Provisional Application No. 63/350,854, filed Jun. 9, 2022, each of which are incorporated herein by reference in their entirety and for all purposes.

BACKGROUND

Methods for acquiring, preparing, and storing tissue sections for either immediate or future analysis have been largely unchanged for decades. For example, when a patient has a biopsy or surgery, the surgeon often removes a portion of tissue for examination by a pathologist. The resected tissue may then be snap-frozen in liquid nitrogen shortly after surgical resection, generating what is commonly referred to as "fresh frozen" tissue. Alternatively, the resected tissue may be preserved in formaldehyde, embedded in paraffin wax, and optionally stored at room temperature, referred to as formalin-fixation and paraffin embedding (FFPE). Both preservation methods are widely used for preserving the macroscopic architecture of cellular structures (e.g., preserve tissue architecture, cell shape, and the components of the cell, such as proteins, DNA, RNA, carbohydrates, and enzymes) in tissue sections. Once a tissue sample has been prepared (e.g., either a fresh frozen sample or FFPE tissue block), a pathologist typically slices the tissue sample into very thin sections (e.g., sectioning using a cryotome, vibratome, or microtome) that are then placed on a glass slide and examined under a microscope. In recent years with the development of additional technologies to further analyze the sample (e.g., spatial gene expression and/or proteomic analyses), extracting or transferring the sample from a glass slide/transitional surface to another medium would be an attractive step in the processing of tissue samples. However, subsequent transfer of the tissue section to another surface often introduces additional damage to the sample. For example, once the tissue section is attached to the first surface (e.g., a typical biopsy slide, such as functionalized and/or a charged glass surface), it may be extremely difficult to transfer again without damaging the tissue due to strong contact forces between the tissue section and attachment surface. Novel approaches for transferring biological specimens while minimizing damage are greatly needed. Disclosed herein, inter alia, are solutions to these and other problems in the art.

BRIEF SUMMARY

In an aspect is provided a method of immobilizing a tissue section to a receiving substrate, wherein the tissue section includes a thickness of about 1 μm to about 50 μm, the method including: contacting the tissue section with a hydrogel carrier substrate to generate a sample-carrier construct including the carrier substrate and the tissue section; contacting the tissue section of the sample-carrier construct with the receiving substrate; and removing the carrier substrate from the sample-carrier construct, thereby immobilizing the tissue section to the receiving substrate.

In an aspect is provided a microplate, including a substrate including a surface, the surface including a plurality of wells separated from each other by interstitial regions on the surface, wherein one or more wells includes a tissue section and a carrier substrate, wherein the tissue section includes a thickness of about 1 μm to about 50 μm and the carrier substrate includes a hydrogel.

In an aspect is provided a method of detecting a biomolecule in a tissue section, the method including: a) immobilizing the tissue section onto a carrier substrate to generate a sample-carrier construct, wherein the carrier substrate includes a first adhesion strength; b) contacting the tissue section of the sample-carrier construct with a receiving substrate to generate an immobilized tissue section, wherein the receiving substrate includes a second adhesion strength, wherein the second adhesion strength is greater than the first adhesion strength; c) removing the carrier substrate from the immobilized tissue section; d) permeabilizing the immobilized tissue section; and e) contacting the biomolecule in the tissue section with a detection agent thereby detecting the biomolecule in the tissue section, wherein the detection agent includes a fluorophore.

In an aspect is provided a method of detecting a biomolecule in a tissue section, the method including: a) immobilizing the tissue section onto a hydrogel carrier substrate to generate a sample-carrier construct; b) contacting the tissue section of the sample-carrier construct with a receiving substrate to generate an immobilized tissue section; c) removing the hydrogel carrier substrate from the immobilized tissue section; d) permeabilizing the immobilized tissue section; and e) contacting the biomolecule in the tissue section with a detection agent thereby detecting a biomolecule in a tissue section, wherein the detection agent includes a fluorophore.

In an aspect is provided a method of obtaining an image of a tissue section, the method including: immobilizing the tissue section onto a hydrogel carrier substrate to generate a sample-carrier construct including the carrier substrate and the tissue section; contacting the tissue section of the sample-carrier construct with a receiving substrate to generate an immobilized tissue section; removing the hydrogel carrier substrate from the immobilized tissue section; and imaging the tissue section, thereby obtaining an image of the tissue section.

In another aspect is provided a method of obtaining an image of a portion of a tissue section, the method including: A) immobilizing the tissue section onto a hydrogel carrier substrate to generate a sample-carrier construct including the carrier substrate and the tissue section; B) removing a portion of the sample-carrier construct, wherein the portion includes a portion of the carrier substrate and a portion of the tissue section; C) contacting the tissue section of the portion of the sample-carrier construct with a receiving substrate to generate an immobilized tissue section; D) removing the hydrogel carrier substrate from the immobilized tissue section; and E) imaging the tissue section, thereby obtaining an image of the portion of a tissue section.

In an aspect is provided a method of capturing a biomolecule from a tissue section, the method including: i) immobilizing the tissue section onto a hydrogel carrier substrate to generate a sample-carrier construct; ii) contacting the tissue section of the sample-carrier construct with a receiving substrate, wherein the receiving substrate includes an immobilized specific-binding agent; and iii) binding the immobilized specific-binding agent to the biomolecule from the tissue section thereby capturing a biomolecule from the tissue section.

In an aspect is provided a method of determining a surgical margin of a tissue to be resected in a subject, the method including: immobilizing a tissue section obtained from the subject onto a hydrogel carrier substrate to generate a sample-carrier construct; contacting the tissue section of the sample-carrier construct with a receiving substrate to generate an immobilized tissue section; removing the hydrogel carrier substrate from the immobilized tissue section; permeabilizing the immobilized tissue section; contacting a biomolecule at a first location in the tissue section with a detection agent thereby detecting the presence of the biomolecule in the first location in the tissue section, wherein the detection agent includes a fluorophore; determining the presence of the biomolecule at one or more different locations in the tissue section by contacting the detection agent at one or more different locations in the tissue section; comparing the presence of the biomolecule in the first location to the presence of the biomolecule in the one or more different locations, and determining the surgical margin of the tissue to be resected from the subject based on the comparison.

BRIEF DESCRIPTION OF THE DRAWINGS

FIG. 2A depicts a sample-carrier construct (i) wherein the sample is embedded in an embedding material, e.g., paraffin wax. The embedding material is then removed, for example when the embedding material is paraffin wax by contacting the construct with an organic solvent such as xylene or heptane, leaving the biological sample on the construct, as illustrated in step (ii) of FIG. 2A. The biological sample of the construct is then contacted with a receiving substrate (e.g., bare or functionalized glass, plastic, polymer receiving substrate), see step (iii) of FIG. 2A, followed by removal of the carrier substrate, see step (iv) of FIG. 2A. Alternatively, the sample-carrier construct may be subjected to fluorogenic and/or chromogenic counterstaining (e.g., H&E staining) methods to aid in visualization and identifying details of the cell types, organelles, structures in the tissue section, see step (ii) of FIG. 2B. The biological sample of the construct is then contacted with a receiving substrate (e.g., bare or functionalized glass, plastic, polymer receiving substrate), see step (iii) of FIG. 2B, followed by removal of the carrier substrate, see step (iv) of FIG. 2B. Shown in FIG. 2C is an overview of selected removal of one or more portions of the construct. To a sample-carrier construct, (i) of FIG. 2C, one or more portions of the construct are removed, for example using a cutting device, and depicted as dashed lines in step (ii) of FIG. 2C. The resulting portions of the construct, illustrated in step (iii) of FIG. 2C, are then contacted with a receiving substrate, such that the biological sample of the portion is in contact with the receiving substrate, as shown in step (iv) of FIG. 2C.

FIG. 5 shows the carrier-assisted transfer methods are successful at transferring a complete tissue section (i.e., Control 1 and Control 2) and portions of tissue sections over a range of temperatures.

FIG. 6A shows an H&E stained human kidney sample that was i) captured on a carrier substrate to form a sample-carrier construct; ii) a portion of the carrier substrate was removed and the portion was mounted on a receiving substrate, iii) the carrier substrate was removed, and iv) the immobilized sample was stained with H&E stain. FIG. 6B shows an H&E stained human kidney sample that was i) captured on a carrier substrate to form a sample-carrier construct, ii) the construct was deparaffinated, iii) a portion of the carrier substrate was removed and the portion was mounted on a receiving substrate, iv) the carrier substrate was removed, and v) the immobilized sample was stained with H&E stain. FIG. 6C shows an H&E stained human kidney sample that was i) captured on a carrier substrate to form a sample-carrier construct, ii) the construct was deparaffinated, iii) the deparaffinated construct was stained with eosin Y stain; iv) a portion of the carrier substrate was removed and the portion was mounted on a receiving substrate, and v) the carrier substrate was removed. The deparaffinated construct of FIG. 6C was stained with $\frac{1}{10}$ of the concentration used in typical eosin Y staining. The boxes are indicative of glomeruli.

FIG. 7A shows tissue sections mounted on an APTES-functionalized wells; and FIG. 7B shows the same tissue sections after the 18 cycles of tissue integrity testing. FIG. 7C shows tissue sections mounted on a (5,6-epoxyhexyl)triethoxysilane (EHTES)-functionalized slide, and FIG. 7D shows the same tissue sections after the 18 cycles of tissue integrity testing. FIG. 7E shows tissue sections mounted on an EHTES and polyethyleneimine (PEI)-functionalized slide, and FIG. 7F shows the same tissue sections after the 18 cycles of tissue integrity testing. FIG. 7G shows tissue sections mounted on a PEI-functionalized slide, and FIG. 7H shows the same tissue sections after the 18 cycles of tissue integrity testing.

FIG. 11A provides a microplate (e.g., a container including 96 wells) with 96 mouse brain tissue sections arranged using the methods described herein. A neonatal mouse brain paraffin block in coronal orientation was sectioned in 5 µm sections. The arranged tissue sections represent approximately 500 µm in the z axis of the tissue. In this embodiment, H&E staining of the mouse brain sections occurred following transfer to the microplate. FIG. 11B provides images of the first three wells and an expanded view of three different regions within one the brain sections demonstrating the transfer methods described herein do not compromise the integrity of the tissue structures.

FIG. 14A illustrates an embodiment described herein for image focusing (e.g., 3D image focusing) using a combination of beads with different fluorophores. In embodiments, one or more fluorescently labelled beads can be added under a tissue section and across the surface of the tissue, in combination with the tissue transfer methods and embodiments described herein. The combination of differentially colored beads (as illustrated in FIG. 14A, e.g., wherein "green beads" are located across the surface of the tissue sample, and wherein "orange beads" are located on the bottom plane of the sample) may be used as fiducial markers for a variety of applications. FIGS. 14B-14C show fluorescent images of an example of two-bead detection across a 5 µm tissue section. The orange beads (OBs) are located under the tissue section, and are detected primarily in the bottom image slices (e.g., the bottom z-slices), whereas the green beads (GBs) are located throughout a variety of Z-axes throughout the tissue section surface.

DETAILED DESCRIPTION

Figure 1:
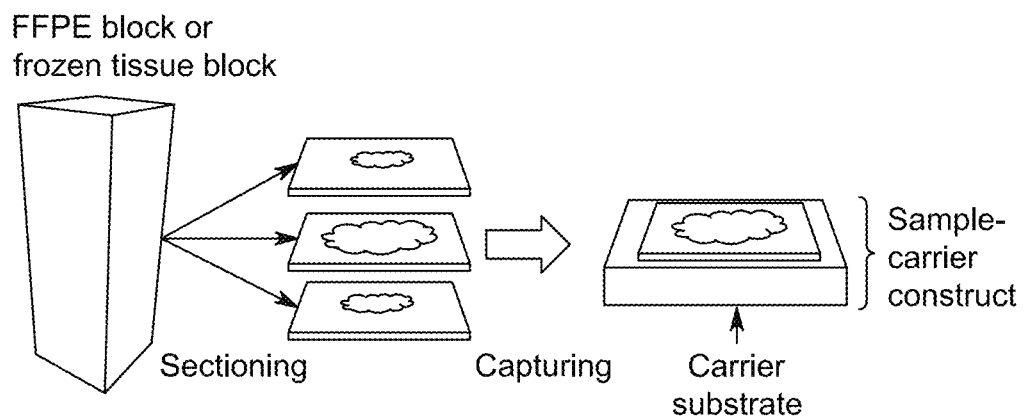
FIG. 1 depicts generating sections and subsequent capture of a biological sample. A sample block, either an FFPE block (i.e., a paraffin embedded biological sample) or fresh frozen tissue block containing a biological sample, is sliced into very thin sections, referred to as sectioning. Individual sections are then be captured using a carrier substrate to generate a sample-carrier construct.

The aspects and embodiments described herein relate to the transfer and manipulation of biological samples (e.g., tissue sections). As described herein, the methods and compositions of this disclosure have many advantages, including greatly enhanced efficiency and speed for tissue testing; and greatly decreased cost for multiple tissue testing.

I. Definitions

All patents, patent applications, articles and publications mentioned herein, both supra and infra, are hereby expressly incorporated herein by reference in their entireties.

Unless defined otherwise herein, all technical and scientific terms used herein have the same meaning as commonly understood by one of ordinary skill in the art to which this disclosure belongs. Various scientific dictionaries that include the terms included herein are well known and available to those in the art. Although any methods and materials similar or equivalent to those described herein find use in the practice or testing of the disclosure, some preferred methods and materials are described. Accordingly, the terms defined immediately below are more fully described by reference to the specification as a whole. It is to be understood that this disclosure is not limited to the particular methodology, protocols, and reagents described, as these may vary, depending upon the context in which they are used by those of skill in the art. The following definitions are provided to facilitate understanding of certain terms used frequently herein and are not meant to limit the scope of the present disclosure.

As used herein, the singular terms "a", "an", and "the" include the plural reference unless the context clearly indicates otherwise. Reference throughout this specification to, for example, "one embodiment", "an embodiment", "another embodiment", "a particular embodiment", "a related embodiment", "a certain embodiment", "an additional embodiment", or "a further embodiment" or combinations thereof means that a particular feature, structure or characteristic described in connection with the embodiment is included in at least one embodiment of the present disclosure. Thus, the appearances of the foregoing phrases in various places throughout this specification are not necessarily all referring to the same embodiment. Furthermore, the particular features, structures, or characteristics may be combined in any suitable manner in one or more embodiments.

As used herein, the term "about" means a range of values including the specified value, which a person of ordinary skill in the art would consider reasonably similar to the specified value. In embodiments, the term "about" means within a standard deviation using measurements generally acceptable in the art. In embodiments, about means a range extending to +/−10% of the specified value. In embodiments, about means the specified value.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements.

In the description, relative terms such as "before," "after," "above," "below," "up," "down," "top" and "bottom" as well as derivative thereof (e.g., "horizontally," "downwardly," "upwardly," etc.) should be construed to refer to the orientation as then described or as shown in the drawing or figure under discussion. These relative terms are for convenience of description and do not require that the system be constructed or operated in a particular orientation.

As used herein, the term "associated" or "associated with" can mean that two or more species are identifiable as being co-located at a point in time. An association can mean that two or more species are or were within a similar container. An association can be an informatics association, where for example digital information regarding two or more species is stored and can be used to determine that one or more of the species were co-located at a point in time. An association can also be a physical association. In some instances, two or more associated species are "tethered", "coated", "attached", or "immobilized" to one another or to a common solid or semisolid support (e.g. a receiving substrate). An association may refer to a relationship, or connection, between two entities. Associated may refer to the relationship between a sample and the DNA molecules, RNA molecules, or polynucleotides originating from or derived from that sample. These relationships may be encoded in oligonucleotide barcodes, as described herein. A polynucleotide is associated with a sample if it is an endogenous polynucleotide, i.e., it occurs in the sample at the time the sample is obtained, or is derived from an endogenous polynucleotide. For example, the RNAs endogenous to a cell are associated with that cell. cDNAs resulting from reverse transcription of these RNAs, and DNA amplicons resulting from PCR amplification of the cDNAs, contain the sequences of the RNAs and are also associated with the cell. The polynucleotides associated with a sample need not be located or synthesized in the sample, and are considered associated with the sample even after the sample has been destroyed (for example, after a cell has been lysed). Barcoding can be used to determine which polynucleotides in a mixture are associated with a particular sample.

As used herein, the term "complementary" or "substantially complementary" refers to the hybridization, base pairing, or the formation of a duplex between nucleotides or nucleic acids. For example, complementarity exists between the two strands of a double stranded DNA molecule or between an oligonucleotide primer and a primer binding site on a single stranded nucleic acid when a nucleotide (e.g., RNA or DNA) or a sequence of nucleotides is capable of base pairing with a respective cognate nucleotide or cognate sequence of nucleotides. As described herein and commonly known in the art the complementary (matching) nucleotide of adenosine (A) is thymidine (T) and the complementary (matching) nucleotide of guanosine (G) is cytosine (C). Thus, a complement may include a sequence of nucleotides that base pair with corresponding complementary nucleotides of a second nucleic acid sequence. The nucleotides of a complement may partially or completely match the nucleotides of the second nucleic acid sequence. Where the nucleotides of the complement completely match each nucleotide of the second nucleic acid sequence, the complement forms base pairs with each nucleotide of the second nucleic acid sequence. Where the nucleotides of the complement partially match the nucleotides of the second nucleic acid sequence only some of the nucleotides of the complement form base pairs with nucleotides of the second nucleic acid sequence. Examples of complementary sequences include coding and non-coding sequences, wherein the non-coding sequence contains complementary nucleotides to the coding sequence and thus forms the complement of the coding sequence. A further example of complementary sequences are sense and antisense sequences, wherein the sense sequence contains complementary nucleotides to the antisense sequence and thus forms the complement of the antisense sequence. "Duplex" means at least two oligonucleotides and/or polynucleotides that are fully or partially complementary undergo Watson-Crick type base pairing among all or most of their nucleotides so that a stable complex is formed.

As described herein, the complementarity of sequences may be partial, in which only some of the nucleic acids match according to base pairing, or complete, where all the nucleic acids match according to base pairing. Thus, two sequences that are complementary to each other, may have a specified percentage of nucleotides that complement one another (e.g., about 60%, preferably 65%, 70%, 75%, 80%, 85%, 90%, 91%, 92%, 93%, 94%, 95%, 96%, 97%, 98%, 99%, or higher complementarity over a specified region). In embodiments, two sequences are complementary when they are completely complementary, having 100% complementarity. In embodiments, sequences in a pair of complementary sequences form portions of a single polynucleotide with non-base-pairing nucleotides (e.g., as in a hairpin structure, with or without an overhang) or portions of separate polynucleotides. In embodiments, one or both sequences in a pair of complementary sequences form portions of longer polynucleotides, which may or may not include additional regions of complementarity.

As used herein, the term "contacting" is used in accordance with its plain ordinary meaning and refers to the process of allowing at least two distinct species (e.g., chemical compounds, biomolecules, nucleotides, binding reagents, or cells) to become sufficiently proximal to react, interact or physically touch. However, the resulting reaction product can be produced directly from a reaction between the added reagents or from an intermediate from one or more of the added reagents that can be produced in the reaction mixture. The term "contacting" may include allowing two species to react, interact, or physically touch, wherein the two species may be a compound, a protein (e.g., an antibody), or enzyme.

"Hybridize" shall mean the annealing of a nucleic acid sequence to another nucleic acid sequence (e.g., one single-stranded nucleic acid (such as a primer) to another nucleic acid) based on the well-understood principle of sequence complementarity. In an embodiment the other nucleic acid is a single-stranded nucleic acid. In some embodiments, one portion of a nucleic acid hybridizes to itself, such as in the formation of a hairpin structure. The propensity for hybridization between nucleic acids depends on the temperature and ionic strength of their milieu, the length of the nucleic acids and the degree of complementarity. The effect of these parameters on hybridization is described in, for example, Sambrook J., Fritsch E. F., Maniatis T., Molecular cloning: a laboratory manual, Cold Spring Harbor Laboratory Press, New York (1989). As used herein, hybridization of a primer, or of a DNA extension product, respectively, is extendable by creation of a phosphodiester bond with an available nucleotide or nucleotide analogue capable of forming a phosphodiester bond, therewith. For example, hybridization can be performed at a temperature ranging from 15° C. to 95° C. In some embodiments, the hybridization is performed at a temperature of about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., or about 95° C. In other embodiments, the stringency of the hybridization can be further altered by the addition or removal of components of the buffered solution.

As used herein, "specifically hybridizes" refers to preferential hybridization under hybridization conditions where two nucleic acids, or portions thereof, that are substantially complementary, hybridize to each other and not to other nucleic acids that are not substantially complementary to either of the two nucleic acids. For example, specific hybridization includes the hybridization of a primer or capture nucleic acid to a portion of a target nucleic acid (e.g., a template, or adapter portion of a template) that is substantially complementary to the primer or capture nucleic acid. In some embodiments nucleic acids, or portions thereof, that are configured to specifically hybridize are often about 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more or 100% complementary to each other over a contiguous portion of nucleic acid sequence. A specific hybridization discriminates over non-specific hybridization interactions (e.g., two nucleic acids that a not configured to specifically hybridize, e.g., two nucleic acids that are 80% or less, 70% or less, 60% or less or 50% or less complementary) by about 2-fold or more, often about 10-fold or more, and sometimes about 100-fold or more, 1000-fold or more, 10,000-fold or more, 100,000-fold or more, or 1,000,000-fold or more. Two nucleic acid strands that are hybridized to each other can form a duplex which includes a double stranded portion of nucleic acid.

As may be used herein, the terms "nucleic acid," "nucleic acid molecule," "nucleic acid sequence," "nucleic acid fragment" and "polynucleotide" are used interchangeably and are intended to include, but are not limited to, a polymeric form of nucleotides covalently linked together that may have various lengths, either deoxyribonucleotides or ribonucleotides, or analogs, derivatives or modifications thereof. Different polynucleotides may have different three-dimensional structures, and may perform various functions, known or unknown. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer. Polynucleotides useful in the methods of the disclosure may include natural nucleic acid sequences and variants thereof, artificial nucleic acid sequences, or a combination of such sequences. As may be used herein, the terms "nucleic acid oligomer" and "oligonucleotide" are used interchangeably and are intended to include, but are not limited to, nucleic acids having a length of 200 nucleotides or less. In some embodiments, an oligonucleotide is a nucleic acid having a length of 2 to 200 nucleotides, 2 to 150 nucleotides, 5 to 150 nucleotides or 5 to 100 nucleotides. The terms "polynucleotide," "oligonucleotide," "oligo" or the like refer, in the usual and customary sense, to a linear sequence of nucleotides. Oligonucleotides are typically from about 5, 6, 7, 8, 9, 10, 12, 15, 25, 30, 40, 50 or more nucleotides in length, up to about 100 nucleotides in length. In some embodiments, an oligonucleotide is a primer configured for extension by a polymerase when the primer is annealed completely or partially to a complementary nucleic acid template. A primer is often a single stranded nucleic acid. In certain embodiments, a primer, or portion thereof, is substantially complementary to a portion of an adapter. In some embodiments, a primer has a length of 200 nucleotides or less. In certain embodiments, a primer has a length of 10 to 150 nucleotides, 15 to 150 nucleotides, 5 to 100 nucleotides, 5 to 50 nucleotides or 10 to 50 nucleotides. In some embodiments, an oligonucleotide may be immobilized to a solid support.

As used herein, the terms "polynucleotide primer" and "primer" refers to any polynucleotide molecule that may hybridize to a polynucleotide template, be bound by a polymerase, and be extended in a template-directed process for nucleic acid synthesis (e.g., amplification and/or sequencing). The primer may be a separate polynucleotide from the polynucleotide template, or both may be portions of the same polynucleotide (e.g., as in a hairpin structure having a 3' end that is extended along another portion of the polynucleotide to extend a double-stranded portion of the hairpin). Primers (e.g., forward or reverse primers) may be attached to a solid support. A primer can be of any length depending on the particular technique it will be used for. For example, PCR primers are generally between 10 and 40 nucleotides in length. The length and complexity of the nucleic acid fixed onto the nucleic acid template may vary. In some embodiments, a primer has a length of 200 nucleotides or less. In certain embodiments, a primer has a length of 10 to 150 nucleotides, 15 to 150 nucleotides, 5 to 100 nucleotides, 5 to 50 nucleotides or 10 to 50 nucleotides. One of skill can adjust these factors to provide optimum hybridization and signal production for a given hybridization procedure. The primer permits the addition of a nucleotide residue thereto, or oligonucleotide or polynucleotide synthesis therefrom, under suitable conditions. In an embodiment the primer is a DNA primer, i.e., a primer consisting of, or largely consisting of, deoxyribonucleotide residues. The primers are designed to have a sequence that is the complement of a region of template/target DNA to which the primer hybridizes. The addition of a nucleotide residue to the 3' end of a primer by formation of a phosphodiester bond results in a DNA extension product. The addition of a nucleotide residue to the 3' end of the DNA extension product by formation of a phosphodiester bond results in a further DNA extension product. In another embodiment the primer is an RNA primer. In embodiments, a primer is hybridized to a target polynucleotide. A "primer" is complementary to a polynucleotide template, and complexes by hydrogen bonding or hybridization with the template to give a primer/template complex for initiation of synthesis by a polymerase, which is extended by the addition of covalently bonded bases linked at its 3' end complementary to the template in the process of DNA synthesis.

Nucleic acids, including e.g., nucleic acids with a phosphorothioate backbone, can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amino acid on a protein or polypeptide through a covalent, non-covalent or other interaction.

The term "messenger RNA" or "mRNA" refers to an RNA that is without introns and is capable of being translated into a polypeptide. The term "RNA" refers to any ribonucleic acid, including but not limited to mRNA, tRNA (transfer RNA), rRNA (ribosomal RNA), and/or noncoding RNA (such as lncRNA (long noncoding RNA)). The term "cDNA" refers to a DNA that is complementary or identical to an RNA, in either single stranded or double stranded form.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

As used herein, the terms "analogue" and "analog", in reference to a chemical compound, refers to compound having a structure similar to that of another one, but differing from it in respect of one or more different atoms, functional groups, or substructures that are replaced with one or more other atoms, functional groups, or substructures. In the context of a nucleotide, a nucleotide analog refers to a compound that, like the nucleotide of which it is an analog, can be incorporated into a nucleic acid molecule (e.g., an extension product) by a suitable polymerase, for example, a DNA polymerase in the context of a nucleotide analogue. The terms also encompass nucleic acids containing known nucleotide analogs or modified backbone residues or linkages, which are synthetic, naturally occurring, or non-naturally occurring, which have similar binding properties as the reference nucleic acid, and which are metabolized in a manner similar to the reference nucleotides. Examples of such analogs include, without limitation, phosphodiester derivatives including, e.g., phosphoramidate, phosphorodiamidate, phosphorothioate (also known as phosphorothioate having double bonded sulfur replacing oxygen in the phosphate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see, e.g., see Eckstein, OLIGONUCLEOTIDES AND ANALOGUES: A PRACTICAL APPROACH, Oxford University Press) as well as modifications to the nucleotide bases such as in 5-methyl cytidine or pseudouridine; and peptide nucleic acid backbones and linkages. Other analog nucleic acids include those with positive backbones; non-ionic backbones, modified sugars, and non-ribose backbones (e.g. phosphorodiamidate morpholino oligos or locked nucleic acids (LNA)), including those described in U.S. Pat. Nos. 5,235,033 and 5,034,506, and Chapters 6 and 7, ASC Symposium Series 580, CARBOHYDRATE MODIFICATIONS IN ANTISENSE RESEARCH, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

As used herein, a "native" nucleotide is used in accordance with its plain and ordinary meaning and refers to a naturally occurring nucleotide that does not include an exogenous label (e.g., a fluorescent dye, or other label) or chemical modification such as may characterize a nucleotide analog. Examples of native nucleotides useful for carrying out procedures described herein include: dATP (2'-deoxyadenosine-5'-triphosphate); dGTP (2'-deoxyguanosine-5'-triphosphate); dCTP (2'-deoxycytidine-5'-triphosphate); dTTP (2'-deoxythymidine-5'-triphosphate); and dUTP (2'-deoxyuridine-5'-triphosphate).

In embodiments, the nucleotides of the present disclosure use a cleavable linker to attach the label to the nucleotide. The use of a cleavable linker ensures that the label can, if required, be removed after detection, avoiding any interfering signal with any labelled nucleotide incorporated subsequently. The use of the term "cleavable linker" is not meant to imply that the whole linker is required to be removed from the nucleotide base. The cleavage site can be located at a position on the linker that ensures that part of the linker remains attached to the nucleotide base after cleavage. The linker can be attached at any position on the nucleotide base provided that Watson-Crick base pairing can still be carried out. In the context of purine bases, it is preferred if the linker is attached via the 7-position of the purine or the preferred deazapurine analogue, via an 8-modified purine, via an N-6 modified adenosine or an N-2 modified guanine. For pyrimidines, attachment is preferably via the 5-position on cytidine, thymidine or uracil and the N-4 position on cytosine.

The term "cleavable linker" or "cleavable moiety" as used herein refers to a divalent or monovalent, respectively, moiety which is capable of being separated (e.g., detached, split, disconnected, hydrolyzed, a stable bond within the moiety is broken) into distinct entities. A cleavable linker is cleavable (e.g., specifically cleavable) in response to external stimuli (e.g., enzymes, nucleophilic/basic reagents, reducing agents, photo-irradiation, electrophilic/acidic reagents, organometallic and metal reagents, or oxidizing reagents). A chemically cleavable linker refers to a linker which is capable of being split in response to the presence of a chemical (e.g., acid, base, oxidizing agent, reducing agent, Pd(0), tris-(2-carboxyethyl) phosphine, dilute nitrous acid, fluoride, tris(3-hydroxypropyl)phosphine), sodium dithionite ($Na_2S_2O_4$), or hydrazine ($N_2H_4$)). A chemically cleavable linker is non-enzymatically cleavable. In embodiments, the cleavable linker is cleaved by contacting the cleavable linker with a cleaving agent. In embodiments, the cleaving agent is a phosphine containing reagent (e.g., TCEP or THPP), sodium dithionite ($Na_2S_2O_4$), weak acid, hydrazine ($N_2H_4$), Pd(0), or light-irradiation (e.g., ultraviolet radiation). In embodiments, cleaving includes removing. A "cleavable site" or "scissile linkage" in the context of a polynucleotide is a site which allows controlled cleavage of the polynucleotide strand (e.g., the linker, the primer, or the polynucleotide) by chemical, enzymatic, or photochemical means known in the art and described herein. A scissile site may refer to the linkage of a nucleotide between two other nucleotides in a nucleotide strand (i.e., an internucleosidic linkage). In embodiments, the scissile linkage can be located at any position within the one or more nucleic acid molecules, including at or near a terminal end (e.g., the 3' end of an oligonucleotide) or in an interior portion of the one or more nucleic acid molecules. In embodiments, conditions suitable for separating a scissile linkage include a modulating the pH and/or the temperature. In embodiments, a scissile site can include at least one acid-labile linkage. For example, an acid-labile linkage may include a phosphoramidate linkage. In embodiments, a phosphoramidate linkage can be hydrolysable under acidic conditions, including mild acidic conditions such as trifluoroacetic acid and a suitable temperature (e.g., 30° C.), or other conditions known in the art, for example Matthias Mag, et al Tetrahedron Letters, Volume 33, Issue 48, 1992, 7319-7322. In embodiments, the scissile site can include at least one photolabile internucleosidic linkage (e.g., o-nitrobenzyl linkages, as described in Walker et al, J. Am. Chem. Soc. 1988, 110, 21, 7170-7177), such as o-nitrobenzyloxymethyl or p-nitrobenzyloxymethyl group(s). In embodiments, the scissile site includes at least one uracil nucleobase. In embodiments, a uracil nucleobase can be cleaved with a uracil DNA glycosylase (UDG) or Formamidopyrimidine DNA Glycosylase Fpg. In embodiments, the scissile linkage site includes a sequence-specific nicking site having a nucleotide sequence that is recognized and nicked by a nicking endonuclease enzyme or a uracil DNA glycosylase.

As used herein, the term "modified nucleotide" refers to nucleotide modified in some manner. Typically, a nucleotide contains a single 5-carbon sugar moiety, a single nitrogenous base moiety and 1 to three phosphate moieties. In embodiments, a nucleotide can include a blocking moiety and/or a label moiety. A blocking moiety on a nucleotide prevents formation of a covalent bond between the 3' hydroxyl moiety of the nucleotide and the 5' phosphate of another nucleotide. A blocking moiety on a nucleotide can be reversible, whereby the blocking moiety can be removed or modified to allow the 3' hydroxyl to form a covalent bond with the 5' phosphate of another nucleotide. A blocking moiety can be effectively irreversible under particular conditions used in a method set forth herein. In embodiments, the blocking moiety is attached to the 3' oxygen of the nucleotide and is independently $-NH_2$, $-CN$, $-CH_3$, $C_2$-$C_6$ allyl (e.g., $-CH_2-CH=CH_2$), methoxyalkyl (e.g., $-CH_2-O-CH_3$), or $-CH_2N_3$. In embodiments, the blocking moiety is attached to the 3' oxygen of the nucleotide and is independently

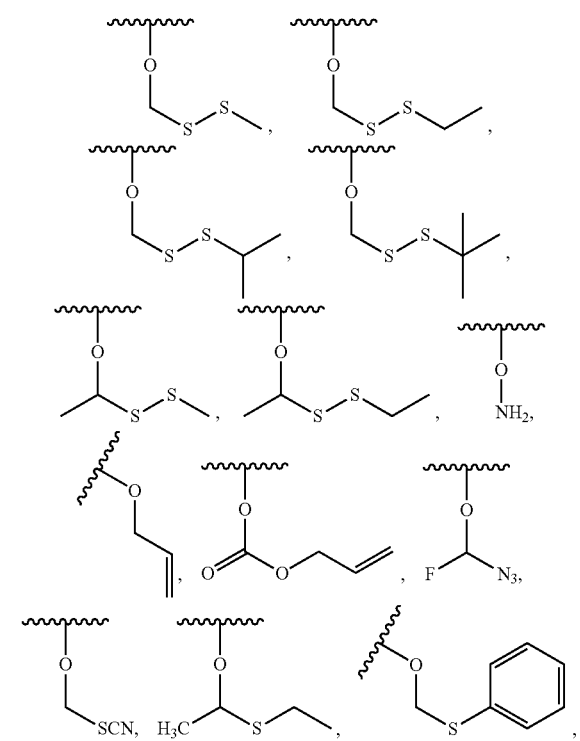

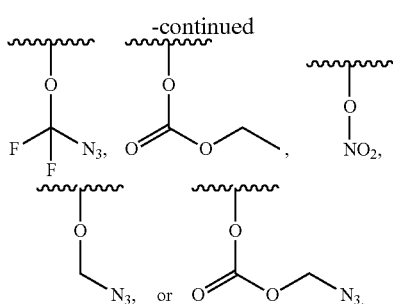

A label moiety of a modified nucleotide can be any moiety that allows the nucleotide to be detected, for example, using a spectroscopic method. Exemplary label moieties are fluorescent labels, mass labels, chemiluminescent labels, electrochemical labels, detectable labels and the like. One or more of the above moieties can be absent from a nucleotide used in the methods and compositions set forth herein. For example, a nucleotide can lack a label moiety or a blocking moiety or both. Examples of nucleotide analogues include, without limitation, 7-deaza-adenine, 7-deaza-guanine, the analogues of deoxynucleotides shown herein, analogues in which a label is attached through a cleavable linker to the 5-position of cytosine or thymine or to the 7-position of deaza-adenine or deaza-guanine, and analogues in which a small chemical moiety is used to cap the OH group at the 3'-position of deoxyribose. Nucleotide analogues and DNA polymerase-based DNA sequencing are also described in U.S. Pat. No. 6,664,079, which is incorporated herein by reference in its entirety for all purposes. Non-limiting examples of detectable labels include labels including fluorescent dyes, biotin, digoxin, haptens, and epitopes. In general, a dye is a molecule, compound, or substance that can provide an optically detectable signal, such as a colorimetric, luminescent, bioluminescent, chemiluminescent, phosphorescent, or fluorescent signal. In embodiments, the dye is a fluorescent dye. Non-limiting examples of dyes, some of which are commercially available, include CF dyes (Biotium, Inc.), Alexa Fluor dyes (Thermo Fisher), DyLight dyes (Thermo Fisher), Cy dyes (GE Healthscience), IRDyes (Li-Cor Biosciences, Inc.), and HiLyte dyes (Anaspec, Inc.). In embodiments, the label is a fluorophore.

In some embodiments, a nucleic acid includes a label. As used herein, the term "label" or "labels" is used in accordance with their plain and ordinary meanings and refer to molecules that can directly or indirectly produce or result in a detectable signal either by themselves or upon interaction with another molecule. Non-limiting examples of detectable labels include fluorescent dyes, biotin, digoxin, haptens, and epitopes. In general, a dye is a molecule, compound, or substance that can provide an optically detectable signal, such as a colorimetric, luminescent, bioluminescent, chemiluminescent, phosphorescent, or fluorescent signal. In embodiments, the label is a dye. In embodiments, the dye is a fluorescent dye. Non-limiting examples of dyes, some of which are commercially available, include CF dyes (Biotium, Inc.), Alexa Fluor dyes (Thermo Fisher), DyLight dyes (Thermo Fisher), Cy dyes (GE Healthscience), IRDyes (Li-Cor Biosciences, Inc.), and HiLyte dyes (Anaspec, Inc.). In embodiments, a particular nucleotide type is associated with a particular label, such that identifying the label identifies the nucleotide with which it is associated. In embodiments, the label is luciferin that reacts with luciferase to produce a detectable signal in response to one or more bases being incorporated into an elongated complementary strand, such as in pyrosequencing. In embodiment, a nucleotide includes a label (such as a dye). In embodiments, the label is not associated with any particular nucleotide, but detection of the label identifies whether one or more nucleotides having a known identity were added during an extension step (such as in the case of pyrosequencing). Examples of detectable agents (i.e., labels) include imaging agents, including fluorescent and luminescent substances, molecules, or compositions, including, but not limited to, a variety of organic or inorganic small molecules commonly referred to as "dyes," "labels," or "indicators." Examples include fluorescein, rhodamine, acridine dyes, Alexa dyes, and cyanine dyes. In embodiments, the detectable moiety is a fluorescent molecule (e.g., acridine dye, cyanine, dye, fluorine dye, oxazine dye, phenanthridine dye, or rhodamine dye). In embodiments, the detectable moiety is a fluorescent molecule (e.g., acridine dye, cyanine, dye, fluorine dye, oxazine dye, phenanthridine dye, or rhodamine dye). The term "cyanine" or "cyanine moiety" as described herein refers to a detectable moiety containing two nitrogen groups separated by a polymethine chain. In embodiments, the cyanine moiety has 3 methine structures (i.e., cyanine 3 or Cy3). In embodiments, the cyanine moiety has 5 methine structures (i.e., cyanine 5 or Cy5). In embodiments, the cyanine moiety has 7 methine structures (i.e., cyanine 7 or Cy7).

The term "nucleoside" refers, in the usual and customary sense, to a glycosylamine including a nucleobase and a five-carbon sugar (ribose or deoxyribose). Non-limiting examples of nucleosides include cytidine, uridine, adenosine, guanosine, thymidine and inosine. Nucleosides may be modified at the base and/or the sugar. The term "nucleotide" refers, in the usual and customary sense, to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA, and hybrid molecules having mixtures of single and double stranded DNA and RNA. Examples of nucleic acid, e.g., polynucleotides contemplated herein include any types of RNA, e.g., mRNA, siRNA, miRNA, and guide RNA and any types of DNA, genomic DNA, plasmid DNA, and minicircle DNA, and any fragments thereof. The term "duplex" in the context of polynucleotides refers, in the usual and customary sense, to double strandedness.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site www.ncbi.nlm.nih.gov/BLAST/or the like). Such sequences are then said to be "substantially identical." This definition also refers to, or may be applied to, the complement of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

As used herein, the term "removable" group, e.g., a label or a blocking group or protecting group, is used in accordance with its plain and ordinary meaning and refers to a chemical group that can be removed from a nucleotide analogue such that a DNA polymerase can extend the nucleic acid (e.g., a primer or extension product) by the incorporation of at least one additional nucleotide. Removal may be by any suitable method, including enzymatic, chemical, or photolytic cleavage. Removal of a removable group, e.g., a blocking group, does not require that the entire removable group be removed, only that a sufficient portion of it be removed such that a DNA polymerase can extend a nucleic acid by incorporation of at least one additional nucleotide using a nucleotide or nucleotide analogue. In general, the conditions under which a removable group is removed are compatible with a process employing the removable group (e.g., an amplification process or sequencing process).

As used herein, the terms "reversible blocking groups" and "reversible terminators" are used in accordance with their plain and ordinary meanings and refer to a blocking moiety located, for example, at the 3' position of a modified nucleotide and may be a chemically cleavable moiety such as an allyl group, an azidomethyl group or a methoxymethyl group, or may be an enzymatically cleavable group such as a phosphate ester. Non-limiting examples of nucleotide blocking moieties are described in applications WO 2004/018497, WO 96/07669, U.S. Pat. Nos. 7,057,026, 7,541,444, 5,763,594, 5,808,045, 5,872,244 and 6,232,465 the contents of which are incorporated herein by reference in their entirety. The nucleotides may be labelled or unlabeled. They may be modified with reversible terminators useful in methods provided herein and may be 3'-O-blocked reversible or 3'-unblocked reversible terminators. In nucleotides with 3'-O-blocked reversible terminators, the blocking group-OR [reversible terminating (capping) group] is linked to the oxygen atom of the 3'-OH of the pentose, while the label is linked to the base, which acts as a reporter and can be cleaved. The 3'-O-blocked reversible terminators are known in the art, and may be, for instance, a 3'-ONH₂ reversible terminator, a 3'-O-allyl reversible terminator, or a 3'-O-azidomethyl reversible terminator. In embodiments, the reversible terminator moiety is attached to the 3'-oxygen of the nucleotide, having the formula:

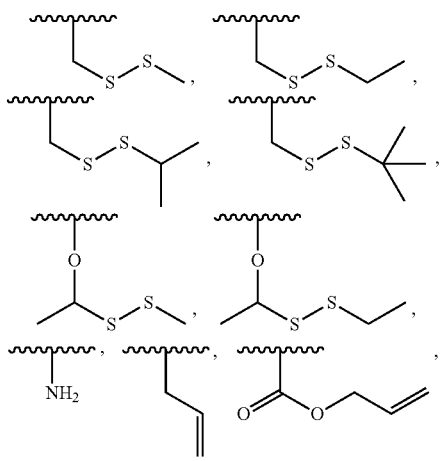

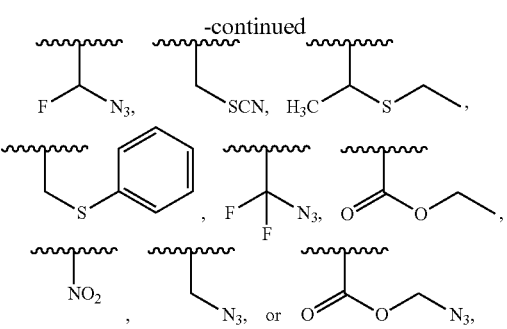

wherein the 3' oxygen of the nucleotide is not shown in the formulae above. The term "allyl" as described herein refers to an unsubstituted methylene attached to a vinyl group (i.e., —CH=CH₂). In embodiments, the reversible terminator moiety is

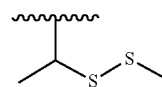

as described in U.S. Pat. No. 10,738,072, which is incorporated herein by reference for all purposes. For example, a nucleotide including a reversible terminator moiety may be represented by the formula:

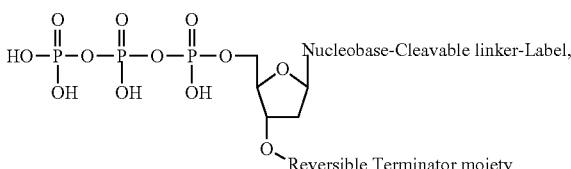

where the nucleobase is adenine or adenine analogue, thymine or thymine analogue, guanine or guanine analogue, or cytosine or cytosine analogue.

In some embodiments, a nucleic acid (e.g., an adapter or a primer) includes a molecular identifier or a molecular barcode. As used herein, the term "molecular barcode" (which may be referred to as a "tag", a "barcode", a "molecular identifier", an "identifier sequence" or a "unique molecular identifier" (UMI)) refers to any material (e.g., a nucleotide sequence, a nucleic acid molecule feature) that is capable of distinguishing an individual molecule in a large heterogeneous population of molecules. In embodiments, a barcode is unique in a pool of barcodes that differ from one another in sequence, or is uniquely associated with a particular sample polynucleotide in a pool of sample polynucleotides. In embodiments, every barcode in a pool of adapters is unique, such that sequencing reads including the barcode can be identified as originating from a single sample polynucleotide molecule on the basis of the barcode alone. In other embodiments, individual barcode sequences may be used more than once, but adapters including the duplicate barcodes are associated with different sequences and/or in different combinations of barcoded adaptors, such that sequence reads may still be uniquely distinguished as originating from a single sample polynucleotide molecule on the basis of a barcode and adjacent sequence information (e.g., sample polynucleotide sequence, and/or one or more adjacent barcodes). In embodiments, barcodes are about or at least about 5, 6, 7, 8, 9, 10, 15, 20, 25, 30, 40, 50, 75 or more nucleotides in length. In embodiments, barcodes are shorter than 20, 15, 10, 9, 8, 7, 6, or 5 nucleotides in length. In embodiments, barcodes are about 10 to about 50 nucleotides in length, such as about 15 to about 40 or about 20 to about 30 nucleotides in length. In a pool of different barcodes, barcodes may have the same or different lengths. In general, barcodes are of sufficient length and include sequences that are sufficiently different to allow the identification of sequencing reads that originate from the same sample polynucleotide molecule. In embodiments, each barcode in a plurality of barcodes differs from every other barcode in the plurality by at least three nucleotide positions, such as at least 3, 4, 5, 6, 7, 8, 9, 10, or more nucleotide positions. In some embodiments, substantially degenerate barcodes may be known as random. In some embodiments, a barcode may include a nucleic acid sequence from within a pool of known sequences. In some embodiments, the barcodes may be pre-defined.

In embodiments, a nucleic acid (e.g., an adapter or primer) includes a sample barcode. In general, a "sample barcode" is a nucleotide sequence that is sufficiently different from other sample barcode to allow the identification of the sample source based on sample barcode sequence(s) with which they are associated. In embodiments, a plurality of nucleotides (e.g., all nucleotides from a particular sample source, or sub-sample thereof) are joined to a first sample barcode, while a different plurality of nucleotides (e.g., all nucleotides from a different sample source, or different subsample) are joined to a second sample barcode, thereby associating each plurality of polynucleotides with a different sample barcode indicative of sample source. In embodiments, each sample barcode in a plurality of sample barcodes differs from every other sample barcode in the plurality by at least three nucleotide positions, such as at least 3, 4, 5, 6, 7, 8, 9, 10, or more nucleotide positions. In some embodiments, substantially degenerate sample barcodes may be known as random. In some embodiments, a sample barcode may include a nucleic acid sequence from within a pool of known sequences. In some embodiments, the sample barcodes may be pre-defined. In embodiments, the sample barcode includes about 1 to about 10 nucleotides. In embodiments, the sample barcode includes about 3, 4, 5, 6, 7, 8, 9, or about 10 nucleotides. In embodiments, the sample barcode includes about 3 nucleotides. In embodiments, the sample barcode includes about 5 nucleotides. In embodiments, the sample barcode includes about 7 nucleotides. In embodiments, the sample barcode includes about 10 nucleotides. In embodiments, the sample barcode includes about 6 to about 10 nucleotides.

As used herein, the term "biomolecule" refers to an agent (e.g., a compound, macromolecule, or small molecule), and the like derived from a biological system (e.g., an organism). The biomolecule may contain multiple individual components that collectively construct the biomolecule, for example, in embodiments, the biomolecule is a polynucleotide wherein the polynucleotide is composed of nucleotide monomers. The biomolecule may be or may include DNA, RNA, organelles, carbohydrates, lipids, proteins, or any combination thereof. These components may be extracellular. In some examples, the biomolecule may be referred to as a clump or aggregate of combinations of components. In some instances, the biomolecule may include one or more constituents of a cell but may not include other constituents of the cell. In embodiments, a biomolecule is a molecule produced by a biological system (e.g., an organism). In embodiments, a biomolecule may be referred to as an analyte. Analytes can be broadly classified into one of two groups: nucleic acid analytes, and non-nucleic acid analytes. Examples of non-nucleic acid analytes include, but are not limited to, lipids, carbohydrates, peptides, proteins, glycoproteins (N-linked or O-linked), lipoproteins, phosphoproteins, specific phosphorylated or acetylated variants of proteins, amidation variants of proteins, hydroxylation variants of proteins, methylation variants of proteins, ubiquitylation variants of proteins, sulfation variants of proteins, viral proteins (e.g., viral capsid, viral envelope, viral coat, viral accessory, viral glycoproteins, viral spike, etc.), extracellular and intracellular proteins, antibodies, and antigen binding fragments. In embodiments, the analytes within a cell can be localized to subcellular locations, including, for example, organelles, e.g., mitochondria, Golgi apparatus, endoplasmic reticulum, chloroplasts, endocytic vesicles, exocytic vesicles, vacuoles, lysosomes, etc. In embodiments, analyte(s) can be peptides or proteins, including antibodies and/or enzymes. In embodiments, an analyte can be detected indirectly, such as through detection of an intermediate agent, for example, a ligation product or an analyte capture agent (e.g., an oligonucleotide-conjugated antibody), such as those described herein.

As used herein, the term "biological system" refers to a virus, cell, cell derivative, cell nucleus, cell organelle, cell constituent and the like derived from a biological sample. Examples of a cell organelle include, without limitation, a nucleus, endoplasmic reticulum, a ribosome, a Golgi apparatus, an endoplasmic reticulum, a chloroplast, an endocytic vesicle, an exocytic vesicle, a vacuole, and a lysosome. The biological system (e.g., an organism) may contain multiple individual components, such as viruses, cells, cell derivatives, cell nuclei, cell organelles and cell constituents, including combinations of different of these and other components. The biological system may include DNA, RNA, organelles, proteins, or any combination thereof. These components may be extracellular. In some examples, the biological system may be referred to as a clump or aggregate of combinations of components. In some instances, the biological system may include one or more constituents of a cell but may not include other constituents of the cell. An example of such constituents include nucleus or an organelle. A cell may be a live or viable cell. The live cell may be capable of being cultured, for example, being cultured when enclosed in a gel or polymer matrix or cultured when including a gel or polymer matrix. A biological system may include a single cell and/or a single nuclei from a cell.

As used herein, the term "DNA polymerase" and "nucleic acid polymerase" are used in accordance with their plain ordinary meanings and refer to enzymes capable of synthesizing nucleic acid molecules from nucleotides (e.g., deoxyribonucleotides). Exemplary types of polymerases that may be used in the compositions and methods of the present disclosure include the nucleic acid polymerases such as DNA polymerase, DNA- or RNA-dependent RNA polymerase, and reverse transcriptase. In some cases, the DNA polymerase is 9°N polymerase or a variant thereof, *E. Coli* DNA polymerase I, Bacteriophage T4 DNA polymerase, Sequenase, Taq DNA polymerase, DNA polymerase from *Bacillus stearothermophilus*, Bst 2.0 DNA polymerase, 9°N polymerase (exo-) A485L/Y409V, Phi29 DNA Polymerase (φ29 DNA Polymerase), T7 DNA polymerase, DNA polymerase II, DNA polymerase III holoenzyme, DNA polymerase IV, DNA polymerase V, VentR DNA polymerase, Therminator™ II DNA Polymerase, Therminator™ III DNA Polymerase, or Therminator™ IX DNA Polymerase. In embodiments, the polymerase is a protein polymerase. Typically, a DNA polymerase adds nucleotides to the 3'-end of a DNA strand, one nucleotide at a time. In embodiments, the DNA polymerase is a Pol I DNA polymerase, Pol II DNA polymerase, Pol III DNA polymerase, Pol IV DNA polymerase, Pol V DNA polymerase, Pol β DNA polymerase, Pol μ DNA polymerase, Pol λ DNA polymerase, Pol σ DNA polymerase, Pol α DNA polymerase, Pol δ DNA polymerase, Pol ε DNA polymerase, Pol η DNA polymerase, Pol ι DNA polymerase, Pol κ DNA polymerase, Pol ζ DNA polymerase, Pol γ DNA polymerase, Pol θ DNA polymerase, Pol ν DNA polymerase, or a thermophilic nucleic acid polymerase (e.g. Therminator γ, 9°N polymerase (exo-), Therminator II, Therminator III, or Therminator IX). In embodiments, the DNA polymerase is a modified archaeal DNA polymerase. In embodiments, the polymerase is a reverse transcriptase. In embodiments, the polymerase is a mutant *P. abyssi* polymerase (e.g., such as a mutant *P. abyssi* polymerase described in WO 2018/148723 or WO 2020/056044). In embodiments, the polymerase is an enzyme described in US 2021/0139884.

As used herein, the term "exonuclease activity" is used in accordance with its ordinary meaning in the art, and refers to the removal of a nucleotide from a nucleic acid by a DNA polymerase. For example, during polymerization, nucleotides are added to the 3' end of the primer strand. Occasionally a DNA polymerase incorporates an incorrect nucleotide to the 3'-OH terminus of the primer strand, wherein the incorrect nucleotide cannot form a hydrogen bond to the corresponding base in the template strand. Such a nucleotide, added in error, is removed from the primer as a result of the 3' to 5' exonuclease activity of the DNA polymerase. In embodiments, exonuclease activity may be referred to as "proofreading." When referring to 3'-5' exonuclease activity, it is understood that the DNA polymerase facilitates a hydrolyzing reaction that breaks phosphodiester bonds at either the 3' end of a polynucleotide chain to excise the nucleotide. In embodiments, 3'-5' exonuclease activity refers to the successive removal of nucleotides in single-stranded DNA in a 3'→5' direction, releasing deoxyribonucleoside 5'-monophosphates one after another. Methods for quantifying exonuclease activity are known in the art, see for example Southworth et al, PNAS Vol 93, 8281-8285 (1996).

As used herein, the term "incorporating" or "chemically incorporating," when used in reference to a primer and cognate nucleotide, refers to the process of joining the cognate nucleotide to the primer or extension product thereof by formation of a phosphodiester bond.

As used herein, the term "template polynucleotide" refers to any polynucleotide molecule that may be bound by a polymerase and utilized as a template for nucleic acid synthesis. A template polynucleotide may be a target polynucleotide. In general, the term "target polynucleotide" refers to a nucleic acid molecule or polynucleotide in a starting population of nucleic acid molecules having a target sequence whose presence, amount, and/or nucleotide sequence, or changes in one or more of these, are desired to be determined. The target sequence may be a portion of a gene, a regulatory sequence, genomic DNA, cDNA, RNA including mRNA, miRNA, rRNA, or others. The target sequence may be a target sequence from a sample or a secondary target such as a product of an amplification reaction. A target polynucleotide is not necessarily any single molecule or sequence. For example, a target polynucleotide may be any one of a plurality of target polynucleotides in a reaction, or all polynucleotides in a given reaction, depending on the reaction conditions. For example, in a nucleic acid amplification reaction with random primers, all polynucleotides in a reaction may be amplified. As a further example, a collection of targets may be simultaneously assayed using polynucleotide primers directed to a plurality of targets in a single reaction. As yet another example, all or a subset of polynucleotides in a sample may be modified by the addition of a primer-binding sequence (such as by the ligation of adapters containing the primer binding sequence), rendering each modified polynucleotide a target polynucleotide in a reaction with the corresponding primer polynucleotide(s). In the context of selective sequencing, "target polynucleotide(s)" refers to the subset of polynucleotide(s) to be sequenced from within a starting population of polynucleotides.

In embodiments, a target polynucleotide is a cell-free polynucleotide. In general, the terms "cell-free," "circulating," and "extracellular" as applied to polynucleotides (e.g. "cell-free DNA" (cfDNA) and "cell-free RNA" (cfRNA)) are used interchangeably to refer to polynucleotides present in a sample from a subject or portion thereof that can be isolated or otherwise manipulated without applying a lysis step to the sample as originally collected (e.g., as in extraction from cells or viruses). Cell-free polynucleotides are thus unencapsulated or "free" from the cells or viruses from which they originate, even before a sample of the subject is collected. Cell-free polynucleotides may be produced as a byproduct of cell death (e.g., apoptosis or necrosis) or cell shedding, releasing polynucleotides into surrounding body fluids or into circulation. Accordingly, cell-free polynucleotides may be isolated from a non-cellular fraction of blood (e.g., serum or plasma), from other bodily fluids (e.g., urine), or from non-cellular fractions of other types of samples.

A nucleic acid can be amplified by a suitable method. The term "amplified" as used herein refers to subjecting a target nucleic acid in a sample to a process that linearly or exponentially generates amplicon nucleic acids having the same or substantially the same (e.g., substantially identical) nucleotide sequence as the target nucleic acid, or segment thereof, and/or a complement thereof. In some embodiments an amplification reaction includes a suitable thermal stable polymerase. Thermal stable polymerases are known in the art and are stable for prolonged periods of time, at temperature greater than 80° C. when compared to common polymerases found in most mammals. In certain embodiments the term "amplified" refers to a method that includes a polymerase chain reaction (PCR). Conditions conducive to amplification (i.e., amplification conditions) are well known and often include at least a suitable polymerase, a suitable template, a suitable primer or set of primers, suitable nucleotides (e.g., dNTPs), a suitable buffer, and application of suitable annealing, hybridization and/or extension times and temperatures. In certain embodiments an amplified product (e.g., an amplicon) can contain one or more additional and/or different nucleotides than the template sequence, or portion thereof, from which the amplicon was generated (e.g., a primer can contain "extra" nucleotides (such as a 5' portion that does not hybridize to the template), or one or more mismatched bases within a hybridizing portion of the primer).

As used herein, the term "rolling circle amplification (RCA)" refers to a nucleic acid amplification reaction that amplifies a circular nucleic acid template (e.g., single-stranded DNA circles) via a rolling circle mechanism. Rolling circle amplification reaction is initiated by the hybridization of a primer to a circular, often single-stranded, nucleic acid template. The nucleic acid polymerase then extends the primer that is hybridized to the circular nucleic acid template by continuously progressing around the circular nucleic acid template to replicate the sequence of the nucleic acid template over and over again (rolling circle mechanism). The rolling circle amplification typically produces concatemers including tandem repeat units of the circular nucleic acid template sequence. The rolling circle amplification may be a linear RCA (LRCA), exhibiting linear amplification kinetics (e.g., RCA using a single specific primer), or may be an exponential RCA (ERCA) exhibiting exponential amplification kinetics. Rolling circle amplification may also be performed using multiple primers (multiply primed rolling circle amplification or MPRCA) leading to hyper-branched concatemers. For example, in a double-primed RCA, one primer may be complementary, as in the linear RCA, to the circular nucleic acid template, whereas the other may be complementary to the tandem repeat unit nucleic acid sequences of the RCA product. Consequently, the double-primed RCA may proceed as a chain reaction with exponential (geometric) amplification kinetics featuring a ramifying cascade of multiple-hybridization, primer-extension, and strand-displacement events involving both the primers. This often generates a discrete set of concatemeric, double-stranded nucleic acid amplification products. The rolling circle amplification may be performed in-vitro under isothermal conditions using a suitable nucleic acid polymerase such as Phi29 DNA polymerase. RCA may be performed by using any of the DNA polymerases that are known in the art (e.g., a Phi29 DNA polymerase, a Bst DNA polymerase, or SD polymerase).

A nucleic acid can be amplified by a thermocycling method or by an isothermal amplification method. In some embodiments a rolling circle amplification method is used. In some embodiments amplification takes place on a solid support (e.g., within a flow cell) where a nucleic acid, nucleic acid library or portion thereof is immobilized. In certain sequencing methods, a nucleic acid library is added to a flow cell and immobilized by hybridization to anchors under suitable conditions. This type of nucleic acid amplification is often referred to as solid phase amplification. In some embodiments of solid phase amplification, all or a portion of the amplified products are synthesized by an extension initiating from an immobilized primer. Solid phase amplification reactions are analogous to standard solution phase amplifications except that at least one of the amplification oligonucleotides (e.g., primers) is immobilized on a solid support.

In some embodiments solid phase amplification includes a nucleic acid amplification reaction including only one species of oligonucleotide primer immobilized to a surface or substrate. In certain embodiments solid phase amplification includes a plurality of different immobilized oligonucleotide primer species. In some embodiments solid phase amplification may include a nucleic acid amplification reaction including one species of oligonucleotide primer immobilized on a solid surface and a second different oligonucleotide primer species in solution. Multiple different species of immobilized or solution-based primers can be used. Non-limiting examples of solid phase nucleic acid amplification reactions include interfacial amplification, bridge PCR amplification, emulsion PCR, WildFire amplification (e.g., US patent publication US20130012399), the like or combinations thereof.

As used herein, the terms "sequencing", "sequence determination", and "determining a nucleotide sequence", are used in accordance with their ordinary meaning in the art, and refer to determination of partial as well as full sequence information of the nucleic acid being sequenced, and particular physical processes for generating such sequence information. That is, the term includes sequence comparisons, fingerprinting, and like levels of information about a target nucleic acid, as well as the express identification and ordering of nucleotides in a target nucleic acid. The term also includes the determination of the identification, ordering, and locations of one, two, or three of the four types of nucleotides within a target nucleic acid. Sequencing produces a sequencing read.

As used herein, the term "sequencing reaction mixture" is used in accordance with its plain and ordinary meaning and refers to an aqueous mixture that contains the reagents necessary to allow dNTP or dNTP analogue (e.g., a modified nucleotide) to add a nucleotide to a DNA strand by a DNA polymerase. In embodiments, the sequencing reaction mixture includes a buffer. In embodiments, the buffer includes an acetate buffer, 3-(N-morpholino) propanesulfonic acid (MOPS) buffer, N-(2-Acetamido)-2-aminoethanesulfonic acid (ACES) buffer, phosphate-buffered saline (PBS) buffer, 4-(2-hydroxyethyl)-1-piperazineethanesulfonic acid (HEPES) buffer, N-(1,1-Dimethyl-2-hydroxyethyl)-3-amino-2-hydroxypropanesulfonic acid (AMPSO) buffer, borate buffer (e.g., borate buffered saline, sodium borate buffer, boric acid buffer), 2-Amino-2-methyl-1,3-propanediol (AMPD) buffer, N-cyclohexyl-2-hydroxyl-3-aminopropanesulfonic acid (CAPSO) buffer, 2-Amino-2-methyl-1-propanol (AMP) buffer, 4-(cyclohexylamino)-1-butanesulfonic acid (CABS) buffer, glycine-NaOH buffer, N-Cyclohexyl-2-aminoethanesulfonic acid (CHES) buffer, tris(hydroxymethyl) aminomethane (Tris) buffer, or a N-cyclohexyl-3-aminopropanesulfonic acid (CAPS) buffer. In embodiments, the buffer is a borate buffer. In embodiments, the buffer is a CHES buffer. In embodiments, the sequencing reaction mixture includes nucleotides, wherein the nucleotides include a reversible terminating moiety and a label covalently linked to the nucleotide via a cleavable linker. In embodiments, the sequencing reaction mixture includes a buffer, DNA polymerase, detergent (e.g., Triton X), a chelator (e.g., EDTA), and/or salts (e.g., ammonium sulfate, magnesium chloride, sodium chloride, or potassium chloride).

As used herein, the term "sequencing cycle" is used in accordance with its plain and ordinary meaning and refers to incorporating one or more nucleotides (e.g., a compound described herein) to the 3' end of a polynucleotide with a polymerase, and detecting one or more labels that identify the one or more nucleotides incorporated. The sequencing may be accomplished by, for example, sequencing by synthesis, pyrosequencing, and the like. In embodiments, a sequencing cycle includes extending a complementary polynucleotide by incorporating a first nucleotide using a polymerase, wherein the polynucleotide is hybridized to a template nucleic acid, detecting the first nucleotide, and identifying the first nucleotide. In embodiments, to begin a sequencing cycle, one or more differently labeled nucleotides and a DNA polymerase can be introduced. Following nucleotide addition, signals produced (e.g., via excitation and emission of a detectable label) can be detected to determine the identity of the incorporated nucleotide (based on the labels on the nucleotides). Reagents can then be added to remove the 3' reversible terminator and to remove labels from each incorporated base. Reagents, enzymes and other substances can be removed between steps by washing. Cycles may include repeating these steps, and the sequence of each cluster is read over the multiple repetitions.

As used herein, the term "extension" or "elongation" is used in accordance with their plain and ordinary meanings and refer to synthesis by a polymerase of a new polynucleotide strand complementary to a template strand by adding free nucleotides (e.g., dNTPs) from a reaction mixture that are complementary to the template in the 5'-to-3' direction. Extension includes condensing the 5'-phosphate group of the dNTPs with the 3'-hydroxy group at the end of the nascent (elongating) DNA strand.

As used herein, the term "sequencing read" is used in accordance with its plain and ordinary meaning and refers to an inferred sequence of nucleotide base pairs (or nucleotide base pair probabilities) corresponding to all or part of a single polynucleotide fragment. A sequencing read may include 10, 20, 30, 40, 50, 60, 70, 80, 90, 100, 150, 200, 250, or more nucleotide base pairs. In embodiments, a sequencing read includes reading a barcode and a template nucleotide sequence. In embodiments, a sequencing read includes reading a template nucleotide sequence. As used herein, the term "sequencing read" refers to an inferred sequence of base pairs (or base pair probabilities) corresponding to all or part of a single DNA fragment. In embodiments, a sequencing read includes reading a barcode and not a template nucleotide sequence. In embodiments, a sequencing read includes a computationally derived string corresponding to the detected label.

As used herein, the term "polymer" refers to macromolecules having one or more structurally unique repeating units. The repeating units are referred to as "monomers," which are polymerized for the polymer. Typically, a polymer is formed by monomers linked in a chain-like structure. A polymer formed entirely from a single type of monomer is referred to as a "homopolymer." A polymer formed from two or more unique repeating structural units may be referred to as a "copolymer." A polymer may be linear or branched, and may be random, block, polymer brush, hyperbranched polymer, bottlebrush polymer, dendritic polymer, or polymer micelles. The term "polymer" includes homopolymers, copolymers, tripolymers, tetra polymers and other polymeric molecules made from monomeric subunits. Copolymers include alternating copolymers, periodic copolymers, statistical copolymers, random copolymers, block copolymers, linear copolymers and branched copolymers. The term "polymerizable monomer" is used in accordance with its meaning in the art of polymer chemistry and refers to a compound that may covalently bind chemically to other monomer molecules (such as other polymerizable monomers that are the same or different) to form a polymer.

Polymers can be hydrophilic, hydrophobic or amphiphilic, as known in the art. Thus, "hydrophilic polymers" are substantially miscible with water and include, but are not limited to, polyethylene glycol and the like. "Hydrophobic polymers" are substantially immiscible with water and include, but are not limited to, polyethylene, polypropylene, polybutadiene, polystyrene, polymers disclosed herein, and the like. "Amphiphilic polymers" have both hydrophilic and hydrophobic properties and are typically copolymers having hydrophilic segment(s) and hydrophobic segment(s). Polymers include homopolymers, random copolymers, and block copolymers, as known in the art. The term "homopolymer" refers, in the usual and customary sense, to a polymer having a single monomeric unit. The term "copolymer" refers to a polymer derived from two or more monomeric species. The term "random copolymer" refers to a polymer derived from two or more monomeric species with no preferred ordering of the monomeric species. The term "block copolymer" refers to polymers having two or homopolymer subunits linked by covalent bond. Thus, the term "hydrophobic homopolymer" refers to a homopolymer which is hydrophobic. The term "hydrophobic block copolymer" refers to two or more homopolymer subunits linked by covalent bonds and which is hydrophobic.

A "receiving substrate" is used according to its plain and ordinary meaning and generally refers to a substantially solid construct with a surface that functions to support a tissue section. A receiving substrate may be composed of any appropriate material such as metal, plastic, glass or polymer based materials.

As used herein, the term "hydrogel" or "hydrogel carrier" refers to a three-dimensional polymeric structure that is substantially insoluble in water, but which is capable of absorbing and retaining water (e.g. large quantities of water) to form a substantially stable, often soft and pliable, structure. In embodiments, water can penetrate in between polymer chains of a polymer network, subsequently causing swelling and the formation of a hydrogel. In embodiments, hydrogels are super-absorbent (e.g., containing more than about 90% water) and can be comprised of natural or synthetic polymers. Hydrogels can contain over 99% water and may include natural or synthetic polymers, or a combination thereof. Hydrogels also possess a degree of flexibility very similar to natural tissue, due to their significant water content. A detailed description of suitable hydrogels may be found in published U.S. patent application No. 20100055733, herein specifically incorporated by reference. By "hydrogel subunits" or "hydrogel precursors" is meant hydrophilic monomers, prepolymers, or polymers that can be crosslinked, or "polymerized", to form a three-dimensional (3D) hydrogel network.

Hydrogels may be prepared by cross-linking hydrophilic biopolymers or synthetic polymers. Thus, in some embodiments, the hydrogel may include a crosslinker. As used herein, the term "crosslinker" refers to a molecule that can form a three-dimensional network when reacted with the appropriate base monomers. Examples of the hydrogel polymers, which may include one or more crosslinkers, include but are not limited to, hyaluronans, chitosans, agar, heparin, sulfate, cellulose, alginates (including alginate sulfate), collagen, dextrans (including dextran sulfate), pectin, carrageenan, polylysine, gelatins (including gelatin type A), agarose, (meth)acrylate-oligolactide-PEO-oligolactide-(meth) acrylate, PEO-PPO-PEO copolymers (Pluronics), poly(phosphazene), poly(methacrylates), poly(N-vinylpyrrolidone), PL(G) A-PEO-PL(G) A copolymers, poly(ethylene imine), polyethylene glycol (PEG)-thiol, PEG-acrylate, acrylamide, N,N'-bis(acryloyl) cystamine, PEG, polypropylene oxide (PPO), polyacrylic acid, poly(hydroxyethyl methacrylate) (PHEMA), poly(methyl methacrylate) (PMMA), poly(N-isopropylacrylamide) (PNIPAAm), poly(lactic acid) (PLA), poly(lactic-co-glycolic acid) (PLGA), polycaprolactone (PCL), poly(vinylsulfonic acid) (PVSA), poly(L-aspartic acid), poly(L-glutamic acid), bisacrylamide, diacrylate, diallylamine, triallylamine, divinyl sulfone, diethyleneglycol diallyl ether, ethyleneglycol diacrylate, polymethyleneglycol diacrylate, polyethyleneglycol diacrylate, trimethylopropoane trimethacrylate, ethoxylated trimethylol triacrylate, or ethoxylated pentaerythritol tetracrylate, or combinations thereof. Thus, for example, a combination may include a polymer and a crosslinker, for example polyethylene glycol (PEG)-thiol/PEG-acrylate, acrylamide/ N,N'-bis(acryloyl) cystamine (BACy), or PEG/polypropylene oxide (PPO). In embodiments, the hydrogel includes chemical crosslinks (e.g., intermolecular or intramolecular joining of two or more molecules by a covalent bond) and may be referred to as a chemical hydrogel. In embodiments, the hydrogel includes physical crosslinks (e.g., intermolecular or intramolecular joining of two or more molecules by a non-covalent bond) and may be referred to as a physical hydrogel. In embodiments, the physical hydrogel include one or more crosslinks including hydrogen bonds, hydrophobic interactions, and/or polymer chain entanglements.

As used herein, the term "interfacial", or "interfacial layer", is used in accordance with its plain ordinary meaning and refers to the boundary between any two bulk phases (gas, liquid, or solid) in contact where the properties differ from the properties of the bulk phases. In embodiments, an interfacial layer includes water. Interfacial water differs from bulk water in a number of properties, for example, interfacial water has a higher heat capacity than bulk water because more energy is necessary to break its hydrogen bonds. The arrangement and structure of the interfacial water layer varies depending on the structure of the hydrophilic and/or hydrophobic surface(s) the water layer is in contact with. Additional properties of interfacial water may be found in, e.g., Mentre P. J. Biol. Phys. and Chem. 2004; 4:115-123 and Tanaka M. Front. Chem. 2020; 8:165, which are incorporated herein by reference in their entirety.

As used herein, the terms "solid support" and "substrate" and "substrate surface" and "solid surface" refers to discrete solid or semi-solid surfaces to which a plurality of functional groups (e.g., bioconjugate reactive moieties or specific binding reagents) may be attached. A solid support may encompass any type of solid, porous, or hollow sphere, ball, cylinder, or other similar configuration composed of plastic, ceramic, metal, or polymeric material (e.g., hydrogel) onto which a nucleic acid may be immobilized (e.g., covalently or non-covalently). A solid support may include a discrete particle that may be spherical (e.g., microspheres) or have a non-spherical or irregular shape, such as cubic, cuboid, pyramidal, cylindrical, conical, oblong, or disc-shaped, and the like. A bead can be non-spherical in shape. A solid support may be used interchangeably with the term "bead." A solid support may further include a polymer or hydrogel on the surface to which the primers are attached. Exemplary solid supports include, but are not limited to, glass and modified or functionalized glass, plastics (including acrylics, polystyrene and copolymers of styrene and other materials, polypropylene, polyethylene, polybutylene, polyurethanes, Teflon™, cyclic olefin copolymers, polyimides etc.), nylon, ceramics, resins, Zeonor, silica or silica-based materials including silicon and modified silicon, carbon, metals, inorganic glasses, optical fiber bundles, photopatternable dry film resists, UV-cured adhesives and polymers. Particularly useful solid supports for some embodiments have at least one surface located on a microplate. Solid surfaces can also be varied in their shape depending on the application in a method described herein. For example, a solid surface useful herein can be planar, or contain regions which are concave or convex. In embodiments, the geometry of the concave or convex regions (e.g., wells) of the solid surface conform to the size and shape of a substantially circular particle to maximize the contact between the particle. In embodiments, the wells of an array are randomly located such that nearest neighbor wells have random spacing between each other. Alternatively, in embodiments the spacing between the wells can be ordered, for example, forming a regular pattern. The term solid substrate is encompassing of a substrate (e.g., a microplate) having a surface including a polymer coating covalently attached thereto.

The term "microplate", "microtiter plate", "multiwell container", or "multiwell plate" as used herein, refers to a substrate including a surface, the surface including a plurality of reaction chambers separated from each other by interstitial regions on the surface. In embodiments, the microplate has dimensions as provided and described by American National Standards Institute (ANSI) and Society for Laboratory Automation And Screening (SLAS); for example the tolerances and dimensions set forth in ANSI SLAS 1-2004 (R2012); ANSI SLAS 2-2004 (R2012); ANSI SLAS 3-2004 (R2012); ANSI SLAS 4-2004 (R2012); and ANSI SLAS 6-2012, which are incorporated herein by reference. The dimensions of the microplate as described herein and the arrangement of the reaction chambers may be compatible with an established format for automated laboratory equipment. In embodiments, the device described herein provides methods for high-throughput screening. High-throughput screening (HTS) refers to a process that uses a combination of modern robotics, data processing and control software, liquid handling devices, and/or sensitive detectors, to efficiently process a large amount of (e.g., thousands, hundreds of thousands, or millions) samples in biochemical, genetic, or pharmacological experiments, either in parallel or in sequence, within a reasonably short period of time (e.g., days). Preferably, the process is amenable to automation, such as robotic simultaneous handling of 96 samples, 384 samples, 1536 samples or more. A typical HTS robot tests up to 100,000 to a few hundred thousand compounds per day. The samples are often in small volumes, such as no more than 1 mL, 500 µl, 200 µl, 100 µl, 50 µl or less. Through this process, one can rapidly identify active compounds, small molecules, antibodies, proteins or polynucleotides in a cell.

The reaction chambers may be provided as wells (alternatively referred to as reaction chambers), for example a microplate may contain 2, 4, 6, 12, 24, 48, 96, 384, or 1536 sample wells. In embodiments, the 96 and 384 wells are arranged in a 2:3 rectangular matrix. In embodiments, the 24 wells are arranged in a 3:8 rectangular matrix. In embodiments, the 48 wells are arranged in a 3:4 rectangular matrix. In embodiments, the reaction chamber is a microscope slide (e.g., a glass slide about 75 mm by about 25 mm). In embodiments the slide is a concavity slide (e.g., the slide includes a depression). In embodiments, the slide includes a coating for enhanced cell adhesion (e.g., poly-L-lysine, silanes, carbon nanotubes, polymers, epoxy resins, or gold). In embodiments, the microplate is about 5 inches by about 3.33 inches, and includes a plurality of 5 mm diameter wells. In embodiments, the microplate is about 5 inches by about 3.33 inches, and includes a plurality of 6 mm diameter wells. In embodiments, the microplate is about 5 inches by about 3.33 inches, and includes a plurality of 7 mm diameter wells. In embodiments, the microplate is about 5 inches by about 3.33 inches, and includes a plurality of 7.5 mm diameter wells. In embodiments, the microplate is 5 inches by 3.33 inches, and includes a plurality of 7.5 mm diameter wells. In embodiments, the microplate is about 5 inches by about 3.33 inches, and includes a plurality of 8 mm diameter wells. In embodiments, the microplate is a flat glass or plastic tray in which an array of wells are formed, wherein each well can hold between from a few microliters to hundreds of microliters of fluid reagents and samples.

The term "surface" is intended to mean an external part or external layer of a substrate. The surface can be in contact with another material such as a gas, liquid, gel, polymer, organic polymer, second surface of a similar or different material, metal, or coat. The surface, or regions thereof, can be substantially flat. The substrate and/or the surface can have surface features such as wells, pits, channels, ridges, raised regions, pegs, posts or the like.

The term "well" refers to a discrete concave feature in a substrate having a surface opening that is completely surrounded by interstitial region(s) of the surface. Wells can have any of a variety of shapes at their opening in a surface including but not limited to round, elliptical, square, polygonal, or star shaped (i.e., star shaped with any number of vertices). The cross section of a well taken orthogonally with the surface may be curved, square, polygonal, hyperbolic, conical, or angular. The wells of a microplate are available in different shapes, for example F-Bottom: flat bottom; C-Bottom: bottom with minimal rounded edges; V-Bottom: V-shaped bottom; or U-Bottom: U-shaped bottom. In embodiments, the well is substantially square. In embodiments, the well is square. In embodiments, the well is F-bottom. In embodiments, the microplate includes 24 substantially round flat bottom wells. In embodiments, the microplate includes 48 substantially round flat bottom wells. In embodiments, the microplate includes 96 substantially round flat bottom wells. In embodiments, the microplate includes 384 substantially square flat bottom wells.

The discrete regions (i.e., features, wells) of the microplate may have defined locations in a regular array, which may correspond to a rectilinear pattern, circular pattern, hexagonal pattern, or the like. In embodiments, the pattern of wells includes concentric circles of regions, spiral patterns, rectilinear patterns, hexagonal patterns, and the like. In embodiments, the pattern of wells is arranged in a rectilinear or hexagonal pattern A regular array of such regions is advantageous for detection and data analysis of signals collected from the arrays during an analysis. These discrete regions are separated by interstitial regions. As used herein, the term "interstitial region" refers to an area in a substrate or on a surface that separates other areas of the substrate or surface. For example, an interstitial region can separate one concave feature of an array from another concave feature of the array. The two regions that are separated from each other can be discrete, lacking contact with each other. In another example, an interstitial region can separate a first portion of a feature from a second portion of a feature. In embodiments the interstitial region is continuous whereas the features are discrete, for example, as is the case for an array of wells in an otherwise continuous surface. The separation provided by an interstitial region can be partial or full separation. In embodiments, interstitial regions have a surface material that differs from the surface material of the wells (e.g., the interstitial region contains a photoresist and the surface of the well is glass). In embodiments, interstitial regions have a surface material that is the same as the surface material of the wells (e.g., both the surface of the interstitial region and the surface of well contain a polymer or copolymer).

As used herein, the term "selective" or "selectivity" or the like of a compound refers to the substance's ability to discriminate between molecular targets. As used herein, the terms "specific", "specifically", "specificity", or the like of a compound refers to the substance's ability to cause a particular action, such as binding, to a particular molecular target with minimal or no action to other substances (e.g., an antibody and antigen). For example, a chemical reagent may selectively modify one nucleotide type in that it reacts with one nucleotide type (e.g., cytosines) and not other nucleotide types (e.g., adenine, thymine, or guanine). When used in the context of sequencing, such as in "selectively sequencing," this term refers to sequencing one or more target polynucleotides from an original starting population of polynucleotides, and not sequencing non-target polynucleotides from the starting population. Typically, selectively sequencing one or more target polynucleotides involves differentially manipulating the target polynucleotides based on known sequence. For example, target polynucleotides may be hybridized to a probe oligonucleotide that may be labeled (such as with a member of a binding pair) or bound to a surface. In embodiments, hybridizing a target polynucleotide to a probe oligonucleotide includes the step of displacing one strand of a double-stranded nucleic acid. Probe-hybridized target polynucleotides may then be separated from non-hybridized polynucleotides, such as by removing probe-bound polynucleotides from the starting population or by washing away polynucleotides that are not bound to a probe. The result is a selected subset of the starting population of polynucleotides, which is then subjected to sequencing, thereby selectively sequencing the one or more target polynucleotides.

The terms "bind" and "bound" as used herein are used in accordance with their plain and ordinary meanings and refer to an association between atoms or molecules. The association can be direct or indirect. For example, bound atoms or molecules may be directly bound to one another, e.g., by a covalent bond or non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). As a further example, two molecules may be bound indirectly to one another by way of direct binding to one or more intermediate molecules (e.g., as in a substrate, bound to a first antibody, bound to an analyte, bound to a second antibody), thereby forming a complex. As used herein, the term "attached" refers to the state of two things being joined, fastened, adhered, connected or bound to each other. For example, a sample such as a cell or tissue, can be attached to a material, such as a hydrogel, polymer, or solid support, by a covalent or non-covalent bond. In embodiments, attachment is a covalent attachment.

"Specific binding" is where the binding is selective between two molecules. A particular example of specific binding is that which occurs between an antibody and an antigen. Typically, specific binding can be distinguished from non-specific when the dissociation constant (KD) is less than about $1\times10^{-5}$ M or less than about $1\times10^{-6}$ M or $1\times10^{-7}$ M. Specific binding can be detected, for example, by ELISA, immunoprecipitation, coprecipitation, with or without chemical crosslinking, two-hybrid assays and the like. In embodiments, specific binding can refer to hybridization of two complementary nucleic acid sequences.

Where a range of values is provided, it is understood that each intervening value, to the tenth of the unit of the lower limit unless the context clearly indicates otherwise, between the upper and lower limit of that range, and any other stated or unstated intervening value in, or smaller range of values within, that stated range is encompassed by such disclosure herein. The upper and lower limits of any such smaller range (within a more broadly recited range) may independently be included in the smaller ranges, or as particular values themselves, and are also encompassed by such disclosure herein, subject to any specifically excluded limit in the stated range. Where the stated range includes one or both of the limits, ranges excluding either or both of those included limits are also included by such disclosure herein.

Provided herein are methods, systems, and compositions for analyzing a sample (e.g., sequencing nucleic acids within a sample) in situ. The term "in situ" is used in accordance with its ordinary meaning in the art and refers to a sample surrounded by at least a portion of its native environment, such as may preserve the relative position of two or more elements. For example, an extracted human cell obtained is considered in situ when the cell is retained in its local microenvironment so as to avoid extracting the target (e.g., nucleic acid molecules or proteins) away from their native environment. An in situ sample (e.g., a cell) can be obtained from a suitable subject. An in situ cell sample may refer to a cell and its surrounding milieu, or a tissue. A sample can be isolated or obtained directly from a subject or part thereof. In embodiments, the methods described herein (e.g., sequencing a plurality of target nucleic acids of a cell in situ) are applied to an isolated cell (i.e., a cell not surrounded by least a portion of its native environment). For the avoidance of any doubt, when the method is performed within a cell (e.g., an isolated cell) the method may be considered in situ. In some embodiments, a sample is obtained indirectly from an individual or medical professional. A sample can be any specimen that is isolated or obtained from a subject or part thereof. A sample can be any specimen that is isolated or obtained from multiple subjects. Non-limiting examples of specimens include fluid or tissue from a subject, including, without limitation, blood or a blood product (e.g., serum, plasma, platelets, buffy coats, or the like), umbilical cord blood, chorionic villi, amniotic fluid, cerebrospinal fluid, spinal fluid, lavage fluid (e.g., lung, gastric, peritoneal, ductal, car, arthroscopic), a biopsy sample, celocentesis sample, cells (blood cells, lymphocytes, placental cells, stem cells, bone marrow derived cells, embryo or fetal cells) or parts thereof (e.g., mitochondrial, nucleus, extracts, or the like), urine, feces, sputum, saliva, nasal mucous, prostate fluid, lavage, semen, lymphatic fluid, bile, tears, sweat, breast milk, breast fluid, the like or combinations thereof. Non-limiting examples of tissues include organ tissues (e.g., liver, kidney, lung, thymus, adrenals, skin, bladder, reproductive organs, intestine, colon, spleen, brain, the like or parts thereof), epithelial tissue, hair, hair follicles, ducts, canals, bone, eye, nose, mouth, throat, car, nails, the like, parts thereof or combinations thereof. A sample may include cells or tissues that are normal, healthy, diseased (e.g., infected), and/or cancerous (e.g., cancer cells). A sample obtained from a subject may include cells or cellular material (e.g., nucleic acids) of multiple organisms (e.g., virus nucleic acid, fetal nucleic acid, bacterial nucleic acid, parasite nucleic acid). A sample may include a cell and RNA transcripts. A sample can include nucleic acids obtained from one or more subjects. In some embodiments a sample includes nucleic acid obtained from a single subject. A subject can be any living or non-living organism, including but not limited to a human, non-human animal, plant, bacterium, fungus, virus, or protist. A subject may be any age (e.g., an embryo, a fetus, infant, child, adult). A subject can be of any sex (e.g., male, female, or combination thereof). A subject may be pregnant. In some embodiments, a subject is a mammal. In some embodiments, a subject is a plant. In some embodiments, a subject is a human subject. A subject can be a patient (e.g., a human patient). In some embodiments a subject is suspected of having a genetic variation or a disease or condition associated with a genetic variation. A "tissue section" as used herein refers to a portion of a biological tissue derived from a biological sample, typically from an organism (e.g., a human or animal subject or patient).

As used herein, the term "fresh," generally in the context of a fresh tissue means that the tissue has recently been obtained from an organism, generally before any subsequent fixation steps, for example, flash freezing or chemical fixation. In embodiments, a fresh tissue is obtained from an organism about 1 second up to about 20 minutes before any fixation steps are performed. In embodiments, a fresh tissue is obtained from an organism about 1 second up to about 60 seconds before any fixation steps are performed. In embodiments, a fresh tissue is obtained from an organism about 30 seconds up to about 60 seconds before any fixation steps are performed. In embodiments, a fresh tissue is obtained from an organism about 1 minutes up to about 20 minutes before any fixation steps are performed. In embodiments, a fresh tissue is obtained from an organism about 1 minutes up to about 10 minutes before any fixation steps are performed. In embodiments, a fresh tissue is obtained from an organism about 1 minutes up to about 5 minutes before any fixation steps are performed. In embodiments, a fresh tissue is obtained from an organism about 30 seconds, about 1 minute, about 2 minutes, about 3 minutes, about 4 minutes, about 5 minutes, about 10 minutes, about 15 minutes, or about 20 minutes before any fixation steps are performed.

As used herein, the term "fix," refers to formation of covalent bonds, such as crosslinks, between biomolecules or within molecules. The process of fixing tissue samples or biological samples (e.g., cells and nuclei) for example, is called "fixation." The agent that causes fixation is generally referred to as a "fixative" or "fixing agent." "Fixed biological samples" (e.g., fixed cells or nuclei) or "fixed tissues" refers to biological samples (e.g., cells or nuclei) or tissues that have been in contact with a fixative under conditions sufficient to allow or result in formation of intra- and inter-molecular crosslinks between biomolecules in the biological sample. Fixation may be reversed and the process of reversing fixation may be referred to as "un-fixing" or "decrosslinking." Unfixing or decrosslinking refers to breaking or reversing the formation of covalent bonds in biomolecules formed by fixatives. In some examples, the tissue fixed is fresh tissue. In some examples, the tissue fixed may be frozen tissue. In some examples, the tissue fixed may not be dissociated. In some examples, the tissue fixed may be dissociated or partially dissociated (e.g., chopped, cut). In some examples, tissue that has been rapidly frozen and, perhaps, cut or chopped into pieces (e.g., small enough to fit into a tube or container used for fixation) may be used. In some examples, tissue may be dissociated or partially dissociated (e.g., cut, chopped) before or during fixation. In some examples, tissue that is fixed may not be dissociated. The frozen biological tissue can be fixed using a fixing agent, which is suitably an organic fixing agent. Suitable organic fixing agents include without limitation alcohols, ketones, aldehydes (e.g., glutaraldehyde), cross-linking agents, disuccinimidyl suberate (DSS), dimethylsuberimidate (DMS), formalin, dimethyladipimidate (DMA), dithiobis(-succinimidyl propionate) (DSP), disuccinimidyl tartrate (DST), ethylene glycol bis(succinimidyl succinate) (EGS), bis(sulfosuccinimidyl) suberate (BS3) and combinations thereof. A particularly suitable fixing agent is a formaldehyde-based fixing agent such as formalin, which is a mixture of formaldehyde and water. The formalin may include about 1% to about 15% by weight formaldehyde and about 85% to about 99% by weight water, suitable about 2% to about 8% by weight formaldehyde and about 92% to about 98% by weight water, or about 4% by weight formaldehyde and about 96% by weight water. In some examples, tissues may be fixed in 4% paraformaldehyde. Other suitable fixing agents will be appreciated by those of ordinary skill in the art (e.g., International PCT App. No. PCT/US2020/066705, which is incorporated herein by reference in its entirety).

As used herein, the term "permeable" refers to a property of a substance that allows certain materials to pass through the substance. "Permeable" may be used to describe a biological sample, such as a cell or nucleus, in which analytes in the biological sample can leave the biological sample. "Permeabilize" is an action taken to cause, for example, a biological sample (e.g., a cell) to release its analytes. In some examples, permeabilization of a biological sample is accomplished by affecting the integrity (e.g., compromising) of a biological sample membrane (e.g., a cellular or nuclear membrane) such as by application of a protease or other enzyme capable of disturbing a membrane allowing analytes to diffuse out of the biological sample. In some embodiments, permeabilizing a biological sample does not release the biomolecules (e.g., proteins and/or nucleic acids) contained within the sample.

As used herein, the term "single biological sample", such as a single cell or a single nucleus generally refers to a biological sample that is not present in an aggregated form or clump. Single biological samples, such as cells and/or nuclei may be the result of dissociating a tissue sample.

As used herein, the term "tissue freezing" is used in accordance with its plain and ordinary meaning and refers to different methods for freezing tissues. In some examples, the methods used may be rapid methods (e.g., "flash freezing" or "snap freezing"). In some examples, tissues may be lowered to temperatures below about −70° C. using these methods. In some examples, rapid freezing may use ultra-cold media. In some examples, an ultracold medium may be liquid nitrogen. In some examples, this type of freezing may preserve tissue integrity, in part by preventing the formation of ice crystals that would affect the tissue morphology. In some examples, an ultracold medium may be dry ice.

As used herein, the term "disease state" is used in accordance with its plain and ordinary meaning and refers to any abnormal biological or aberrant state of a cell or organism. The presence of a disease state may be identified by the same collection of biological constituents used to determine the cell's biological state. In general, a disease state will be detrimental to a biological system. A disease state may be a consequence of, inter alia, an environmental pathogen, for example a viral infection (e.g., HIV/AIDS, hepatitis B, hepatitis C, influenza, measles, etc.), a bacterial infection, a parasitic infection, a fungal infection, or infection by some other organism. A disease state may also be the consequence of some other environmental agent, such as a chemical toxin or a chemical carcinogen. As used herein, a disease state further includes genetic disorders wherein one or more copies of a gene is altered or disrupted, thereby affecting its biological function. Exemplary genetic diseases include, but are not limited to polycystic kidney disease, familial multiple endocrine neoplasia type I, neurofibromatoses, Tay-Sachs disease, Huntington's disease, sickle cell anemia, thalassemia, and Down's syndrome, as well as others (see, e.g., The Metabolic and Molecular Bases of Inherited Diseases, 7th ed., McGraw-Hill Inc., New York). Other exemplary diseases include, but are not limited to, cancer, hypertension, Alzheimer's disease, neurodegenerative diseases, and neuropsychiatric disorders such as bipolar affective disorders or paranoid schizophrenic disorders. Disease states are monitored to determine the level or severity (e.g., the stage or progression) of one or more disease states of a subject and, more specifically, detect changes in the biological state of a subject which are correlated to one or more disease states (see, e.g., U.S. Pat. No. 6,218,122, which is incorporated by reference herein in its entirety). In embodiments, methods provided herein are also applicable to monitoring the disease state or states of a subject undergoing one or more therapies. Thus, the present disclosure also provides, in some embodiments, methods for determining or monitoring efficacy of a therapy or therapies (i.e., determining a level of therapeutic effect) upon a subject. In embodiments, methods of the present disclosure can be used to assess therapeutic efficacy in a clinical trial, e.g., as an early surrogate marker for success or failure in such a clinical trial. Within eukaryotic cells, there are hundreds to thousands of signaling pathways that are interconnected. For this reason, perturbations in the function of proteins within a cell have numerous effects on other proteins and the transcription of other genes that are connected by primary, secondary, and sometimes tertiary pathways. This extensive interconnection between the function of various proteins means that the alteration of any one protein is likely to result in compensatory changes in a wide number of other proteins. In particular, the partial disruption of even a single protein within a cell, such as by exposure to a drug or by a disease state which modulates the gene copy number (e.g., a genetic mutation), results in characteristic compensatory changes in the transcription of enough other genes that these changes in transcripts can be used to define a "signature" of particular transcript alterations which are related to the disruption of function, e.g., a particular disease state or therapy, even at a stage where changes in protein activity are undetectable.

As used herein, the term "surgical margin" is used in accordance with its plain and ordinary meaning and refers to tissue including the outermost layer of tissue (e.g., border) of tissue excised (or being excised) from a subject during surgery to remove a tumor. A surgical margin may also be referred to herein as a resection margin. For example, the one or more tissue sections peripheral to a tumor may include a surgical margin.

The terms "polypeptide," "peptide" and "protein" are used interchangeably herein to refer to a polymer of amino acid residues, wherein the polymer may optionally be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymer. A protein may refer to a protein expressed in a cell.

A polypeptide, or a cell is "recombinant" when it is artificial or engineered, or derived from or contains an artificial or engineered protein or nucleic acid (e.g., non-natural or not wild type). For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant.

As used herein, a "single cell" refers to one cell. Single cells useful in the methods described herein can be obtained from a tissue of interest, or from a biopsy, blood sample, or cell culture. Additionally, cells from specific organs, tissues, tumors, neoplasms, or the like can be obtained and used in the methods described herein. In general, cells from any population can be used in the methods, such as a population of prokaryotic or eukaryotic organisms, including bacteria or yeast.

As used herein, the term "tissue" is used in accordance with its plain and ordinary meaning and refers to an organization of cells in a structure, where the structure generally functions as a unit in an organism (e.g., mammals) and may carry out specific functions. In some examples, cells in a tissue are configured in a mass and may not be free from one another. This disclosure describes methods of obtaining single biological samples (e.g., cells or nuclei) from tissues that can be used in various single biological samples (e.g., single-cell/nucleus) workflows. In some examples, blood cells (e.g., lymphocytes) can be considered a tissue. However, blood cells, like lymphocytes, generally are free from one another in the blood. The methods disclosed herein can be used to process those cells to obtain cells and/or nuclei, although dissociation steps may not be necessary when using those types of tissues. Generally, any type of tissue can be used in the methods described herein. Examples of tissues that may be used in the disclosed methods include, but are not limited to connective, epithelial, muscle and nervous tissue. In some examples, the tissues are from mammals. Tissues that contain any type of cells may be used. For example, tissues from abdomen, bladder, brain, esophagus, heart, intestine, kidney, liver, lung, lymph node, olfactory bulb, ovary, pancreas, skin, spleen, stomach, testicle, and the like. The tissue may be normal or tumor tissue (e.g., malignant). This example is not meant to be limiting. Although the conditions used in the disclosed may not be identical for different types of tissue, the methods may be applied to any tissue. The tissues used in the disclosed methods may be in various states. In some examples, the tissues used in the disclosed methods may be fresh, frozen, or fixed.

The term "cellular component" is used in accordance with its ordinary meaning in the art and refers to any organelle, nucleic acid, protein, or analyte that is found in a prokaryotic, eukaryotic, archaeal, or other organismic cell type. Examples of cellular components (e.g., a component of a cell) include RNA transcripts, proteins, membranes, lipids, and other analytes. In embodiments, a cellular component is a biomolecule.

A "gene" refers to a polynucleotide that is capable of conferring biological function after being transcribed and/or translated.

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay, etc.) from one location to another. For example, kits include one or more enclosures (e.g., boxes) containing the relevant reaction reagents and/or supporting materials. As used herein, the term "fragmented kit" refers to a delivery system including two or more separate containers that each contain a subportion of the total kit components. The containers may be delivered to the intended recipient together or separately. For example, a first container may contain an enzyme for use in an assay, while a second container contains oligonucleotides. In contrast, a "combined kit" refers to a delivery system containing all of the components of a reaction assay in a single container (e.g., in a single box housing each of the desired components). The term "kit" includes both fragmented and combined kits.

As used herein the term "determine" can be used to refer to the act of ascertaining, establishing or estimating. A determination can be probabilistic. For example, a determination can have an apparent likelihood of at least 50%, 75%, 90%, 95%, 98%, 99%, 99.9% or higher. In some cases, a determination can have an apparent likelihood of 100%. An exemplary determination is a maximum likelihood analysis or report. As used herein, the term "identify," when used in reference to a thing, can be used to refer to recognition of the thing, distinction of the thing from at least one other thing or categorization of the thing with at least one other thing. The recognition, distinction or categorization can be probabilistic. For example, a thing can be identified with an apparent likelihood of at least 50%, 75%, 90%, 95%, 98%, 99%, 99.9% or higher. A thing can be identified based on a result of a maximum likelihood analysis. In some cases, a thing can be identified with an apparent likelihood of 100%.

The terms "bioconjugate group," "bioconjugate reactive moiety," and "bioconjugate reactive group" refer to a chemical moiety which participates in a reaction to form a bioconjugate linker (e.g., covalent linker). Non-limiting examples of bioconjugate reactive groups and the resulting bioconjugate reactive linkers may be found in the Bioconjugate Table below:

| Bioconjugate reactive group 1 (e.g., electrophilic bioconjugate reactive moiety) | Bioconjugate reactive group 2 (e.g., nucleophilic bioconjugate reactive moiety) | Resulting Bioconjugate reactive linker |
| --- | --- | --- |
| activated esters | amines/anilines | carboxamides |
| acrylamides | thiols | thioethers |
| acyl azides | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | carboxamides |
| aryl halides | thiols | thiophenols |
| aryl halides | amines | aryl amines |
| aziridines | thiols | thioethers |
| boronates | glycols | boronate esters |
| carbodiimides | carboxylic acids | N-acylureas or anhydrides |
| diazoalkanes | carboxylic acids | esters |
| epoxides | thiols | esters |
| haloacetamides | thiols | thioethers |
| haloplatinate | amino | thioethers |
| haloplatinate | heterocycle | platinum complex |
| haloplatinate | thiol | platinum complex |
| halotriazines | amines/anilines | platinum complex |
| halotriazines | alcohols/phenols | aminotriazines |
| halotriazines | thiols | triazinyl ethers |
| imido esters | amines/anilines | triazinyl thioethers |
| isocyanates | amines/anilines | amidines |
| isocyanates | alcohols/phenols | ureas |
| isothiocyanates | amines/anilines | urethanes |
| maleimides | thiols | thioureas |
| phosphoramidites | alcohols | thioethers |
| silyl halides | alcohols | phosphite esters |
| sulfonate esters | amines/anilines | silyl ethers |
| sulfonate esters | thiols | alkyl amines |
| sulfonate esters | carboxylic acids | thioethers |
| sulfonate esters | alcohols | esters |
| sulfonyl halides | amines/anilines | ethers |
| sulfonyl halides | phenols/alcohols | sulfonamides sulfonate esters |

As used herein, the term "bioconjugate reactive moiety" and "bioconjugate reactive group" refers to a moiety or group capable of forming a bioconjugate (e.g., covalent linker) as a result of the association between atoms or molecules of bioconjugate reactive groups. The association can be direct or indirect. For example, a conjugate between a first bioconjugate reactive group (e.g., —NH₂, —COOH, —N-hydroxysuccinimide, or -maleimide) and a second bioconjugate reactive group (e.g., sulfhydryl, sulfur-containing amino acid, amine, amine sidechain containing amino acid, or carboxylate) provided herein can be direct, e.g., by covalent bond or linker (e.g., a first linker of second linker), or indirect, e.g., by non-covalent bond (e.g., electrostatic interactions (e.g., ionic bond, hydrogen bond, halogen bond), van der Waals interactions (e.g., dipole-dipole, dipole-induced dipole, London dispersion), ring stacking (pi effects), hydrophobic interactions and the like). In embodiments, bioconjugates or bioconjugate linkers are formed using bioconjugate chemistry (i.e., the association of two bioconjugate reactive groups) including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the first bioconjugate reactive group (e.g., malcimide moiety) is covalently attached to the second bioconjugate reactive group (e.g., a sulfhydryl). In embodiments, the first bioconjugate reactive group (e.g., haloacetyl moiety) is covalently attached to the second bioconjugate reactive group (e.g., a sulfhydryl). In embodiments, the first bioconjugate reactive group (e.g., pyridyl moiety) is covalently attached to the second bioconjugate reactive group (e.g., a sulfhydryl). In embodiments, the first bioconjugate reactive group (e.g., —N-hydroxysuccinimide moiety) is covalently attached to the second bioconjugate reactive group (e.g., an amine). In embodiments, the first bioconjugate reactive group (e.g., maleimide moiety) is covalently attached to the second bioconjugate reactive group (e.g., a sulfhydryl). In embodiments, the first bioconjugate reactive group (e.g., -sulfo-N-hydroxysuccinimide moiety) is covalently attached to the second bioconjugate reactive group (e.g., an amine).

Useful bioconjugate reactive groups used for bioconjugate chemistries herein include, for example: (a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters; (b) hydroxyl groups which can be converted to esters, ethers, aldehydes, etc.; (c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom; (d) dienophile groups which are capable of participating in Diels-Alder reactions such as, for example, maleimido or maleimide groups; (c) aldehyde or ketone groups such that subsequent derivatization is possible via formation of carbonyl derivatives such as, for example, imines, hydrazones, semicarbazones or oximes, or via such mechanisms as Grignard addition or alkyllithium addition; (f) sulfonyl halide groups for subsequent reaction with amines, for example, to form sulfonamides; (g) thiol groups, which can be converted to disulfides, reacted with acyl halides, or bonded to metals such as gold, or react with maleimides; (h) amine or sulfhydryl groups (e.g., present in cysteine), which can be, for example, acylated, alkylated or oxidized; (i) alkenes, which can undergo, for example, cycloadditions, acylation, Michael addition, etc.; (j) epoxides, which can react with, for example, amines and hydroxyl compounds; (k) phosphoramidites and other standard functional groups useful in nucleic acid synthesis; (l) metal silicon oxide bonding; (m) metal bonding to reactive phosphorus groups (e.g., phosphines) to form, for example, phosphate diester bonds.; (n) azides coupled to alkynes using copper catalyzed cycloaddition click chemistry; (o) biotin conjugate can react with avidin or strepavidin to form a avidin-biotin complex or streptavidin-biotin complex.

The term "covalent linker" is used in accordance with its ordinary meaning and refers to a divalent moiety which connects at least two moieties to form a molecule.

The term "non-covalent linker" is used in accordance with its ordinary meaning and refers to a divalent moiety which includes at least two molecules that are not covalently linked to each other but are capable of interacting with each other via a non-covalent bond (e.g., electrostatic interactions (e.g., ionic bond, hydrogen bond, halogen bond) or van der Waals interactions (e.g., dipole-dipole, dipole-induced dipole, London dispersion). In embodiments, the non-covalent linker is the result of two molecules that are not covalently linked to each other that interact with each other via a non-covalent bond.

The term "protein-specific binding agent" refers to an agent to a protein or polypeptide molecule, or portion thereof, capable of selectively binding or interacting with a protein. In embodiments, a protein-specific binding agent specifically binds a particular protein (e.g., a protein antigen or epitope thereof). In embodiments a protein-specific binding agent is an immunoglobulin (IgA, IgD, IgE, IgG, or IgM). Intact immunoglobulins, also known as antibodies, are typically tetrameric glycosylated proteins composed of two light (L) chains of approximately 25 kDa each, and two heavy (H) chains of approximately 50 kDa each. In embodiments, the protein binding moiety is an antigen-specific antibody. Non-limiting examples of protein-specific binding agent encompassed within the term "antigen-specific antibody" used herein include: (i) an Fab fragment, a monovalent fragment consisting of the VL, VH, CL and CHI domains; (ii) an F(ab')2 fragment, a bivalent fragment including two Fab fragments linked by a disulfide bridge at the hinge region; (iii) an Fd fragment consisting of the VH and CHI domains; (iv) an Fv fragment consisting of the VL and VH domains of a single arm of an antibody, (v) a dAb fragment, which consists of a VH domain; and (vi) an isolated CDR. Furthermore, although the two domains of the Fv fragment, VL and VH, are coded for by separate genes, they may be recombinantly joined by a synthetic linker, creating a single protein chain in which the VL and VH domains pair to form monovalent molecules (known as single chain Fv (scFv)). The most commonly used linker is a 15-residue (Gly4Ser) 3 peptide, but other linkers are also known in the art. Single chain antibodies are also intended to be encompassed within the terms "protein-specific binding agent," of an antibody. The antibody can also be a polyclonal antibody, monoclonal antibody, chimeric antibody, antigen-binding fragment, Fc fragment, single chain antibodies, or any derivatives thereof. In embodiments, the protein-specific binding agent is the antigen-binding site (e.g., fragment antigen-binding (Fab) variable region) of an antibody. The term "antigen-binding site" of an antibody (or simply "antibody portion"), as used herein, refers to one or more fragments of an antibody that retains the ability to specifically bind to an antigen. It has been shown that the antigen-binding function of an antibody can be performed by fragments of a full-length antibody.

An "antibody" (Ab) is a protein that binds specifically to a particular substance, known as an "antigen" (Ag). An "antibody" or "antigen-binding fragment" is an immunoglobulin that binds a specific "epitope." The term encompasses polyclonal, monoclonal, and chimeric antibodies. In nature, antibodies are generally produced by lymphocytes in response to immune challenge, such as by infection or immunization. An "antigen" (Ag) is any substance that reacts specifically with antibodies or T lymphocytes (T cells). An antibody may include the entire antibody as well as any antibody fragments capable of binding the antigen or antigenic fragment of interest. Examples include complete antibody molecules, antibody fragments, such as Fab, F(ab') 2, CDRs, VL, VH, and any other portion of an antibody which is capable of specifically binding to an antigen. Antibodies used herein are immunospecific for, and therefore specifically and selectively bind to, for example, proteins either detected (e.g., biological targets of interest) or used for detection (e.g., probes containing oligonucleotide barcodes) in the methods and devices as described herein.

As used herein, the term "control" or "control experiment" is used in accordance with its plain and ordinary meaning and refers to an experiment in which the subjects, cells, tissues, or reagents of the experiment are treated as in a parallel experiment except for omission of a procedure, reagent, or variable of the experiment. In some instances, the control is used as a standard of comparison in evaluating experimental effects. In embodiments, a control cell is the same cell type as the cell being examined, wherein the control cell does not include the variable or is subjected to conditions being examined.

Typically, the concentration and molecular weight of the hydrogel subunit(s) will depend on the selected polymer and the desired characteristics, e.g., pore size, swelling properties, conductivity, elasticity/stiffness (Young's modulus), biodegradability index, etc., of the hydrogel network into which they will be polymerized. For example, it may be desirable for the hydrogel to include pores of sufficient size to allow the passage of macromolecules, e.g., proteins, nucleic acids, or small molecules as described in greater detail below, into the specimen. The ordinarily skilled artisan will be aware that pore size generally decreases with increasing concentration of hydrogel subunits and generally increases with an increasing ratio of hydrogel subunits to crosslinker, and will prepare a hydrogel composition that includes a concentration of hydrogel subunits that allows the passage of such macromolecules. As another example, it may be desirable for the hydrogel to have a particular stiffness, e.g., to provide stability in handling the embedded specimen, e.g., a Young's Modulus (also referred to herein as a compression modulus) of about 2-70 kN/m$^2$, for example, about 2 kN/m$^2$, about 4 kN/m$^2$, about 7 kN/m$^2$, about 10 kN/m$^2$, about 15 kN/m$^2$, about 20 kN/m$^2$, about 40 kN/m$^2$, but typically not more than about 70 kN/m$^2$. The ordinarily skilled artisan will be aware that the elasticity of a hydrogel network may be influenced by a variety of factors, including the branching of the polymer, the concentration of hydrogel subunits, and the degree of cross-linking, and will prepare a hydrogel composition that includes a concentration of hydrogel subunits to provide such desired elasticity. Thus, for example, the hydrogel composition may include an acrylamide monomer at a concentration of from about 1% w/v to about 20% w/v, e.g., about 2% to about 15%, about 3% to about 10%, about 4% to about 8%, and a concentration of bisacrylamide crosslinker in the range of about 0.01% to about 0.075%, e.g., 0.01%, 0.02%, 0.025%, 0.03%, 0.04%, 0.05%, 0.06%, or 0.075%; or, for example, the hydrogel composition may include PEG prepolymers having a molecular weight ranging from at least about 2.5K to about 50K, e.g., 2.5K or more, 3.5K or more, 5K or more, 7.5K or more, 10K or more, 15K or more, 20K or more, but typically not more than about 50K, at a concentration in a range from about 1% w/w to about 50% w/w, e.g., 1% or more, 5% or more, 7.5% or more, 10% or more, 15% or more, 20% or more, 30% or more, 40% or more, and usually not more than about 50%. Concentrations of hydrogel subunits that provide desired hydrogel characteristics may be readily determined by methods in the art or as described in the working examples below.

The term "image" is used according to its ordinary meaning and refers to a representation of all or part of an object. The representation may be an optically detected reproduction. For example, an image can be obtained from fluorescent, luminescent, scatter, or absorption signals. The part of the object that is present in an image can be the surface or other xy plane of the object. Typically, an image is a 2 dimensional representation of a 3 dimensional object. An image may include signals at differing intensities (i.e., signal levels). An image can be provided in a computer readable format or medium. An image is derived from the collection of focus points of light rays coming from an object (e.g., the sample), which may be detected by any image sensor.

As used herein, the term "signal" is intended to include, for example, fluorescent, luminescent, scatter, or absorption impulse or electromagnetic wave transmitted or received. Signals can be detected in the ultraviolet (UV) range (about 200 to 390 nm), visible (VIS) range (about 391 to 770 nm), infrared (IR) range (about 0.771 to 25 microns), or other range of the electromagnetic spectrum. The term "signal level" refers to an amount or quantity of detected energy or coded information. For example, a signal may be quantified by its intensity, wavelength, energy, frequency, power, luminance, or a combination thereof. Other signals can be quantified according to characteristics such as voltage, current, electric field strength, magnetic field strength, frequency, power, temperature, etc. Absence of signal is understood to be a signal level of zero or a signal level that is not meaningfully distinguished from noise.

The term "xy coordinates" refers to information that specifies location, size, shape, and/or orientation in an xy plane. The information can be, for example, numerical coordinates in a Cartesian system. The coordinates can be provided relative to one or both of the x and y axes or can be provided relative to another location in the xy plane (e.g., a fiducial). The term "xy plane" refers to a 2 dimensional area defined by straight line axes x and y. When used in reference to a detecting apparatus and an object observed by the detector, the xy plane may be specified as being orthogonal to the direction of observation between the detector and object being detected.

The term "adhesion strength" or "attachment strength" as used herein refers to the interfacial force bonding two materials together. The adhesion strength may refer to the minimal amount of force necessary to detach and/or remove the two materials. Means for quantifying adhesion strength are known in the art, for example with a pull-off adhesion test. A pull-off adhesion test measures the resistance of a substance (e.g., a tissue sample) from a substrate (e.g., a carrier substrate) when a perpendicular tensile force is applied to the substance. As outlined in the American Society for Testing and Materials (ASTM) D4541 (and similarly in BS EN ISO 4624), the test may include attaching a test dolly to the substance (e.g., the tissue sample) and then pulling the dolly by exerting a force perpendicular to the surface in an effort to remove the dolly with the substance from the substrate. An alternative testing approach is outlined in ASTM D6677 which utilizes a utility knife to peel the substance away from the substrate and ASTM D3359 which uses a pressure sensitive tape. The peel strength tests employed for examining the strength of Band-Aid® bonds is provided in ASTM D903, ASTM D1876, and ASTM F2258, each of which are incorporated herein by reference and may be used for measuring the adhesion strength as described herein. Instruments for performing such measurements include the monotonic uniaxial tensile testing device provided by Bose® Biodynamic Test Instrument, Minnetonka, MN, for example by employing at a constant rate (e.g., 0.05 mm/sec) and continuously recording the load response (e.g., 200 measurements/sec) to the point of macroscopic failure, or the Avery Adhesive Test (AAT).

As used herein, the term "resected" or "resection" is used in accordance with its plain and ordinary meaning and refers to removal of part or all of a tissue or an organ from a subject, typically through surgical removal.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

II. Compositions & Kits

In an aspect is provided a microplate, including a substrate including a surface, the surface including a plurality of wells separated from each other by interstitial regions on the surface, wherein one or more wells includes a tissue section and a carrier substrate, wherein the tissue section includes a thickness of about 1 µm to about 50 µm and the carrier substrate includes a hydrogel.

In an aspect is provided a microplate assembly. In embodiments, the microplate assembly includes a microplate receiver frame defining a pocket. In embodiments, the microplate assembly includes at least one microplate section and a planar support positioned on a bottom of the at least one microplate section. In embodiments, the microplate assembly includes integrated unit, wherein the frame and microplate section are fused together or otherwise inseparable. For example, the microplate assembly may include a microwell insert, wherein a plurality of wells are bored directly into the microwell insert. The integrated unit may have dimensions as provided and described by American National Standards Institute (ANSI) and Society for Laboratory Automation And Screening (SLAS); for example the tolerances and dimensions set forth in ANSI SLAS 1-2004 (R2012); ANSI SLAS 2-2004 (R2012); ANSI SLAS 3-2004 (R2012); ANSI SLAS 4-2004 (R2012); and ANSI SLAS 6-2012, which are incorporated herein by reference. The microplate insert does not necessarily include any wells. For example, the microplate insert may be configured to retain a microscope slide. In embodiments, the microwell insert includes a thermoplastic. In embodiments, the microwell insert includes a thermoplastic polyetherimide (PEI), for example ULTEM™ PEI PolyEtherImide (PEI). In embodiments, the microwell insert is glass. In embodiments, the microwell insert is ceramic. In embodiments, the microwell insert is steel. In embodiments, the microwell insert is glass, wherein the plurality of wells are bored directly into the glass.

In embodiments, the microplate (e.g., a microplate array) includes 2, 4, 6, 12, 24, 48, 96, 384 or 1536 wells. In embodiments, the microplate array includes 24, 48, 96, or 384 wells. In embodiments, the microplate array includes 24 wells. In embodiments, the microplate array includes 48 wells. In embodiments, the microplate array includes 96 wells. In embodiments, the microplate array includes 384 wells. In embodiments, the dimensions of the microplate conform to the standards provided by the American National Standards Institute (ANSI) and Society For Laboratory Automation And Screening (SLAS); for example the tolerances and dimensions set forth in ANSI SLAS 1-2004 (R2012); ANSI SLAS 2-2004 (R2012); ANSI SLAS 3-2004 (R2012); ANSI SLAS 4-2004 (R2012); and ANSI SLAS 6-2012. In embodiments, the microplate has a rectangular shape that measures 127.7 mm±0.5 mm in length by 85.4 mm±0.5 mm in width, and includes 6, 12, 24, 48, or 96 wells. In embodiments, the microplate has a rectangular shape that measures 127.7 mm±0.5 mm in length by 85.4 mm±0.5 mm in width, and includes 6, 12, 24, 48, or 96 wells, wherein each well has an average diameter of about 5-7 mm. In embodiments, the microplate has a rectangular shape that measures 127.7 mm±0.5 mm in length by 85.4 mm±0.5 mm in width, and includes 6, 12, 24, 48, or 96 wells, wherein each well has an average diameter of about 6 mm. In embodiments, the microplate includes wells that are formatted for compatibility with automated reagent loading equipment (e.g., pipetting robots) that exists and are in common usage in laboratories and manufacturing facilities.

In some embodiments, the wells of the array are separated from each other by about 1 mm to about 10 mm. In embodiments, the well is about 3 mm in diameter. In embodiments, the well is about 3.6 mm in diameter. In embodiments, the well is about 4 mm in diameter. In embodiments, the well is about 5 mm in diameter. In embodiments, the well is about 6 mm in diameter. In embodiments, the well is about 6.5 mm in diameter. In embodiments, the well is about 7 mm in diameter. In embodiments, the well is about 7.5 mm in diameter. In embodiments, the well is about 8 mm in diameter. In embodiments, the well is 5 mm in diameter. In embodiments, the well is 6 mm in diameter. In embodiments, the well is 6.5 mm in diameter. In embodiments, the well is 7 mm in diameter. In embodiments, the well is 7.5 mm in diameter. In embodiments, the well is 8 mm in diameter. In embodiments, the well is about 6 to 12 mm in depth. It is also understood that the size of the wells on the array can be of various sizes and will ultimately depend on the systems and/or apparatus used to analyze later reactions.

In embodiments, the microplate and wells are comprised of the same material. Though typically glass, suitable microplate materials may include polymeric materials, plastics, silicon, quartz (fused silica), Borofloat® glass, silica, silica-based materials, carbon, metals, an optical fiber or optical fiber bundles, sapphire, or plastic materials such as COCs and epoxies. The material can be selected based on properties desired for a particular use. For example, materials that are transparent to a desired wavelength of radiation are useful for analytical techniques that will utilize radiation of the desired wavelength. Conversely, it may be desirable to select a material that does not pass radiation of a certain wavelength (e.g., being opaque, absorptive, or reflective). In embodiments, at least a portion of the bottom of the wells is transparent and the sides (i.e., walls) of the wells are opaque. In embodiments, the material of the microplate is selected due to the ability to conduct thermal energy. In embodiments, the microplate and wells as used herein may be referred to as the receiving substrate.

Commercial microplates are typically made from plastic polymers (e.g., polypropylene). However, common plastic polymers, such as polypropylene and polyethylene, are susceptible to degradations issues. Thermal degradation, photodegradation, oxidative degradation, and UV degradation can occur, limiting the service life of a plastic microplate. Moreover, solvent compatibility with a range of solvents is required for certain types of analyses. Degradation generally involves changes to the molecular weight and/or structure of the plastic. Other property changes include a reduction in ductility and embrittlement, chalking, color changes, cracking, and a general reduction in desirable physical properties. Biological analyses often require incubation with abrasive chemicals and/or significant thermal shifts (e.g., about 20° C. to about 100° C.). The systems and devices used herein utilize microplates that are stable to temperature shifts and/or chemicals. Biological analyses often require subjecting the sample to significant thermal changes. For example, nucleic acid amplification and/or epitope expression may require cycling between room temperatures (e.g., 20° C. to 25° C.) to an elevated temperature (e.g., 90° C. to 120° C.). Plastic microplates (e.g., polystyrene, polypropylene, cyclic olefin copolymer, or cyclic olefin plastic microplates) are susceptible to warping and thermal degradation. Experiments with plastic microplates fused to an optically clear (COC/COP, glass, or quartz) bottom supports over these temperature ranges resulted in significant sample contamination. Without wishing to be bound by any theory, the different thermal expansion between the planar support (i.e., the glass bottom) and the fused well frame resulted in shearing, separating the well frame from the planar support, resulting in well-to-well leakage. In embodiments, the microwell insert is resistant to chemical degradation. Chemical durability is measured according to known methods in the art, for example via measuring weight loss per surface area following contact with a chemical (e.g., HCl). In embodiments, the microwell insert is capable of contacting xylene without significant degradation (e.g., without significant weight loss). In embodiments, the microwell insert is capable of contacting HCl, $HNO_3$, HF, and/or NaOH, without significant degradation (e.g., without significant weight loss). In embodiments, the microwell insert is capable of contacting organic solvents, such as hexanes or xylenes. Such chemicals can react with the microplate polymers (i.e., oxidization, reaction with functional groups, catalyze de-polymerization), or be absorbed into the bulk microplate material and soften/swell the microplate.

Microplates with clear-bottom wells facilitate optical measurements from the bottom, e.g., inverted high-resolution microscopy and imaging. For optical detection modalities, an optically transparent planar support is useful. Microplate color may be tuned to maximize the signal-to-background ratio. Black microplates are well-suited for fluorescence-based readouts; the black color can reduce well-to-well crosstalk, while also reducing background autofluorescence. In embodiments, the microplate includes a thermoplastic. In embodiments, the microplate includes a thermoplastic polyetherimide (PEI), for example ULTEM™ PEI PolyEtherImide (PEI). In embodiments, the microplate is glass. In embodiments, the microplate is ceramic. In embodiments, the microplate includes steel attached to a glass bottom. In embodiments, the microplate is glass, wherein a plurality of wells are bored directly into the glass. In embodiments, the microplate does not degrade at temperatures greater than 50° C., 60° C., 70° C., 80° C., 90° C., 100° C., 110° C., or 120° C. In embodiments, the microplate does not degrade at temperatures greater than 50° C., 60° C., 70° C., 80° C., 90° C., or 100° C. In embodiments, the microplate does not degrade at 100° C. In embodiments, the microplate bonded to the planar support does not degrade or result in sample contamination at elevated temperatures (e.g., 80° C.-120° C.). The microplate may be used to detect biomolecules (e.g., nucleic acids). Typically, the nucleic acids need to be amplified. In embodiments the term "amplified" refers to a method that includes a polymerase chain reaction (PCR). Conditions conducive to amplification (i.e., amplification conditions) are well known and often include at least a suitable polymerase, a suitable template, a suitable primer or set of primers, suitable nucleotides (e.g., dNTPs), a suitable buffer, and application of suitable annealing, hybridization and/or extension times and temperatures. Amplification conditions may cycle between different temperatures, often involving a large temperature gradient (e.g., 20° C.-40° C.). Additionally, samples embedded in formalin may require additional protocols to render biomolecules available. Heat induced epitope retrieval (HIER) uses heat coupled with buffered solutions to recover antigen reactivity in formalin fixed paraffin embedded tissue samples. Typical HIER methods include increasing the temperature from 25° C. to 95° C.-120° C., if utilizing a water bath or pressure enhanced temperature device (e.g., a pressure cooker). In embodiments, the microplate includes a microplate insert and a planar support attached to the microplate insert. In embodiments, a the planar support can include glass (e.g., a glass slide) that has been coated with a substance or otherwise modified to confer conductive properties to the glass. In some embodiments, a glass slide can be coated with a conductive coating. In some embodiments, a conductive coating includes tin oxide (TO) or indium tin oxide (ITO). In some embodiments, a conductive coating includes a transparent conductive oxide (TCO). In some embodiments, a conductive coating includes aluminum doped zinc oxide (AZO). In some embodiments, a conductive coating includes fluorine doped tin oxide (FTO).

In embodiments, the microplate includes a plurality of wells. In embodiments, each well includes about 10,000 to 100,000 cells per well. In embodiments, each well includes at least 1000, 2000, 3000, 4000, 5000, 6000, 7000, 8000, 9000 or at least 10,000 cells per well. In embodiments, each well includes about 10,000, 20,000, 30,000, 40,000, 50,000, 60,000, 70,000, 80,000, 90,000 or at least 100,000 cells per well.

In embodiments, the well contains a gel and/or a polymeric matrix. The term "gel" in this context refers to a semi-rigid solid that is permeable to liquids and gases. Exemplary gels include, but are not limited to, those having a colloidal structure, such as agarose; polymer mesh structure, such as gelatin; or cross-linked polymer structure, such as polyacrylamide or a derivative thereof. Analytes, such as polynucleotides, can be attached to a gel or polymer material via covalent or non-covalent means. Exemplary methods and reactants for attaching nucleic acids to gels are described, for example, in US 2011/0059865 which is incorporated herein by reference. The analytes, sample, tissue, or cell can include nucleic acids and the nucleic acids can be attached to the gel or polymer via their 3' oxygen, 5' oxygen, or at other locations along their length such as via a base moiety of the 3' terminal nucleotide, a base moiety of the 5' nucleotide, and/or one or more base moieties elsewhere in the molecule. In embodiments, the microplate includes a polymer layer (alternatively referred to as a polymer coating). In embodiments, the microplate includes a polymer layer, wherein the polymer layer includes an amphiphilic copolymer. The term "amphiphilic copolymer" is used in accordance with its ordinary meaning and refers to a copolymer composed of polymerized hydrophilic (e.g., PEG monomers) and hydrophobic monomers (e.g., alkoxysilyl or (poly(propylene oxide) monomers). Amphiphilic copolymers can have both hydrophilic and hydrophobic properties. In embodiments, the polymer layer includes an amphiphilic acrylate copolymer or amphiphilic methacrylate copolymer. In embodiments, the amphiphilic polymer includes a poloxamer. In some embodiments, the poloxamer is a polyoxyethylene-polyoxypropylene copolymer.

In embodiments, the tissue section may be referred to herein as a biological sample. In embodiments, the thickness of the biological sample is about 1 μm to about 20 μm. In embodiments, the thickness of the biological sample is about 5 μm to about 12 μm. In embodiments, the thickness of the biological sample is about 8 μm to about 15 μm. In embodiments, the thickness of the biological sample is about 1 μm, about 2 μm, about 3 μm, about 4 μm, about 5 μm, about 6 μm, about 7 μm, about 8 μm, about 9 μm, about 10 μm, about 11 μm, about 12 μm, about 13 μm, about 14 μm, or about 15 μm. In embodiments, the thickness of the biological sample is about 1 μm. In embodiments, the thickness of the biological sample is about 2 μm. In embodiments, the thickness of the biological sample is about 3 μm. In embodiments, the thickness of the biological sample is about 4 μm. In embodiments, the thickness of the biological sample is about 5 μm. In embodiments, the thickness of the biological sample is about 6 μm. In embodiments, the thickness of the biological sample is about 7 μm. In embodiments, the thickness of the biological sample is about 8 μm. In embodiments, the thickness of the biological sample is about 9 μm. In embodiments, the thickness of the biological sample is about 10 μm. In embodiments, the thickness of the biological sample is about 11 μm. In embodiments, the thickness of the biological sample is about 12 μm. In embodiments, the thickness of the biological sample is about 13 μm. In embodiments, the thickness of the biological sample is about 14 μm. In embodiments, the thickness of the biological sample is about 15 μm. In embodiments, the thickness of the biological sample is less than about 10 μm. In embodiments, the thickness of the biological sample is less about 6 μm, 7 μm, 8 μm, 9 μm or 10 μm.

The present disclosure provides kits for carrying out the methods of the present disclosure. The kits may include one or more of the following: fixative; carrier substrate (e.g., agarose, amylose, amylopectin, alginate, gelatin, cellulose, polyolefin, polyethylene glycol, polyvinyl alcohol, and/or acrylate polymers and copolymers); a surface including a plurality of wells separated from each other by interstitial regions on the surface, clearing reagents; nucleic acid probes, in situ hybridization buffer, labeled and/or unlabeled antibodies, buffers, e.g. buffer for fixing, washing, clearing, and/or staining specimens; mounting medium; embedding molds; dissection tools; etc. The subject reagents and kits thereof may vary greatly and may include a sub-set of the foregoing reagents. In embodiments, the kits include specialized well-plates, and reagents for sample preparation.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, digital storage medium, etc., on which the information has been recorded. Yet another means that may be present is a website address which may be used via the Internet to access the information at a removed site. Any convenient means may be present in the kits.

In an aspect is provided a composition including an alcohol (e.g., polyvinyl alcohol), a glycol (e.g., polyethylene glycol), and a hydrogel, wherein the hydrogel includes a cell. In embodiments, the composition is stored at or below 0° C. (i.e., the composition is frozen and solid). In embodiments, the composition is stored at or about 0° C., -10° C., -20° C., 40° C., -60° C., -70° C., or -80° C. In embodiments, the composition is formed by mixing a cell and a hydrogel together to form an embedded cell, followed by contacting the embedded cell with an aqueous solution including the alcohol and the glycol (e.g., 10% polyvinyl alcohol and about 4% polyethylene glycol). In embodiments, the composition further includes sucrose (e.g., 30% sucrose). In embodiments, the alcohol and glycol are an optimal cutting temperature (OCT) reagent (e.g., Tissue Freezing Medium (TFM) available from Leica Microsystems, Catalog #14020108926). An OCT reagent are characterized as being generally non-reactive with biological materials and having a high degree of viscosity due to the presence of viscosity generating substances such as polyvinyl alcohol and polyethylene glycol (see, e.g., O.C.T. sold by Tissue Tek® (product code 4583) which is composed of 10.24% polyvinyl alcohol, 4.26% polyethylene glycol and 85.50% non-reactive ingredients). The OCT compounds function to rapidly freeze biological samples and typically include viscosity agents such as about 5% to about 20% polyvinyl alcohol and/or about 1% to about 10% polyethylene glycol.

In embodiments, the hydrogel surrounds and/or encapsulates the cell. In embodiments, the cell is attached to the hydrogel via a covalent linker. In embodiments, the cell is non-covalently attached to the hydrogel. In embodiments, the hydrogel is a hydrogel described herein. In embodiments, the hydrogel is a polymer composition including 3 to 20% acrylamide and N,N-dimethylacrylamide. Any suitable hydrogel may be used, for example a hydrogel including poly(2-hydroxyethyl methacrylate) (PHEMA), optionally crosslinked with polyethylene glycol dimethacrylate; 2-hydroxyethyl methacrylate (HEMA) optionally crosslinked with TEGDMA (triethylene glycol dimethacrylate); polyethylene glycol methacrylate (PEGMA), optionally crosslinked with TEGDMA (triethylene glycol dimethacrylate); a copolymer of methacrylic acid (MAA) and polyethylene glycol methacrylate (PEGMA), optionally crosslinked with tetra(ethylene glycol) dimethacrylate; or poly(N-isopropyl acrylamide) (PNIPAM), optionally crosslinked with N,N-methylene bisacrylamide. Additional hydrogels include a polymer such as poly(hydroxyethyl methacrylate) (PHEMA), poly(glyceryl methacrylate) (PGMA), poly(hydroxypropyl methacrylate) (PHPMA), polyacrylamide (PAM), polymethacrylamide (PMAM), polyvinyl alcohol (PVA), polyacrylic acid (PAA), polyvinyl pyrrolidone (PVP), poly(ε-caprolactone) (PCL), poly(ethyleneimine) (PEI), poly(N,N-dimethylacrylamide) (PDMAM), poly(2-methoxyethyl acrylate) (PMEA), or a copolymer thereof. Polymer chains in a hydrogel may be crosslinked with each other chemically via covalent bonds or physically via non-covalent interactions to produce the network structure. The physical cross-linking involves hydrogen bonding, hydrophobic interactions, crystallinity, and ionic interactions. In chemically cross-linked hydrogels, covalent bonds cross-link individual polymer chains. Any suitable crosslinker may be used, for example N,N-methylene bisacrylamide, N,N-ethylene bisacrylamide, 1,4-Bis(acryloyl) piperazine, triethylene glycol dimethacrylate (TEGDMA), 1,1,1-trimethylolpropane trimethacrylate (TMPTMA), poly(ethylene glycol) dimethacrylate (PEGDMA), glyoxal, or tetramethylethylenediamineor N,N'-Bis(acryloyl) cystamine. In embodiments, the composition includes a tissue sample. In embodiments, the composition includes a plurality of cells.

In an aspect is provided a composition including a tissue section attached to a carrier substrate, wherein the carrier substrate includes a first adhesion strength; the tissue section attached to a receiving substrate, wherein the receiving substrate includes a second adhesion strength, wherein the second adhesion strength is greater than the first adhesion strength. In embodiments, the tissue section is immediately adjacent to both the carrier substrate as described herein and the carrier substrate as described herein. In embodiments, the tissue section includes a fluorescent particle (e.g., a fluorescent bead). In embodiments, the fluorescent particle is on the top (e.g., the surface of the tissue section in contact with the carrier substrate) and the bottom (e.g., the surface of the tissue section in contact with the receiving substrate) of the tissue section.

In an aspect is provided a kit. In embodiments, the kit is to support analysis of single cells and tissue sections on the device described herein. In embodiments, the kits enable multiomics analysis, including RNA transcription, protein expression, and targeted gene sequencing. In embodiments, the kits include a microplate, and reagents for sample preparation, purification, amplification, and sequencing readout. In embodiments, the kits for protein detection include DNA-conjugated antibodies.

In an aspect is provided a kit, including the plurality of particles, adapters, primers, and enzymes as described herein. Generally, the kit includes one or more containers providing a composition and one or more additional reagents (e.g., a buffer suitable for polynucleotide extension and/or sequencing.

In embodiments, amplification reagents and other reagents may be provided in lyophilized form. In embodiments, amplification reagents and other reagents may be provided in a container that includes wells within which the lyophilized reagent may be reconstituted.

In embodiments the kits are for use in accordance with any of the devices, systems, or methods disclosed herein, and including one or more elements thereof. In embodiments, a kit includes labeled nucleotides including differently labeled nucleotides, enzymes, buffers, oligonucleotides, and related solvents and solutions. In embodiments, the kit includes an oligonucleotide primer (e.g., an oligonucleotide primer as described herein). The kit may also include a template nucleic acid (DNA and/or RNA), one or more primer polynucleotides, nucleoside triphosphates (including, e.g., deoxyribonucleotides, dideoxynucleotides, ribonucleotides, labeled nucleotides, and/or modified nucleotides), buffers, salts, and/or labels (e.g., fluorophores). In embodiments, the kit includes components useful for circularizing template polynucleotides using a ligation enzyme (e.g., Circligase enzyme, Taq DNA Ligase, HiFi Taq DNA Ligase, T4 ligase, or Ampligase DNA Ligase). For example, such a kit further includes the following components: (a) reaction buffer for controlling pH and providing an optimized salt composition for a ligation enzyme (e.g., Circligase enzyme, Taq DNA Ligase, HiFi Taq DNA Ligase, T4 ligase, or Ampligase DNA Ligase), and (b) ligation enzyme cofactors. In embodiments, the kit further includes instructions for use thereof. In embodiments, kits described herein include a polymerase. In embodiments, the polymerase is a DNA polymerase. In embodiments, the DNA polymerase is a thermophilic nucleic acid polymerase. In embodiments, the DNA polymerase is a modified archaeal DNA polymerase. In embodiments, the kit includes a sequencing solution. In embodiments, the sequencing solution include labeled nucleotides including differently labeled nucleotides, wherein the label (or lack thereof) identifies the type of nucleotide. For example, each adenine nucleotide, or analog thereof; a thymine nucleotide; a cytosine nucleotide, or analog thereof; and a guanine nucleotide, or analog thereof may be labeled with a different fluorescent label. In embodiments, the kit includes a modified terminal deoxynucleotidyl transferase (TdT) enzyme.

In embodiments, the kit includes a sequencing polymerase, and one or more amplification polymerases. In embodiments, the sequencing polymerase is capable of incorporating modified nucleotides. In embodiments, the polymerase is a DNA polymerase. In embodiments, the DNA polymerase is a Pol I DNA polymerase, Pol II DNA polymerase, Pol III DNA polymerase, Pol IV DNA polymerase, Pol V DNA polymerase, Pol β DNA polymerase, Pol μ DNA polymerase, Pol λ DNA polymerase, Pol σ DNA polymerase, Pol α DNA polymerase, Pol δ DNA polymerase, Pol ε DNA polymerase, Pol η DNA polymerase, Pol ι DNA polymerase, Pol κ DNA polymerase, Pol ζ DNA polymerase, Pol γ DNA polymerase, Pol θ DNA polymerase, Pol ν DNA polymerase, or a thermophilic nucleic acid polymerase (e.g., Terminator γ, 9°N polymerase (exo-), Terminator II, Terminator III, or Terminator IX). In embodiments, the DNA polymerase is a thermophilic nucleic acid polymerase. In embodiments, the DNA polymerase is a modified archaeal DNA polymerase. In embodiments, the polymerase is a reverse transcriptase. In embodiments, the polymerase is a mutant *P. abyssi* polymerase (e.g., such as a mutant *P. abyssi* polymerase described in WO 2018/148723 or WO 2020/056044, each of which are incorporated herein by reference for all purposes). In embodiments, the kit includes a strand-displacing polymerase. In embodiments, the kit includes a strand-displacing polymerase, such as a phi29 polymerase, phi29 mutant polymerase or a thermostable phi29 mutant polymerase.

In embodiments, the kit includes a buffered solution. Typically, the buffered solutions contemplated herein are made from a weak acid and its conjugate base or a weak base and its conjugate acid. For example, sodium acetate and acetic acid are buffer agents that can be used to form an acetate buffer. Other examples of buffer agents that can be used to make buffered solutions include, but are not limited to, Tris, bicine, tricine, HEPES, TES, MOPS, MOPSO and PIPES. Additionally, other buffer agents that can be used in enzyme reactions, hybridization reactions, and detection reactions are known in the art. In embodiments, the buffered solution can include Tris. With respect to the embodiments described herein, the pH of the buffered solution can be modulated to permit any of the described reactions. In some embodiments, the buffered solution can have a pH greater than pH 7.0, greater than pH 7.5, greater than pH 8.0, greater than pH 8.5, greater than pH 9.0, greater than pH 9.5, greater than pH 10, greater than pH 10.5, greater than pH 11.0, or greater than pH 11.5. In other embodiments, the buffered solution can have a pH ranging, for example, from about pH 6 to about pH 9, from about pH 8 to about pH 10, or from about pH 7 to about pH 9. In embodiments, the buffered solution can include one or more divalent cations. Examples of divalent cations can include, but are not limited to, $Mg^{2+}$, $Mn^{2+}$, $Zn^{2+}$, and $Ca^{2+}$. In embodiments, the buffered solution can contain one or more divalent cations at a concentration sufficient to permit hybridization of a nucleic acid. In embodiments, the buffered solution can contain one or more divalent cations at a concentration sufficient to permit hybridization of a nucleic acid. In embodiments, the buffered solution includes about 10 mM Tris, about 20 mM Tris, about 30 mM Tris, about 40 mM Tris, or about 50 mM Tris. In embodiments the buffered solution includes about 50 mM NaCl, about 75 mM NaCl, about 100 mM NaCl, about 125 mM NaCl, about 150 mM NaCl, about 200 mM NaCl, about 300 mM NaCl, about 400 mM NaCl, or about 500 mM NaCl. In embodiments, the buffered solution includes about 0.05 mM EDTA, about 0.1 mM EDTA, about 0.25 mM EDTA, about 0.5 mM EDTA, about 1.0 mM EDTA, about 1.5 mM EDTA or about 2.0 mM EDTA. In embodiments, the buffered solution includes about 0.01% Triton X-100, about 0.025% Triton X-100, about 0.05% Triton X-100, about 0.1% Triton X-100, or about 0.5% Triton X-100. In embodiments, the buffered solution includes 20 mM Tris pH 8.0, 100 mM NaCl, 0.1 mM EDTA, 0.025% Triton X-100. In embodiments, the buffered solution includes 20 mM Tris pH 8.0, 150 mM NaCl, 0.1 mM EDTA, 0.025% Triton X-100. In embodiments, the buffered solution includes 20 mM Tris pH 8.0, 300 mM NaCl, 0.1 mM EDTA, 0.025% Triton X-100. In embodiments, the buffered solution includes 20 mM Tris pH 8.0, 400 mM NaCl, 0.1 mM EDTA, 0.025% Triton X-100. In embodiments, the buffered solution includes 20 mM Tris pH 8.0, 500 mM NaCl, 0.1 mM EDTA, 0.025% Triton X-100.

In embodiments, the kit includes one or more sequencing reaction mixtures. In embodiments, the sequencing reaction mixture includes a buffer. In embodiments, the buffer includes an acetate buffer, 3-(N-morpholino) propanesulfonic acid (MOPS) buffer, N-(2-Acetamido)-2-aminoethanesulfonic acid (ACES) buffer, phosphate-buffered saline (PBS) buffer, 4-(2-hydroxyethyl)-1-piperazineethanesulfonic acid (HEPES) buffer, N-(1,1-Dimethyl-2-hydroxyethyl)-3-amino-2-hydroxypropanesulfonic acid (AMPSO) buffer, borate buffer (e.g., borate buffered saline, sodium borate buffer, boric acid buffer), 2-Amino-2-methyl-1,3-propanediol (AMPD) buffer, N-cyclohexyl-2-hydroxyl-3-aminopropanesulfonic acid (CAPSO) buffer, 2-Amino-2-methyl-1-propanol (AMP) buffer, 4-(Cyclohexylamino)-1-butanesulfonic acid (CABS) buffer, glycine-NaOH buffer, N-Cyclohexyl-2-aminoethanesulfonic acid (CHES) buffer, tris(hydroxymethyl) aminomethane (Tris) buffer, or a N-cyclohexyl-3-aminopropanesulfonic acid (CAPS) buffer. In embodiments, the buffer is a borate buffer. In embodiments, the buffer is a CHES buffer. In embodiments, the sequencing reaction mixture includes nucleotides, wherein the nucleotides include a reversible terminating moiety and a label covalently linked to the nucleotide via a cleavable linker. In embodiments, the sequencing reaction mixture includes a buffer, DNA polymerase, detergent (e.g., Triton X), a chelator (e.g., EDTA), and/or salts (e.g., ammonium sulfate, magnesium chloride, sodium chloride, or potassium chloride).

The term "kit" includes both fragmented and combined kits. In embodiments, the kit includes, without limitation, nucleic acid primers, probes, adapters, enzymes, and the like, and are each packaged in a container, such as, without limitation, a vial, tube or bottle, in a package suitable for commercial distribution, such as, without limitation, a box, a sealed pouch, a blister pack and a carton. The package typically contains a label or packaging insert indicating the uses of the packaged materials. As used herein, "packaging materials" includes any article used in the packaging for distribution of reagents in a kit, including without limitation containers, vials, tubes, bottles, pouches, blister packaging, labels, tags, instruction sheets and package inserts.

Adapters and/or primers may be supplied in the kits ready for use, as concentrates-requiring dilution before use, or in a lyophilized or dried form requiring reconstitution prior to use. If required, the kits may further include a supply of a suitable diluent for dilution or reconstitution of the primers and/or adapters. Optionally, the kits may further include supplies of reagents, buffers, enzymes, and dNTPs for use in carrying out nucleic acid amplification and/or sequencing. Further components which may optionally be supplied in the kit include sequencing primers suitable for sequencing templates prepared using the methods described herein.

In embodiments, the kit includes a receiving substrate (e.g., a receiving substrate as described herein). For example, the receiving substrate is a microplate. In embodiments, the receiving substrate includes a plurality of wells, wherein one or more wells include a functionalized glass surface or a functionalized plastic surface. In embodiments, the receiving substrate includes a container suitable for air- and moisture-sensitive components (e.g., the receiving substrate is packaged under nitrogen or argon). In embodiments, the kit includes a carrier substrate (e.g., a hydrogel carrier substrate) as described herein. In embodiments, the kit includes a cutting device (e.g., a punch biopsy device). For example, a cutting device refers to a hollow, circular scalpel used to cut into portion of the tissue sample and/or the carrier substrate, which may be turned clockwise and counterclockwise to cut down about 4 millimeters (mm). In embodiments, the cutting device includes a circular hollow blade attached to a handle ranging, wherein the diameter of the circular hollow blade is about 0.5 mm to about 10 mm. In embodiments, the cutting device is disposable. In embodiments, the cutting device is reusable. In embodiments, the cutting device includes a plunger to aid in ejection of the cut section. In embodiments, the kit includes one or more detection agents (e.g., a detection agent as described herein, for example a fluorescent oligonucleotide probe and/or sequencing reagents).

In embodiments, the kit can further include one or more biological stain(s) (e.g., any of the biological stains as described herein). For example, the kit can further include eosin and hematoxylin. In other examples, the kit can include a biological stain such as acridine orange, Bismarck brown, carmine, coomassie blue, cresyl violet, DAPI, eosin, ethidium bromide, acid fuchsine, hematoxylin, Hoechst stains, iodine, methyl green, methylene blue, neutral red, Nile blue, Nile red, osmium tetroxide, propidium iodide, rhodamine, safranin, or any combination thereof.

III. Methods

In an aspect is provided a method of detecting a biomolecule in a tissue section, the method including: a) immobilizing the tissue section onto a carrier substrate to generate a sample-carrier construct, wherein the carrier substrate includes a first adhesion strength; b) contacting the tissue section of the sample-carrier construct with a receiving substrate to generate an immobilized tissue section, wherein the receiving substrate includes a second adhesion strength, wherein the second adhesion strength is greater than the first adhesion strength; c) removing the carrier substrate from the immobilized tissue section; d) optionally permeabilizing the immobilized tissue section; and e) contacting the biomolecule in the tissue section with a detection agent thereby detecting the biomolecule in the tissue section. In embodiments, the detection agent includes a fluorophore. In embodiments, the second adhesion strength is greater than the first adhesion strength to enable differential release of the carrier substrate from the immobilized tissue section. In embodiments, step c) occurs prior to step e). In embodiments, step c) occurs prior to step d).

In embodiments, the adhesion strength between the tissue section and the receiving substrate (e.g., the second adhesion strength) is greater than the adhesion strength between the carrier substrate and the tissue section (e.g., the first adhesion strength), such that the transfer of the tissue section occurs following contact between the tissue section and the receiving substrate. For example, removal of the carrier substrate from the immobilized tissue section does not remove the immobilized tissue section from the receiving substrate, as the second adhesion strength is greater than the first adhesion strength.

In embodiments, the second adhesion strength is at least 20%, at least 40%, at least 60%, or at least 80% greater than the first adhesion strength. In embodiments, the second adhesion strength is at least 20% greater than the first adhesion strength. In embodiments, the second adhesion strength is at least 40% greater than the first adhesion strength. In embodiments, the second adhesion strength is at least 60% greater than the first adhesion strength. In embodiments, the second adhesion strength is at least 80% greater than the first adhesion strength.

In embodiments, the first adhesion strength differs from the second adhesion strength by about 20%, 30%, 40%, 50%, 60%, 70%, 80%, 90%, or more. In embodiments, the first adhesion strength differs from the second adhesion strength by at least about 20%. In embodiments, the first adhesion strength differs from the second adhesion strength by at least about 30%. In embodiments, the first adhesion strength differs from the second adhesion strength by at least about 40%. In embodiments, the first adhesion strength differs from the second adhesion strength by at least about 50%. In embodiments, the first adhesion strength differs from the second adhesion strength by at least about 60%. In embodiments, the first adhesion strength differs from the second adhesion strength by at least about 70%. In embodiments, the first adhesion strength differs from the second adhesion strength by at least about 80%. In embodiments, the first adhesion strength differs from the second adhesion strength by at least about 90%.

In embodiments, the sample-carrier construct includes uniform adhesion (e.g., areas of uniform adhesion in the interface) between the tissue section and the carrier substrate. In embodiments, the sample-carrier construct includes non-uniform adhesion (e.g., areas of non-uniform adhesion in the interface) between the tissue section and the carrier substrate. In embodiments, the sample-carrier construct includes both uniform and non-uniform adhesion (e.g., includes areas with both uniform and non-uniform adhesion in the interface) between the tissue section and the carrier substrate. By "uniform adhesion" it is meant that the adhesion strength is consistent and not variable, for example, across all or most of the points of contact between the tissue section and the carrier substrate. By "non-uniform adhesion" it is means that there is at least some variability in the adhesion strength, for example, across all or some points of contact between the tissue section and the carrier substrate. The interface (e.g., all or some points of contact) between the tissue section and the carrier substrate may include both uniform and non-uniform adhesion, that is to say, regions of the interface where the adhesion strength is consistent (e.g., minimally variable) and regions of the interface wherein the adhesion strength is different and/or inconsistent (e.g., the adhesion strength across the non-uniform region(s) is different that the adhesion strength across the uniform region). Without wishing to be bound by theory, the adhesion strength may be non-uniform for a variety of reason, for example, non-planar tissue sections, microscopic air pockets between the tissue section and the carrier substrate, microscopic imperfections across the carrier substrate, and/or varying concentrations of bioconjugate reactive moieties present across the surface of the tissue section.

In embodiments, the immobilized tissue section includes uniform adhesion (e.g., areas of uniform adhesion in the interface) between the tissue section and the receiving substrate. In embodiments, the immobilized tissue section includes non-uniform adhesion (e.g., areas of non-uniform adhesion in the interface) between the tissue section and the receiving substrate. In embodiments, the immobilized tissue section includes non-uniform adhesion (e.g., includes areas with both uniform and non-uniform adhesion in the interface) between the tissue section and the receiving substrate. By "uniform adhesion" it is meant that the adhesion strength is consistent and not variable, for example, across all or most of the points of contact between the tissue section and the receiving substrate. By "non-uniform adhesion" it is means that there is at least some variability in the adhesion strength, for example, across all or some points of contact between the tissue section and the receiving substrate. The interface (e.g., all or some points of contact) between the tissue section and the receiving substrate may include both uniform and non-uniform adhesion, that is to say, regions of the interface where the adhesion strength is consistent (e.g., minimally variable) and regions of the interface wherein the adhesion strength is different and/or inconsistent (e.g., the adhesion strength across the non-uniform region(s) is different that the adhesion strength across the uniform region). Without wishing to be bound by theory, the adhesion strength may be non-uniform for a variety of reason, for example, non-planar tissue sections, microscopic air pockets between the tissue section and the receiving substrate, microscopic imperfections across the receiving substrate, and/or varying concentrations of bioconjugate reactive moieties present across the surface of the tissue section.

In embodiments, a stimulus (e.g., a physical stimulus, such as physical pressure, or a chemical, light, or electrical stimulus) is applied to the sample-carrier construct to increase the first adhesion strength (e.g., to immobilize the tissue section onto the carrier substrate). In embodiments, a stimulus (e.g., a physical stimulus, such as physical pressure, or a chemical, light, or electrical stimulus) is applied to the sample-carrier construct upon, or immediately after, contact with the receiving substrate (e.g., a stimulus is applied to the immobilized tissue section) to increase the second adhesion strength. In embodiments, a stimulus is applied to the sample-carrier construct upon, or immediately after, contact with the receiving substrate that decreases the first adhesion strength. In embodiments, a stimulus is applied to the sample-carrier construct upon, or immediately after, contact with the receiving substrate that decreases the first adhesion strength and increases the second adhesion strength.

In embodiments, the first adhesion strength is in a range such that the immobilization of the tissue section onto the carrier substrate is reversible (e.g., the tissue section is not damaged to an unacceptable degree following contact of the tissue section with the receiving substrate and removal of the carrier substrate). In embodiments, the second adhesion strength is in a range such that the movement of the tissue section upon, or immediately after, contact with the receiving substrate is restricted. In embodiments, the first adhesion strength of the carrier substrate is low upon immobilization of the tissue section onto the carrier substrate, such that the tissue section may be repositioned on the carrier substrate (e.g., repositioned without damaging the tissue section to an unacceptable degree).

In embodiments, the first adhesion strength of the carrier substrate increases (e.g., increases over time) after immobilization of the tissue section onto the carrier substrate (e.g., in response to a stimulus, such as a physical or chemical stimulus). In embodiments, the second adhesion strength of the receiving substrate increases (e.g., increases over time) after immobilization of the tissue section onto the receiving substrate (e.g., in response to a stimulus, such as a physical or chemical stimulus). In embodiments, the first adhesion strength of the carrier substrate decreases (e.g., decreases over time) and the second adhesion strength of the receiving substrate increases (e.g., increases over time) after immobilization of the tissue section onto the receiving substrate (e.g., in response to a stimulus, such as a physical or chemical stimulus).

In embodiments, the adhesion strength (e.g., the first adhesion strength and/or the second adhesion strength) may be measured as a shear strength or a tensile strength. For example, shear strength is the strength of a material against the type of yield when the material fails under a shear load. A shear load is a force that tends to produce a sliding failure on a material along a plane that is parallel to the direction of the force. In embodiments, the shear strength is less than about 0.1 kPa to 2 MPa. In embodiments, the shear strength is less than 2 MPa, less than 1 MPa, less than 500 kPa, less than 200 kPa, less than 100 kPa, less than 10 kPa, less than 1 kPa, or less than 0.1 kPa.

In an aspect is provided a method of detecting a biomolecule in a tissue section, the method including: a) immobilizing the tissue section onto a hydrogel carrier substrate to generate a sample-carrier construct; b) contacting the tissue section of the sample-carrier construct with a receiving substrate to generate an immobilized tissue section; c) removing the hydrogel carrier substrate from the immobilized tissue section; d) optionally permeabilizing the immobilized tissue section; and e) contacting the biomolecule in the tissue section with a detection agent thereby detecting the biomolecule in a tissue section. In embodiments, permeabilizing the immobilized tissue section allows access to the biomolecule within the immobilized tissue section. In embodiments, permeabilizing includes contacting the immobilized tissue section with a detergent. In embodiments, permeabilizing includes modulating the temperature (e.g., freezing or heating) of the immobilized tissue section. In embodiments, the detection agent includes a fluorophore. In embodiments, step c) occurs prior to step e). In embodiments, step c) occurs prior to step d).

In embodiments, the method further includes permeabilizing the tissue section of the sample-carrier construct prior to binding the immobilized specific binding agent to the biomolecule. Methods for permeabilization are known in the art, as exemplified by Cremer et al., The Nucleus: Volume 1: Nuclei and Subnuclear Components, R. Hancock (cd.) 2008; and Larsson et al., Nat. Methods (2010) 7:395-397, the content of each of which is incorporated herein by reference in its entirety. In embodiments, the tissue section is cleared (e.g., digested) of proteins, lipids, or proteins and lipids. In embodiments, permeabilizing the tissue section does not release the biomolecules (e.g., the one or more biomolecules) from within the tissue section. For example, after a fixation process (e.g. formaldehyde cross-linking), proteins and nucleic acids are immobilized within the cells of a tissue section, and are therefore not liberated into the environment following permeabilization of the cells.

Imaging deep into a tissue volume is problematic due to inherently fluorescent molecules present in the tissue or introduced during processing which give rise to autofluorescence that masks fluorescently labelled structures of interest. Typically, autofluorescence decreases image quality by lowering the signal to noise ratio across multiple fluorescence channels and undermines sharp images. Autofluorescence may arise from endogenous fluorescent biomolecules (NADPH, collagen, flavins, tyrosine, and others) or be introduced by the formation of Schiffs bases during fixation with aldehydes (e.g., glutaraldehyde and paraformaldehyde). Additional light scattering is provided by various cellular components, such as ribosomes, nuclei, nucleoli, mitochondria, lipid droplets, membranes, myelin, cytoskeletal components, and extracellular matrix components such as collagen and elastin.

In embodiments, the tissue is cleared using a solvent-based clearing approach. Solvent-based clearing techniques typically includes two steps: 1) dehydration (e.g., contacting the sample with methanol with or without hexane or, tetrahydrofurane (THF) alone) and 2) clearing by refractive index matching to the remaining dehydrated tissue's index (e.g., contacting the tissue sample with methylsalicilate, benzyl alcohol, benzyl benzoate, dichloromethane, or dibenzyl ether). Alternatively, the initial dehydration may be performed using phosphate buffered saline (PBS), detergent, and dimethyl sulfoxide (DMSO). In embodiments, the tissue is cleared by contacting the tissue sample with an aqueous solution containing sucrose, fructose, 2,2'-thiodiethanol (TDE), or formamide.

In embodiments, the tissue is cleared utilizing the 3D imaging of solvent-cleared organs (3DISCO) method as described in Ertürk A et al. Nat Protoc. 2012 November; 7 (11): 1983-95, which is incorporated herein by reference. For example, a sample is incubated overnight in 50% v/v tetrahydrofuran/$H_2O$ (THF), followed by incubation for at least one hour 80% THF/$H_2O$ and followed by incubation in a 100% THE solution. This is then followed by contacting the sample with dichloromethane (DCM) and an incubation in dibenzyl ether (DBE) until clear.

In embodiments, the tissue is cleared according to a known technique in the art, for example CLARITY (Chung K., et al. Nature 497, 332-337 (2013)), PACT-PARS (Yang B et al. Cell 158, 945-958 (2014).), CUBIC (Susaki E. A. et al. Cell 157, 726-739 (2014)., 18), ScaleS (Hama H., et al. Nat. Neurosci. 18, 1518-1529 (2015)), OPTIClear (Lai H. M., et al. Nat. Commun. 9, 1066 (2018)), Ce3D (Li W., et al. Proc. Natl. Acad. Sci. U.S.A. 114, E7321-E7330 (2017)), BABB (Dodt H. U. et al. Nat. Methods 4, 331-336 (2007)), iDISCO (Renier N., et al. Cell 159, 896-910 (2014)), uDISCO (Pan C., et al. Nat. Methods 13, 859-867 (2016)), FluoClearBABB (Schwarz M. K., et al. PLOS ONE 10, c0124650 (2015)), Ethanol-ECi (Klingberg A., et al. J. Am. Soc. Nephrol. 28, 452-459 (2017)), and PEGASOS (Jing D. et al. Cell Res. 28, 803-818 (2018)).

In embodiments, the tissue section is contacted with an alkaline solution containing a combination of 2,2'-thiodiethanol (TDE), DMSO, D-sorbitol, and Tris. In embodiments, the tissue section is contacted with an aqueous solution including 20% (vol/vol) DMSO, 40% (vol/vol) TDE, 20% (wt/vol) sorbitol, and 6% (wt/vol, equal to 0.5 M) Tris base. In embodiments, the tissue section is contacted with an aqueous solution including 25% (wt/wt) urea, 25% (wt/wt) N,N,N',N'-Tetrakis (2-hydroxypropyl) ethylenediamine, and 15% (wt/wt) Triton X-100. In embodiments, the tissue section is contact with an aqueous solution including 9.1 M urea, 22.5% (wt/vol) D-sorbitol, and 5% (wt/vol) Triton X-100. In embodiments, the tissue section is contact with an aqueous solution including 30% (wt/vol) urea, 20% (wt/vol) D-sorbitol, and 5% (wt/vol) glycerol dissolved in DMSO. In embodiments, the tissue section is contact with an aqueous solution according to the protocols described in Shan, Q H., Qin, X Y., Zhou, N. et al. BMC Biol 20, 77 (2022).

In embodiments, the biological sample can be permeabilized using any of the methods described herein (e.g., using any of the detergents described herein, e.g., SDS and/or N-lauroylsareosine sodium salt solution) before or after enzymatic treatment (e.g., treatment with any of the enzymes described herein, e.g., trypin, proteases (e.g., pepsin and/or proteinase K)). In embodiments, the biological sample can be permeabilized by contacting the sample with a permeabilization solution. In some embodiments, the biological sample is permeabilized by exposing the sample to greater than about 1.0 w/v % (e.g., greater than about 2.0 w/v %, greater than about 3.0 w/v %, greater than about 4.0 w/v %, greater than about 5.0 w/v %, greater than about 6.0 w/v %, greater than about 7.0 w/v %, greater than about 8.0 w/v %, greater than about 9.0 w/v %, greater than about 10.0 w/v %, greater than about 11.0 w/v %, greater than about 12.0 w/v %, or greater than about 13.0 w/v %) sodium dodecyl sulfate (SDS) and/or N-lauroylsareosine or N-lauroylsareosine sodium salt. In some embodiments, the biological sample can be permeabilized by exposing the sample (e.g., for about 5 minutes to about 1 hour, about 5 minutes to about 40 minutes, about 5 minutes to about 30 minutes, about 5 minutes to about 20 minutes, or about 5 minutes to about 10 minutes) to about 1.0 w/v % to about 14.0 w/v % (e.g., about 2.0 w/v % to about 14.0 w/v %, about 2.0 w/v % to about 12.0 w/v %, about 2.0 w/v % to about 10.0 w/v %, about 4.0 w/v % to about 14.0 w/v %, about 4.0 w/v % to about 12.0 w/v %, about 4.0 w/v % to about 10.0 w/v %, about 6.0 w/v % to about 14.0 w/v %, about 6.0 w/v % to about 12.0 w/v %, about 6.0 w/v % to about 10.0 w/v %, about 8.0 w/v % to about 14.0 w/v %, about 8.0 w/v % to about 12.0 w/v %, about 8.0 w/v % to about 10.0 w/v %, about 10.0% w/v % to about 14.0 w/v %, about 10.0 w/v % to about 12.0 w/v %, or about 12.0 w/v % to about 14.0 w/v %) SDS and/or N-lauroylsareosine salt solution and/or proteinase K (e.g., at a temperature of about 4% to about 35° C., about 4° C. to about 25° C., about 4° C. to about 20° C., about 4° C. to about 10° C., about 10° C. to about 25° C., about 10° C. to about 20° C., about 10° C. to about 15° C., about 35° C. to about 50° C., about 35° C. to about 45° C., about 35° C. to about 40° C., about 40° C. to about 50° C., about 40° C. to about 45° C., or about 45° C. to about 50° C.).

In embodiments, the method further includes removing the carrier substrate from the immobilized tissue section prior to contacting the biomolecule in the tissue section with a detection agent. In embodiments, the method further includes removing the carrier substrate from the immobilized tissue section during contacting the biomolecule in the tissue section with a detection agent.

In embodiments, the method further includes removing the carrier substrate from the immobilized tissue section prior to permeabilizing the immobilized tissue section. In embodiments, the method further includes removing the carrier substrate from the immobilized tissue section during permeabilization of the immobilized tissue section. In embodiments, the method includes removing paraffin after removing the carrier substrate.

In embodiments, generating a sample-carrier construct includes forming a plurality of non-covalent bonds between the tissue section and the carrier substrate. In embodiments, the carrier substrate includes water molecules attached to the surface of the carrier substrate.

In embodiments, the method includes contacting the tissue sample in a water bath. For example, the tissue sample is placed in a warm water bath, wherein the water bath temperature is set to about 40-50° C. (e.g., 42° C.), and the tissue sample floats on the surface of the water (e.g., floating for several seconds or up to a few minutes to allow the section to spread open and remove any wrinkles). In embodiments, the method includes contacting the tissue sample with the carrier substrate and attaching (e.g., non-covalently attaching) the tissue sample to the carrier substrate. Methods for transferring tissue sections via a water bath are known in the art, see for example Qin et al. (Qin C, et al. The Cutting and Floating Method for Paraffin-embedded Tissue for Sectioning. J Vis Exp. 2018 Sep. 5; (139): 58288.) which is incorporated herein by reference, and may include additional tools such as forceps and brushes to minimize wrinkles, air bubbles, or damage.

In embodiments, the carrier substrate includes a compression modulus greater than about 100 kPa. In embodiments, the carrier substrate includes a compression modulus greater than about 250 kPa. In embodiments, the carrier substrate includes a compression modulus greater than about 500 kPa. In embodiments, the carrier substrate includes a compression modulus greater than about 750 kPa. In embodiments, the carrier substrate includes a compression modulus greater than about 1 MPa. In embodiments, the carrier substrate includes a compression modulus greater than about 1.5 MPa. In embodiments, the carrier substrate includes a compression modulus greater than about 2 MPa. In embodiments, the carrier substrate includes a compression modulus of about 5 kPa.

In embodiments, the carrier substrate includes a compression modulus of about 25 kPa. In embodiments, the carrier substrate includes a compression modulus of about 50 kPa. In embodiments, the carrier substrate includes a compression modulus of about 100 kPa. In embodiments, the carrier substrate includes a compression modulus of about 250 kPa. In embodiments, the carrier substrate includes a compression modulus of about 500 kPa. In embodiments, the carrier substrate includes a compression modulus of about 750 kPa. In embodiments, the carrier substrate includes a compression modulus of about 1 MPa. In embodiments, the carrier substrate includes a compression modulus of about 1.5 MPa. In embodiments, the carrier substrate includes a compression modulus of about 2 MPa.

In embodiments, generating an immobilized tissue section includes forming a plurality of covalent bonds between the tissue section and the receiving substrate. In embodiments, the plurality of covalent bonds include amide and imide bonds. In embodiments, the plurality of covalent bonds include amide bonds. In embodiments, the plurality of covalent bonds include imide bonds.

In embodiments, the receiving substrate includes (3-aminopropyl)triethoxysilane (APTES), (3-Aminopropyl) trimethoxysilane (APTMS), γ-Aminopropylsilatrane (APS), N-(6-aminohexyl)aminomethyltriethoxysilane (AHAMTES), polyethylenimine (PEI), 5,6-epoxyhexyltriethoxysilane, or triethoxysilylbutyraldehyde, or a combination thereof. In embodiments, the receiving substrate includes (3-aminopropyl)triethoxysilane (APTES). In embodiments, the receiving substrate includes (3-Aminopropyl) trimethoxysilane (APTMS). In embodiments, the receiving substrate includes γ-Aminopropylsilatrance (APS). In embodiments, the receiving substrate includes N-(6-aminohexyl)aminomethyltriethoxysilane (AHAMTES). In embodiments, the receiving substrate surface includes polyethylenimine (PEI). In embodiments, the receiving substrate includes 5,6-epoxyhexyltriethoxysilane. In embodiments, the receiving substrate includes triethoxysilylbutyraldehyde. In embodiments, the receiving substrate is a functionalized glass surface or a functionalized plastic surface. In embodiments, the functionalized glass surface is functionalized with APTES, APTMS, APS, or AHAMTES.

In embodiments, the biomolecule is a nucleic acid sequence, carbohydrate, or protein. In embodiments, the biomolecule is a nucleic acid sequence. In embodiments, contacting the biomolecule (e.g., step e)) includes detecting the biomolecule by hybridizing one or more fluorescent probes to the biomolecule and detecting the one or more fluorescent probes. In embodiments, contacting the biomolecule (e.g., step e)) includes hybridizing a sequencing primer to the biomolecule and sequencing the biomolecule. In embodiments, sequencing includes (a) extending a sequencing primer by incorporating a labeled nucleotide, or labeled nucleotide analogue and (b) detecting the label to generate a signal for each incorporated nucleotide or nucleotide analogue. Some SBS embodiments include detection of a proton released upon incorporation of a nucleotide into an extension product. For example, sequencing based on detection of released protons can use an electrical detector and associated techniques that are commercially available from Ion Torrent (Guilford, Conn., a Life Technologies subsidiary) or sequencing methods and systems described in US 2009/0026082; US 2009/0127589; US 2010/0137143; or US 2010/0282617, each of which is incorporated herein by reference.

In embodiments, sequencing includes extending a sequencing primer to incorporate a nucleotide containing a detectable label that indicates the identity of a nucleotide in the target polynucleotide, detecting the detectable label, and repeating the extending and detecting of steps. In embodiments, the methods include sequencing one or more bases of a target nucleic acid by extending a sequencing primer hybridized to a target nucleic acid (e.g., an amplification product of a target nucleic acid). In embodiments, the sequencing includes sequencing-by-synthesis, sequencing-by-binding, sequencing by ligation, sequencing-by-hybridization, or pyrosequencing, and generates a sequencing read. In embodiments, generating a sequencing read includes executing a plurality of sequencing cycles, each cycle including extending the sequencing primer by incorporating a nucleotide or nucleotide analogue using a polymerase and detecting a characteristic signature indicating that the nucleotide or nucleotide analogue has been incorporated.

In SBS, extension of a nucleic acid primer along a nucleic acid template is monitored to determine the sequence of nucleotides in the template. The underlying chemical process can be catalyzed by a polymerase, wherein fluorescently labeled nucleotides are added to a primer (thereby extending the primer) in a template dependent fashion such that detection of the order and type of nucleotides added to the primer can be used to determine the sequence of the template. A plurality of different nucleic acid fragments that have been attached at different locations of an array can be subjected to an SBS technique under conditions where events occurring for different templates can be distinguished due to their location in the array. In embodiments, the sequencing step includes annealing and extending a sequencing primer to incorporate a detectable label that indicates the identity of a nucleotide in the target polynucleotide, detecting the detectable label, and repeating the extending and detecting steps. In embodiments, the methods include sequencing one or more bases of a target nucleic acid by extending a sequencing primer hybridized to a target nucleic acid (e.g., an amplification product produced by the amplification methods described herein). In embodiments, the sequencing step may be accomplished by a sequencing-by-synthesis (SBS) process. In embodiments, sequencing comprises a sequencing by synthesis process, where individual nucleotides are identified iteratively, as they are polymerized to form a growing complementary strand. In embodiments, nucleotides added to a growing complementary strand include both a label and a reversible chain terminator that prevents further extension, such that the nucleotide may be identified by the label before removing the terminator to add and identify a further nucleotide. Such reversible chain terminators include removable 3' blocking groups, for example as described in U.S. Pat. Nos. 10,738,072, 7,541,444 and 7,057,026. Once such a modified nucleotide has been incorporated into the growing polynucleotide chain complementary to the region of the template being sequenced, there is no free 3'-OH group available to direct further sequence extension and therefore the polymerase cannot add further nucleotides. Once the identity of the base incorporated into the growing chain has been determined, the 3' block may be removed to allow addition of the next successive nucleotide. By ordering the products derived using these modified nucleotides it is possible to deduce the DNA sequence of the DNA template. Non-limiting examples of suitable labels are described in U.S. Pat. Nos. 8,178,360, 5,188,934 (4,7-dichlorofluorscein dyes); 5,366,860 (spectrally resolvable rhodamine dyes); 5,847,162 (4,7-dichlororhodamine dyes); 4,318,846 (ether-substituted fluorescein dyes); 5,800,996 (energy transfer dyes); 5,066,580 (xanthene dyes); and 5,688,648 (energy transfer dyes); and the like.

Sequencing includes, for example, detecting a sequence of signals. Examples of sequencing include, but are not limited to, sequencing by synthesis (SBS) processes in which reversibly terminated nucleotides carrying fluorescent dyes are incorporated into a growing strand, complementary to the target strand being sequenced. In embodiments, the nucleotides are labeled with up to four unique fluorescent dyes. In embodiments, the nucleotides are labeled with at least two unique fluorescent dyes. In embodiments, the readout is accomplished by epifluorescence imaging. A variety of sequencing chemistries are available, non-limiting examples of which are described herein.

In embodiments, sequencing includes a plurality of sequencing cycles. In embodiments, sequencing includes 10 to 100 sequencing cycles. In embodiments, sequencing includes 50 to 100 sequencing cycles. In embodiments, sequencing includes 50 to 300 sequencing cycles. In embodiments, sequencing includes 50 to 150 sequencing cycles. In embodiments, sequencing includes at least 10, 20, 30 40, or 50 sequencing cycles. In embodiments, sequencing includes at least 10 sequencing cycles. In embodiments, sequencing includes 10 to 20 sequencing cycles. In embodiments, sequencing includes 10, 11, 12, 13, 14, or 15 sequencing cycles. In embodiments, sequencing includes (a) extending a sequencing primer by incorporating a labeled nucleotide, or labeled nucleotide analogue and (b) detecting the label to generate a signal for each incorporated nucleotide or nucleotide analogue. In embodiments, detecting includes two-dimensional (2D) or three-dimensional (3D) fluorescent microscopy. Suitable imaging technologies are known in the art, as exemplified by Larsson et al., Nat. Methods (2010) 7:395-397 and associated supplemental materials, the entire content of which is incorporated by reference herein in its entirety. In embodiments of the methods provided herein, the imaging is accomplished by confocal microscopy. Confocal fluorescence microscopy involves scanning a focused laser beam across the sample, and imaging the emission from the focal point through an appropriately-sized pinhole. This suppresses the unwanted fluorescence from sections at other depths in the sample. In embodiments, the imaging is accomplished by multi-photon microscopy (e.g., two-photon excited fluorescence or two-photon-pumped microscopy). Unlike conventional single-photon emission, multi-photon microscopy can utilize much longer excitation wavelength up to the red or near-infrared spectral region. This lower energy excitation requirement enables the implementation of semiconductor diode lasers as pump sources to significantly enhance the photostability of materials. Scanning a single focal point across the field of view is likely to be too slow for many sequencing applications. To speed up the image acquisition, an array of multiple focal points can be used. The emission from each of these focal points can be imaged onto a detector, and the time information from the scanning mirrors can be translated into image coordinates. Alternatively, the multiple focal points can be used just for the purpose of confining the fluorescence to a narrow axial section, and the emission can be imaged onto an imaging detector, such as a CCD, EMCCD, or s-CMOS detector. A scientific grade CMOS detector offers an optimal combination of sensitivity, readout speed, and low cost. One configuration used for confocal microscopy is spinning disk confocal microscopy. In 2-photon microscopy, the technique of using multiple focal points simultaneously to parallelize the readout has been called Multifocal Two-Photon Microscopy (MTPM). Several techniques for MTPM are available, with applications typically involving imaging in biological tissue. In embodiments of the methods provided herein, the imaging is accomplished by light sheet fluorescence microscopy (LSFM). In embodiments, detecting includes 3D structured illumination (3DSIM). In 3DSIM, patterned light is used for excitation, and fringes in the Moiré pattern generated by interference of the illumination pattern and the sample, are used to reconstruct the source of light in three dimensions. In order to illuminate the entire field, multiple spatial patterns are used to excite the same physical area, which are then digitally processed to reconstruct the final image. See York, Andrew G., et al. "Instant super-resolution imaging in live cells and embryos via analog image processing." Nature methods 10.11 (2013): 1122-1126 which is incorporated herein by reference. In embodiments, detecting includes selective planar illumination microscopy, light sheet microscopy, emission manipulation, pinhole confocal microscopy, aperture correlation confocal microscopy, volumetric reconstruction from slices, deconvolution microscopy, or aberration-corrected multifocus microscopy. In embodiments, detecting includes digital holographic microscopy (see for example Manoharan, V. N. Frontiers of Engineering: Reports on Leading-edge Engineering from the 2009 Symposium, 2010, 5-12, which is incorporated herein by reference). In embodiments, detecting includes confocal microscopy, light sheet microscopy, or multi-photon microscopy.

Use of the sequencing method outlined above is a non-limiting example, as essentially any sequencing methodology which relies on successive incorporation of nucleotides into a polynucleotide chain can be used. Suitable alternative techniques include, for example, pyrosequencing methods, FISSEQ (fluorescent in situ sequencing), MPSS (massively parallel signature sequencing), or sequencing by ligation-based methods.

In embodiments, generating a sequencing read includes determining the identity of the nucleotides in the template polynucleotide (or complement thereof). In embodiments, a sequencing read, e.g., a first sequencing read or a second sequencing read, includes determining the identity of a portion (e.g., 1, 2, 5, 10, 20, 50 nucleotides) of the total template polynucleotide. In embodiments the first sequencing read determines the identity of 5-10 nucleotides and the second sequencing read determines the identity of more than 5-10 nucleotides (e.g., 11 to 200 nucleotides). In embodiments the first sequencing read determines the identity of more than 5-10 nucleotides (e.g., 11 to 200 nucleotides) and the second sequencing read determines the identity of 5-10 nucleotides. In embodiments, following the generation of a sequencing read, subsequent extension is performed using a plurality of standard (e.g., non-modified) dNTPs until the complementary strand is copied. In other embodiments, following the generation of a sequencing read, subsequent extension is performed using a plurality of dideoxy nucleotide triphosphates (ddNTPs) to prevent further extension of the first sequencing read product during a second sequencing read. In embodiments, following the identification of at least 5-10 (e.g., 11 to 200 nucleotides, or up to 1000 nucleotides), subsequent extension is performed using a plurality of standard (e.g., non-modified) dNTPs until the complementary strand is copied. In embodiments, following the identification of at least 5-10 (e.g., 11 to 200 nucleotides, or up to 1000 nucleotides), subsequent extension is performed using a plurality of dideoxy nucleotide triphosphates (ddNTPs) to prevent further extension of the sequencing read product.

In embodiments, the detection agent includes a label. In embodiments, the detection agent includes a fluorescent label. In embodiments, the detection agent includes an oligonucleotide barcode (e.g., a 5 to 15 nucleotide sequence). In embodiments, the oligonucleotide barcode includes at least two primer binding sequences. In embodiments, the oligonucleotide barcode includes an amplification primer binding sequence. In embodiments, the oligonucleotide barcode includes a sequencing primer binding sequence. The amplification primer binding sequence refers to a nucleotide sequence that is complementary to a primer useful in initiating amplification (i.e., an amplification primer). Likewise, a sequencing primer binding sequence is a nucleotide sequence that is complementary to a primer useful in initiating sequencing (i.e., a sequencing primer). Primer binding sequences usually have a length in the range of between 3 to 36 nucleotides, also 5 to 24 nucleotides, also from 14 to 36 nucleotides. In embodiments, an amplification primer and a sequencing primer are complementary to the same primer binding sequence, or overlapping primer binding sequences. In embodiments, an amplification primer and a sequencing primer are complementary to different primer binding sequences. In embodiments, the primer binding sequence is complementary to a fluorescent in situ hybridization (FISH) probe. FISH probes may be custom designed using known techniques in the art, see for example Gelali, E., et al. Nat Commun 10, 1636 (2019). In embodiments, the detection probe is an oligonucleotide including a barcode sequence. In embodiments the oligonucleotide further includes a primer binding sequence.

In embodiments, contacting the biomolecule (e.g., step e)) includes hybridizing a padlock probe to two adjacent nucleic acid sequences of the biomolecule, wherein the padlock probe is a single-stranded polynucleotide having a 5' and a 3' end, the padlock probe includes at least one oligonucleotide barcode, and wherein the padlock probe includes a primer binding sequence. In embodiments, the method further includes ligating the 5' and 3' ends of the padlock probe to form a circular polynucleotide.

In embodiments, contacting the biomolecule (e.g., step e)) includes hybridizing a padlock probe to a nucleic acid sequence of the biomolecule, wherein the padlock probe is a single-stranded polynucleotide having a 5' and a 3' end, wherein the 3' end hybridizes to a first complementary region of the biomolecule and the 5' end hybridizes to a second complementary region of the biomolecule. In embodiments, the padlock probe includes a primer binding sequence. In embodiments, the method further includes extending the 3' end of the padlock probe along the nucleic acid sequence of the biomolecule to generate a complementary sequence and ligating the complementary sequence to the 5' end of the padlock probe thereby forming a circular oligonucleotide.

In embodiments, the method includes sequencing an endogenous nucleic acid of a cell, the method including: contacting the cell with a polynucleotide probe including a first region and a second region, hybridizing the first region of the polynucleotide probe to a first sequence of the endogenous nucleic acid, and hybridizing the second region of the polynucleotide probe to a second sequence of the endogenous nucleic acid, thereby forming a complex including the polynucleotide probe hybridized to the endogenous nucleic acid, wherein the endogenous nucleic acid includes a target sequence between the first sequence and the second sequence; extending the polynucleotide probe with nucleotides (e.g., deoxynucleotide triphosphates (dNTPs)) along the target sequence to generate a complement of the target sequence, and ligating the complement of the target sequence to the polynucleotide probe thereby forming a circular oligonucleotide; amplifying the circular oligonucleotide to form an extension product including one or more copies of the target sequence; and sequencing the one or more copies of the target sequence in the cell.

A variety of sequencing methodologies can be used such as sequencing-by-synthesis (SBS), pyrosequencing, sequencing by ligation (SBL), or sequencing by hybridization (SBH). Pyrosequencing detects the release of inorganic pyrophosphate (PPi) as particular nucleotides are incorporated into a nascent nucleic acid strand (Ronaghi, et al., Analytical Biochemistry 242 (1), 84-9 (1996); Ronaghi, Genome Res. 11 (1), 3-11 (2001); Ronaghi et al. Science 281 (5375), 363 (1998); U.S. Pat. Nos. 6,210,891; 6,258,568; and. 6,274,320, each of which is incorporated herein by reference in its entirety). In pyrosequencing, released Ppi can be detected by being converted to adenosine triphosphate (ATP) by ATP sulfurylase, and the level of ATP generated can be detected via light produced by luciferase. In this manner, the sequencing reaction can be monitored via a luminescence detection system. In both SBL and SBH methods, target nucleic acids, and amplicons thereof, that are present at features of an array are subjected to repeated cycles of oligonucleotide delivery and detection. SBL methods, include those described in Shendure et al. Science 309:1728-1732 (2005); U.S. Pat. Nos. 5,599,675; and 5,750,341, each of which is incorporated herein by reference in its entirety; and the SBH methodologies are as described in Bains et al., Journal of Theoretical Biology 135 (3), 303-7 (1988); Drmanac et al., Nature Biotechnology 16, 54-58 (1998); Fodor et al., Science 251 (4995), 767-773 (1995); and WO 1989/10977, each of which is incorporated herein by reference in its entirety.

In embodiments, sequencing is performed according to a "sequencing-by-binding" method (see, e.g., U.S. Pat. Pubs. US2017/0022553 and US2019/0048404, each of which is incorporated herein by reference in its entirety), which refers to a sequencing technique wherein specific binding of a polymerase and cognate nucleotide to a primed template nucleic acid molecule (e.g., blocked primed template nucleic acid molecule) is used for identifying the next correct nucleotide to be incorporated into the primer strand of the primed template nucleic acid molecule. The specific binding interaction need not result in chemical incorporation of the nucleotide into the primer. In some embodiments, the specific binding interaction can precede chemical incorporation of the nucleotide into the primer strand or can precede chemical incorporation of an analogous, next correct nucleotide into the primer. Thus, detection of the next correct nucleotide can take place without incorporation of the next correct nucleotide. As used herein, the "next correct nucleotide" (sometimes referred to as the "cognate" nucleotide) is the nucleotide having a base complementary to the base of the next template nucleotide. The next correct nucleotide will hybridize at the 3'-end of a primer to complement the next template nucleotide. The next correct nucleotide can be, but need not necessarily be, capable of being incorporated at the 3' end of the primer. For example, the next correct nucleotide can be a member of a ternary complex that will complete an incorporation reaction or, alternatively, the next correct nucleotide can be a member of a stabilized ternary complex that does not catalyze an incorporation reaction. A nucleotide having a base that is not complementary to the next template base is referred to as an "incorrect" (or "non-cognate") nucleotide.

In embodiments, the sequencing method relies on the use of modified nucleotides that can act as reversible reaction terminators. Once the modified nucleotide has been incorporated into the growing polynucleotide chain complementary to the region of the template being sequenced there is no free 3'-OH group available to direct further sequence extension and therefore the polymerase cannot add further nucleotides. Once the identity of the base incorporated into the growing chain has been determined, the 3' reversible terminator may be removed to allow addition of the next successive nucleotide. These such reactions can be done in a single experiment if each of the modified nucleotides has attached a different label, known to correspond to the particular base, to facilitate discrimination between the bases added at each incorporation step. Alternatively, a separate reaction may be carried out containing each of the modified nucleotides separately.

In embodiments, the method further includes terminating extension by incorporating one or more unmodified dNTPs and/or one or more ddNTPs into the 3' end of the extension strand. In embodiments, the method further includes terminating extension by incorporating one or more unmodified dNTPs. In embodiments, the method further includes terminating extension by incorporating one or more ddNTPs into the 3' end of the extension strand.

The modified nucleotides may carry a label (e.g., a fluorescent label) to facilitate their detection. Each nucleotide type may carry a different fluorescent label. However, the detectable label need not be a fluorescent label. Any label can be used which allows the detection of an incorporated nucleotide. One method for detecting fluorescently labeled nucleotides includes using laser light of a wavelength specific for the labeled nucleotides, or the use of other suitable sources of illumination. The fluorescence from the label on the nucleotide may be detected (e.g., by a CCD camera, CMOS camera, or other suitable detection means).

In embodiments, the method includes detecting a protein in a cell, the method including: contacting a cell with a specific binding reagent (e.g., antibody, single-chain Fv fragment (scFv), antibody fragment-antigen binding (Fab), or an aptamer) and binding the specific binding reagent to the protein, wherein the specific binding reagent includes an oligonucleotide; hybridizing a first sequence of a polynucleotide to the oligonucleotide, and hybridizing a second sequence of the polynucleotide to the oligonucleotide, thereby forming a complex including the polynucleotide hybridized to the oligonucleotide, wherein the oligonucleotide includes a barcode sequence between the first sequence and the second sequence; extending the polynucleotide along the barcode sequence to generate a complement of the barcode sequence, and ligating the complement of the barcode sequence to the polynucleotide thereby forming a circular oligonucleotide; amplifying the circular oligonucleotide to form an extension product including one or more copies of the barcode sequence; and sequencing the one or more copies of the barcode sequence in the cell, thereby detecting the protein.

In embodiments, contacting the biomolecule includes hybridizing a padlock probe to a nucleic acid sequence of the biomolecule, wherein the padlock probe is a single-stranded polynucleotide having a 5' and a 3' end, wherein the 3' end hybridizes to a first complementary region of the nucleic acid sequence and the 5' end hybridizes to a second complementary region of the RNA molecule. In embodiments, the padlock probe includes a primer binding sequence. In embodiments, the method further includes extending the 3' end of the padlock probe along the nucleic acid sequence of the biomolecule to generate a complementary sequence and ligating the complementary sequence to the 5' end of the padlock probe thereby forming a circular oligonucleotide.

In embodiments, the second complementary region is about 5 to about 75 nucleotides in the 5' direction with respect to the first complementary region. In embodiments, the second complementary region is about 10 to about 100 nucleotides in the 5' direction with respect to the first complementary region. In embodiments, the second complementary region is about 5, 10, 15, 20, 25, 30, 35, 40, 45, 50, 55, 60, 65, 70, 75, 80, 85, 90, 95, 100, or more nucleotides in the 5' direction with respect to the first complementary region.

In embodiments, the detection agent includes a padlock probe. Padlock probes are specialized ligation probes, examples of which are known in the art, see for example Nilsson M, et al. Science. 1994; 265 (5181): 2085-2088), and has been applied to detect transcribed RNA in cells, see for example Christian A T, et al. Proc Natl Acad Sci USA. 2001; 98 (25): 14238-14243, both of which are incorporated herein by reference in their entireties. In embodiments, the padlock probe is approximately 50 to 200 nucleotides. In embodiments, a padlock probe has a first domain that is capable of hybridizing to a first target sequence domain, and a second ligation domain, capable of hybridizing to an adjacent second sequence domain. The configuration of the padlock probe is such that upon ligation of the first and second ligation domains of the padlock probe, the probe forms a circular polynucleotide, and forms a complex with the sequence (i.e., the sequence it hybridized to, the target sequence) wherein the target sequence is "inserted" into the loop of the circle. Padlock probes are useful for the methods provided herein and include, for example, padlock probes for genomic analyses, as exemplified by Gore, A. et al. Nature 471, 63-67 (2011); Porreca, G. J. et al. Nat Methods 4, 931-936 (2007); Li, J. B. et al. Genome Res 19, 1606-1615 (2009), Zhang, K. et al. Nat Methods 6, 613-618 (2009); Noggle, S. et al. Nature 478, 70-75 (2011); and Li, J. B. et al. Science 324, 1210-1213 (2009), the content of each of which is incorporated by reference in its entirety.

In embodiments, the padlock probe is a single-stranded polynucleotide having a 5' and a 3' end, wherein the padlock probe includes at least one oligonucleotide barcode. In embodiments, the padlock probe includes a primer binding sequence. In embodiments, the padlock probe includes a primer binding sequence from a known set of primer binding sequences. In embodiments, the padlock probe includes only one primer binding sequence, wherein the primer binding sequence serves as the amplification primer binding sequence and sequencing primer binding sequence. In embodiments, the padlock probe includes at least two primer binding sequences from a known set of primer binding sequences. In embodiments, the padlock probe includes two or more primer binding sequences from a known set of primer binding sequences. In embodiments, the padlock probe includes up to 50 different primer binding sequences from a known set of primer binding sequences. In embodiments, the padlock probe includes up to 10 different primer binding sequences from a known set of primer binding sequences. In embodiments, the padlock probe includes up to 5 different primer binding sequences from a known set of primer binding sequences. In embodiments, the padlock probe includes two or more sequencing primer binding sequences from a known set of sequencing primer binding sequences. In embodiments, the padlock probe includes 1, 2, 3, 4, 5, 6, 7, 8, 9, or 10 primer binding sequences from a known set of primer binding sequences. In embodiments, the padlock probe includes two or more different primer binding sequences from a known set of primer binding sequences. In embodiments, the padlock probe includes 1, 2, 3, 4, 5, 6, 7, 8, 9, or 10 different primer binding sequences from a known set of primer binding sequences. In embodiments, the padlock probe includes 2 to 5 primer binding sequences from a known set of primer binding sequences. In embodiments, the padlock probe includes 2 to 5 different primer binding sequences from a known set of primer binding sequences. In embodiments, the padlock probe includes 2 to 5 sequencing primer binding sequences from a known set of sequencing primer binding sequences. In embodiments, the padlock probe includes 2 to 5 different sequencing primer binding sequences from a known set of sequencing primer binding sequences.

In embodiments, the padlock probe includes one oligonucleotide barcode, and one primer binding sequence. In embodiments, the padlock probe includes at least two (optionally different) oligonucleotide barcodes, and at least two different primer binding sequences. In embodiments, the padlock probe includes at least two (optionally different) oligonucleotide barcodes, and at least two different sequencing primer binding sequences. In embodiments, the padlock probe includes two different oligonucleotide barcodes and two different sequencing primer binding sequences. In embodiments, the padlock probe includes identical oligonucleotide barcodes and two different sequencing primer binding sequences.

In embodiments, the method further includes ligating the 5' and 3' ends of the padlock probe to form a circular polynucleotide (i.e., a polynucleotide that is a continuous strand lacking free 5' and 3' ends). In embodiments, the method includes ligating the 5' and 3' ends of the padlock probe to form a circular polynucleotide, wherein the circular polynucleotide includes the target nucleic acid. In embodiments, the method includes ligating the 5' and 3' ends of the padlock probe to form a circular polynucleotide, wherein the circular polynucleotide includes the oligonucleotide barcode. In embodiments, the ligation includes enzymatic ligation. In embodiments, ligating includes enzymatic ligation including a ligation enzyme (e.g., Circligase enzyme, Taq DNA Ligase, HiFi Taq DNA Ligase, T4 ligase, PBCV-1 DNA Ligase (also known as SplintR ligase) or Ampligase DNA Ligase). Non-limiting examples of ligases include DNA ligases such as DNA Ligase I, DNA Ligase II, DNA Ligase III, DNA Ligase IV, T4 DNA ligase, T7 DNA ligase, T3 DNA Ligase, *E. coli* DNA Ligase, PBCV-1 DNA Ligase (also known as SplintR ligase) or a Taq DNA Ligase. In embodiments, the ligase enzyme includes a T4 DNA ligase, T4 RNA ligase 1, T4 RNA ligase 2, T3 DNA ligase or T7 DNA ligase. In embodiments, the enzymatic ligation is performed by a mixture of ligases. In embodiments, the ligation enzyme is selected from the group consisting of T4 DNA ligase, T4 RNA ligase 1, T4 RNA ligase 2, RtcB ligase, T3 DNA ligase, T7 DNA ligase, Taq DNA ligase, PBCV-1 DNA Ligase, a thermostable DNA ligase (e.g., 5'AppDNA/RNA ligase), an ATP dependent DNA ligase, an RNA-dependent DNA ligase (e.g., SplintR ligase), and combinations thereof.

In embodiments, ligating includes chemical ligation (e.g., enzyme-free, click-mediated ligation). In embodiments, the oligonucleotide primer includes a first bioconjugate reactive moiety capable of bonding upon contact with a second (complementary) bioconjugate reactive moiety. In embodiments, the oligonucleotide primer includes an alkynyl moiety at the 3' and an azide moiety at the 5' end that, upon hybridization to the target nucleic acid react to form a triazole linkage during suitable reaction conditions. Reaction conditions and protocols for chemical ligation techniques that are compatible with nucleic acid amplification methods are known in the art, for example El-Sagheer, A. H., & Brown, T. (2012). *Accounts of chemical research*, 45 (8), 1258-1267; Manuguerra I. et al. *Chem Commun (Camb).* 2018; 54 (36): 4529-4532; and Odch, F., et al. (2019). *Molecules (Basel, Switzerland)*, 25 (1), 3, each of which is incorporated herein by reference in their entirety.

In embodiments, the method includes amplifying the circular polynucleotide by extending an amplification primer with a strand-displacing polymerase, wherein the primer extension generates an extension product including multiple complements of the circular polynucleotide. In embodiments, the method of amplifying includes an isothermal amplification method. In embodiments, the method of amplifying includes rolling circle amplification (RCA) or rolling circle transcription (RCT). In embodiments, the method of amplifying is rolling circle amplification (RCA). In embodiments, amplifying includes exponential rolling circle amplification (eRCA). Exponential RCA is similar to the linear process except that it uses a second primer (e.g., one or more immobilized oligonucleotide(s)) having a sequence that is identical to at least a portion of the circular template (Lizardi et al. Nat. Genet. 19:225 (1998)). This two-primer system achieves isothermal, exponential amplification. Exponential RCA has been applied to the amplification of non-circular DNA through the use of a linear probe that binds at both of its ends to contiguous regions of a target DNA followed by circularization using DNA ligase (Nilsson et al. Science 265 (5181): 208 5 (1994)).

Optionally, the rolling circle amplification reaction can be done with modified nucleotides that contain chemical groups that serve as attachment points to the cell or the matrix in which the cell is embedded (e.g. a hydrogel). The attachment of the amplified product to the matrix can help confine & fix the amplicon to a small volume. In embodiments, amplification reactions include standard dNTPs and a modified nucleotide (e.g., amino-allyl dUTP, 5-TCO-PEG4-dUTP, C8-Alkyne-dUTP, 5-Azidomethyl-dUTP, 5-Vinyl-dUTP, or 5-Ethynyl dLTTP). For example, during amplification a mixture of standard dNTPs and aminoallyl deoxyuridine 5'-triphosphate (dUTP) nucleotides may be incorporated into the amplicon and subsequently cross-linked to the cell protein matrix by using a cross-linking reagent (e.g., an amine-reactive crosslinking agent with PEG spacers, such as (PEGylated bis(sulfosuccinimidyl) suberate) (BS(PEG) 9)).

In embodiments, the method does not include ligation or amplification. For example, the method includes hybridizing a probe nucleic acid to the target (i.e., to a complementary region or gene of interest), wherein the probe nucleic acid is branched DNA or a concatemer and includes at least one sequencing primer binding sequence and a plurality of oligonucleotide barcodes. In embodiments, the probe nucleic acid includes a plurality of identical barcodes. In embodiments, associating an oligonucleotide barcode with each of the plurality of targets includes hybridizing a probe nucleic acid, wherein the probe nucleic acid includes branched DNA or a concatemer and includes at least one sequencing primer binding sequence and a plurality of oligonucleotide barcodes. In embodiments, the probe nucleic acid includes a plurality of identical oligonucleotide barcodes. In embodiments, the probe nucleic acid includes two or more complementary sequences to the target. In embodiments, the probe nucleic acid includes two or more different oligonucleotide barcodes.

In embodiments, the probe nucleic acid includes a two or more complementary sequences to the target. In embodiments, the probe nucleic acid includes two or more different oligonucleotide barcodes. In embodiments, the probe includes a primer binding sequence from a known set of primer binding sequences. In embodiments, the probe includes a sequencing primer binding sequence from a known set of sequencing primer binding sequences In embodiments, the detection agent includes a protein-specific binding agent. In embodiments, the detection agent includes a protein-specific binding agent bound to a nucleic acid sequence, bioconjugate reactive moiety, an enzyme, or a label. In embodiments, the protein-specific binding agent is an antibody, single domain antibody, single-chain Fv fragment (scFv), antibody fragment-antigen binding (Fab), affimer, or an aptamer.

In embodiments, the method includes detecting a plurality of biomolecules. In embodiments, the biomolecules are proteins or carbohydrates. In embodiments, the biomolecules are proteins. In embodiments, the biomolecules are carbohydrates. In embodiments when the biomolecules are proteins and/or carbohydrates, the method includes contacting the proteins with a specific binding reagent, wherein the specific binding reagent includes an oligonucleotide barcode. In embodiments, the specific binding reagent includes an antibody, single-chain Fv fragment (scFv), antibody fragment-antigen binding (Fab), or an aptamer. In embodiments, the specific binding reagent is a peptide, a cell penetrating peptide, an aptamer, a DNA aptamer, an RNA aptamer, an antibody, an antibody fragment, a light chain antibody fragment, a single-chain variable fragment (scFv), a lipid, a lipid derivative, a phospholipid, a fatty acid, a triglyceride, a glycerolipid, a glycerophospholipid, a sphingolipid, a saccharolipid, a polyketide, a polylysine, polyethyleneimine, diethylaminoethyl (DEAE)-dextran, cholesterol, or a sterol moiety. In embodiments, the specific binding reagent interacts (e.g., contacts, or binds) with one or more specific binding reagents in or on the cell. Carbohydrate-specific antibodies are known in the art, see for example Kappler, K., Hennet, T. Genes Immun 21, 224-239 (2020).

In embodiments, the biomolecule is a nucleic acid sequence. In embodiments, the method further includes amplifying the nucleic acid sequence to generate amplification products. In embodiments, the method includes detecting the amplification products.

In embodiments, the barcode is at least 5, 6, 7, 8, 9, 10, 11, 12, 13, 14, or 15 nucleotides in length. In embodiments, the barcode is 5, 6, 7, 8, 9, 10, 11, 12, 13, 14, or 15 nucleotides in length. In embodiments, the barcode is 10 to 15 nucleotides in length. An oligonucleotide barcode is at least about 1, 2, 3, 4, 5, 6, 7, 8, 9, 10, 15, 20, 25, 30, 35, 40, 45, 50 or more nucleotides in length. An oligonucleotide barcode can be at most about 300, 200, 100, 90, 80, 70, 60, 50, 40, 30, 20, 15, 12, 10, 9, 8, 7, 6, 5, 4 or fewer or more nucleotides in length. In embodiments, an oligonucleotide barcode includes between about 5 to about 8, about 5 to about 10, about 5 to about 15, about 5 to about 20, about 10 to about 150 nucleotides. In embodiments, an oligonucleotide barcode includes between 5 to 8, 5 to 10, 5 to 15, 5 to 20, 10 to 150 nucleotides. In embodiments, an oligonucleotide barcode is less than 10 nucleotides. In embodiments, an oligonucleotide barcode is about 10 nucleotides. In embodiments, an oligonucleotide barcode is 10 nucleotides. An oligonucleotide barcode may include a unique sequence (e.g., a barcode sequence) that gives the oligonucleotide barcode its identifying functionality. The unique sequence may be random or non-random. Attachment of the barcode sequence to a nucleic acid of interest (i.e., the target) may associate the barcode sequence with the nucleic acid of interest. The barcode may then be used to identify the nucleic acid of interest during sequencing, even when other nucleic acids of interest (e.g., including different oligonucleotide barcodes) are present. In embodiments, the oligonucleotide barcode consists only of a unique barcode sequence. In embodiments, the 5' end of a barcoded oligonucleotide is phosphorylated. In embodiments, the oligonucleotide barcode is known (i.e., the nucleic sequence is known before sequencing) and is sorted into a basis-set according to their Hamming distance. Oligonucleotide barcodes can be associated with a target of interest by knowing, a priori, the target of interest, such as a gene or protein. In embodiments, the oligonucleotide barcodes further include one or more sequences capable of specifically binding a gene or nucleic acid sequence of interest. For example, in embodiments, the oligonucleotide barcode include a sequence capable of hybridizing to mRNA, e.g., one containing a poly-T sequence (e.g., having several T's in a row, e.g., 4, 5, 6, 7, 8, or more T's). In embodiments, the padlock probe is at least about 50, 60, 70, 80, 90, 100, 110, 120, 130 or more nucleotides in length. In embodiments, the padlock probe is at most about 300, 200, 100, 90, 80, or fewer or more nucleotides in length. In embodiments, the total length of the padlock probe is about 80, 90, 100, 110, 120, 130, or 140 nucleotides in length.

In embodiments, the oligonucleotide barcode is taken from a "pool" or "set" or "basis-set" of potential oligonucleotide barcode sequences. The set of oligonucleotide barcodes may be selected using any suitable technique, e.g., randomly, or such that the sequences allow for error detection and/or correction, or having a particular feature, such as by being separated by a certain distance (e.g., Hamming distance). In embodiments, the method includes selecting a basis-set of oligonucleotide barcodes having a specified Hamming distance (e.g., a Hamming distance of 10; a Hamming distance of 5). The pool may have any number of potential barcode sequences, e.g., at least 100, at least 300, at least 500, at least 1,000, at least 3,000, at least 5,000, at least 10,000, at least 30,000, at least 50,000, at least 100,000, at least 300,000, at least 500,000, or at least 1,000,000 barcode sequences.

In embodiments, the method further includes digesting the tissue section by contacting the sample-carrier construct with an endopeptidase. In embodiments, the endopeptidase is pepsin.

In an aspect is provided a method of obtaining an image of a tissue section, the method including: immobilizing the tissue section onto a hydrogel carrier substrate to generate a sample-carrier construct including the carrier substrate and the tissue section; contacting the tissue section of the sample-carrier construct with a receiving substrate to generate an immobilized tissue section; removing the hydrogel carrier substrate from the immobilized tissue section; and imaging the tissue section, thereby obtaining an image of the tissue section.

In another aspect is provided a method of obtaining an image of a portion of a tissue section, the method including: A) immobilizing the tissue section onto a hydrogel carrier substrate to generate a sample-carrier construct including the carrier substrate and the tissue section; B) removing a portion of the sample-carrier construct, wherein the portion includes a portion of the carrier substrate and a portion of the tissue section; C) contacting the tissue section of the portion of the sample-carrier construct with a receiving substrate to generate an immobilized tissue section; D) removing the hydrogel carrier substrate from the immobilized tissue section; and E) imaging the tissue section, thereby obtaining an image of the portion of the tissue section.

In embodiments, prior to imaging (e.g., step E)), the method further includes permeabilizing the immobilized tissue section. In embodiments, prior to imaging (e.g., step E)), the method does not include permeabilizing the immobilized tissue section. In embodiments, prior to imaging (e.g., step E)), the method further includes contacting the immobilized tissue section with one or more imaging reagents or stains. In embodiments, following permeabilization, the tissue section is contacted with one or more imaging reagents or stains. In embodiments, the tissue section is contacted with one or more imaging reagents or stains without permeabilization. In embodiments, the imaging reagents or stains include hematoxylin and eosin (H&E) staining reagents. In embodiments, the imaging (e.g., step E)) includes phase-contrast microscopy, bright-field microscopy, Nomarski differential-interference-contrast microscopy, dark field microscopy, electron microscopy, or cryo-electron microscopy. In embodiments, the imaging reagents or stains include phase-contrast microscopy, bright-field microscopy, Nomarski differential-interference-contrast microscopy, or dark field microscopy imaging reagents. In embodiments, the light transmittance of the sample is measured. For example, light transmittance may be measured with a visible near-infrared optical fiber spectrometer, wherein a circular spot of light (e.g., diameter, 5 mm) is irradiated on the central part a sample and the transmitted light is collected using an optical sensor.

In embodiments, the imaging reagents or stains include electron microscopy (e.g., transmission electron microscopy or scanning electron microscopy) or cryo-electron microscopy imaging reagents. Examples of electron microscopy contrast agents may include one or more heavy metals (e.g., gold particles, colloidal gold particles, uranium, lead, platinum, and/or osmium) and/or antibodies bound to one or more types of heavy metals (e.g., gold particles, colloidal gold particles, uranium, lead, platinum, and/or osmium). For example, immunogold labels that may be used to contact the tissue section include may include different antibodies bound to gold particles of different sizes to image different molecules of interest. Optionally, the method may include contacting the tissue section with heavy metals. Heavy metals that may be used to stain additional features of interest and/or provide contrast between different structures in the tissue section may include uranium, lead, platinum, and/or osmium (see, e.g., U.S. Pat. Pubs. 2019/0355550 and 2013/0344500, each of which is incorporated herein by reference in its entirety).

In an aspect is provided a method of capturing a biomolecule from a tissue section, the method including: i) immobilizing the tissue section onto a hydrogel carrier substrate to generate a sample-carrier construct; ii) contacting the tissue section of the sample-carrier construct with a receiving substrate, wherein the receiving substrate includes an immobilized specific-binding agent; and iii) binding the immobilized specific-binding agent to the biomolecule from the tissue section thereby capturing a biomolecule from the tissue section.

In embodiments, the method includes removing the hydrogel carrier substrate. In embodiments, the method includes not removing the hydrogel carrier substrate. In embodiments, the method includes dissolving the hydrogel carrier substrate.

In embodiments, the receiving substrate includes a plurality of immobilized specific binding agents (e.g., immobilized oligonucleotides as described herein or immobilized proteins capable of specifically hybridizing a target of interest). In embodiments, the biomolecule is a target nucleic acid sequence. In embodiments, the immobilized specific-binding agent includes an oligonucleotide complementary to the target nucleic acid sequence. In embodiments, the immobilized specific-binding agent includes a poly(T) sequence. In embodiments, the immobilized specific-binding agent includes a spatial barcode, unique molecule identifying sequence, cleavable site, an amplification primer binding sequence, or a combination thereof. In embodiments, the method further includes extending with a polymerase the target nucleic acid sequence bound to the immobilized specific binding agent. In embodiments, the method further includes digesting the tissue section by contacting the sample-carrier construct with an endopeptidase. In embodiments, the immobilized specific binding agents are attached to the solid support via a linker.

In an aspect is provided a method of immobilizing a tissue section to a receiving substrate, wherein the tissue section includes a thickness of about 1 µm to about 50 µm, the method including: contacting the tissue section with a hydrogel carrier substrate to generate a sample-carrier construct including the carrier substrate and the tissue section; contacting the tissue section of the sample-carrier construct with the receiving substrate; and removing the carrier substrate from the sample-carrier construct, thereby immobilizing the tissue section to the receiving substrate.

In embodiments, the temperature of the carrier substrate is at or below the temperature of the tissue section. In embodiments, the temperature of the carrier substrate is about (e.g., within 10%) of the temperature of the carrier substrate. In embodiments, the temperature of the carrier substrate is reduced to about −40° C., −50° C., −60° C., −70° C., or −80° C. prior to contacting the tissue section to the carrier substrate.

In embodiments, substantially all of the tissue section is immobilized to the receiving substrate. In embodiments, greater than 90%, greater than 95%, greater than 96%, greater than 97%, greater than 98%, or greater than 99% of the tissue section is immobilized to the receiving substrate. In embodiments, greater than 90% of the tissue section is immobilized to the receiving substrate. In embodiments, greater than 95% of the tissue section is immobilized to the receiving substrate. In embodiments, greater than 96% of the tissue section is immobilized to the receiving substrate. In embodiments, greater than 97% of the tissue section is immobilized to the receiving substrate. In embodiments, greater than 98% of the tissue section is immobilized to the receiving substrate. In embodiments, greater than 99% of the tissue section is immobilized to the receiving substrate. In embodiments, about 100% of the tissue section is immobilized to the receiving substrate.

In another aspect is provided a method of immobilizing a portion of a tissue section to a receiving substrate, wherein the tissue section includes a thickness of about 1 µm to about 50 µm, the method including: contacting the tissue section with a hydrogel carrier substrate to generate a sample-carrier construct including the carrier substrate and the tissue section; removing a portion of the sample-carrier construct, wherein the portion includes a portion of the carrier substrate and a portion of the tissue section; contacting the tissue section of the portion of the sample-carrier construct with the receiving substrate thereby immobilizing the tissue section to the receiving substrate.

In embodiments, the thickness of the tissue section is about 1 µm to about 20 µm. In embodiments, the thickness of the tissue section is about 5 µm to about 12 µm. In embodiments, the thickness of the tissue section is about 8 µm to about 15 µm. In embodiments, the thickness of the tissue section is about 1 µm, about 2 µm, about 3 µm, about 4 µm, about 5 µm, about 6 µm, about 7 µm, about 8 µm, about 9 µm, about 10 µm, about 11 µm, about 12 µm, about 13 µm, about 14 µm, or about 15 µm. In embodiments, the thickness of the tissue section is about 1 µm. In embodiments, the thickness of the tissue section is about 2 µm. In embodiments, the thickness of the tissue section is about 3 µm. In embodiments, the thickness of the tissue section is about 4 µm. In embodiments, the thickness of the tissue section is about 5 µm. In embodiments, the thickness of the tissue section is about 6 µm. In embodiments, the thickness of the tissue section is about 7 µm. In embodiments, the thickness of the tissue section is about 8 µm. In embodiments, the thickness of the tissue section is about 9 µm. In embodiments, the thickness of the tissue section is about 10 µm. In embodiments, the thickness of the tissue section is about 11 µm. In embodiments, the thickness of the tissue section is about 12 µm. In embodiments, the thickness of the tissue section is about 13 µm. In embodiments, the thickness of the tissue section is about 14 μm. In embodiments, the thickness of the tissue section is about 15 μm.

In embodiments, the tissue section includes a tissue or a cell (e.g. plurality of cells such as blood cells). In embodiments, the tissue section includes one or more cells.

In embodiments, the tissue section is embedded in an embedding material including paraffin wax, polyepoxide polymer, polyacrylic polymer, agar, gelatin, celloidin, cryogel, optimal cutting temperature (OCT) compositions, glycols, or a combination thereof. In embodiments, the tissue section is embedded in an embedding material including paraffin wax. In embodiments, the OCT composition includes about 10% polyvinyl alcohol and about 4% polyethylene glycol. In embodiments, the OCT composition includes sucrose (e.g., 30% sucrose). In embodiments, the OCT composition is Tissue Freezing Medium (TFM) available from Leica Microsystems, Catalog #14020108926.

In embodiments, the tissue section is an artificial tissue section, wherein the artificial tissue section includes one or more cells suspended in a hydrogel. In embodiments, the artificial tissue section includes one or more cells suspended in a hydrogel that is embedded in an optimal cutting temperature (OCT) composition. In embodiments, the artificial tissue section is prepared according to the following method: the sample containing the biomolecule of interest (e.g., a cell or a particle) is embedded in a crosslinked hydrogel (e.g., a polymer composition including 3 to 20% acrylamide and N,N-dimethylacrylamide). Any suitable hydrogel may be used, for example a hydrogel including poly(2-hydroxyethyl methacrylate) (PHEMA), optionally crosslinked with polyethylene glycol dimethacrylate; 2-hydroxyethyl methacrylate (HEMA) optionally crosslinked with TEGDMA (triethylene glycol dimethacrylate); polyethylene glycol methacrylate (PEGMA), optionally crosslinked with TEGDMA (triethylene glycol dimethacrylate); a copolymer of methacrylic acid (MAA) and polyethylene glycol methacrylate (PEGMA), optionally crosslinked with tetra(ethylene glycol) dimethacrylate; or poly(N-isopropyl acrylamide) (PNIPAM), optionally crosslinked with N,N-methylene bisacrylamide. Additional hydrogels include a polymer such as poly(hydroxyethyl methacrylate) (PHEMA), poly(glyceryl methacrylate) (PGMA), poly(hydroxypropyl methacrylate) (PHPMA), polyacrylamide (PAM), polymethacrylamide (PMAM), polyvinyl alcohol (PVA), polyacrylic acid (PAA), polyvinyl pyrrolidone (PVP), poly(ε-caprolactone) (PCL), poly(ethyleneimine) (PEI), poly(N,N-dimethylacrylamide) (PDMAM), poly(2-methoxyethyl acrylate) (PMEA), or a copolymer thereof. Polymer chains in a hydrogel may be crosslinked with each other chemically via covalent bonds or physically via non-covalent interactions to produce the network structure. The physical cross-linking involves hydrogen bonding, hydrophobic interactions, crystallinity, and ionic interactions. In chemically cross-linked hydrogels, covalent bonds cross-link individual polymer chains. Any suitable crosslinker may be used, for example N,N-methylene bisacrylamide, N,N-ethylene bisacrylamide, 1,4-Bis(acryloyl) piperazine, triethylene glycol dimethacrylate (TEGDMA), 1,1,1-trimethylolpropane trimethacrylate (TMPTMA), poly(ethylene glycol) dimethacrylate (PEGDMA), glyoxal, or tetramethylethylenediamineor N,N'-Bis(acryloyl) cystamine.

Following hydrogel embedding, the sample was frozen in OCT at −80° C. The frozen OCT-hydrogel complex was then sectioned (e.g., tissue sections of 5 μm and 9 μm thickness were derived). It is known that OCT compounds may impact PCR amplification, see for example Turbett and Sellner (Diagn Mol Pathol. 1997 October; 6 (5): 298-303), so embedding the biological sample in a hydrogel first helps protect the sample from downstream effects from the OCT.

In embodiments, the tissue section is embedded in an embedding material including a polyepoxide polymer. In embodiments, the tissue section is embedded in an embedding material including polyacrylic polymer. In embodiments, the tissue section is embedded in an embedding material including agar. In embodiments, the tissue section is embedded in an embedding material including gelatin. In embodiments, the tissue section is embedded in an embedding material including celloidin. In embodiments, the tissue section is embedded in an embedding material including a cryogel. In embodiments, the tissue section is embedded in an embedding material including an optimal cutting temperature (OCT) compositions. In embodiments, the tissue section is embedded in an embedding material including one or more glycols.

In embodiments, the method further includes removing the embedding material. In embodiments, the method further includes removing the embedding material prior to contacting the tissue section of the sample-carrier construct with the receiving substrate (e.g., step C)). For example, if the embedding material is paraffin wax, the embedding material is removed by contacting the sample-carrier construct with a hydrocarbon solvent, such as xylene or hexane, followed by two or more washes with decreasing concentrations of an alcohol, such as ethanol.

In embodiments, the carrier substrate includes a hydrogel. In embodiments, the carrier substrate includes agarose, amylose, amylopectin, alginate, gelatin, cellulose, polyolefin, polyethylene glycol, polyvinyl alcohol, and/or acrylate polymers and copolymers thereof. In embodiments, the carrier substrate includes agarose, amylose, or amylopectin. In embodiments, the carrier substrate includes agarose. In embodiments, the carrier substrate includes amylose. In embodiments, the carrier substrate includes amylopectin. In embodiments, the carrier substrate includes alginate. In embodiments, the carrier substrate includes gelatin. In embodiments, the carrier substrate includes cellulose. In embodiments, the carrier substrate includes polyolefin. In embodiments, the carrier substrate includes polyethylene glycol. In embodiments, the carrier substrate includes polyvinyl alcohol. In embodiments, the carrier substrate includes acrylate polymers and copolymers thereof.

In embodiments, the carrier substrate includes about 2% to about 10% agarose. In embodiments, the carrier substrate includes about 2% agarose. In embodiments, the carrier substrate includes about 3% agarose. In embodiments, the carrier substrate includes about 4% agarose. In embodiments, the carrier substrate includes about 5% agarose. In embodiments, the carrier substrate includes about 6% agarose. In embodiments, the carrier substrate includes about 7% agarose. In embodiments, the carrier substrate includes about 8% agarose. In embodiments, the carrier substrate includes about 9% agarose. In embodiments, the carrier substrate includes about 10% agarose.

In embodiments, the carrier substrate further includes a support scaffold.

In embodiments, the carrier substrate includes a hydrogel. In embodiments, the hydrogel carrier substrate includes agarose, alginate, gelatin, cellulose, polyolefin, polyethylene glycol, polyvinyl alcohol, and/or acrylate polymers and copolymers. In embodiments, the hydrogel carrier substrate includes agarose, amylose, or amylopectin. In embodiments, the hydrogel carrier substrate includes acrylamide, methacrylate and methacrylamide polymers and copolymers thereof. Any suitable hydrogel may be used as a carrier substrate, for example a hydrogel including poly(2-hydroxyethyl methacrylate) (PHEMA), optionally crosslinked with polyethylene glycol dimethacrylate; 2-hydroxyethyl methacrylate (HEMA) optionally crosslinked with TEGDMA (triethylene glycol dimethacrylate); polyethylene glycol methacrylate (PEGMA), optionally crosslinked with TEGDMA (triethylene glycol dimethacrylate); a copolymer of methacrylic acid (MAA) and polyethylene glycol methacrylate (PEGMA), optionally crosslinked with tetra(ethylene glycol) dimethacrylate; or poly(N-isopropyl acrylamide) (PNIPAM), optionally crosslinked with N,N-methylene bisacrylamide. Additional hydrogels include a polymer such as poly(hydroxyethyl methacrylate) (PHEMA), poly(glyceryl methacrylate) (PGMA), poly(hydroxypropyl methacrylate) (PHPMA), polyacrylamide (PAM), polymethacrylamide (PMAM), polyvinyl alcohol (PVA), polyacrylic acid (PAA), polyvinyl pyrrolidone (PVP), poly(ε-caprolactone) (PCL), poly(ethyleneimine) (PEI), poly(N,N-dimethylacrylamide) (PDMAM), poly(2-methoxyethyl acrylate) (PMEA), or a copolymer thereof. Polymer chains in a hydrogel may be crosslinked with each other chemically via covalent bonds or physically via non-covalent interactions to produce the network structure. The physical cross-linking involves hydrogen bonding, hydrophobic interactions, crystallinity, and ionic interactions. In chemically cross-linked hydrogels, covalent bonds cross-link individual polymer chains. Any suitable crosslinker may be used, for example N,N-methylene bisacrylamide, N,N-ethylene bisacrylamide, 1,4-Bis(acryloyl) piperazine, triethylene glycol dimethacrylate (TEGDMA), 1,1,1-trimethylolpropane trimethacrylate (TMPTMA), poly(ethylene glycol) dimethacrylate (PEGDMA), glyoxal, or tetramethylethylenediamineor N,N'-Bis(acryloyl) cystamine.

In embodiments, the carrier substrate and/or the receiving substrate is sterile prior to immobilizing the tissue section onto the carrier substrate. In embodiments, the hydrogel carrier substrate is sterile prior to immobilizing the tissue section onto the carrier substrate. In embodiments, the carrier substrate is sterilized prior to contact with the tissue section. In embodiments, the receiving substrate is sterilized prior to contact with the tissue section. In embodiments, the hydrogel carrier substrate is sterilized prior to contact with the tissue section Methods of sterilization include, but are not limited to, steam autoclaving (e.g., sterilization in an autoclave under a standard condition at 121° C. for 30 min), ethanol sterilization, and gamma irradiation, as described further in Han X. Biointerphases. 2017; 12 (2): 02C411 and Galante R et al., J. Biomed. Mater. Res. B Appl. Biomater. 2018; 106 (6): 2472-2492, each of which is incorporated herein by reference.

In embodiments, the carrier substrate includes a semisolid foam. In embodiments, the carrier substrate includes a polythioketal-based polyurethane (PTK-UR) foam scaffold. In embodiments, the carrier substrate includes hydroxypropyl methylcellulose (HPMC) and polyvinylpyrrolidone (PVP). In embodiments, the carrier substrate includes dry ice (i.e., solid carbon dioxide). In embodiments, the carrier substrate includes ice (i.e., frozen water).

In embodiments, the hydrogel carrier substrate includes an agarose gel. Agarose gels can be made at different weight percentages by varying the amount of purified agarose in solution prior to gelation, which alters the microstructure and subsequent bulk mechanical behavior significantly. Agarose gels are typically categorized by their weight percentages, meaning that a 1% agarose gel is defined by 1 g of agarose powder (agar) per 100 mL of buffer solution. The type of buffer solution used to make agarose is generally a TBE buffer, which is a tris base, boric acid, and EDTA (ethylene diamine tetraacetic acid) mixture produced at various concentrations in water. In embodiments, the hydrogel carrier substrate includes less than about 5% agarose. In embodiments, the hydrogel carrier substrate includes less than about 4% agarose. In embodiments, the hydrogel carrier substrate includes less than about 3% agarose. In embodiments, the hydrogel carrier substrate includes less than about 2% agarose. In embodiments, the hydrogel carrier substrate includes more than about 5% agarose.

In embodiments, the hydrogel carrier substrate is contacted with glycerol (e.g., a 50-80% solution of glycerol. Without wishing to be bound by any theory, it is hypothesized that saturating hydrogel carrier substrate with glycerol reduced damage to frozen tissue samples, possibly by changing the surface tension or hydrophobicity. In embodiments, the hydrogel carrier substrate is stored in a glycerol solution prior to use.

In embodiments, the hydrogel carrier substrate further includes a support scaffold (e.g., the hydrogel carrier substrate forms part of a multi-layer substrate). In embodiments, the support scaffold is forms a rigid backing for the hydrogel carrier substrate. In embodiments, the support scaffold includes a thermoplastic elastomer. In embodiments, the support scaffold includes a polyester. In embodiments, the support scaffold includes polyethylene terephthalate. In embodiments, the support scaffold includes biaxially-oriented polyethylene terephthalate. In embodiments, the support scaffold is non-porous. In embodiments, the support scaffold is solid.

In embodiments, the support scaffold includes a thermo-responsive polymer, chemically-responsive polymer, light-responsive polymer, or pH-responsive polymer. In embodiments, the support scaffold includes a thermo-responsive polymer. In embodiments, the support scaffold includes a chemically-responsive polymer. In embodiments, the support scaffold includes a light-responsive polymer. In embodiments, the support scaffold includes a pH-responsive polymer.

In embodiments, the method further includes removing the support scaffold from the hydrogel carrier substrate. For example, in response to a change in pH, a support scaffold including a pH-responsive polymer as described herein degrades (e.g., the pH-responsive polymer degrades and/or debonds in responds to a change in pH), allowing for removal of at least part (e.g., 25% up to 99%) of the support scaffold from the hydrogel carrier substrate. In embodiments, removing the support scaffold from the hydrogel carrier substrate removes between about 25% to about 99% of the support scaffold. In embodiments, removing the support scaffold from the hydrogel carrier substrate removes about 25%, about 30%, about 35%, about 40%, about 45%, about 50%, about 55%, about 60%, about 65%, about 70%, about 75%, about 80%, about 85%, about 90%, about 95%, or about 99% of the support scaffold. In embodiments, removing the support scaffold from the hydrogel carrier substrate removes about 100% of the support scaffold.

Thermo-responsive polymers undergo reversible volume-phase transitions in response to changes in their surrounding temperatures (see, Lim H L et al. Biomater. Sci. 2014; 2:603, which is incorporated herein by reference in its entirety). In embodiments, the thermo-responsive polymer includes a homopolymer or copolymer of acrylamide, methacrylamide, N-ethyl acrylamide, N-n-propyl acrylamide, N-n-propyl methacrylamide, N-isopropyl acrylamide, N-isopropyl methacrylamide, N-cyclopropyl acrylamide, N-cyclopropyl methacrylamide, N-ethoxyethyl acrylamide, N-ethoxyethyl methacrylamide, N-tetrahydrofurfuryl acrylamide, N-tetrahydro furfuryl methacrylamide, N,N-dimethyl (meth)acrylamide, N,N-ethylmethyl acrylamide, N,N-diethyl acrylamide, 1-(1-oxo-2-propenyl)-pyrrolidine, 1-(1-oxo-2-propenyl)-piperidine, 4-(1-oxo-2-propenyl)-morpholine, 1-(1-oxo-2-methyl-2-propenyl)-pyrrolidine, 1-(1-oxo-2-methyl-2-propenyl)-piperidine, 4-(1-oxo-2-methyl-2-propenyl)-morpholine, methyl vinyl ether, or a combination thereof. Additional examples of thermo-responsive polymers may be found, for example, in U.S. Pat. Pubs. US2008/0160559 and US2014/0255333, which are incorporated herein by reference in their entirety.

In embodiments, the chemically-responsive polymer is responsive to chemical stimuli, for example, changes in ionic strength, pH, solvent composition, and molecular species in the external solution/environment. In embodiments, the chemically-responsive polymer is a pH-responsive polymer. In embodiments, the pH-responsive polymer includes methyl acrylate, ethyl acrylate, vinyl acrylate, propyl acrylate, butyl acrylate, hexyl acrylate, octyl acrylate, decyl acrylate, dodecyl acrylate, myristyl acrylate, lauryl acrylate, cetyl acrylate, stearyl acrylate, methyl methacrylate, ethyl methacrylate, propyl methacrylate, butyl methacrylate, isobutyl methacrylate, hexyl methacrylate, 2-ethylhexyl-(meth) acrylate, phenyl methacrylate, octyl methacrylate, decyl methacrylate, dodecyl methacrylate, myristyl methacrylate, lauryl methacrylate, cetyl methacrylate, stearyl methacrylate, or a combination thereof. Additional examples of pH-sensitive polymers may be found, for example in U.S. Pat. Pubs. US2005/0154165 and US2005/0137372, which are incorporated herein by reference in their entirety.

In embodiments, the light-responsive polymer includes different modes of actions that can be stimulated by light, such as photoisomerization, photocleavage, photodimerization, photorearrangement, and photoconjugation. For example, an azobenzene group undergoes a reversible cis-trans isomerization upon UV irradiation, while photochromic chromophores like coumarin, anthracene, and cinnamoyl groups undergo reversible dimerization upon UV irradiation. Specifically, polymers containing coumarin, anthracene, and cinnamoyl moieties undergo photodimerization reaction when irradiated with long-wavelength UV light ($\lambda$=300-365 nm), and photoreversible0 cleavage upon exposure to short-wavelength UV light ($\lambda$=254 nm) (see, Mohamed M A et al. Progress in Polymer Science. 2019; 98:101147, which is incorporated herein by reference in its entirety). In embodiments, the light-responsive polymer is capable of changing its physical and/or chemical properties such as elasticity, viscosity, shape and swelling degree, for example, upon light irradiation. In various embodiments, the light-responsive polymer includes light reactive groups such as photochromic moieties. In some embodiments, light-sensitive chromophores such as azobenzenes are added into a polymer network, thereby making embodiments of the polymer sensitive to UV light. In some embodiments, photocleavable groups are immobilized into a polymer network, thereby making embodiments of the polymer sensitive to UV light. In other embodiments, chlorophyllin chromophore is introduced into a polymer, e.g. a poly(N-isopropylacrylamide) (PNIPAM) so that it becomes sensitive to visible light. Additional examples of light-responsive polymers may be found in, for example, U.S. Pat. Pub. US2006/0257629 and PCT Pub. WO2016/123480, each of which is incorporated herein by reference in its entirety.

In embodiments, the pH-responsive polymer includes polymers each intramolecularly having an acidic functional group such as a carboxylic acid or a sulfonic acid group, or a basic functional group such as a primary amine, a secondary amine, or a tertiary amine. Specific examples are polymers as polymerized products of monomers such as acrylic acid, methacrylic acid, vinyl acetate, maleic acid, vinylsulfonic acid, styrenesulfonic acid, vinylpyridine, vinylaniline, vinylimidazole, aminoethyl acrylate, methylaminoethyl acrylate, dimethylaminoethyl acrylate, ethylaminoethyl acrylate, ethylmethylaminoethyl acrylate, diethylaminoethyl acrylate, aminoethyl methacrylate, methylaminoethyl methacrylate, dimethylaminoethyl methacrylate, ethylaminoethyl methacrylate, ethylmethylaminoethyl methacrylate, diethylaminoethyl methacrylate, aminopropyl acrylate, methylaminopropyl acrylate, dimethylaminopropyl acrylate, ethylaminopropyl acrylate, ethylmethylaminopropyl acrylate, diethylaminespropyl acrylate, aminopropyl methacrylate, methylaminopropyl methacrylate, dimethylaminopropyl methacrylate, ethylaminopropyl methacrylate, ethylmethylaminopropyl methacrylate, diethylaminopropyl methacrylate, dimethylaminoethylacrylamide, and dimethylaminopropylacrylamide. Additional examples of pH-responsive polymers may be found, for example, in U.S. Pat. Pub. US2007/0196492, which is incorporated herein by reference in its entirety.

In embodiments, the hydrogel is a crosslinked hydrogel (e.g., contacting the polymers of a hydrogel with a cross-linking agent that covalently bonds one or more of the polymer chains together). Crosslinking between polymer chains affects their physical properties, such as the elasticity, viscosity, solubility, glass transition temperature (Tg), strength, toughness, and melting point, of the hydrogel. The crosslinked polymers have a higher Tg due to limited rotational motion between the polymer chains. Cross-linking increases the molecular weight of the polymer chains as well as restricts the translational movement; hence the solubility of the polymer decreases.

In embodiments, the hydrogel carrier substrate does not include a resin adhesive. In embodiments, the hydrogel carrier substrate does not include a resin adhesive on the surface that contacts the tissue section. Non-limiting examples of resin adhesives include glue (e.g., Elmer's glue), polyurethanes, cyanoacrylate, and epoxies. In embodiments, the hydrogel carrier substrate does not include a cyanoacrylate (e.g., methoxyisopropylcyanoacrylate, octylcyanoacrylate, or methoxyisopropylcyanoacrylate). In embodiments, the hydrogel carrier substrate does not include protein and/or lipids. Foreign proteins and lipids may negatively impact the detection biomolecules within the sample. In preferred embodiments, the hydrogel carrier substrate does not deposit a detectable remnant following immobilization on the receiving substrate.

When considering a carrier substrate as a two-dimensional body, i.e., neglecting its thickness, the mechanical properties in the absence of anisotropies can be characterized by one or more elastic constants according to continuum elasticity theory. One such elastic constant is the Young's modulus (alternatively referred to as an elastic modulus). In principle, the Young's modulus of a carrier substrate can be measured by finding a relationship between a force applied to the carrier substrate and the resultant deformation. On a macroscale, the Young's modulus is usually obtained by measuring the stress-strain curves of a substrate specimen through the compression method or the tensile method and then finding the slope of the curve.

In embodiments, the carrier substrate includes a Young's modulus of about 5 kPa to about 30 kPa. In embodiments, the carrier substrate includes a Young's modulus of about 5 kPa to about 20 kPa. In embodiments, the carrier substrate includes a Young's modulus of about 5 kPa to about 15 kPa. In embodiments, the carrier substrate includes a Young's modulus of about 5 kPa, about 10 kPa, about 15 kPa, about 20 kPa, about 25 kPa, or about 30 kPa. In embodiments, the carrier substrate includes a Young's modulus of about 5 kPa. In embodiments, the carrier substrate includes a Young's modulus of about 10 kPa. In embodiments, the carrier substrate includes a Young's modulus of about 15 kPa. In embodiments, the carrier substrate includes a Young's modulus of about 20 kPa. In embodiments, the carrier substrate includes a Young's modulus of about 25 kPa. In embodiments, the carrier substrate includes a Young's modulus of about 30 kPa. In embodiments, the Young's modulus is quantified according to known techniques in the art (e.g., the indentation test). For example, the indentation test employs the use of an indenter which comes in to contact with and applies a perpendicular force on a small area of the carrier substrate. Alternatively, the Young's Modulus of thin elastic membranes of materials can be determined using Diaphragm tests, where the membrane is clamped at two ends and inflated in the form of a dome while the pressure of suction is controlled by a pressure controller.

In embodiments, the carrier substrate includes interfacial water, wherein the interfacial water is on the surface, such that the interfacial water is between the carrier substrate and the tissue section when forming a sample-carrier construct.

In embodiments, the carrier substrate includes about 80% to about 99% water. In embodiments, the carrier substrate includes about 80% to about 95% water. In embodiments, the carrier substrate includes about 80% to about 90% water. In embodiments, the carrier substrate includes about 80% to about 85% water. In embodiments, the carrier substrate includes about 80%, about 85%, about 90%, about 91%, about 92%, about 93%, about 94%, about 95%, about 96%, about 97%, about 98%, or about 99% water. In embodiments, the carrier substrate includes about 80% water. In embodiments, the carrier substrate includes about 85% water. In embodiments, the carrier substrate includes about 90% water. In embodiments, the carrier substrate includes about 91% water. In embodiments, the carrier substrate includes about 92% water. In embodiments, the carrier substrate includes about 93% water. In embodiments, the carrier substrate includes about 94% water. In embodiments, the carrier substrate includes about 95% water. In embodiments, the carrier substrate includes about 96% water. In embodiments, the carrier substrate includes about 97% water. In embodiments, the carrier substrate includes about 98% water. In embodiments, the carrier substrate includes about 99% water.

In embodiments, the hydrogel carrier substrate includes a Young's modulus of about 5 kPa to about 30 kPa. In embodiments, the hydrogel carrier substrate includes a Young's modulus of about 5 kPa to about 20 kPa. In embodiments, the hydrogel carrier substrate includes a Young's modulus of about 5 kPa to about 15 kPa. In embodiments, the hydrogel carrier substrate includes a Young's modulus of about 5 kPa, about 10 kPa, about 15 kPa, about 20 kPa, about 25 kPa, or about 30 kPa. In embodiments, the hydrogel carrier substrate includes a Young's modulus of about 5 kPa. In embodiments, the hydrogel carrier substrate includes a Young's modulus of about 10 kPa. In embodiments, the hydrogel carrier substrate includes a Young's modulus of about 15 kPa. In embodiments, the hydrogel carrier substrate includes a Young's modulus of about 20 kPa. In embodiments, the hydrogel carrier substrate includes a Young's modulus of about 25 kPa. In embodiments, the hydrogel carrier substrate includes a Young's modulus of about 30 kPa. In embodiments, the Young's modulus is quantified according to known techniques in the art (e.g., the indentation test). For example, the indentation test employs the use of an indenter which comes in to contact with and applies a perpendicular force on a small area of the carrier substrate. Alternatively, the Young's Modulus of thin elastic membranes of materials can be determined using Diaphragm tests, where the membrane is clamped at two ends and inflated in the form of a dome while the pressure of suction is controlled by a pressure controller.

In embodiments, the sample-carrier construct includes interfacial water, wherein the interfacial water is between the carrier substrate and the tissue section. In embodiments, the sample-carrier construct includes interfacial water, wherein the interfacial water is between the hydrogel carrier substrate and the tissue section.

In embodiments, the hydrogel carrier substrate includes interfacial water, wherein the interfacial water is on the surface, such that the interfacial water is between the carrier substrate and the tissue section when forming a sample-carrier construct.

In embodiments, the hydrogel carrier substrate includes about 80% to about 99% water. In embodiments, the hydrogel carrier substrate includes about 80% to about 95% water. In embodiments, the hydrogel carrier substrate includes about 80% to about 90% water. In embodiments, the hydrogel carrier substrate includes about 80% to about 85% water. In embodiments, the hydrogel carrier substrate includes about 80%, about 85%, about 90%, about 91%, about 92%, about 93%, about 94%, about 95%, about 96%, about 97%, about 98%, or about 99% water. In embodiments, the hydrogel carrier substrate includes about 80% water. In embodiments, the hydrogel carrier substrate includes about 85% water. In embodiments, the hydrogel carrier substrate includes about 90% water. In embodiments, the hydrogel carrier substrate includes about 91% water. In embodiments, the hydrogel carrier substrate includes about 92% water. In embodiments, the hydrogel carrier substrate includes about 93% water. In embodiments, the hydrogel carrier substrate includes about 94% water. In embodiments, the hydrogel carrier substrate includes about 95% water. In embodiments, the hydrogel carrier substrate includes about 96% water. In embodiments, the hydrogel carrier substrate includes about 97% water. In embodiments, the hydrogel carrier substrate includes about 98% water. In embodiments, the hydrogel carrier substrate includes about 99% water.

In embodiments, prior to contacting the tissue section of the sample-carrier construct with the receiving substrate, a portion of the sample-carrier construct is removed. Removal of a portion of the sample-carrier construct may be performed, for example, with a cutting device. The cutting device may include a sharp blade, and the cutting may be performed manually, or may be automated. In other embodiments, removal of a portion of the sample-carrier construct may be performed, for example, through the use of photon or acoustic energy (see, e.g., U.S. Pat. Pubs. US2004/0247777 and US2016/0025604, each of which is incorporated herein by reference in its entirety). In embodiments, a portion of the hydrogel carrier substrate is cut and removed from the total substrate.

In embodiments, the receiving substrate includes a functionalized glass surface or a functionalized plastic surface. Functionalization, as used herein, refers to a modification of the original surface. For example, functionalization may include topographical modifications (e.g., groves, posts, etching), chemical modifications (e.g., binding one or more compounds to the surface to alter the surface charge or bioconjugate reactive moieties on the surface), biological modifications (e.g., immobilizing one or more heparin proteins, heparin sulfate binding proteins, peptide sequences, growth factors, fibronectin, laminin, or collagen), or plasma treatment on reactive glass to generate bioconjugate reactive moieties on the surface.

In embodiments, the receiving substrate is functionalized with an RGD peptide or YIGSR peptide. RGD peptide is one of the most physiologically ubiquitous binding motifs commonly used, which is found in many natural adhesive proteins such as fibronectin, vitronectin, laminin and collagen type I.

In embodiments, the receiving substrate is functionalized with one or more synthetic chemical molecules. In embodiments, the receiving substrate includes dimethyl sulfoxide (DMSO), all-trans retinoic acid (RA), dynorphin B, ascorbic acid. In embodiments, the receiving substrate includes one or more bioconjugate reactive moieties (e.g., carboxyl or amine groups) on the surface of the receiving substrate. In embodiments, the receiving substrate includes a glass solid support that is functionalized by contacting the glass solid support in triethanolamine buffer containing glutaraldehyde and 1-hydroxbenzol (HOBt), followed by contacting with 1-ethyl-3-(3-dimethylaminopropyl) carbodiimide (EDC) and/or N-hydroxysuccinimide (NHS). In embodiments, the functionalized glass surface includes (3-aminopropyl)triethoxysilane (APTES), (3-Aminopropyl) trimethoxysilane (APTMS), γ-Aminopropylsilatrane (APS), N-(6-aminohexyl)aminomethyltriethoxysilane (AHAMTES), polyethylenimine (PEI), 5,6-epoxyhexyltriethoxysilane, or triethoxysilylbutyraldehyde, or a combination thereof. In embodiments, the functionalized glass surface includes (3-aminopropyl)triethoxysilane (APTES). In embodiments, the functionalized glass surface includes (3-Aminopropyl) trimethoxysilane (APTMS). In embodiments, the functionalized glass surface includes γ-Aminopropylsilatrane (APS). In embodiments, the functionalized glass surface includes N-(6-aminohexyl)aminomethyltriethoxysilane (AHAMTES). In embodiments, the functionalized glass surface includes polyethylenimine (PEI). In embodiments, the functionalized glass surface includes 5,6-epoxyhexyltriethoxysilane. In embodiments, the functionalized glass surface includes triethoxysilylbutyraldehyde. In embodiments, the receiving substrate is a functionalized glass surface or a functionalized plastic surface. In embodiments, the functionalized glass surface is functionalized with APTES, APTMS, APS, or AHAMTES.

In embodiments, the tissue is immobilized to the receiving substrate by covalently binding the tissue to one or more bioconjugate reactive moieties of the receiving substrate. In embodiments, the tissue is immobilized to the receiving substrate by non-covalently binding the tissue to the receiving substrate. For non-covalent binding, the tissue sections attach to the receiving substrate surface due to surface interactions, such as Van der Waal forces, electrostatic forces, hydrophobic interactions and hydrogen bonds. The physical adsorption efficiency can be enhanced by treating the material with air plasma to increase its hydrophilicity.

In embodiments, prior to contacting the tissue section with the receiving substrate, the sample-carrier construct is stored for one or more days. In embodiments, the sample-carrier construct is stored for 1 to 90 days. In embodiments, the sample-carrier construct is stored for greater than 90 days. In embodiments, the sample-carrier construct is stored for 1 to 30 days. In embodiments, the sample-carrier construct is stored for 1, 5, 7, 14, 21, 30, 45, 60, 75, 90, or more days. In embodiments, the sample-carrier construct is stored at less than about 25° C. In embodiments, the sample-carrier construct is stored at less than about 5° C. In embodiments, the sample-carrier construct is stored at about 4° C. In embodiments, the sample-carrier construct is stored in the dark (e.g., in the absence of light, such as visible light or UV light).

In embodiments, removing the carrier substrate includes thermally removing, chemically removing, or enzymatically removing. In embodiments, removing the carrier substrate includes thermally removing. In embodiments, removing the carrier substrate includes chemically removing. In embodiments, removing the carrier substrate includes enzymatically removing. Thermally removing, for example, may include heating the carrier substrate to facilitate its detachment from the tissue section. In embodiments, thermally removing the carrier substrate includes heating the carrier substrate to about 40° C. up to about 70° C. In embodiments, thermally removing the carrier substrate includes heating the carrier substrate to about 40° C. In embodiments, thermally removing the carrier substrate includes heating the carrier substrate to about 42° C. In embodiments, thermally removing the carrier substrate includes heating the carrier substrate to about 45° C. In embodiments, thermally removing the carrier substrate includes heating the carrier substrate to about 48° C. In embodiments, thermally removing the carrier substrate includes heating the carrier substrate to about 50° C. In embodiments, thermally removing the carrier substrate includes heating the carrier substrate to about 55° C. In embodiments, thermally removing the carrier substrate includes heating the carrier substrate to about 60° C. In embodiments, thermally removing the carrier substrate includes heating the carrier substrate to about 65° C. In embodiments, thermally removing the carrier substrate includes heating the carrier substrate to about 70° C. In embodiments, chemically removing the carrier substrate may include the use of, for example, alcohols, acids, oxygen, ozone, or peroxides in combination with physical action (e.g., heat, light, ultrasound, or mechanical energy). In embodiments, enzymatically removing the carrier substrate may include treatment with a, for example, proteinase, protease, hydrolase, carboxylesterase, agarose, or chitinase. In embodiments, removing the carrier substrate includes physically removing (e.g., mechanically pulling or lifting to remove the carrier substrate).

In embodiments, removing the hydrogel carrier substrate includes thermally removing, chemically removing, or enzymatically removing. In embodiments, removing the hydrogel carrier substrate includes thermally removing. In embodiments, removing the hydrogel carrier substrate includes chemically removing. In embodiments, removing the hydrogel carrier substrate includes enzymatically removing. Thermally removing, for example, may include heating the hydrogel carrier substrate to facilitate its detachment from the tissue section. In embodiments, thermally removing the hydrogel carrier substrate includes heating the hydrogel carrier substrate to about 40° C. up to about 70° C. In embodiments, thermally removing the hydrogel carrier substrate includes heating the hydrogel carrier substrate to about 40° C. In embodiments, thermally removing the hydrogel carrier substrate includes heating the hydrogel carrier substrate to about 42° C. In embodiments, thermally removing the hydrogel carrier substrate includes heating the hydrogel carrier substrate to about 45° C. In embodiments, thermally removing the hydrogel carrier substrate includes heating the hydrogel carrier substrate to about 48° C. In embodiments, thermally removing the hydrogel carrier substrate includes heating the hydrogel carrier substrate to about 50° C. In embodiments, thermally removing the hydrogel carrier substrate includes heating the hydrogel carrier substrate to about 55° C. In embodiments, thermally removing the hydrogel carrier substrate includes heating the hydrogel carrier substrate to about 60° C. In embodiments, thermally removing the hydrogel carrier substrate includes heating the hydrogel carrier substrate to about 65° C. In embodiments, thermally removing the hydrogel carrier substrate includes heating the hydrogel carrier substrate to about 70° C. In embodiments, chemically removing the hydrogel carrier substrate may include the use of, for example, alcohols, acids, oxygen, ozone, or peroxides in combination with physical action (e.g., heat, light, ultrasound, or mechanical energy). In embodiments, enzymatically removing the hydrogel carrier substrate may include treatment with a, for example, proteinase, protease, hydrolase, carboxylesterase, agarose, or chitinase. In embodiments, removing the hydrogel carrier substrate includes physically removing (e.g., mechanically pulling or lifting to remove the hydrogel carrier substrate).

In embodiments, the receiving substrate includes a functionalized glass surface or a functionalized plastic surface. In embodiments, the functionalized glass surface includes (3-aminopropyl)triethoxysilane (APTES), (3-Aminopropyl) trimethoxysilane (APTMS), γ-Aminopropylsilatrane (APS), N-(6-aminohexyl)aminomethyltriethoxysilane (AHAMTES), polyethylenimine (PEI), 5,6-epoxyhexyltriethoxysilane, or triethoxysilylbutyraldehyde, or a combination thereof.

In embodiments, prior to contacting the tissue section with the receiving substrate, the sample-carrier construct is stored for one or more days. In embodiments, the sample-carrier construct is stored for 1 to 90 days. In embodiments, the sample-carrier construct is stored for 1 to 30 days. In embodiments, the sample-carrier construct is stored at less than about 25° C. In embodiments, the sample-carrier construct is stored at less than about 5° C. In embodiments, the sample-carrier construct is stored at about 4° C.

Tissue sections include tissue or organ samples obtained from a subject, e.g., a mammal. In certain embodiments, the subject is diagnosed with a disease or disorder, such as a cancerous tumor, or considered at risk of having or developing the disease or disorder. Tissue sections may also be obtained from healthy donors, e.g., as normal control samples. In certain embodiments, both a disease tissue (e.g., a tumor tissue) sample and a normal sample are obtained from the same subject. In particular embodiments, the tissue section is obtained from a patient, e.g., a mammal such as a human. In other embodiments, a tissue section is obtained from an animal model of disease. Various animal models of disease are known and available in the art. Particular animal models of cancer include but are not limited to xenograft, syngeneic, and PDx models, e.g., in mice or rats. Animal models may also include human cells, cancerous or otherwise, introduced into animal models wherein tumor properties, progress, and treatment may be assessed. In vitro 3D tissue arrangements, organoids, and stem or iPS-cell-derived 3D compositions are also relevant models, and these may include human or other animal cells, for example.

In embodiments, the tissue section includes a tissue or a cell. Biological tissue samples suitable for use with the methods and systems described herein generally include any type of tissue samples collected from living or dead subjects, such as, for example, tumor tissue and autopsy samples. Tissue samples may be collected and processed using the methods and systems described herein and subjected to microscopic analysis immediately following processing, or may be preserved and subjected to microscopic analysis at a future time, e.g., after storage for an extended period of time. In some embodiments, the methods described herein may be used to preserve tissue samples in a stable, accessible and fully intact form for future analysis. For example, tissue samples, such as, e.g., human tumor tissue samples, may be processed as described herein and cleared to remove a plurality of cellular components, such as, e.g., lipids, and then stored for future analysis. In some embodiments, the methods and systems described herein may be used to analyze a fresh tissue section. In some embodiments, the methods and systems described herein may be used to analyze a previously-preserved (e.g., previously fixed) or stored tissue section (e.g., tissue sample). For example, in some embodiments a previously-preserved tissue sample that has not been subjected to a sample preparation process described herein may be processed and analyzed as described herein. In particular methods, a tissue sample is frozen prior to being processed as described herein.

In certain embodiments, tissue sections are tumor tissue samples. Tumor samples may contain only tumor cells, or they may contain both tumor cells and non-tumor cells. In particular embodiments, a tissue section includes only non-tumor cells. In particular embodiments, the tumor is a solid tumor. In particular embodiments, the tissue section is obtained from or includes an adrenal cortical cancer, anal cancer, aplastic anemia, bileduct cancer, bladder cancer, bone cancer, bone metastasis, brain tumor, brain cancer, breast cancer, childhood cancer, cancer of unknown primary origin, Castleman disease, cervical cancer, colon/rectal cancer, endometrial cancer, esophagus cancer, Ewing family of tumors, eye cancer, gallbladder cancer, gastrointestinal carcinoid tumors, gastrointestinal stromal tumors, gestational trophoblastic disease, head or neck cancer, Kaposi sarcoma, renal cell carcinoma, laryngeal and hypopharyngeal cancer, liver cancer, non-small cell lung cancer, small cell lung cancer, lung carcinoid tumor, lymphoma of the skin, malignant mesothelioma, myelodysplasia syndrome, nasal cavity or paranasal sinus cancer, nasopharyngeal cancer, neuroblastoma, oral cavity or oropharyngeal cancer, osteosarcoma, ovarian cancer, pancreatic cancer, penile cancer, pituitary tumors, prostate cancer, retinoblastoma, rhabdomyosarcoma, salivary gland cancer, sarcoma in adult soft tissue, basal or squamous cell skin cancer, melanoma, small intestine cancer, stomach cancer, testicular cancer, throat cancer, thymus cancer, thyroid cancer, uterine sarcoma, vaginal cancer, vulvar cancer, Waldenstrom macroglobulinemia, Wilms tumor and secondary cancers caused by cancer treatment, is a tissue section obtained from a subject diagnosed with or suspected of having any of these tumors or cancers.

The methods of the invention can be used to characterize a cancer or metastasis thereof, including without limitation, a carcinoma, a sarcoma, a lymphoma or leukemia, a germ cell tumor, a blastoma, or other cancers. Carcinomas include without limitation epithelial neoplasms, squamous cell neoplasms squamous cell carcinoma, basal cell neoplasms basal cell carcinoma, transitional cell papillomas and carcinomas, adenomas and adenocarcinomas (glands), adenoma, adenocarcinoma, linitis plastica insulinoma, glucagonoma, gastrinoma, vipoma, cholangiocarcinoma, hepatocellular carcinoma, adenoid cystic carcinoma, carcinoid tumor of appendix, prolactinoma, oncocytoma, hurthle cell adenoma, renal cell carcinoma, grawitz tumor, multiple endocrine adenomas, endometrioid adenoma, adnexal and skin appendage neoplasms, mucoepidermoid neoplasms, cystic, mucinous and serous neoplasms, cystadenoma, pseudomyxoma peritonei, ductal, lobular and medullary neoplasms, acinar cell neoplasms, complex epithelial neoplasms, warthin's tumor, thymoma, specialized gonadal neoplasms, sex cord stromal tumor, thecoma, granulosa cell tumor, arrhenoblastoma, sertoli leydig cell tumor, glomus tumors, paraganglioma, pheochromocytoma, glomus tumor, nevi and melanomas, melanocytic nevus, malignant melanoma, melanoma, nodular melanoma, dysplastic nevus, lentigo maligna melanoma, superficial spreading melanoma, and malignant acral lentiginous melanoma. Sarcoma includes without limitation Askin's tumor, botryodies, chondrosarcoma, Ewing's sarcoma, malignant hemangio endothelioma, malignant schwannoma, osteosarcoma, soft tissue sarcomas including: alveolar soft part sarcoma, angiosarcoma, cystosarcoma phyllodes, dermatofibrosarcoma, desmoid tumor, desmoplastic small round cell tumor, epithelioid sarcoma, extraskeletal chondrosarcoma, extraskeletal osteosarcoma, fibrosarcoma, hemangiopericytoma, hemangiosarcoma, kaposi's sarcoma, leiomyosarcoma, liposarcoma, lymphangiosarcoma, lymphosarcoma, malignant fibrous histiocytoma, neurofibrosarcoma, rhabdomyosarcoma, and synovialsarcoma. Lymphoma and leukemia include without limitation chronic lymphocytic leukemia/small lymphocytic lymphoma, B-cell prolymphocytic leukemia, lymphoplasmacytic lymphoma (such as waldenstrom macroglobulinemia), splenic marginal zone lymphoma, plasma cell myeloma, plasmacytoma, monoclonal immunoglobulin deposition diseases, heavy chain diseases, extranodal marginal zone B cell lymphoma, also called malt lymphoma, nodal marginal zone B cell lymphoma (nmzl), follicular lymphoma, mantle cell lymphoma, diffuse large B cell lymphoma, mediastinal (thymic) large B cell lymphoma, intravascular large B cell lymphoma, primary effusion lymphoma, burkitt lymphoma/leukemia, T cell prolymphocytic leukemia, T cell large granular lymphocytic leukemia, aggressive NK cell leukemia, adult T cell leukemia/lymphoma, extranodal NK/T cell lymphoma, nasal type, enteropathy-type T cell lymphoma, hepatosplenic T cell lymphoma, blastic NK cell lymphoma, mycosis fungoides/sezary syndrome, primary cutaneous CD30-positive T cell lymphoproliferative disorders, primary cutaneous anaplastic large cell lymphoma, lymphomatoid papulosis, angioimmunoblastic T cell lymphoma, peripheral T cell lymphoma, unspecified, anaplastic large cell lymphoma, classical hodgkin lymphomas (nodular sclerosis, mixed cellularity, lymphocyte-rich, lymphocyte depleted or not depleted), and nodular lymphocyte-predominant hodgkin lymphoma. Germ cell tumors include without limitation germinoma, dysgerminoma, seminoma, nongerminomatous germ cell tumor, embryonal carcinoma, endodermal sinus tumor, choriocarcinoma, teratoma, polyembryoma, and gonadoblastoma. Blastoma includes without limitation nephroblastoma, medulloblastoma, and retinoblastoma. Other cancers include without limitation labial carcinoma, larynx carcinoma, hypopharynx carcinoma, tongue carcinoma, salivary gland carcinoma, gastric carcinoma, adenocarcinoma, thyroid cancer (medullary and papillary thyroid carcinoma), renal carcinoma, kidney parenchyma carcinoma, cervix carcinoma, uterine corpus carcinoma, endometrium carcinoma, chorion carcinoma, testis carcinoma, urinary carcinoma, melanoma, brain tumors such as glioblastoma, astrocytoma, meningioma, medulloblastoma and peripheral neuroectodermal tumors, gall bladder carcinoma, bronchial carcinoma, multiple myeloma, basalioma, teratoma, retinoblastoma, choroidea melanoma, seminoma, rhabdomyosarcoma, craniopharyngeoma, osteosarcoma, chondrosarcoma, myosarcoma, liposarcoma, fibrosarcoma, Ewing sarcoma, and plasmocytoma.

In a further embodiment, the cancer under analysis may be a lung cancer including non-small cell lung cancer and small cell lung cancer (including small cell carcinoma (oat cell cancer), mixed small cell/large cell carcinoma, and combined small cell carcinoma), colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemia, lymphoma, myeloma, or a solid tumor.

Tissue sections may be obtained from a subject by any means known and available in the art. In particular embodiments, a tissue section, e.g., a tumor tissue sample, is obtained from a subject by fine needle aspiration, core needle biopsy, stereotactic core needle biopsy, vacuum-assisted core biopsy, or surgical biopsy. In particular embodiments, the surgical biopsy is an incisional biopsy, which removes only part of the suspicious area. In other embodiments, the surgical biopsy is an excisional biopsy, which removes the entire diseased tissue (e.g., tumor) or abnormal area. In particular embodiments, an excisional tumor tissue sample is obtained from a tumor that has been excised with the intent to "cure" a patient in the case of early stage disease, wherein in other embodiments, the excisional tumor tissue sample is obtained from an excised bulk of primary tumor in later stage disease. Tumor tissue samples may include primary tumor tissue, metastastic tumor tissue and/or secondary tumor tissue. Tumor tissue samples may be cell cultures, e.g., cultures of tumor-derived cell lines. In certain embodiments, a tissue section is a cell line, e.g., a cell pellet of a cultured cell line, such as a tumor cell line. In particular embodiments, the cell line or cell pellet is frozen or was previously frozen. Such cell lines and pellets are useful, e.g., as positive or negative controls for imaging with various reagents. Tumor tissue samples may also be xenograft tumors, e.g., tumors obtained from animals administered with tumor cells, e.g., a human tumor cell line. In certain embodiments, a first tumor tissue sample from a subject is a primary tumor tissue sample obtained during an initial surgery intended to remove the entire tumor, and a second tumor tissue sample is obtained from the same subject is a metastatic tumor tissue sample or a secondary tumor tissue sample obtained during a later surgery.

Tissue sections, e.g., tumor tissue samples, may be obtained surgically or using a laparoscope. A tissue section may be a tissue sample obtained from any part of the body to examine it for disease or injury, e.g., presence of cancer tissue or cells, or the extent or characteristics thereof. In particular embodiments, the tissue section includes abdominal tissue, bone, bone marrow, breast tissue, endometrial tissue, kidney tissue, liver tissue, lung or chest tissue, lymph node, nerve tissue, skin, testicular tissue, head or neck tissue, or thyroid tissue. In certain embodiments, the tissue is obtained from brain, breast, skin, bone, joint, skeletal muscle, smooth muscle, red bone marrow, thymus, lymphatic vessel, thoracic duct, spleen, lymph node, nasal cavity, pharynx, larynx, trachea, bronchus, lung, oral cavity, esophagus, liver, stomach, small intestine, large intestine, rectum, anus, spinal cord, nerve, pineal gland, pituitary gland, thyroid gland, thymus, adrenal gland, pancreas, ovary, testis, heart, blood vessel, kidney, uterus, urinary bladder, urethra, prostate gland, penis, prostate, testis, scrotum, ductus deferens, mammary glands, ovary, uterus, vagina, or uterine tube.

In particular embodiments, a tissue section has a size greater than sections typically examined by traditional pathology thin section or immunohistochemical analysis, which are typically in the range of 4-10 microns thick. In certain embodiments, a tissue section is greater than 20 microns, greater than 50 microns, greater than 100 microns, greater than 200 microns, greater than 500 microns, greater than 1 mm, greater than 2 mm, greater than 5 mm, greater than 10 mm or greater than 20 mm in thickness and/or length. In particular embodiments, the tissue section has a length and/or a thickness between 20 microns and 20 mm, between 20 microns and 10 mm, or between 50 microns and 1 mm. In certain embodiments, a tissue section is a cubic sample with each side greater than 10 microns, greater than 20 microns, greater than 50 microns, greater than 100 microns, greater than 200 microns, greater than 500 microns, greater than 1 mm, greater than 2 mm, greater than 5 mm, greater than 10 mm, or greater than 2 mm in thickness and/or length. In some embodiments, a tissue section is thinner, e.g., from about 4-10 or 4-20 microns in thickness.

RNA, including mRNA, is highly susceptible to degradation upon exposure to one or more RNAses. RNAses are present in a wide range of locations, including water, many reagents, laboratory equipment and surfaces, skin, and mucous membranes. Working with RNA often requires preparing an RNAse-free environment and materials, as well as taking precautions to avoid introducing RNAses into an RNAse-free environment. These precautions include, but are not limited to, cleaning surfaces with an RNAse cleaning product (e.g., RNASEZAP™ and other commercially available products or 0.5% sodium dodecyl sulfate [SDS] followed by 3% $H_2O_2$); using a designated workspace, materials, and equipment (e.g., pipets, pipet tips); using barrier tips; baking designated glassware (e.g., 300° C. for 2 hours) prior to use; treating enzymes, reagents, and other solutions (e.g., with diethyl pyrocarbonate [DEPC] or dimethyl pyrocarbonate [DMPC]) or using commercially available, certified RNAse-free water or solutions, or ultrafiltered water (e.g., for Tris-based solutions); including an RNAse inhibitor while avoiding temperatures or denaturing conditions that could deactivate the inhibitor); and wearing clean gloves (while avoiding contaminated surfaces) and a clean lab coat.

In embodiments, the tissue section forms part of a tissue in situ. In embodiments, the tissue section includes one or more prokaryotic cells. In embodiments, the tissue section includes one or more eukaryotic cells. In embodiments, the tissue section includes a bacterial cell (e.g., a bacterial cell or bacterial spore), a fungal cell (e.g., a fungal spore), a plant cell, or a mammalian cell. In embodiments, the tissue section includes a stem cell. In embodiments, the stem cell is an embryonic stem cell, a tissue-specific stem cell, a mesenchymal stem cell, or an induced pluripotent stem cell. In embodiments, the tissue section includes an endothelial cell, muscle cell, myocardial, smooth muscle cell, skeletal muscle cell, mesenchymal cell, epithelial cell; hematopoietic cell, such as lymphocytes, including T cell, e.g., (Th1 T cell, Th2 T cell, Th0 T cell, cytotoxic T cell); B cell, pre-B cell; monocytes; dendritic cell; neutrophils; or a macrophage. In embodiments, the tissue section includes a stem cell, an immune cell, a cancer cell (e.g., a circulating tumor cell or cancer stem cell), a viral-host cell, or a cell that selectively binds to a desired target. In embodiments, the cell includes a T cell receptor gene sequence, a B cell receptor gene sequence, or an immunoglobulin gene sequence. In embodiments, the cell includes a Toll-like receptor (TLR) gene sequence. In embodiments, the cell includes a gene sequence corresponding to an immunoglobulin light chain polypeptide and a gene sequence corresponding to an immunoglobulin heavy chain polypeptide. In embodiments, the tissue section includes a genetically modified cell. In embodiments, the tissue section includes a circulating tumor cell or cancer stem cell.

In embodiments, the tissue section includes a prokaryotic cell. In embodiments, the tissue section includes a bacterial cell. In embodiments, the bacterial cell is a *Bacteroides, Clostridium, Faecalibacterium, Eubacterium*, Ruminococcus, Peptococcus, *Peptostreptococcus*, or *Bifidobacterium* cell. In embodiments, the bacterial cell is a *Bacteroides fragilis, Bacteroides melaninogenicus, Bacteroides oralis, Enterococcus faecalis, Escherichia coli, Enterobacter* sp., *Klebsiella* sp., *Bifidobacterium bifidum, Staphylococcus aureus, Lactobacillus, Clostridium perfringens, Proteus mirabilis, Clostridium tetani, Clostridium septicum, Pseudomonas aeruginosa, Salmonella enterica, Faecalibacterium prausnitzii, Peptostreptococcus* sp., or *Peptococcus* sp. cell. In embodiments, tissue section includes a fungal cell. In embodiments, the fungal cell is a *Candida, Saccharomyces, Aspergillus, Penicillium, Rhodotorula, Trametes, Pleospora, Sclerotinia, Bullera*, or a *Galactomyces* cell.

In embodiments, the tissue section includes a viral-host cell. A "viral-host cell" is used in accordance with its ordinary meaning in virology and refers to a cell that is infected with a viral genome (e.g., viral DNA or viral RNA). The cell, prior to infection with a viral genome, can be any cell that is susceptible to viral entry. In embodiments, the viral-host cell is a lytic viral-host cell. In embodiments, the viral-host cell is capable of producing viral protein. In embodiments, the viral-host cell is a lysogenic viral-host cell. In embodiments, the cell is a viral-host cell including a viral nucleic acid sequence, wherein the viral nucleic acid sequence is from a *Hepadnaviridae, Adenoviridae, Herpesviridae, Poxviridae, Parvoviridae, Reoviridae, Coronaviridae, Retroviridae* virus.

In embodiments, the tissue section includes an adherent cell (e.g., epithelial cell, endothelial cell, or neural cell). Adherent cells are usually derived from tissues of organs and attach to a substrate (e.g., epithelial cells adhere to an extracellular matrix coated substrate via transmembrane adhesion protein complexes). Adherent cells typically require a substrate, e.g., tissue culture plastic, which may be coated with extracellular matrix (e.g., collagen and laminin) components to increase adhesion properties and provide other signals needed for growth and differentiation. In embodiments, the tissue section includes a neuronal cell, an endothelial cell, epithelial cell, germ cell, plasma cell, a muscle cell, peripheral blood mononuclear cell (PBMC), a myocardial cell, or a retina cell. In embodiments, the tissue section includes a suspension cell (e.g., a cell free-floating in the culture medium, such a lymphoblast or hepatocyte). In embodiments, the tissue section includes a glial cell (e.g., astrocyte, radial glia), pericyte, or stem cell (e.g., a neural stem cell). In embodiments, the tissue section includes a neuronal cell. In embodiments, the tissue section includes an endothelial cell. In embodiments, the tissue section includes an epithelial cell. In embodiments, the tissue section includes a germ cell. In embodiments, the tissue section includes a plasma cell. In embodiments, the tissue section includes a muscle cell. In embodiments, the tissue section includes a peripheral blood mononuclear cell (PBMC). In embodiments, the tissue section includes a myocardial cell. In embodiments, the tissue section includes a retina cell. In embodiments, the tissue section includes a lymphoblast. In embodiments, the tissue section includes a hepatocyte. In embodiments, the tissue section includes a glial cell. In embodiments, the tissue section includes an astrocyte. In embodiments, the tissue section includes a radial glia. In embodiments, the tissue section includes a pericyte. In embodiments, the tissue section includes a stem cell. In embodiments, the tissue section includes a neural stem cell.

In embodiments, the tissue section includes a cell bound to a known antigen. In embodiments, the cell is a cell that selectively binds to a desired target, wherein the target is an antibody, or antigen binding fragment, an aptamer, affimer, non-immunoglobulin scaffold, small molecule, or genetic modifying agent. In embodiments, the cell is a leukocyte (i.e., a white-blood cell). In embodiments, leukocyte is a granulocyte (neutrophil, eosinophil, or basophil), monocyte, or lymphocyte (T cells and B cells). In embodiments, the cell is a lymphocyte. In embodiments, the cell is a T cell, an NK cell, or a B cell.

In embodiments, the tissue section includes an immune cell. In embodiments, the immune cell is a granulocyte, a mast cell, a monocyte, a neutrophil, a dendritic cell, or a natural killer (NK) cell. In embodiments, the immune cell is an adaptive cell, such as a T cell, NK cell, or a B cell. In embodiments, the cell includes a T cell receptor gene sequence, a B cell receptor gene sequence, or an immunoglobulin gene sequence. In embodiments, the immune cell is a granulocyte. In embodiments, the immune cell is a mast cell. In embodiments, the immune cell is a monocyte. In embodiments, the immune cell is a neutrophil. In embodiments, the immune cell is a dendritic cell. In embodiments, the immune cell is a natural killer (NK) cell. In embodiments, the immune cell is a T cell. In embodiments, the immune cell is a B cell. In embodiments, the cell includes a T cell receptor gene sequence. In embodiments, the cell includes a B cell receptor gene sequence. In embodiments, the cell includes an immunoglobulin gene sequence. In embodiments, the plurality of target nucleic acids includes non-contiguous regions of a nucleic acid molecule. In embodiments, the non-contiguous regions include regions of a VDJ recombination of a B cell or T cell.

In embodiments, the tissue section includes a cancer cell. In embodiments, the cancer is lung cancer, colorectal cancer, skin cancer, colon cancer, pancreatic cancer, breast cancer, cervical cancer, lymphoma, leukemia, or a cancer associated with aberrant K-Ras, aberrant APC, aberrant Smad4, aberrant p53, or aberrant TGFβ. In embodiments, the cancer cell includes a ERBB2, KRAS, TP53, PIK3CA, or FGFR2 gene. In embodiments, the cancer cell includes a cancer-associated gene (e.g., an oncogene associated with kinases and genes involved in DNA repair) or a cancer-associated biomarker. A "biomarker" is a substance that is associated with a particular characteristic, such as a disease or condition. A change in the levels of a biomarker may correlate with the risk or progression of a disease or with the susceptibility of the disease to a given treatment. In embodiments, the cancer is Acute Myeloid Leukemia, Adrenocortical Carcinoma, Bladder Urothelial Carcinoma, Breast Ductal Carcinoma, Breast Lobular Carcinoma, Cervical Carcinoma, Cholangiocarcinoma, Colorectal Adenocarcinoma, Esophageal Carcinoma, Gastric Adenocarcinoma, Glioblastoma Multiforme, Head and Neck Squamous Cell Carcinoma, Hepatocellular Carcinoma, Kidney Chromophobe Carcinoma, Kidney Clear Cell Carcinoma, Kidney Papillary Cell Carcinoma, Lower Grade Glioma, Lung Adenocarcinoma, Lung Squamous Cell Carcinoma, Mesothelioma, Ovarian Serous Adenocarcinoma, Pancreatic Ductal Adenocarcinoma, Paraganglioma & Pheochromocytoma, Prostate Adenocarcinoma, Sarcoma, Skin Cutaneous Melanoma, Testicular Germ Cell Cancer, Thymoma, Thyroid Papillary Carcinoma, Uterine Carcinosarcoma, Uterine Corpus Endometrioid Carcinoma, or Uveal Melanoma. In embodiments, the cancer-associated gene is a nucleic acid sequence identified within The Cancer Genome Atlas Program, accessible at www.cancer.gov/tcga.

In embodiments, the cancer-associated biomarker is MDC, NME-2, KGF, P1GF, Flt-3L, HGF, MCP1, SAT-1, MIP-1-b, GCLM, OPG, TNF RII, VEGF-D, ITAC, MMP-10, GPI, PPP2R4, AKRIB1, Amy1A, MIP-1b, P-Cadherin, or EPO. In embodiments, the cancer-associated gene is a AKT1, AKT2, AKT3, ALK, AR, ARAF, ARID1A, ATM, ATR, ATRX, AXL, BAP1, BRAF, BRCA1, BRCA2, BTK, CBL, CCND1, CCND2, CCND3, CCNE1, CDK12, CDK2, CDK4, CDK6, CDKN1B, CDKN2A, CDKN2B, CHEK1, CHEK2, CREBBP, CSF1R, CTNNB1, DDR2, EGFR, ERBB2, ERBB3, ERBB4, ERCC2, ERG, ESR1, ETV1, ETV4, ETV5, EZH2, FANCA, FANCD2, FANC1, FBXW7, FGF19, FGF3, FGFR1, FGFR2, FGFR3, FGFR4, FGR, FLT3, FOXL2, GATA2, GNA11, GNAQ, GNAS, H3F3A, HIST1H3B, HNF1A, HRAS, IDH1, IDH2, IGF1R, JAK1, JAK2, JAK3, KDR, KIT, KNSTRN, KRAS, MAGOH, MAP2K1, MAP2K2, MAP2K4, MAPK1, MAX, MDM2, MDM4, MED12, MET, MLH1, MRE11A, MSH2, MSH6, MTOR, MYB, MYBL1, MYC, MYCL, MYCN, MYD88, NBN, NF1, NF2, NFE2L2, NOTCH1, NOTCH2, NOTCH3, NOTCH4, NRAS, NRG1, NTRK1, NTRK2, NTRK3, NUTM1, PALB2, PDGFRA, PDGFRB, PIK3CA, PIK3CB, PIK3R1, PMS2, POLE, PPARG, PPP2RIA, PRKACA, PRKACB, PTCH1, PTEN, PTPN11, RAC1, RAD50, RAD51, RAD51B, RAD51C, RAD51D, RAF1, RB1, RELA, RET, RHEB, RHOA, RICTOR, RNF43, ROS1, RSPO2, RSPO3, SETD2, SF3B1, SLX4, SMAD4, SMARCA4, SMARCB1, SMO, SPOP, SRC, STAT3, STK11, TERT, TOP1, TP53, TSC1, TSC2, U2AF1, or XPO1 gene. In embodiments, the cancer-associated gene is a ABL1, AKT1, ALK, APC, ATM, BRAF, CDH1, CDKN2A, CSF1R, CTNNB1, EGFR, ERBB2, ERBB4, EZH2, FBXW7, FGFR1, FGFR2, FGFR3, FLT3, GNA11, GNAQ, GNAS, HNFIA, HRAS, IDH1, IDH2, JAK2, JAK3, KDR, KIT, KRAS, MET, MLH1, MPL, NOTCH1, NPM1, NRAS, PDGFRA, PIK3CA, PTEN, PTPN11, RB1, RET, SMAD4, SMARCB1, SMO, SRC, STK11, TP53, or VHL gene. In embodiments, the tissue section includes a cell (e.g., a T cell) within a tumor. In embodiments, the tissue section includes a non-allogenic cell (i.e., native cell to the subject) within a tumor. In embodiments, the tissue section includes a tumor infiltrating lymphocyte (TIL). In embodiments, the tissue section includes an allogenic cell. In embodiments, the tissue section includes a circulating tumor cell.

In embodiments, the tissue section is obtained from a subject (e.g., human or animal tissue). Once obtained, the tissue section is placed in an artificial environment in plastic or glass containers supported with specialized medium containing essential nutrients and growth factors to support proliferation. In embodiments, the tissue section is permeabilized and immobilized to a solid support surface. In embodiments, the tissue section is permeabilized and immobilized to an array (i.e., to discrete locations arranged in an array). In embodiments, the tissue section is immobilized to a solid support surface. In embodiments, the surface includes a patterned surface (e.g., suitable for immobilization of a plurality of cells in an ordered pattern. The discrete regions of the ordered pattern may have defined locations in a regular array, which may correspond to a rectilinear pattern, circular pattern, hexagonal pattern, or the like. These discrete regions are separated by interstitial regions. As used herein, the term "interstitial region" refers to an area in a substrate or on a surface that separates other areas of the substrate or surface. In embodiments, a plurality of cells are immobilized on a patterned surface that have a mean or median separation from one another of about 10-20 μm. In embodiments, a plurality of cells are immobilized on a patterned surface that have a mean or median separation from one another of about 10-20; 10-50; or 100 μm. In embodiments, a plurality of cells are arrayed on a substrate. In embodiments, a plurality of cells are immobilized in a 96-well microplate having a mean or median well-to-well spacing of about 8 mm to about 12 mm (e.g., about 9 mm). In embodiments, a plurality of cells are immobilized in a 384-well microplate having a mean or median well-to-well spacing of about 3 mm to about 6 mm (e.g., about 4.5 mm).

In embodiments, the tissue section is attached to the receiving substrate via a bioconjugate reactive linker. In embodiments, the tissue section is attached to the substrate via a specific binding reagent. In embodiments, the specific binding reagent includes an antibody, single-chain Fv fragment (scFv), antibody fragment-antigen binding (Fab), or an aptamer. In embodiments, the specific binding reagent includes an antibody, or antigen binding fragment, an aptamer, affimer, or non-immunoglobulin scaffold. In embodiments, the specific binding reagent is a peptide, a cell penetrating peptide, an aptamer, a DNA aptamer, an RNA aptamer, an antibody, an antibody fragment, a light chain antibody fragment, a single-chain variable fragment (scFv), a lipid, a lipid derivative, a phospholipid, a fatty acid, a triglyceride, a glycerolipid, a glycerophospholipid, a sphingolipid, a saccharolipid, a polyketide, a polylysine, polyethyleneimine, diethylaminoethyl (DEAE)-dextran, cholesterol, or a sterol moiety. Substrates may be prepared for selective capture of particular cells of the tissue section. For example, a substrate containing a plurality of bioconjugate reactive moieties or a plurality of specific binding reagents, optionally in an ordered pattern, contacts a plurality of cells of the tissue section. Only cells of the tissue section containing complementary bioconjugate reactive moieties or complementary specific binding reagents are capable of reacting, and thus adhering, to the substrate.

In embodiments, the receiving substrate includes a coating for enhanced biomolecule adhesion. Coatings for enhanced biomolecule adhesion are known, for example extracellular matrix proteins such as collagen type I, fibronectin, and laminin mediate specific binding of the cell to the protein. Poly-D-Lysine (PDL), a synthetically produced biomolecule, belongs to the non-specific adhesion-promoting polypeptides. PDL is typically used to promote cell adhesion, especially during washing steps, as well as to enhance cell vitality and proliferation during serum-reduced or serum-free cultivation.

In embodiments, the methods are performed in situ in tissue sections that have been prepared according to methodologies known in the art. Methods for permeabilization and fixation of cells and tissue samples are known in the art, as exemplified by Cremer et al., The Nucleus: Volume 1: Nuclei and Subnuclear Components, R. Hancock (cd.) 2008; and Larsson et al., Nat. Methods (2010) 7:395-397, the content of each of which is incorporated herein by reference in its entirety. In embodiments, the tissue section is cleared (e.g., digested) of proteins, lipids, or proteins and lipids.

In embodiments, the tissue section is exposed to paraformaldehyde (i.e., by contacting the cell with paraformaldehyde). Any suitable permeabilization and fixation technologies can be used for making the cell available for the detection methods provided herein. In embodiments the method includes affixing single cells or tissues to a transparent substrate. Exemplary tissue include those from skin tissue, muscle tissue, bone tissue, organ tissue and the like. In embodiments, the method includes immobilizing the tissue section in situ to a substrate and permeabilized for delivering probes, enzymes, nucleotides and other components required in the reactions. In embodiments, the tissue section includes many cells from a tissue section in which the original spatial relationships of the cells are retained. In embodiments, the tissue section in situ is within a Formalin-Fixed Paraffin-Embedded (FFPE) sample. In embodiments, the tissue section is subjected to paraffin removal methods, such as methods involving incubation with a hydrocarbon solvent, such as xylene or hexane, followed by two or more washes with decreasing concentrations of an alcohol, such as ethanol. The tissue section may be rehydrated in a buffer, such as PBS, TBS or MOPs. In embodiments, the FFPE sample is incubated with xylene and washed using ethanol to remove the embedding wax, followed by treatment with Proteinase K to permeabilized the tissue. In embodiments, the tissue section is fixed with a chemical fixing agent. In embodiments, the chemical fixing agent is formaldehyde or glutaraldehyde. In embodiments, the chemical fixing agent is glyoxal or dioxolane. In embodiments, the chemical fixing agent includes one or more of ethanol, methanol, 2-propanol, acetone, and glyoxal. In embodiments, the chemical fixing agent includes formalin, Greenfix®, Greenfix® Plus, UPM, CyMol®, HOPE®, CytoSkelFix™, F-Solv®, FincFIX®, RCL2/KINFix, UMFIX, Glyo-Fixx®, Histochoice®, or PAXgene®. In embodiments, the tissue section is fixed within a synthetic three-dimensional matrix (e.g., polymeric material). In embodiments, the synthetic matrix includes polymeric-crosslinking material. In embodiments, the material includes polyacrylamide, poly-ethylene glycol (PEG), poly(acrylate-co-acrylic acid) (PAA), or Poly(N-isopropylacrylamide) (NIPAM).

In embodiments, the fixed tissue may be frozen tissue. The frozen biological tissue can be fixed using a fixing agent, which is suitably an organic fixing agent. In some embodiments, the fixing agent can be chilled and can be at a temperature of about 0° C. to about 100° C., suitably about zero to about 50° C., or about 1° C. to about 50° C. The fixing agent can be chilled by placing it over a bed of ice to maintain its temperature as close to 0° C. as possible. The frozen biological tissue can be treated with the fixing agent using any suitable technique, suitably by immersing it in the fixing agent for a period of time. Depending on the type and size of the biological tissue sample, the treatment time can range from about 5 minutes to about 60 minutes, suitably about 10 minutes to about 30 minutes, or about 15 minutes to about 25 minutes, or about 20 minutes. In some embodiments, treatment time may be overnight. During fixing, the snap-frozen tissue will thaw but will suitably remain at a low temperature due to the low temperature environment of the fixing agent.

In some embodiments, the type/identity of a fixation agent, the amount/concentration of a fixation agent, the temperature at which it is used, the duration for which it is used, and the like, may be empirically determined or titrated. These parameters, and others, may need to be varied to obtain optimal results for different tissues, for different organisms, or for different days on which an experiment is performed. Insufficient fixation (e.g., too little fixing agent, too low temperature, too short duration) may not, for example, stabilize/preserve the cells/organelles/analytes of tissues. Excess fixation (e.g., too much fixing agent, too high temperature, too long duration) may result in the single biological samples (e.g., cells/nuclei) obtained from the methods not yielding good results in single biological sample (e.g., single-cell or single nucleus) workflows or assays in which the biological samples (e.g., cells or nuclei) are used. Generally, the quality of data obtained in these workflows/assays may be a good measure of the extent of the fixation process.

In some embodiments, the fixative can be diluted in a buffer, e.g., saline, phosphate buffer (PB), phosphate buffered saline (PBS), citric acid buffer, potassium phosphate buffer, etc., usually at a concentration of about 1-10%, e.g. 1%, 2%, 3%, 4%, 5%, 6%, 7%, 8%, or 10%, for example, 4% paraformaldehyde/0.1 M phosphate buffer; 2% paraformaldehyde/0.2% picric acid/0.1 M phosphate buffer; 4% paraformaldehyde/0.2% periodate/1.2% lysine in 0.1 M phosphate buffer; 4% paraformaldehyde/0.05% glutaraldehyde in phosphate buffer; etc. The type of fixative used and the duration of exposure to the fixative can depend on the sensitivity of the molecules of interest in the tissue section to denaturation by the fixative, and can be readily determined using conventional histochemical or immunohistochemical techniques, for example as described in Buchwalow and Bocker. Immunohistochemistry: Basics and Methods. Springer-Verlag Berlin Heidelberg 2010.

During the fixing, the biological tissue sample can be periodically cut into successively smaller segments while it is submerged in the fixation solution, to facilitate perfusion and fixation of the biological tissue sample by the organic fixing agent. For example, the tissue sample may have an initial length, width and/or diameter of about 0.25 cm to about 1.5 cm or may be initially cut into segments having such suitable dimensions. After a first periodic interval, the tissue sample or segments can be cut into smaller segments, and the smaller segments can remain immersed in the fixing agent. This process can be repeated after a second periodic interval, after a third periodic interval, after a fourth periodic interval, and so on. The periodic intervals can range from about 1 to about 10 minutes, or about 2 to about 8 minutes, or about 4 to about 6 minutes. The sum of the periodic intervals can equal the entire fixing time and can range from about 5 to about 60 minutes, or about 10 to about 30 minutes, or about 15 to about 25 minutes, for example. The resulting fixed tissue segments can have a length, width and/or diameter in a range of less than 1 mm to about 10 mm, by way of example. In some embodiments, the tissue is not cut into smaller segments during fixation. In some embodiments, this may be performed prior to fixation. In some embodiments, this may be performed after fixation.

Once the biological tissue segments have been sufficiently fixed, the fixation process may be stopped and/or the tissue may be removed from the fixation and the tissue may be washed. Generally, fixation is stopped to cease additional activity of the fixative on the tissue. Fixation may also be stopped so that any subsequent biochemical reactions performed on the tissue (e.g., enzymatic cell dissociation) can function. In some embodiments, the tissue segments may be treated or contacted with a quenching medium to quench the fixation. The term "quenching" means to stop the fixation reaction, i.e., the chemical interactions that cause the fixation. Quenching the fixation can be accomplished by immersing the fixed tissue segments in a suitable quenching medium. The fixation quenching medium can be chilled and can have a temperature of about 0° C. to about 100° C., or about 1° C. to about 50° C. In embodiments, the quenching medium is a phosphate buffer solution (PBS). One suitable phosphate buffer solution is 1×PBS, available from Sigma Aldrich Corp. 1×PBS has a pH of about 7.4 and the following composition in water: NaCl—137 mM, KCl—2.7 mM, $Na_2HPO_4$—10 mM, $KH_2PO_4$—1.8 mM. In one embodiment, the phosphate buffer solution can be combined with fetal bovine serum (FBS) to aid in quenching the fixation reaction. FBS is the liquid fraction of clotted blood from fetal calves, depleted of cells, fibrin and clotting factors, but containing many nutritional and macromolecular factors essential for cell growth. Bovine serum albumin (BSA) is the major component of FBS. The fetal bovine serum can be combined with the phosphate buffer solution at a concentration of about 1% to about 25% by weight FBS and about 75% to about 99% by weight PBS, suitably about 5% to about 15% by weight FBS and about 85% to about 95% by weight PBS, or about 10% by weight FBS and about 90% by weight PBS. In another embodiment, a solution of concentrated ethanol in water can be used instead of the PBS in the quenching medium. The ethanol solution can contain about 50% to about 90% by weight ethanol, or about 55% to about 85% by weight ethanol, or about 60% to about 80% by weight ethanol, or about 70% by weight ethanol. In some embodiments, fixation may be quenched using a quenching solution that does not contain serum. In some examples, Tris-based buffers may be used. In some examples, PBS+50 mM Tris pH 8.0+0.02% BSA (RNAse free)+0.1 U/ul of RNAse Inhibitor may be used. In some examples, the tissue may be removed from the fixative and washed using a quenching solution or biological buffer.

In embodiments, the tissue section is lysed to release nucleic acid or other materials from the cells. For example, the tissue section may be lysed using reagents (e.g., a surfactant such as Triton-X or SDS, an enzyme such as lysozyme, lysostaphin, zymolase, cellulase, mutanolysin, glycanases, proteases, mannase, proteinase K, etc.) or a physical lysing mechanism a physical condition (e.g., ultrasound, ultraviolet light, mechanical agitation, etc.). The cells may release, for instance, DNA, RNA, mRNA, proteins, or enzymes. The cells may arise from any suitable source. For instance, the cells may be any cells for which nucleic acid from the cells is desired to be studied or sequenced, etc., and may include one, or more than one, cell type. The cells may be for example, from a specific population of cells, such as from a certain organ or tissue (e.g., cardiac cells, immune cells, muscle cells, cancer cells, etc.), cells from a specific individual or species (e.g., human cells, mouse cells, bacteria, etc.), cells from different organisms, cells from a naturally-occurring sample (e.g., pond water, soil, etc.), or the like. In some cases, the cells may be dissociated from tissue. In embodiments, the method does not include dissociating the cell from the tissue or the cellular microenvironment. In embodiments, the method does not include lysing the tissue section.

In embodiments, a permeabilization solution can contain additional reagents or a biological sample may be treated with additional reagents in order to optimize biological sample permeabilization. In some embodiments, an additional reagent is an RNA protectant. As used herein, the term "RNA protectant" typically refers to a reagent that protects RNA from RNA nucleases (e.g., RNases). Any appropriate RNA protectant that protects RNA from degradation can be used. A non-limiting example of an RNA protectant includes organic solvents (e.g., at least 60%, 65%, 70%, 75%, 80%, 85%, 90%, or 95% v/v organic solvent), which includes ethanol, methanol, propan-2-ol, acetone, trichloroacetic acid, propanol, polyethylene glycol, acetic acid, or a combination thereof. In embodiments, the RNA protectant includes ethanol, methanol and/or propan-2-ol, or a combination thereof. In embodiments, the RNA protectant includes RNAlater ICE (ThermoFisher Scientific). In embodiments, the RNA protectant includes a salt. The salt may include ammonium sulfate, ammonium bisulfate, ammonium chloride, ammonium acetate, cesium sulfate, cadmium sulfate, cesium iron (II) sulfate, chromium (III) sulfate, cobalt (II) sulfate, copper (II) sulfate, lithium chloride, lithium acetate, lithium sulfate, magnesium sulfate, magnesium chloride, manganese sulfate, manganese chloride, potassium chloride, potassium sulfate, sodium chloride, sodium acetate, sodium sulfate, zinc chloride, zinc acetate and zinc sulfate. In some embodiments, the biological sample is treated with one or more RNA protectants before, contemporaneously with, or after permeabilization.

In embodiments, the method further includes subjecting the tissue section to expansion microscopy methods and techniques (e.g., prior to detection). Expansion allows individual targets (e.g., mRNA or RNA transcripts) which are densely packed within a cell, to be resolved spatially in a high-throughput manner. Expansion microscopy techniques are known in the art and can be performed as described in US 2016/0116384 and Chen et al., Science, 347, 543 (2015), each of which are incorporated herein by reference in their entirety.

In embodiments, the method does not include subjecting the tissue section to expansion microscopy. Typically, expansion microscopy techniques utilize a swellable polymer or hydrogel (e.g., a synthetic matrix-forming material) which can significantly slow diffusion of enzymes and nucleotides. Matrix (e.g., synthetic matrix) forming materials include polyacrylamide, cellulose, alginate, polyamide, cross-linked agarose, cross-linked dextran or cross-linked polyethylene glycol. The matrix forming materials can form a matrix by polymerization and/or crosslinking of the matrix forming materials using methods specific for the matrix forming materials and methods, reagents and conditions known to those of skill in the art. Additionally, expansion microscopy techniques may render the temperature of the cell sample difficult to modulate in a uniform, controlled manner. Modulating temperature provides a useful parameter to optimize amplification and sequencing methods. In embodiments, the method does not include an exogenous matrix.

In embodiments, the method includes imaging the immobilized tissue section. In embodiments, the method further includes an imaging modality, immunofluorescence (IF), or immunohistochemistry modality (e.g., immunostaining). In embodiments, the method includes ER staining (e.g., contacting the tissue section with a cell-permeable dye which localizes to the endoplasmic reticula), Golgi staining (e.g., contacting the tissue section with a cell-permeable dye which localizes to the Golgi), F-actin staining (e.g., contacting the tissue section with a phalloidin-conjugated dye that binds to actin filaments), lysosomal staining (e.g., contacting the tissue section with a cell-permeable dye that accumulates in the lysosome via the lysosome pH gradient), mitochondrial staining (e.g., contacting the tissue section with a cell-permeable dye which localizes to the mitochondria), nucleolar staining, or plasma membrane staining. For example, the method includes live cell imaging (e.g., obtaining images of the tissue section) prior to or during fixing, immobilizing, and permeabilizing the tissue section. Immunohistochemistry (IHC) is a powerful technique that exploits the specific binding between an antibody and antigen to detect and localize specific antigens in cells and tissue, commonly detected and examined with the light microscope. Known IHC modalities may be used, such as the protocols described in Magaki, S., Hojat, S. A., Wei, B., So, A., & Yong, W. H. (2019). *Methods in molecular biology* (Clifton, N.J.), 1897, 289-298, which is incorporated herein by reference. In embodiments, the additional imaging modality includes bright field microscopy, phase contrast microscopy, Nomarski differential-interference-contrast microscopy, or dark field microscopy. In embodiments, the method further includes determining the cell morphology of the tissue section (e.g., the cell boundary or cell shape) using known methods in the art. For example, to determining the cell boundary includes comparing the pixel values of an image to a single intensity threshold, which may be determined quickly using histogram-based approaches as described in Carpenter, A. et al Genome Biology 7, R100 (2006) and Arce, S., Sci Rep 3, 2266 (2013)). By "microscopic analysis" is meant the analysis of a specimen using techniques that provide for the visualization of aspects of a specimen that cannot be seen with the unaided eye, i.e., that are not within the resolution range of the normal human eye. Such techniques may include, without limitation, optical microscopy, e.g., bright field, oblique illumination, dark field, phase contrast, differential interference contrast, interference reflection, epifluorescence, confocal microscopy, CLARITY-optimized light sheet microscopy (COLM), light field microscopy, tissue expansion microscopy, etc., laser microscopy, such as, two photon microscopy, electron microscopy, and scanning probe microscopy. By "preparing a biological specimen for microscopic analysis" is generally meant rendering the specimen suitable for microscopic analysis at an unlimited depth within the specimen. In embodiments, the immobilized tissue section is imaged using "optical sectioning" techniques, such as laser scanning confocal microscopes, laser scanning 2-Photon microscopy, parallelized confocal (i.e. spinning disk), computational image deconvolution methods, and light sheet approaches. Optical sectioning microscopy methods provide information about single planes of a volume by minimizing contributions from other parts of the volume and do so without physical sectioning. The resulting "stack" of such optically sectioned images, represents a full reconstruction of the 3-dimensional features of a tissue volume. A typical confocal microscope includes a 10×/0.5 objective (dry; working distance, 2.0 mm) and/or a 20×/0.8 objective (dry; working distance, 0.55 mm), with a s z-step interval of 1 to 5 μm. A typical light sheet fluorescence microscope includes an sCMOS camera, a 2×/0.5 objective lens, and zoom microscope body (magnification range of ×0.63 to ×6.3). For entire scanning of whole samples, the z-step interval is 5 or 10 μm, and for image acquisition in the regions of interest, an interval in the range of 2 to 5 μm may be used.

To microscopically visualize tissue sections prepared by the subject methods, in some embodiments the tissue section is embedded in a mounting medium. Mounting medium is typically selected based on its suitability for the reagents used to visualize the cellular biomolecules, the refractive index of the tissue section, and the microscopic analysis to be performed. For example, for phase-contrast work, the refractive index of the mounting medium should be different from the refractive index of the specimen, whereas for bright-field work the refractive indexes should be similar. As another example, for epifluorescence work, a mounting medium should be selected that reduces fading, photobleaching or quenching during microscopy or storage. In certain embodiments, a mounting medium or mounting solution may be selected to enhance or increase the optical clarity of the cleared tissue specimen. Nonlimiting examples of suitable mounting media that may be used include glycerol, CC/Mount™, Fluoromount™ Fluoroshield™, ImmunHistoMount™, Vectashield™, Permount™, Acrytol™, CureMount™, FocusClear™, or equivalents thereof.

The biological targets or molecules to be detected can be any biological molecules including but not limited to proteins, nucleic acids, lipids, carbohydrates, ions, or multi-component complexes containing any of the above. Examples of subcellular targets include organelles, e.g., mitochondria, Golgi apparatus, endoplasmic reticulum, chloroplasts, endocytic vesicles, exocytic vesicles, vacuoles, lysosomes, etc. Exemplary nucleic acid targets can include genomic DNA of various conformations (e.g., A-DNA, B-DNA, Z-DNA), mitochondria DNA (mtDNA), mRNA, tRNA, rRNA, hRNA, miRNA, and piRNA. For example, following immobilization on the receiving substrate, the sections may be fixed with methanol, permeabilized with 0.025% Triton in PBS solution, and stained with primary antibodies directed against vimentin (fibroblasts) and macrophages, followed by secondary antibody labeling (e.g., Alexa-594 conjugated secondary antibodies). Additional counterstaining may be performed, for example using 4,6-diamidino-2-phenylindole (DAPI) mounting media to counterstain nuclei.

In embodiments, the collection of information (e.g., sequencing information and cell morphology) is referred to as a signature. The term "signature" may encompass any gene or genes, protein or proteins, or epigenetic element(s) whose expression profile or whose occurrence is associated with a specific cell type, subtype, or cell state of a specific cell type or subtype within a population of cells. It is to be understood that also when referring to proteins (e.g., differentially expressed proteins), such may fall within the definition of "gene" signature. Levels of expression or activity or prevalence may be compared between different cells in order to characterize or identify for instance signatures specific for cell (sub) populations. Increased or decreased expression or activity of signature genes may be compared between different cells in order to characterize or identify for instance specific cell (sub) populations.

In embodiments, the methods described herein may further include constructing a 3-dimensional pattern of abundance, expression, and/or activity of each target from spatial patterns of abundance, expression, and/or activity of each target of multiple samples. In embodiments, the multiple samples can be consecutive tissue sections of a 3-dimensional tissue sample.

In embodiments, the method further includes digesting the tissue section by contacting the sample-carrier construct with an endopeptidase. In embodiments, the endopeptidase is pepsin.

In embodiments, the method further includes removing the embedding material from the sample. For example, if the embedding material is paraffin wax, the embedding material is removed by contacting the sample-carrier construct with a hydrocarbon solvent, such as xylene or hexane, followed by two or more washes with decreasing concentrations of an alcohol, such as ethanol.

In embodiments, the method includes measuring changes in the amount of biomaterial present in a well relative to a control (e.g., a sample obtained at a different time point or exposed to alternate conditions). As used herein, "biomaterial" refers to any biological material produced by an organism. In some embodiments, biomaterial includes secretions, extracellular matrix, proteins, lipids, organelles, membranes, cells, portions thereof, and combinations thereof. In some embodiments, cellular material includes secretions, extracellular matrix, proteins, lipids, organelles, membranes, cells, portions thereof, and combinations thereof. In some embodiments, biomaterial includes viruses. In some embodiments, the biomaterial is a replicating virus and thus includes virus infected cells.

In embodiments, additional methods may be performed to further characterize the sample. For example, in addition to sequencing, the method includes protein analysis, lipid analysis, metabolite analysis (e.g., glucose analysis), or measuring the transcriptomic profile, gene expression activity, genomic profile, protein expression activity, proteomic profile, protein interaction activity, cellular receptor expression activity, lipid profile, lipid activity, carbohydrate profile, microvesicle activity, glucose activity, and combinations thereof.

In an aspect is provided a method of determining a surgical margin of a tissue to be resected in a subject, the method including: immobilizing a tissue section obtained from the subject onto a hydrogel carrier substrate to generate a sample-carrier construct; contacting the tissue section of the sample-carrier construct with a receiving substrate to generate an immobilized tissue section; removing the hydrogel carrier substrate from the immobilized tissue section; permeabilizing the immobilized tissue section; contacting a biomolecule at a first location in the tissue section with a detection agent thereby detecting the presence of the biomolecule in the first location in the tissue section; determining the presence of the biomolecule at one or more different locations in the tissue section by contacting the detection agent at one or more different locations in the tissue section; comparing the presence of the biomolecule in the first location to the presence of the biomolecule in the one or more different locations, and determining the surgical margin of the tissue to be resected from the subject based on the comparison. In embodiments, the detection agent includes a fluorophore In embodiments, the method includes comparing the presence of a plurality of biomolecules at the first location in the tissue section to the presence of the plurality of biomolecules at one or more different locations in the tissue section (i.e., detecting or identifying the presence of the plurality of biomolecules at two or more different locations in the tissue section), and determining a surgical margin of the tissue (e.g., a sample of the tissue surrounding a tumor, or other diseased tissue) to be resected from a subject based on the comparison, for example, if the presence of the biomolecule (or plurality of biomolecules) is being used for determination of the surgical margin of the tissue.

In embodiments, the biomolecule (e.g., the one or more biomolecules) are not detected in the one or more different locations in the tissue section. For example, the one or more different locations may not contain diseased cells (e.g., cells including the biomolecule of interest). In such a case, the lack of the presence of the biomolecule indicates that the location should not be resected from the subject.

In certain embodiments, the tissue sample includes one or more tissue sections. Typically, the tissue sample includes more than one tissue section (e.g., serial sections). Typically, the tissue sample includes one or more tissue sections peripheral to the tumor. In certain embodiments, the one or more tissue sections are topographically marked. For example, the one or more sections may be marked (e.g., notched) to maintain orientation. The one or more sections may be marked to allow them to be located to the wound during or after surgery. More than one section may be marked to allow different sections to be distinguished from each other. The one or more sections may be used to map the margin of the tumor.

In certain embodiments, the tissue sample includes one or more horizontal sections of the tumor. In certain embodiments, the tissue sample includes horizontal sections of tissue peripheral to the tumor. In certain embodiments, the tissue sample includes (or may be deemed to be at risk of including) tumor positive tissue. For example, the one or more sections of tissue peripheral to the tumor may include (or be suspected of including) the margin (e.g., outermost layer) of the tumor. For example, the tissue may include the outermost boundary of tumor positive tissue. The tissue may further include tumor negative tissue adjacent to the tumor boundary.

In some embodiments, the tissue to be resected is a tumor (e.g., a malignant or a benign tumor). In some embodiments, the tumor is a solid tumor. In some embodiments, the subject is suspected of having a cancer. In some embodiments, the subject has been previously diagnosed or identified as having a cancer (e.g., any of the exemplary cancers described herein). In some embodiments, the tissue to be resected can include a tumor (e.g., a malignant tumor) of any of the types of cancer described herein.

In some embodiments of any one of the methods described herein, the biomolecule is a tumor biomarker. In some embodiments, the biomolecule is a tumor antigen. Exemplary tumor antigens include, but are not limited to, melanoma-associated antigen (MAGE) series of antigens (e.g., MAGE-C1 (cancer/testis antigen CT7), MAGE-B1 antigen (MAGE-XP antigen, DAM10), MAGE-B2 antigen (DAME), MAGE-2 antigen, MAGE-4a antigen, and MAGE-4b antigen), tyrosinase, glycoprotein 100 (gp100), disialoganglioside GD-2, disialoganglioside 0-acetylated GD-3, ganglioside GM-2, epidermal growth factor receptor (EGFR), vascular endothelial growth factor receptor (VEGFR), mutant B-Raf antigen associated with melanoma and colon cancer, human epidermal growth factor receptor-2 (HER-2/neu) antigen, melanoma-associated antigen recognized by T cells (MART-1) (e.g., MART-1 26-35 peptide or MART-1 27-35 peptide), protein kinase C-binding protein, reverse transcriptase protein, A-kinase-anchoring protein (AKAP protein), vaccinia-related kinase Serine/Threonine Kinase 1 (VRK1), fucosyltransferase (T6-7), zinc finger protein 258 (T11-6), p53-binding protein (T1-52), T5-15 (KIAA1735), T5-13 (Sosl), T11-5 (hypothetical protein MGC4170), T11-9 (hypothetical protein AF225417), T11-3 (trap ankyrin repeat), T7-1 (KIAA1288), a mutant or wild type ras peptide, Homo sapiens telomerase ferment (hTRT), cytokeratin-19 (CYFRA21-1), squamous cell carcinoma antigen 1 (SCCA-1), protein T4-A, squamous cell carcinoma antigen 2 (SCCA-2), ovarian carcinoma antigen CA125 (1A1-3B) (KIAA0049), cell surface-associated MUCIN 1 (e.g., tumor-associated MUCIN, carcinoma-associated MUCIN, polymorphic epithelial MUCIN peanut-reactive urinary MUCIN, polymorphic epithelial mucin (PEM), PEMT, episialin, tumor-associated epithelial membrane antigen, epithelial membrane antigen (EMA), H23 antigen (H23AG), PUM, and breast carcinoma-associated antigen DF3), CTCL tumor antigen sel-1, CTCL tumor antigen se14-3, CTCL tumor antigen se20-4, CTCL tumor antigen se20-9, CTCL tumor antigen se33-1, CTCL tumor antigen se37-2, CTCL tumor antigen se57-1, CTCL tumor antigen se89-1, prostate-specific membrane antigen, 5T4 oncofetal trophoblast glycoprotein, Orf73 Kaposi's sarcoma-associated herpesvirus, colon cancer antigen NY-CO-45, lung cancer antigen NY-LU-12 variant A, cancer associated surface antigen, adenocarcinoma antigen ART1, paraneoplastic associated brain-testis-cancer antigen (onconeuronal antigen MA2; parancoplastic neuronal antigen), neuro-oncological ventral antigen 2 (NOVA2), hepatocellular carcinoma antigen gene 520, tumor-associated antigen CO-029, tumor-associated antigen MAGE-X2, synovial sarcoma antigen, X breakpoint 2, squamous cell carcinoma antigen recognized by T cell, serologically defined colon cancer antigen 1, serologically defined breast cancer antigen NY-BR-15, serologically defined breast cancer antigen NY-BR-16, chromogranin A, parathyroid secretory protein 1, pancreatic cancer-associated antigen (DUPAN-2), carbohydrate antigen CA 19-9, carbohydrate antigen CA 72-4, carbohydrate antigen CA 195, and carcinoembryonic antigen (CEA).

In embodiments, the biomolecule (e.g., one or more biomolecules detected) includes CD4, CD68, CD20, CD11c, CD8, HLA-DR, Ki67, CD45RO, PanCK, CD3c, CD44, CD45, HLA-A, CD14, CD56, CD57, CD19, CD2, CD1a, CD107a, CD21, Pax5, FOXP3, Granzyme B, CD38, CD39, CD79a, TIGIT, TOX, TP63, S100A4, TFAM, GP100, LaminB1, CK19, CK17, GATA3, SOX2, Bcl2, EpCAM, Caveolin, CD163, CD11b, MPO, CD141, iNOS, PD-1, PD-L1, ICOS, TIM3, LAG3, IDO1, CD40, HLA-E, IFNG, CD69, E-cadherin, CD31, Histone $H_3$, Beta-actin, Podoplanin, SMA, Vimentin, Collagen IV, CD34, Beta-catenin, MMP-9, ZEB1, ASCT2, Na/K ATPase, HK1, LDHA, G6PD, IDH2, GLUT1, pNRF2, ATPA5, SDHA, Citrate Synthase, CPT1A, PARP, BAK, BCL-XL, BAX, BAD, Cytochrome c, LC3B, Beclin-1, $H_2$AX, pRPS6, PCNA, Cyclin D1, HLA-DPB1, LEF1, GAL9, CD138, MC Tryptase, OX40, ZAP70, CD7, CIQa, CCR6, CD15, AXL, and/or CD227.

In some embodiments, the tissue to be resected is an infected tissue, a necrotic tissue, or a diseased tissue. In some embodiments, the biomolecule can be associated with an infection, necrosis, inflammation, or disease. Non-limiting examples of such biomolecules are known in the art.

In some embodiments, the methods provided herein include comparing the presence of the biomolecule at the location in the tissue sample to presence of the biomolecule at different location(s) in the tissue sample, and determining the size and site of a tissue to be resected from the subject based on the comparison. In some embodiments, the different location(s) in the tissue sample are reference location(s). In some embodiments, the reference location(s) in the tissue sample are locations of healthy tissue. In some embodiments, the reference location(s) in the tissue sample are locations of non-cancerous tissue. In some embodiments, the reference location(s) in the tissue sample are locations of non-tumor tissue. In some embodiments, the reference location(s) in the tissue sample are locations with no abnormalities such as tumor, cancer, necrosis, inflammation, infection, or disease.

In some embodiments, the presence of the biomolecule at the location in the tissue sample is significantly different from the presence of the biomolecule at the different location(s) in the tissue. In some embodiments, the presence of the biomolecule at the location in the tissue sample is significantly greater than the presence of the biomolecule at the different location(s) in the tissue sample. In some embodiments, the presence of the biomolecule at the location in the tissue sample is significantly less than the presence of the biomolecule at the different location(s) in the tissue sample.

In some embodiments, the location at the tissue sample is determined to be resected if the presence of the biomolecule at the location in the tissue sample is significantly different from the presence of the biomolecule at the different location (s). In some embodiments, the location at the tissue sample is determined to be resected if the presence of the biomolecule at the location in the tissue sample is significantly greater than the presence of the biomolecule at the different location(s). In some embodiments, the location at the tissue sample is determined to be resected if the presence of the biomolecule at the location in the tissue sample is significantly less than the presence of the biomolecule at the different location(s).

In some embodiments, the presence of the biomolecule at the location in the tissue sample is about 0.1-fold to about 100-fold (e.g., about 0.1-fold to about 90-fold, about 0.1-fold to about 80-fold, about 0.1-fold to about 70-fold, about 0.1-fold to about 60-fold, about 0.1-fold to about 50-fold, about 0.1-fold to about 40-fold, about 0.1-fold to about 30-fold, about 0.1-fold to about 20-fold, about 0.1-fold to about 15-fold, about 0.1-fold to about 10-fold, about 0.1-fold to about 8-fold, about 0.1-fold to about 6-fold, about 0.1-fold to about 5-fold, about 0.1-fold to about 4-fold, about 0.1-fold to about 3-fold, about 0.1-fold to about 2-fold, about 0.1-fold to about 1.5-fold, about 0.1-fold to about 1-fold, about 0.1-fold to about 0.8-fold, about 0.1-fold to about 0.6-fold, about 0.1-fold to about 0.4-fold, about 0.1-fold to about 0.2-fold, about 1-fold to about 100-fold, about 1-fold to about 90-fold, about 1-fold to about 80-fold, about 1-fold to about 70-fold, about 1-fold to about 60-fold, about 1-fold to about 50-fold, about 1-fold to about 40-fold, about 1-fold to about 30-fold, about 1-fold to about 20-fold, about 1-fold to about 15-fold, about 1-fold to about 10-fold, about 1-fold to about 8-fold, about 1-fold to about 6-fold, about 1-fold to about 5-fold, about 1-fold to about 4-fold, about 1-fold to about 3-fold, about 1-fold to about 2-fold, about 1-fold to about 1.5-fold, about 5-fold to about 100-fold, about 5-fold to about 90-fold, about 5-fold to about 80-fold, about 5-fold to about 70-fold, about 5-fold to about 60-fold, about 5-fold to about 50-fold, about 5-fold to about 40-fold, about 5-fold to about 30-fold, about 5-fold to about 20-fold, about 5-fold to about 15-fold, about 5-fold to about 10-fold, about 5-fold to about 8-fold, about 5-fold to about 6-fold, about 10-fold to about 100-fold, about 10-fold to about 90-fold, about 10-fold to about 80-fold, about 10-fold to about 70-fold, about 10-fold to about 60-fold, about 10-fold to about 50-fold, about 10-fold to about 40-fold, about 10-fold to about 30-fold, about 10-fold to about 20-fold, about 10-fold to about 15-fold, about 15-fold to about 100-fold, about 15-fold to about 90-fold, about 15-fold to about 80-fold, about 15-fold to about 70-fold, about 15-fold to about 60-fold, about 15-fold to about 50-fold, about 15-fold to about 40-fold, about 15-fold to about 30-fold, about 15-fold to about 20-fold, about 20-fold to about 100-fold, about 20-fold to about 90-fold, about 20-fold to about 80-fold, about 20-fold to about 70-fold, about 20-fold to about 60-fold, about 20-fold to about 50-fold, about 20-fold to about 40-fold, about 20-fold to about 30-fold, about 30-fold to about 40-fold, about 40-fold to about 100-fold, about 40-fold to about 90-fold, about 40-fold to about 80-fold, about 40-fold to about 70-fold, about 40-fold to about 60-fold, about 40-fold to about 50-fold, about 50-fold to about 100-fold, about 50-fold to about 90-fold, about 50-fold to about 80-fold, about 50-fold to about 70-fold, about 50-fold to about 60-fold, about 60-fold to about 100-fold, about 60-fold to about 90-fold, about 60-fold to about 80-fold, about 60-fold to about 70-fold, about 70-fold to about 100-fold, about 70-fold to about 90-fold, about 70-fold to about 80-fold, about 80-fold to about 100-fold, about 80-fold to about 90-fold, or about 90-fold to about 100-fold) greater than the presence of the biomolecule at the different location(s).

In some embodiments, the presence of certain biomarkers associated with a cancer and/or disease (e.g., breast cancer biomarkers in ductal carcinoma) at a location in a tissue sample are evaluated. If the presence of certain biomarkers associated with a cancer and/or disease are below a threshold value for those biomarkers, the location in the tissue sample is considered "clear." If the presence of certain biomarkers associated with a cancer and/or disease are above a threshold value for those biomarkers, the location in the tissue sample is considered within the margin of tissue to be resected. Additional examples of biomolecule and/or biomolecule comparisons that may be performed in determining tumor surgical margins are described in, e.g., U.S. Pat. Pub. 2022/0098576, which is incorporated herein by reference in its entirety.

In some embodiments, a location at the tissue sample includes about 1 to about 100,000 (e.g., about 1 to about 90,000, about 1 to about 80,000, about 1 to about 70,000, about 1 to about 60,000, about 1 to about 50,000, about 1 to about 40,000, about 1 to about 30,000, about 1 to about 20,000, about 1 to about 10,000, about 1 to about 9,000, about 1 to about 8,000, about 1 to about 7,000, about 1 to about 6,000, about 1 to about 5,000, about 1 to about 4,000, about 1 to about 3,000, about 1 to about 2,000, about 1 to about 1,000, about 1 to about 900, about 1 to about 800, about 1 to about 700, about 1 to about 600, about 1 to about 500, about 1 to about 400, about 1 to about 300, about 1 to about 200, about 1 to about 100, about 1 to about 90, about 1 to about 80, about 1 to about 70, about 1 to about 60, about 1 to about 50, about 1 to about 40, about 1 to about 30, about 1 to about 20, about 1 to about 10, about 100 to about 100,000, about 100 to about 90,000, about 100 to about 80,000, about 100 to about 70,000, about 100 to about 60,000, about 100 to about 50,000, about 100 to about 40,000, about 100 to about 30,000, about 100 to about 20,000, about 100 to about 10,000, about 100 to about 9,000, about 100 to about 8,000, about 100 to about 7,000, about 100 to about 6,000, about 100 to about 5,000, about 100 to about 4,000, about 100 to about 3,000, about 100 to about 2,000, about 100 to about 1,000, about 100 to about 900, about 100 to about 800, about 100 to about 700, about 100 to about 600, about 100 to about 500, about 100 to about 400, about 100 to about 300, about 100 to about 200, about 1,000 to about 100,000, about 1,000 to about 90,000, about 1,000 to about 80,000, about 1,000 to about 70,000, about 1,000 to about 60,000, about 1,000 to about 50,000, about 1000 to about 40,000, about 1,000 to about 30,000, about 1,000 to about 20,000, about 1,000 to about 10,000, about 1000 to about 9,000, about 1,000 to about 8,000, about 1,000 to about 7,000, about 1000 to about 6,000, about 1,000 to about 5,000, about 1,000 to about 4,000, about 1000 to about 3,000, about 1,000 to about 2,000, 10,000 to about 100,000, about 10,000 to about 90,000, about 10,000 to about 80,000, about 10,000 to about 70,000, about 10,000 to about 60,000, about 10000 to about 50,000, about 10,000 to about 40,000, about 10,000 to about 30,000, about 10,000 to about 20,000) cells.

In some embodiments, additional methods are used in combination with the methods described herein to determine the site and size of the tissue to be resected in a subject. In some embodiments, medical imaging modalities such as computed tomography (CT) and magnetic resonance imaging (MRI) are used in combination with the methods described herein. In some embodiments, a position emission tomography (PET) is used in combination with the methods described herein. For example, an initial scanning of a cancer patient and/or imaging of a tissue sample from a cancer patient can be performed using, e.g., MRI, CT, and/or PET prior to the methods described herein, and a preliminary assessment of a surgical margin can be performed. The initial information can provide guidance on, e.g., where to obtain the tissue sample for use in the methods described herein, the size of the tissue sample, and/or the number of tissue samples needed. In another example, a follow-up scanning and/or imaging can be performed using e.g., MRI, CT, and/or PET after the methods described herein are performed. The follow-up scanning and/or imaging provide information on, e.g., the clearance of the cancerous and/or diseased tissue, and whether there are residual cancerous and/or diseased tissue. Any other suitable methods known in the art can also be used in combination with the methods described herein.

Some embodiments of any of the methods described herein can further include obtaining the tissue sample from the subject (e.g., obtain a biopsy from the subject).

In some embodiments, at least a portion of the tissue to be resected includes cancer cell(s), pre-cancerous cell(s), necrotic cell(s), infected cell(s), and/or diseased tissue. In some embodiments, at least 80%, at least 85%, at least 90%, at least 95%, at least 99%, or 100% of the tissue to be resected includes one or more of cancer cell(s), pre-cancerous cell(s), necrotic cell(s), infected cell(s), and disease tissue.

EXAMPLES

Example 1. Carrier-Assisted Tissue Section Transfer

Biopsies and cytology specimens typically include cell and tissue sections and are a major component of disease research and clinical pathology. Unstained slides derived from formalin-fixed paraffin-embedded (FFPE) tissue sections may be analyzed using hematoxylin and eosin (H&E) histology techniques, immunohistochemistry/immunofluorescence assays and protocols, and chromogenic or fluorescent in situ hybridization methods. H&E staining of FFPE sections reviewed by a pathologist are highly valuable to ensure the presence of suitable lesional cells for molecular and other analyses (Sy J and Ang L C. Methods Mol. Biol. 2019; 1897:269-278). In addition to standard morphology-based imaging, more current approaches are interrogating the spatial and structural context of specimens. For example, in situ gene expression approaches, such as those commercialized by 10× Genomics, Interpace Biosciences, Thermo Fisher Scientific, and others represent an emerging area of spatial genomics. In addition, multiplexed in situ proteomic expression approaches such as those commercialized by Akoya Biosciences, Fluidigm, Ionpath, and others are developing complementary spatial proteomics approaches. For example, in situ gene expression methods typically involve attaching a section of a frozen tissue of interest to patterned microarrays carrying spatially barcoded oligo-dT primers that capture the polyadenylated transcriptome contained within the tissue section. Each spot on the microarray contains a capture probe with a spatial barcode unique to that spot allowing the individual sequencing reads to be mapped to the originating spot. After cDNA synthesis on the surface via reverse transcription, the tissue is removed and the mRNA-cDNA hybrids are released from the array to be prepared for sequencing on a separate platform; see Vickovic, S., et al. Nat. Methods 16, 987-990 (2019) for greater detail on the approach. In parallel, multiplex protein measurements in situ enable profiling multiple detectable tags simultaneously (e.g., cyclical immunostaining).

A number of new techniques have been described for reading out RNA transcription levels in tissue sections directly (i.e., in situ), without requiring spatial barcoding, based on single molecule fluorescence in situ hybridization. These include MERFISH (Multiplexed Error-Robust Fluorescence In Situ Hybridization), STARmap (Spatially-resolved Transcript Amplicon Readout mapping), FISSEQ, BaristaSeq, seq-FISH (Sequential Fluorescence In Situ Hybridization) and others (see for example Chen, K. H., et al. (2015). Science, 348 (6233), aaa6090; Wang, G., Moffitt, J. R. & Zhuang, X. Sci Rep. 2018; 8, 4847; Wang X. et al; Science, 2018; 27, Vol 361, Issue 6400, caat5691; Cai, M. Dissertation, (2019) UC San Diego. ProQuest ID: Cai_ucsd_0033D_18822; and Sansone, A. Nat Methods 16, 458; 2019). In these techniques, individual RNA transcripts are individually resolved, typically with pre-amplification or requiring multiple instances of labeled probes. Some of these techniques have been combined with super-resolution microscopy, expansion microscopy, or both, to increase the resolution and allow more transcripts to be resolved and thus counted.

Methods for acquiring, preparing, and storing tissue sections for either immediate or future analysis have been largely unchanged for decades. For example, when a patient has a biopsy or surgery, the surgeon often removes a portion of tissue for examination by a pathologist. Typically when dealing with biopsy samples, the recommended approach is to process the samples by embedding individually in a supporting material such as a paraffin block or freezing the sample. The resected tissue may be snap-frozen in liquid nitrogen shortly after surgical resection, generating what is commonly referred to as "fresh frozen" tissue. Freshly obtained tissue samples require snap freezing to prevent RNA degradation and avoid crystal formation, which can cause physical damage to the tissue architecture. Once frozen, tissue samples are embedded in a freezing and embedding compound, referred to as optimal cutting temperature (OCT), to preserve the structure of the tissue and provide structural support during subsequent cryosectioning. Alternatively, preservation techniques such as formalin-fixation and paraffin embedding (FFPE) are widely used for preserving the macroscopic architecture of cellular structures (e.g., preserve tissue architecture, cell shape, and the components of the cell, such as proteins, carbohydrates, and enzymes) in tissue sections but are known to damage and alter nucleic acids. Prolonged formalin fixation causes the crosslinking of proteins and nucleic acids and random breakages in nucleotide sequences rendering downstream analyses a challenge. Fresh frozen tissue is the preferred sample for detecting gene mutations due to its superiority in preserving DNA, while FFPE tissue provides the benefits of case of storage and preservation of cellular and architectural morphology. However, the fixation and archiving process in FFPE often leads to the cross-linking, degradation, and fragmentation of DNA molecules (Gao X H et al. Front. Oncol. 2020; 10:310). In recent years with the development of additional technologies to further analyze the sample (e.g., spatial gene expression and/or proteomic analyses), extracting or transferring the sample from a glass slide/transitional surface to another medium would be an attractive step in the processing of tissue samples. However, subsequent transfer of the tissue section to another surface often introduces additional damage to the sample. For example, once the tissue section is attached to the first surface (e.g., a typical biopsy slide, such as a charged glass surface), it may be extremely difficult to transfer again without damaging the tissue due to strong contact forces between the tissue section and attachment surface. Novel approaches for transferring biological specimens while minimizing damage are greatly needed.

Tissue samples, such as those taken by biopsy, are commonly formalin-fixed and paraffin embedded (FFPE) to allow for extended storage of the samples and the structure of the cell and sub-cellular components to be maintained. In such FFPE processing, the samples are typically fixed in a formalin solution (e.g., a 10% formalin solution may contain 3.7% formaldehyde and 1.0 to 1.5% methanol), which creates crosslinks between nucleic acids, between proteins and/or between nucleic acids and proteins. Afterward, the sample is dehydrated, e.g., by placing the sample in an alcohol, and exposed xylene. The sample is then embedded in paraffin, where the sample is surrounded by paraffin which replaces the xylene in the sample. The paraffin embedded sample (i.e., an FFPE block) can then be stored for extended periods of days, months, or years. At a desired time, the samples may then be transferred to a vessel or other system for further processing.

Once a tissue sample has been obtained and preserved (e.g., either a fresh frozen tissue block or FFPE tissue block), a scientist typically slices the tissue sample into very thin sections (e.g., sectioning using a microtome, vibratome, or cryotome). A vibratome (i.e., a vibrating microtome) is an instrument that uses a vibrating blade to cut thin slices of material, for example, from about 10 μm to about 300 μm in thickness (e.g., product number E0977 from Beyotime), or from about 1 mm to about 40 mm (e.g., model #VT1000S from Leica Biosystems). FFPE tissue sections, for example, are placed in a warm water bath and then mounted onto a glass slide following sectioning from a tissue block. The water bath temperature may be set about 5-10° C. below the melting point of paraffin (e.g., the water bath temperature is maintained at about 40-50° C.), and the tissue section is floated for several seconds or up to a few minutes to allow the section to spread open and remove any wrinkles prior to contacting the receiving substrate (i.e., the glass slide). The water bath temperature is highly dependent upon the ambient temperature in the room, the humidity, and the melting temperature of the wax. Typical water bath temperatures include about 37° C. to about 50° C. The temperature should be selected such that the water bath temperature is lower than the melting temperature of the wax, but high enough so that the section completely flattens out for even transfer. Once on the slide, the tissue section is baked at 50-60° C., to improve adherence to the slide. Next, the tissue section may be inspected under a microscope for proper positioning of the section prior to further processing. This process (i.e., mounting a tissue section onto a glass slide) leads to a strong attachment between the tissue section and the glass slide.

Transferring intact regions of interest from a tissue section into a vessel or another slide would be very advantageous for downstream analysis. Though it would be desirable to be able to transfer undamaged tissue sections from a prepared glass slide after sectioning, current technology is limited. Subsequent transfer of the tissue section, or regions of interest, from the glass slide to another surface often introduces additional damage to the sample. For example, once the tissue section is attached to the first surface (e.g., a typical biopsy slide, such as a charged glass surface), it may be extremely difficult to transfer again without damaging the tissue section due to strong contact forces between the tissue section and attachment surface. Being able to effectively transfer tissue sections without damage or loss of material is critical when working with rare and valuable samples such as tissue biopsy specimens.

Current commercial solutions for spatial transcriptome analyses, such as the Visium Spatial Gene Expression method, requires that one to four sections be captured on a single slide using traditional approaches. A user interested in analyzing 4 FFPE samples using the Visium platform would need to float each corresponding tissue section in a water bath and catch them individually on the patterned slide, for example, in the small 6.5×6.5 mm oligo-patterned areas provided in a Visium Spatial Gene Expression Slide (10× Genomics, Item #PN-2000233). Not only are these protocols labor intensive, obtaining proper alignment and placement on the patterns slide is difficult due to the mobility of the tissue section on the surface of the as the water bath. Complicating matters, following capture and immobilization of a first tissue section, the sections may move again while retrieving subsequent tissue sections. Accordingly, the Visium for FFPE tissue protocol does not prevent the immobilized tissue sections from folding, wrinkling, or moving out of the specified target capture regions on the slide during this process.

Unique challenges arise when working with fresh frozen tissue sections. Usually upon contact with the slide, the frozen tissue sections melt and bind to the surface of the slide. To prevent the temperature differential, maintaining the slides at a reduced temperature (e.g., −20° C.) reduces tissue section thawing and allows for proper placement, however the tissue strongly adheres to the slide upon increasing the temperature. These issues are further complicated when attempting to place tissue sections into a concave well (e.g., a well of a microtiter plate). For example, the tissue sections may adhere to the walls of the wells due to various forces (e.g., electrostatic forces) that may interact with the tissue section during the transfer and mounting process. The methods described herein describe approaches that overcome existing challenges in tissue transfer-associated damage through the introduction of a carrier layer between the tissue section and the attachment surface and allow for effective transfer of tissue sections to both slides and multi-well plates (e.g., a 6-well, 12-well, 24-well, 48-well, or 96-well plate) without significant physical damage to the tissue section.

Given the challenges described supra, few commercial solutions exist for transferring frozen tissue sections onto a slide. One offering for transferring frozen tissue sections is the CryoJane Tape-Transfer System from Leica Biosystems, which uses adhesive coated slides and adhesive tapes to capture sections (see, e.g., Yang Y et al. J. Orthop. Translat. 2020; 26:92-100, which is incorporated herein by reference in its entirety). Briefly, a strip of cold adhesive tape is affixed to the trimmed frozen tissue block and a section is then cut onto the tape. The tape with the frozen tissue section is then placed on a pre-coated cold adhesive slide. UV light is then applied to the slide, converting the adhesive coating into a hard, solvent-resistant plastic, and the tape is then peeled away. Other cryofilm-based approaches have been commercialized for similar processing of tissue sections, such as Cryofilm (#C-MK001-C2, cryofilm type 2C (9) 3.5 cm, Section lab, Hiroshima, Japan), as described in Ticha P et al. Scientific Reports. 2020; 10:19510 and Kawamoto T. Arch. Histol. Cytol. 2003; 66 (2): 123-143, each of which is incorporated by reference herein in its entirety. Recent modifications to the cryofilm protocol include a "sticker method", which combines cryofilm with OCT-embedded tissue samples to transfer tissue sections, instead of freeze-embedding of the tissue sample with CMC gel in hexane using a stainless-steel container, and subsequent UV light treatment (see, Ryu B et al. Journal of Neuroscience Methods. 2019; 328:108436, which is incorporated herein by reference in its entirety). These adhesive-based frozen tissue section methods have a number of shortcomings that may affect downstream analyses. First, the films are applied at the time of sectioning the tissue, slowing down the tissue sectioning process for which timing is critical given the fragile nature of frozen tissue. Secondly, these tape-based methods rely on adhesive compounds which, following mounting of the tape-transferred tissue section, are removed with organic solvents (e.g., hexane), and may therefore not be compatible with commercial multi-well plates, many of which have poor chemical compatibility with organic solvents (e.g., multi-well plates made from polystyrene). These studies on adhesive tape-based transfer of frozen tissue sections also did not explore the stability of the tissue sections after transferring, for example, stability after heating and cooling the transferred tissue section. Adhesive removal, and treatment with solvents, may impact the structural integrity of the tissue sections when subjected to thermal variation.

The methods described herein are applicable to both freshly cut tissue and frozen tissue samples, as well as preserved samples, and are compatible with a broad range of downstream applications such as in situ sequencing and proteomic analysis. In lieu of a glass slide, tissue sections are first mounted on a carrier substrate, forming a sample-carrier construct. An overview of this process is provided in FIG. 1, for example. In embodiments, the carrier substrate includes a hydration layer (i.e., interfacial water layer) between the tissue section and the carrier substrate hydrated prior to transfer to a final substrate (e.g., a charged glass slide). In contrast to the adhesive tape-based methods discussed supra, the carrier substrate described herein is free of adhesives and does not require UV curing following transfer to the final substrate. Reducing the strength of the tissue section adherence to the carrier substrate facilitates subsequent detachment and transference without damaging the tissue. Maintaining hydration of the tissue section is also useful for facilitating transfer from the carrier substrate to the final target surface. Under hydrated conditions, the tissue section is more likely to have complete contact with a hydration layer surface of the carrier substrate while exhibiting reduced contact forces, in comparison to dehydrated conditions. After dehydration, ideally once the tissue section is transferred to the final surface, strong surface interactions (e.g., van der Waals and/or electrostatic interactions) result in the tissue section being retained on the surface. For example, the carrier substrate may include agarose or gelatin.

Figure 2A:
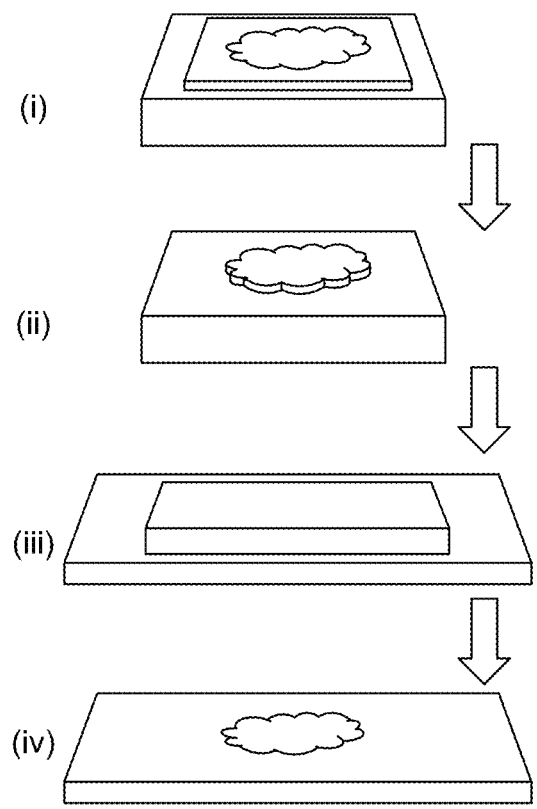
FIGS. 2A-2C illustrate different workflows for the sample-carrier constructs. For example.
Figure 2B:
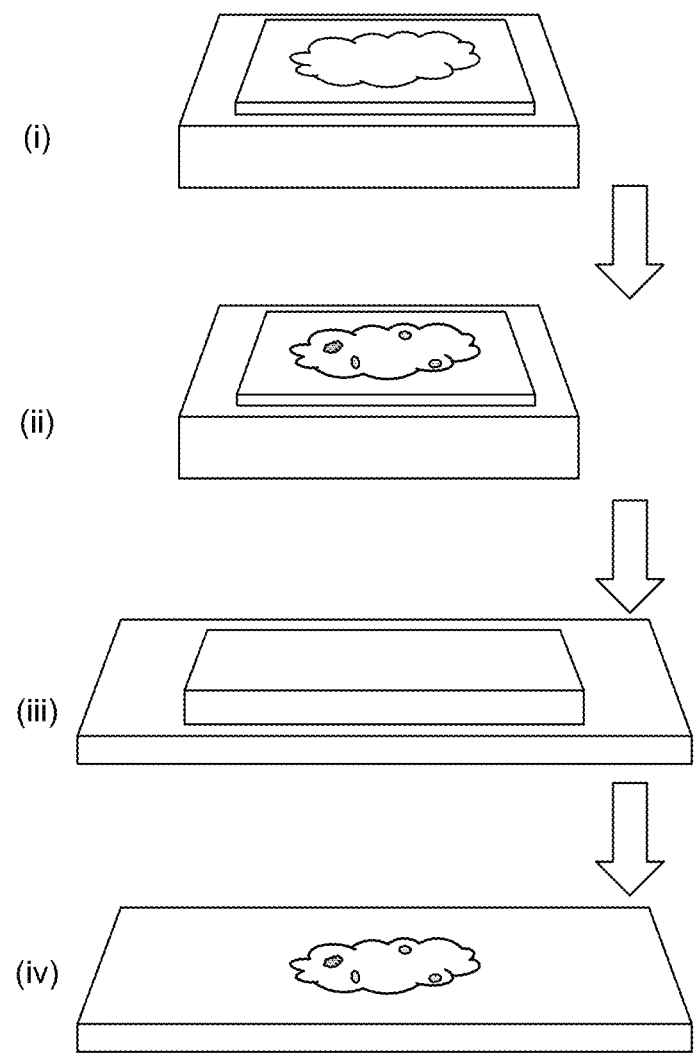
Figure 2C:
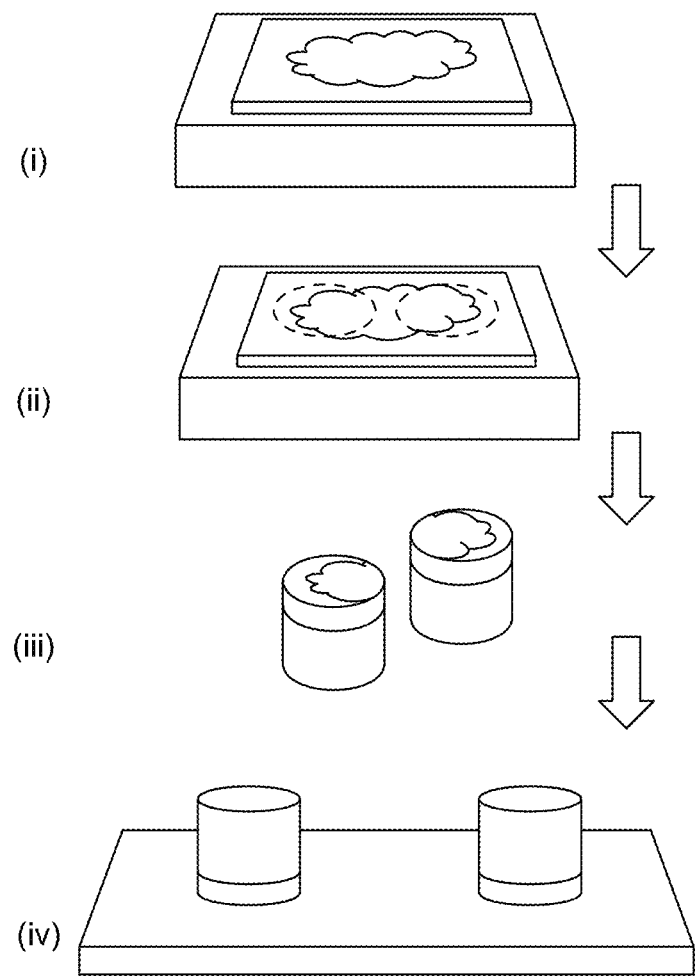
Figure 3A:
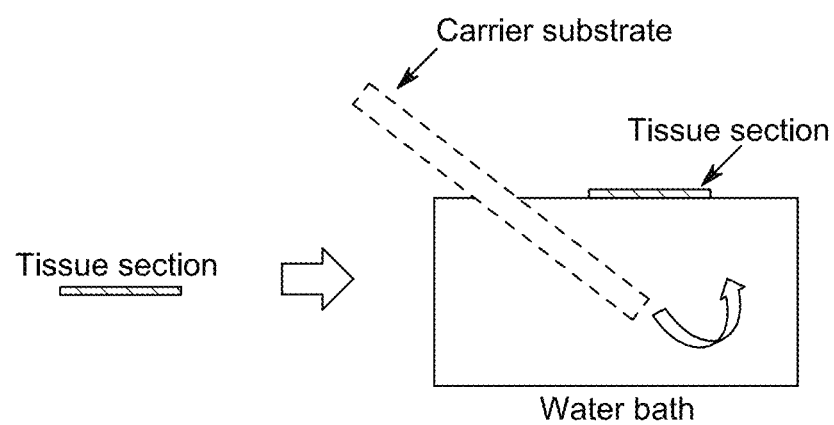
FIGS. 3A-3B describes tissue section transfer techniques. In an embodiment, a carrier substrate (e.g., a hydrophilic polymeric gel) is used to facilitate tissue section transfer. As illustrated, a tissue section, for example, an FFPE tissue section is placed in a water bath and then caught with a carrier substrate, yielding a sample-carrier construct (FIG. 3A). In embodiments, the carrier substrate maintains a hydrated interfacial surface (i.e., a plurality of water molecules at the surface forming an interstitial water layer) depicted as a solid bar between the tissue section and the carrier substrate. Without wishing to be bound by any theory, the interfacial water is useful at facilitating transfer and does not significantly affect the structural integrity of the tissue section upon subsequent transfer. The hydrophobicity of the carrier substrate may impact how the sample is captured. In embodiments, a substantially hydrophilic carrier substrate is at least partially submerged into the water bath, and the tissue section is attracted to the substrate and may be pulled out of the water bath. Alternatively, a substantially hydrophobic carrier substrate is at least partially submerged into the water bath and pushed up against the tissue section to promote adherence. The resulting construct is then applied to a receiving substrate (e.g., bare or functionalized glass, plastic, polymer receiving substrate) such that the tissue section can contact and become immobilized on the receiving substrate (FIG. 3B). Following transfer of the tissue section, the carrier substrate is removed. The bound FFPE tissue section may then be subjected additional manipulation (e.g., deparaffinization), and/or analyses (e.g., tissue labeling, and imaging) as required by the specific application.
Figure 3B:
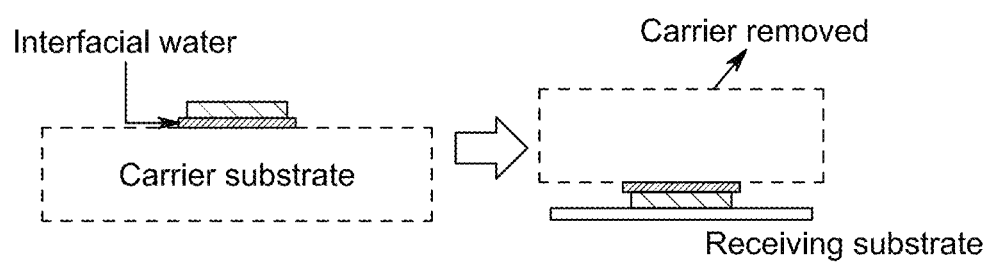

The sample-carrier construct can undergo additional manipulations, see for example FIGS. 2A-2C that illustrate different workflows for the sample-carrier constructs. For example, FIG. 2A depicts a sample-carrier construct (i) wherein the sample is embedded in an embedding material, e.g., paraffin wax. The embedding material is then removed, for example when the embedding material is paraffin wax by contacting the construct with an organic solvent such as xylene or heptane, leaving the tissue section on the construct, as illustrated in step (ii) of FIG. 2A. The tissue section of the construct is then contacted with a receiving substrate (e.g., bare or functionalized glass, plastic, polymer receiving substrate), see step (iii) of FIG. 2A, followed by removal of the carrier substrate, see step (iv) of FIG. 2A. Alternatively, the sample-carrier construct may be subjected to fluorogenic and/or chromogenic counterstaining (e.g., H&E staining) methods to aid in visualization and identifying details of the cell types, organelles, structures in the tissue section. The tissue section of the construct is then contacted with a receiving substrate (e.g., bare or functionalized glass, plastic, polymer receiving substrate), see step (iii) of FIG. 2B, followed by removal of the carrier substrate, see step (iv) of FIG. 2B. Shown in FIG. 2C is an overview of selected removal of one or more portions of the construct. To a sample-carrier construct, (i) of FIG. 2C, one or more portions of the construct are removed, for example using a cutting device, and depicted as dashed lines in step (ii) of FIG. 2C. The resulting portions of the construct, illustrated in step (iii) of FIG. 2C, are then contacted with a receiving substrate, such that the tissue section of the portion is in contact with the receiving substrate, as shown in step (iv) of FIG. 2C.

Figure 4A:
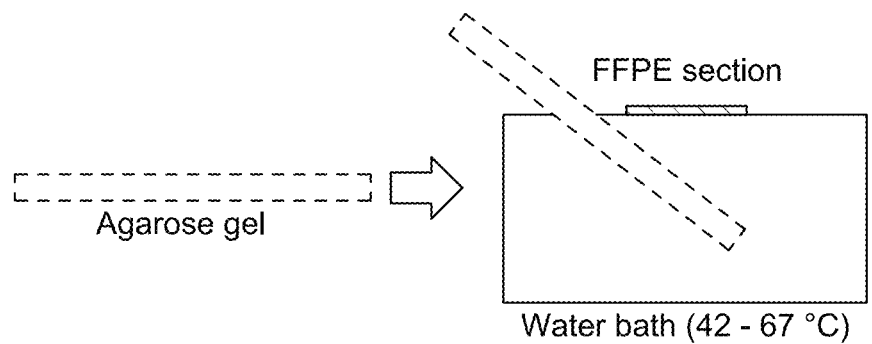
FIGS. 4A-4C presents a diagram of an embodiment described herein using a carrier substrate for tissue section transfer onto a glass slide. In this embodiment, the carrier substrate is an agarose gel and is prepared and placed in a warm water bath (e.g., maintained at a temperature between 42° C. and 67° C.), as shown in FIG. 4A. An FFPE tissue section floats in the water bath, followed by contacting the tissue section with the agarose gel to layer it atop the agarose. The tissue section and agarose gel (collectively referred to as a sample-carrier construct) are removed from the warm water bath and allowed to cool without completely drying out. A portion of the construct is removed, for example using a cutting device, e.g., a hole punch or cutting blade. Multiple portions may be made from a single tissue section. The portions (i.e., cutouts) are then mounted onto a functionalized glass slide by bringing the tissue section in contact with the glass surface. The glass, tissue section, and agarose are then heated to facilitate removal of the agarose gel while retaining the tissue section on the glass surface.
Figure 4B:
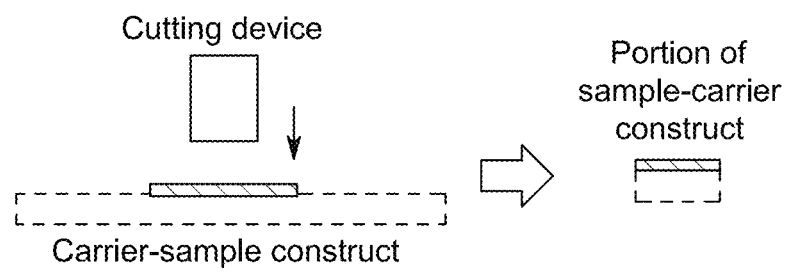
Figure 4C:
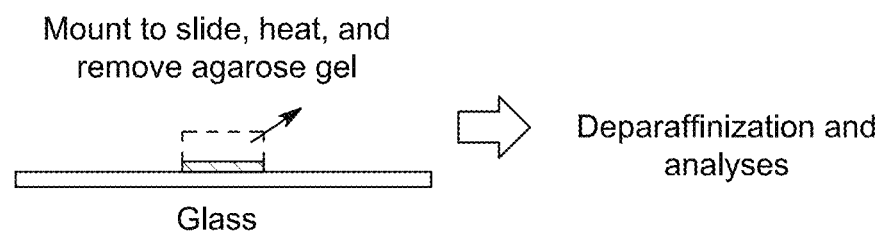
Figure 8:
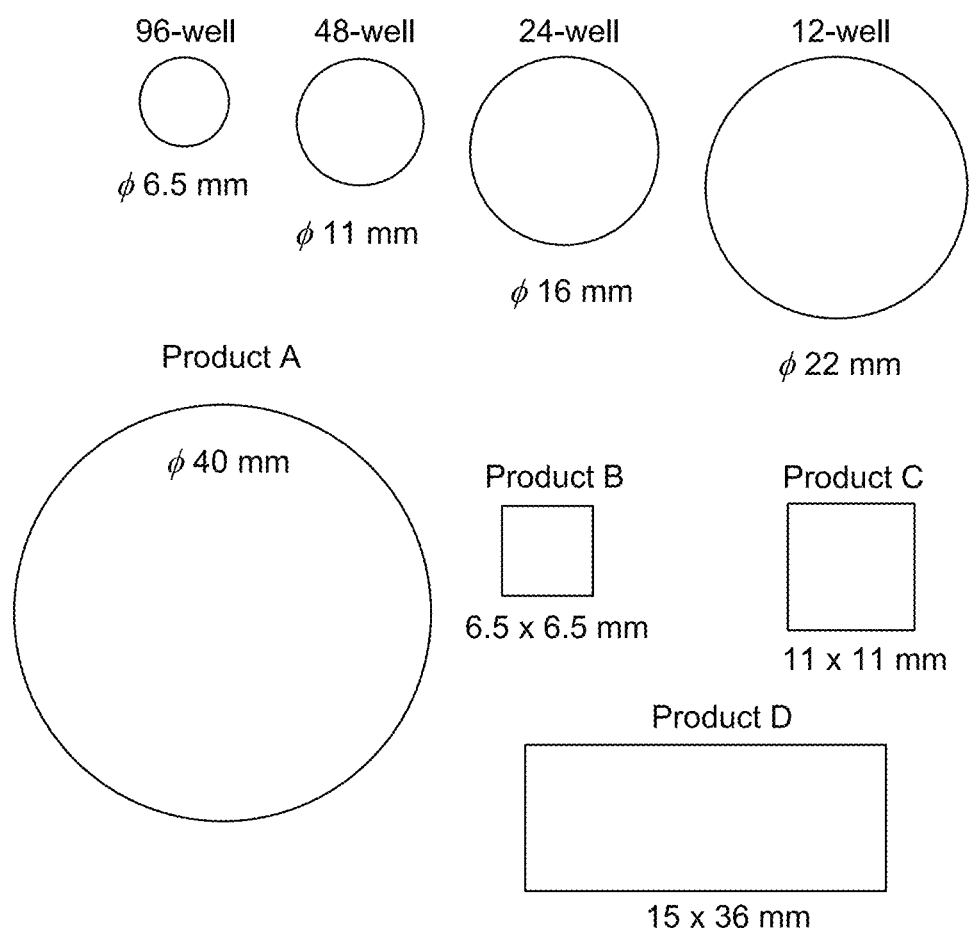
FIG. 8 is an illustration comparing the diameter and dimensions of individual wells in 96-well, 48-well, 24-well, and 12-well plates, and tissue capture areas of several commercial products. The methods described herein may be cut to any of the dimensions depicted in FIG. 8.

In an embodiment, the tissue section is transferred from a carrier substrate (e.g., a hydrophilic polymeric layer) to a receiving substrate (e.g., charged glass surface). In embodiments, the carrier substrate includes agarose, gelatin, polyacrylamide, or any suitable hydrogel. In embodiments, the carrier substrate includes a hydrophilic surface (e.g., an interfacial water layer). The hydrophilic surface maintains the tissue section wet at the point of contact with the underlying attachment surface and prevents damage to the tissue during the transfer process. As an example, an agarose gel layer with similar dimensions to the charged glass slide is prepared for use as a carrier substrate using methods described. The concentration of agarose is chosen to provide optimal support for the tissue section to be transferred, and to prevent tissue section distortion during subsequent transfer steps. For example, an agarose gel medium is prepared by dissolving agarose powder in boiling deionized water such that the final concentration of the agarose gel is between 2% to 5%. The dissolved agarose is then poured into a 4-well plate mold and cooled to cast the gel. In embodiments, and depending on the thickness of the tissue section, an agarose concentration of at least 5% or higher may be preferable preferred when facilitating tissue transfer to avoid fracturing the agarose layer. Once the agarose surface is prepared, the agarose surface and tissue section (e.g., a FFPE tissue section) are contacted in a warm water bath (e.g., a water bath with a temperature setpoint of about 42° C.) such that the FFPE section can become captured on the surface of the agarose gel layer (see, e.g., FIGS. 3A-3B and FIGS. 4A-4C). The agarose contacted FFPE section is then removed from the incubation bath and allowed to cool. Portions of the agarose-FFPE construct are then cut and removed, (e.g., punched-out using a small hole punch with sharp edges), and subsequently mounted on a charged glass slide such that the FFPE section is contacted directly with the glass surface (see FIG. 2C and FIGS. 4B-4C). The removed portion may be cut according to any dimension depending on the application, for example the diameter and dimensions of individual portions may be suitable for use in 96-well, 48-well, 24-well, and 12-well plates. The methods described herein may be cut to any of the dimensions depicted in FIG. 8. The agarose-tissue section cutout is then heated (e.g., heated to anywhere between 42° C. or 67° C.) to facilitate release of the agarose layer from the slide, leaving behind the FFPE tissue section on the glass slide.

Figure 12:
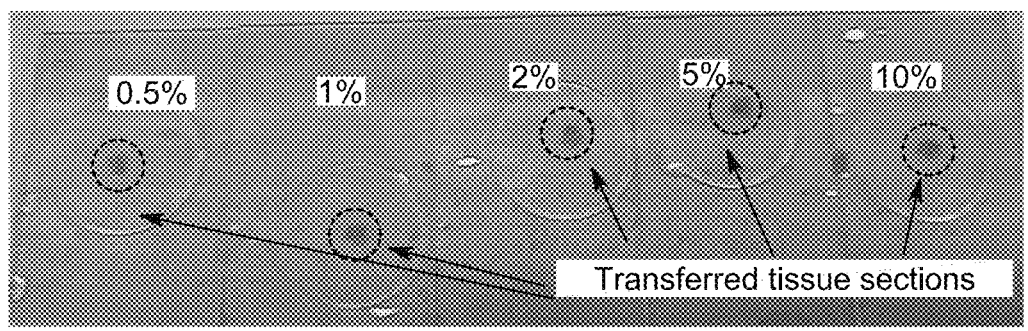
FIG. 12 shows a photograph of several tissue section samples transferred from a series of agarose gel layers. Each agarose gel layer contained a different weight percentage of agarose (e.g., 0.5%, 1%, 2%, 5%, or 10%, as indicated in the photograph). The tissue section cutouts were generated from human kidney tumor tissue sections transferred from the different agarose polymeric gels (i.e., following the protocol illustrated in FIG. 2C and FIGS. 4B-4C). All tissue sections were deparaffinated and stained with eosin Y for 10 sec prior to imaging to provide contrast in the images.

When considering a carrier substrate for effective tissue transfer onto a receiving substrate, for example, the carrier substrate composition (e.g., the percentage of agarose in an agarose gel layer) should withstand manipulation (e.g., have a Young's modulus to support handling by a user during tissue section catching, cutting, and transferring, wherein the Young's modulus is between about 5 kPa to about 2.5 MPa, or more) while effectively transferring the tissue section onto the receiving substrate. As illustrated in FIG. 12, several tissue section samples were transferred from a series of agarose gel layers, wherein each agarose gel layer contained a different weight percentage of agarose (e.g., 0.5%, 1%, 2%, 5%, or 10%, as indicated in the photograph). Both 0.5% and 1% agarose gel layers effectively transferred the tissue sections, as shown in FIG. 12, but may require additional care while handling due to their low expected compression modulus (e.g., about 5 kPa and about 40 kPa, respectively), in contrast with the 2%, 5%, and 10% agarose gel layers, each of which have a higher expected compression modulus (e.g., about 100 kPa, about 900 kPa, and about 2.5 MPa, respectively). An agarose gel layer with a higher compression modulus of about 100 kPa to about 1 MPa, or more, may therefore provide easier handling while retaining effective tissue transfer properties as described herein. Additional information on the mechanical properties of agarose gels is described, e.g., in Normand V et al. Biomacromolecules. 2000; 1 (4): 730-8, which is incorporated herein by reference in its entirety.

In another embodiment, a fresh frozen tissue section is prepared using a cryostat with a temperature setpoint of about −15° C. to about −25° C. The tissue section is then mounted directly onto a carrier substrate (e.g., an agarose polymeric layer) to transfer it onto a glass slide or multiwell plate, bypassing the water bath floating step that described supra for FFPE tissue section transfers. As described in FIG. 8, the capture regions of various sizes of multiwell plates and commercial slides can vary in surface area, and each may be suitable for use in an embodiment of the invention. As the polymeric layer has reversible adherence to the fresh frozen tissue section, the issues that typically exist when mounting frozen tissue sections onto glass slides (e.g., rapid melting and binding) are overcome using the methods described herein.

Figure 5:
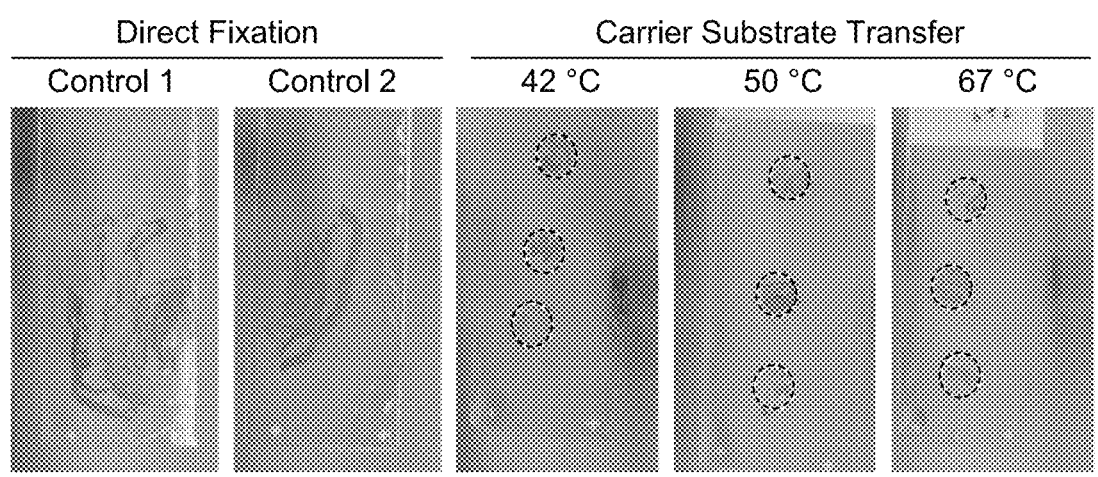
FIG. 5 shows a series of photographs of several agarose layers containing tissue samples. The first two images show two control slides prepared by direct fixation of the complete tissue section onto the slides (e.g., the process depicted in FIG. 3B). The next three slides represent tissue section cutouts generated from tissue sections transferred with an agarose polymeric gel as the carrier substrate (i.e., following the protocol illustrated in FIG. 2C and FIGS. 4B-4C), and then heated to either 42° C., 50° C., or 67° C. prior to removal of the agarose layer. All tissue sections were deparaffinated and stained with eosin Y for 10 sec prior to imaging to provide contrast in the images.

FFPE tissue sections were transferred using agarose as a carrier substrate. Briefly, once the agarose-FFPE constructs were cut out and placed on a glass slide, several temperatures were assessed for removing the agarose. The slides were incubated at either 42° C., 50° C., or 67° C. for about 10-15 min, and subsequently the agarose layer was removed using tweezers, leaving the intact tissue on the glass slide (see, e.g., FIG. 5). FIG. 5 shows a series of photographs of several agarose layers containing tissue samples. The first two images show two control slides prepared by direct fixation of the complete tissue section onto the slides (e.g., the process depicted in FIG. 3B). The next three slides represent tissue section cutouts generated from tissue sections transferred with an agarose polymeric gel as the carrier substrate (i.e., following the protocol illustrated in FIG. 2C and FIGS. 4B-4C), and then heated to either 42° C., 50° C., or 67° C. prior to removal of the agarose layer. All tissue sections were deparaffinated and stained with eosin Y for 10 sec prior to imaging to provide contrast in the images. FIG. 5 shows the carrier-assisted transfer methods are successful at transferring a complete tissue section (i.e., Control 1 and Control 2) and portions of tissue sections over a range of temperatures.

Figure 6A:
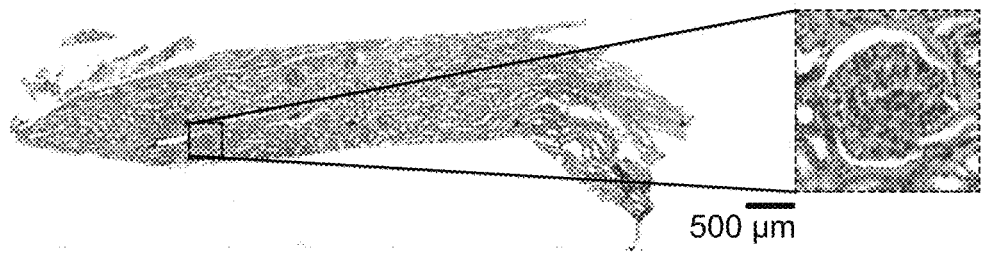
FIGS. 6A-6C show human kidney samples.
Figure 6B:
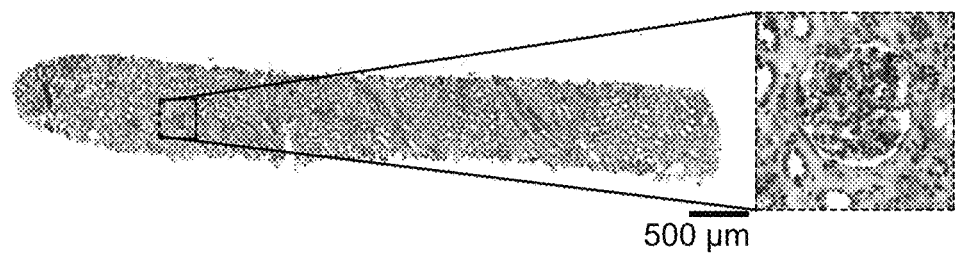
Figure 6C:
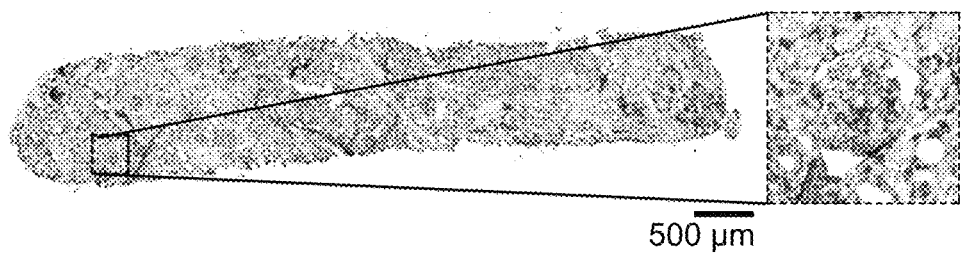

In another example, 5 μm thick sections of human kidney FFPE samples were generated and transferred using an agarose polymeric layer onto functionalized glass substrates as described herein. See FIGS. 6A-6C. FIG. 6A shows an H&E stained human kidney sample that was i) captured on a carrier substrate to form a sample-carrier construct; ii) a portion of the carrier substrate was removed and the portion was mounted on a receiving substrate, iii) the carrier substrate was removed, and iv) the immobilized sample was stained with H&E stain. FIG. 6B shows an H&E stained human kidney sample that was i) captured on a carrier substrate to form a sample-carrier construct, ii) the construct was deparaffinated, iii) a portion of the carrier substrate was removed and the portion was mounted on a receiving substrate, iv) the carrier substrate was removed, and v) the immobilized sample was stained with H&E stain. FIG. 6C shows an H&E stained human kidney sample that was i) captured on a carrier substrate to form a sample-carrier construct, ii) the construct was deparaffinated, iii) the deparaffinated construct was stained with eosin Y stain; iv) a portion of the carrier substrate was removed and the portion was mounted on a receiving substrate, and v) the carrier substrate was removed. The deparaffinated construct of FIG. 6C was stained with 1/10 of the concentration used in typical eosin Y staining. The boxes are indicative of glomeruli. Each slide was baked at 50° C. for 15 min followed by incubating at 60° C. for 30 min. Deparaffinization was performed with xylene, followed by 4% PFA fixation for 1 hr at room temperature, two water washes, and staining. Using the procedures described herein, it was found that the human kidney tissue section transferred using an agarose polymeric layer to a glass slide was flat and had intact morphological features (e.g., intact glomeruli).

Various properties of the carrier substrate being used may be optimized for more effective transfer of the tissue section, including the stiffness of the hydrophilic material, for example, whether the layer forms a softer or harder gel. The thickness of the gel may also contribute to whether there is any deformation of the tissue section while it is being cut from the construct. The methods presented herein describe a novel approach to transferring fresh or preserved tissue sections onto a final medium (e.g., a receiving substrate, such as a functionalized glass slide) that minimizes tissue damage and is scalable, flexible, and also compatible with the conventional lab equipment and consumables, enabling easy adaptation and automation.

Example 2. Tissue Transfer and Surface Functionalization

Preparing a surface for tissue section mounting is a critical step in minimizing loss of tissue material during subsequent processing. For example, repeated exposure to immunohistochemistry reagents and solvents used during analysis may lead to loss of cellular or tissue section material if the tissue section is weakly bound to the surface. The conditions involved in in situ sequencing processes also involve elevated pH and incubation temperatures, in addition to the addition and removal of various fluids repeatedly. Lack of strong binding of the tissue section to the surface may therefore lead to detachment of the tissue section during in situ sequencing. Some common methods of preparing a surface for tissue section mounting, for example, a glass slide, include plasma treatment and functionalization with charged moieties. To determine the optimal surface functionalization conditions, we performed a comparison of several surface functionalization reagents, including (3-aminopropyl)triethoxysilane (APTES), (5,6-epoxyhexyl)triethoxysilane (EHTES), polyethyleneimine (PEI), or a combination thereof. Tissue sections were then transferred to the functionalized glass slide surfaces using the methods described herein, and tissue integrity cycles in the presence of various buffers performed to assess for any tissue section detachment from the treated glass slides.

Glass functionalization: Glass slides were washed three times in an acetone/ethanol bath while being sonicated. The glass slides were then oxygen plasma-treated (100 mTorr for vacuum, 1 Torr oxygen injection for 3 mins, plasma treatment at high power for 6 mins). Glass slides were then submerged in EtOH with either 1% APTES or 1% EHTES and incubated overnight. Following the overnight treatment, the slides were washed three times with EtOH and dried with an air gun. For PEI functionalization, the slides were incubated with 50 µg/mL in deionized water for 30 min followed by three washes with deionized water.

Tissue transfer and deparaffinization: Mouse intestine FFPE tissue sections were prepared and mounted on an agarose layer using the transfer methods described in Example 1. The agarose-mounted tissue sections were stored at 4° C. for about 2 months prior to being cut into 6.5 mm diameter portions (i.e., to fit in a well of a 96-well plater, see FIG. 8 for various comparative well dimensions) using a blade and transferred to each of the functionalized glass slides. 24 portions were cut and transferred to each glass slide. Following tissue section transfer, the slides were baked at 50° C. for 15 mins and the agarose layer removed. The slides were then baked at 60° C. for 30 mins and placed in dark storage at room temperature overnight. The tissue sections were then deparaffinized using xylene followed by 100% EtOH incubation. The slides were dried at 37° C. for 15 mins.

Plate assembly and rehydration: The slides were then assembled onto a bottomless 96-well plate. The slides were attached to the 96-well plate using a Kapton double-sided adhesive cut using a Silhouette Curio cutter. Samples were then serially incubated in 100%, 96%, and 70% EtOH for 5 mins each followed by incubation in deionized water.

H&E staining: Tissue sections were then fixed with 4% PFA in PBS for 30 min. Samples were then H&E stained using methods known in the art and imaged using a color camera.

Figure 7A:
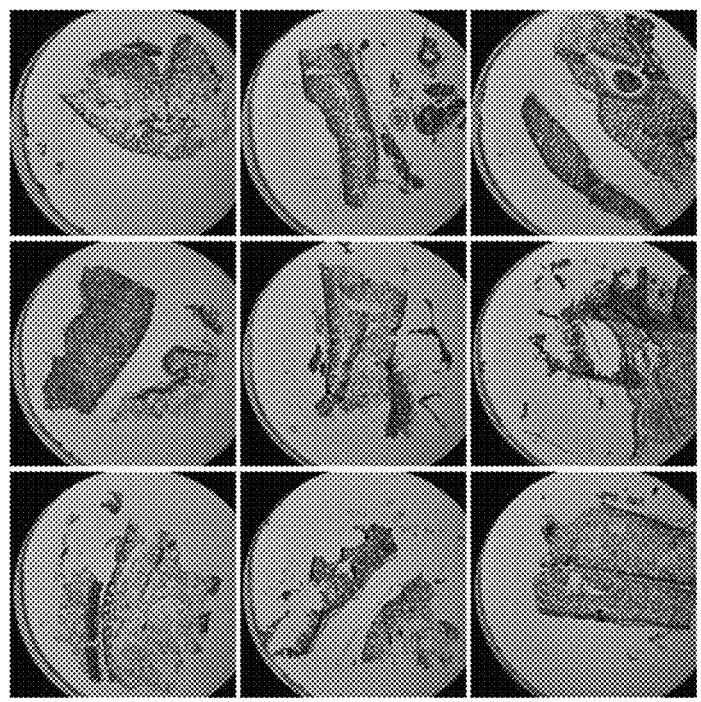
FIGS. 7A-7H are images of H&E-stained tissue sections mounted on functionalized glass slides in a 96-well plate and subjected to 18 cycles of heat and chemical treatment, consistent with DNA sequencing reaction conditions, referred to as tissue integrity tests.
Figure 7B:
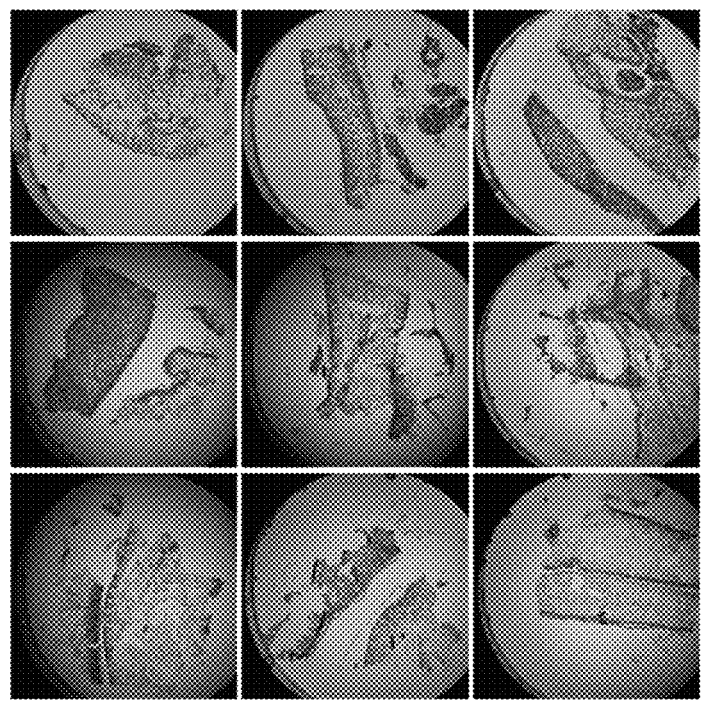
Figure 7C:
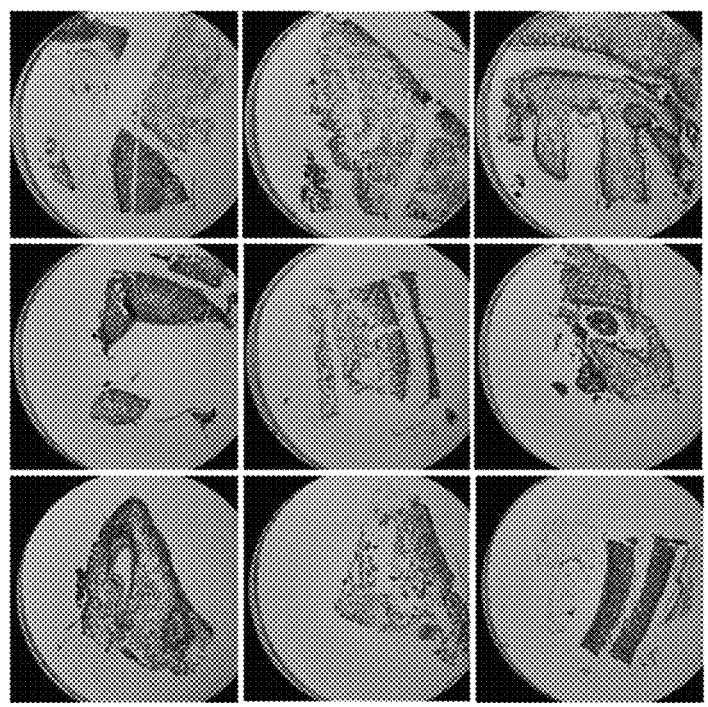
Figure 7D:
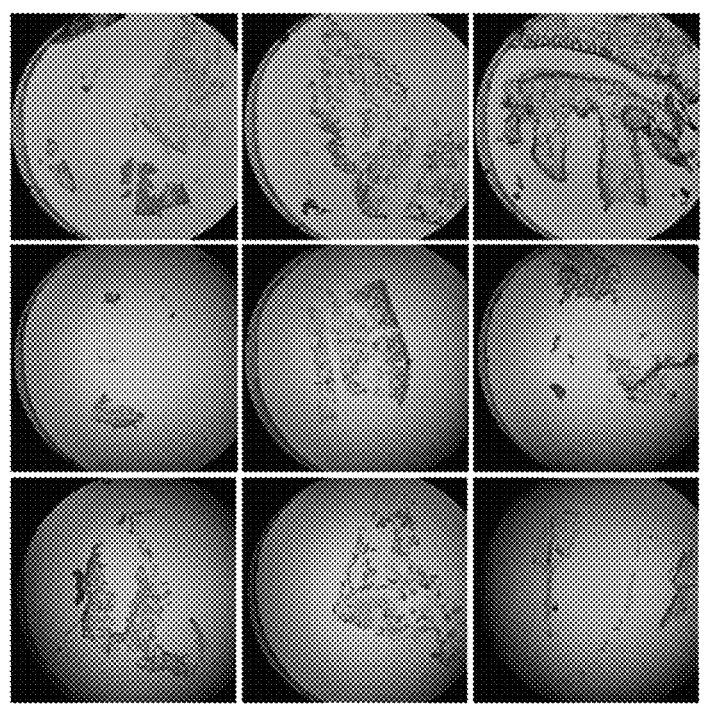
Figure 7E:
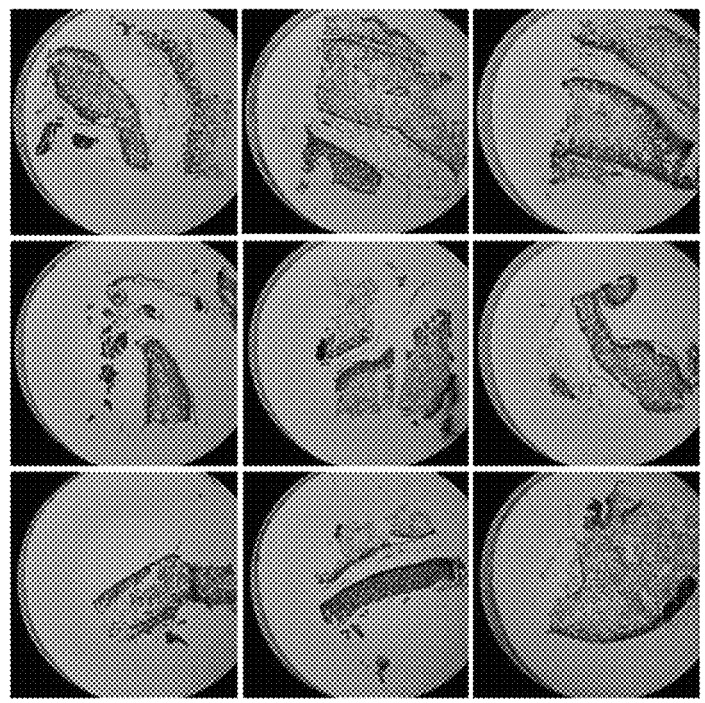
Figure 7F:
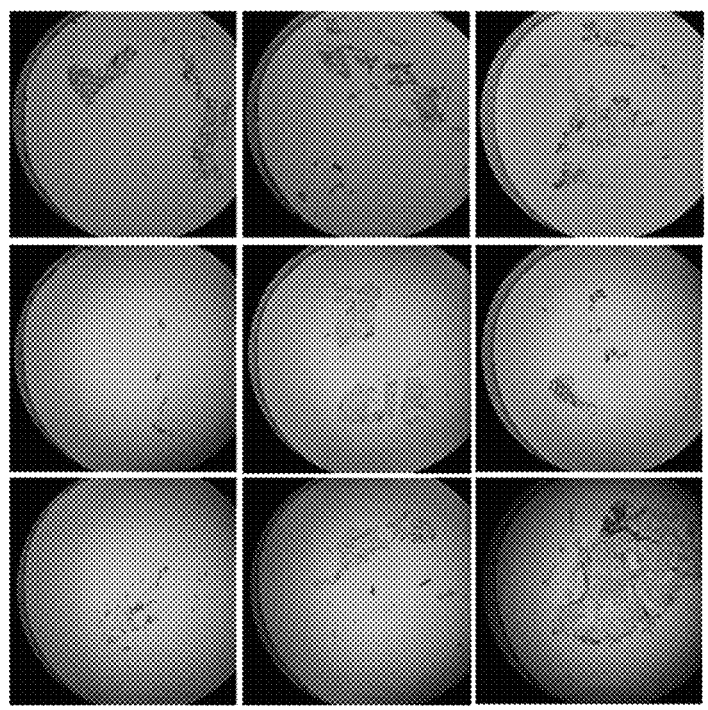
Figure 7G:
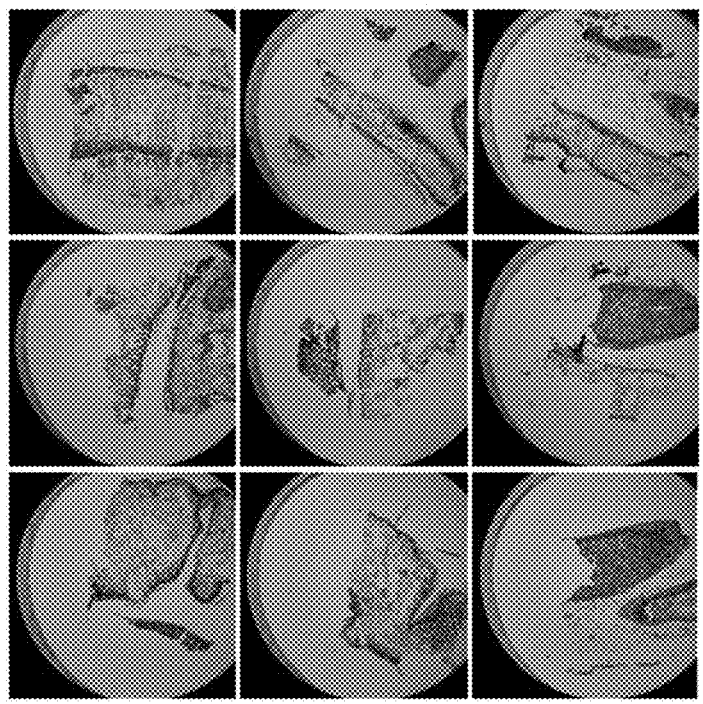
Figure 7H:
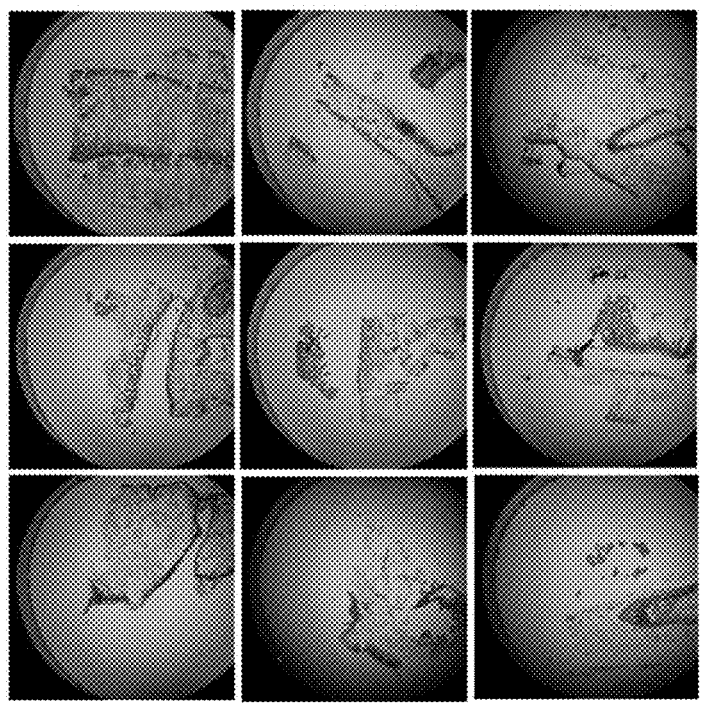

Tissue integrity tests: The 96-well plate was then subjected to 18 cycles of heat and chemical treatment, consistent with conditions useful for DNA sequencing reactions. The wells were exposed to different buffers and different reagents commonly used in amplification and sequencing reactions. For example, each cycle included a 60 sec incubation in an amplification buffer, a 240 sec incubation in sequencing buffer, a 420 sec incubation in a reducing agent, with all incubations performed at 55° C. At the end of each cycle, room temperature wash buffer was applied, and the subsequent cycle initiated. Following the integrity cycles, the tissue sections were then H&E stained and imaged using a color camera (see, FIGS. 7A-7H). FIGS. 7A-7H are images of H&E-stained tissue sections mounted on functionalized glass slides in a 96-well plate and subjected to 18 cycles of heat and chemical treatment, consistent with DNA sequencing reaction conditions, referred to as tissue integrity tests. FIG. 7A shows tissue sections mounted on an APTES-functionalized wells; and FIG. 7B shows the same tissue sections after the 18 cycles of tissue integrity testing. FIG. 7C shows tissue sections mounted on a (5,6-epoxyhexyl) triethoxysilane (EHTES)-functionalized slide, and FIG. 7D shows the same tissue sections after the 18 cycles of tissue integrity testing. FIG. 7E shows tissue sections mounted on an EHTES and polyethyleneimine (PEI)-functionalized slide, and FIG. 7F shows the same tissue sections after the 18 cycles of tissue integrity testing. FIG. 7G shows tissue sections mounted on a PEI-functionalized slide, and FIG. 7H shows the same tissue sections after the 18 cycles of tissue integrity testing.

Constructing a receiving substrate capable of surviving thermal/chemical cycling is useful for retaining the tissue during subsequent analyses. As shown in FIGS. 7A-7B, tissue sections mounted on APTES-functionalized surfaces did not appear to have any significant tissue loss or degradation after 18 cycles. In contrast, the EHTES (FIGS. 7C-7D), EHTES+PEI (FIGS. 7E-7F), and PEI (FIGS. 7G-7H) treated surfaces exhibited greater loss of tissue section material following the thermal/chemical cycling. Without wishing to be bound by any theory, the APTES-functionalized surface successfully retained a majority of the tissue due to the positive charge of the amines covalently bound to the glass which facilitate strong attachment forces and preventing tissue section detachment. PEI attaches to the tissue via an electrostatic bonding, and was likely washed away during the integrity testing. These results indicate that the tissue transfer methods of the invention are compatible with downstream in situ analytical approaches, including immunohistochemistry and multiwell plate sequencing.

Example 3. Biomolecule Detection

A wealth of information is reflected in the temporal and spatial variation of gene and protein expression among cells. Cellular macromolecules such as nucleic acids and proteins, occupy precise positions in cells and tissues, and a great deal of information is lost when these molecules are extracted. The methods available today for RNA sequence analysis (RNA-Seq) have the capacity to quantify the abundance of RNA molecules in a population of cells with great sensitivity. Current methods for single-cell RNA and protein analysis typically involve some method for "barcoding" the content of individual cells, followed by pooling the content and sequencing on a commercial DNA sequencing device (e.g., Illumina NextSeq™ 500/550, MiSeq™, HiSeq™ 2500/3000/4000, or NovaSeq™). The barcoding can be done in individual wells on a microplate (e.g., a microplate with 96, 384, or 1536 wells), and more recently droplet-based methods are emerging as an essential tool for single-cell genomics research (see for example, Klein A. and Macosko E. Lab Chip. 2017; 17 (15): 2540-2541; and Zheng, G. X., et al. Nature communications, 2017; 8, 14049). Briefly, droplet-based methods begin with isolating a cell from a sample (e.g., a tissue) and encapsulating the cell in a droplet where unique identifying oligonucleotides (i.e., barcodes) are incorporated into the genomic sequence, often while converting RNAs to cDNAs during reverse transcription. These barcodes uniquely label the cDNA and identify the cellular origin. The cDNAs are then extracted and undergo standard library preparation for sequencing before being sequenced on a commercial sequencer. mRNA expression is then quantified by counting the number of barcodes that mapped to each cell.

These methods have found wide application dissecting transcriptomic heterogeneity, and can handle upwards of 10,000 cells in an automated format, however they have several limitations and drawbacks. For example, if the cells of interest originate from a tissue sample, all information about the spatial distribution of the cells within the tissue is lost in the process of dissociating and isolating the cells prior to barcoding them. Often information about the intracellular distribution of analytes within the cellular microenvironment is also lost. This information can be vital to designing therapeutic approaches to cancers, for example, where the tumor microenvironment often creates spatial gradients of nutrients and metabolic byproducts. Droplet-based techniques are capable of barcoding and sequencing tens of thousands of cells (e.g., 10-50 thousand cells) in a single experiment but current approaches require generation of custom microfluidic devices, reagents, and sample preparation techniques (e.g., as found in the disclosures RE41,780 and US 2015/0225778). Additionally, due to the digital "counting" nature of the sequencing readout, hundreds of sequencing reads/cell are required to get information about the expression of less abundant genes. For example, if a particular abundant gene is transcribed into 500 copies of RNA, the abundant gene will dominate the sequencing run resulting in relatively inefficient use of sequencing capacity. However, cells can associate with multiple barcodes which significantly impacts single-cell analyses and rare cell events (Lareau, C. A., et al. (2020) *Nature communications,* 11 (1), 866).

Described herein are methods for addressing these and other problems in the art. An aspect of the invention is to allow the readout of multiple RNA transcripts. In embodiments, the method includes targeting specific RNA sequences, and "translating" them to a DNA barcode, with a means for local amplification. The method includes selecting barcodes that are widely spaced in the combinatorial space of possible barcodes (large Hamming distance). The method may include sequencing or otherwise detecting the barcodes. The methods described herein (for example within the aspects and embodiments) reveal the distribution of specific RNA molecules in cells and tissues. In this way, patterns of differential gene expression may be observed which aids in the understanding of a particular gene's function, and ultimately the phenotype of the cell. The human genome contains on the order of 25,000 genes which work in concert to produce on the order of 1,000,000 distinct proteins. A single mass spectrometry experiment can identify about 2,000 proteins or 0.2% of the total (Mirza, S. P., & Olivier, M. (2008). Physiological genomics, 33 (1), 3-11), highlighting the need for novel approaches to identify more proteins. Certainly, when one considers the levels of mRNA are not proportional to the expression level of the proteins they code for, it is beneficial to determine the proteome of a sample (e.g., a cell).

Figure 14A:
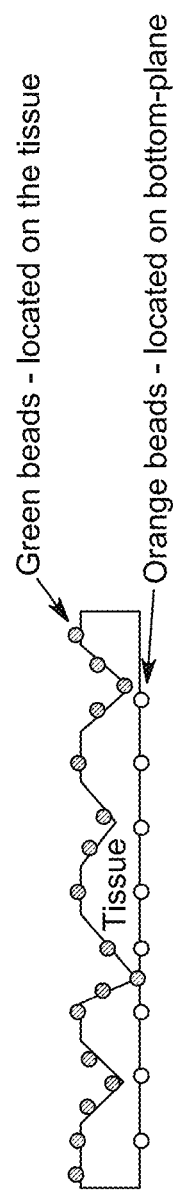
FIGS. 14A-14C.
Figure 14B:
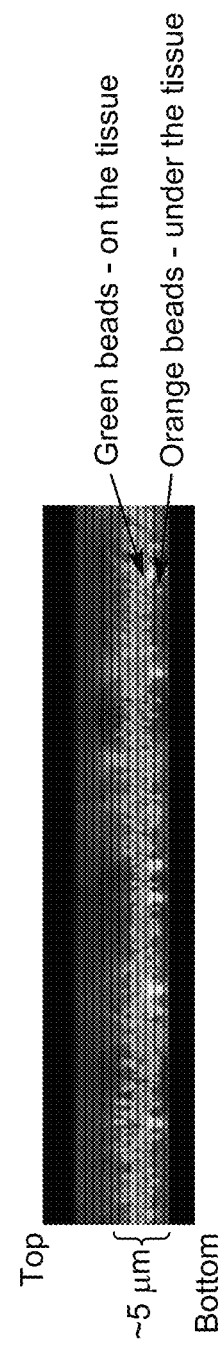
Figure 14C:
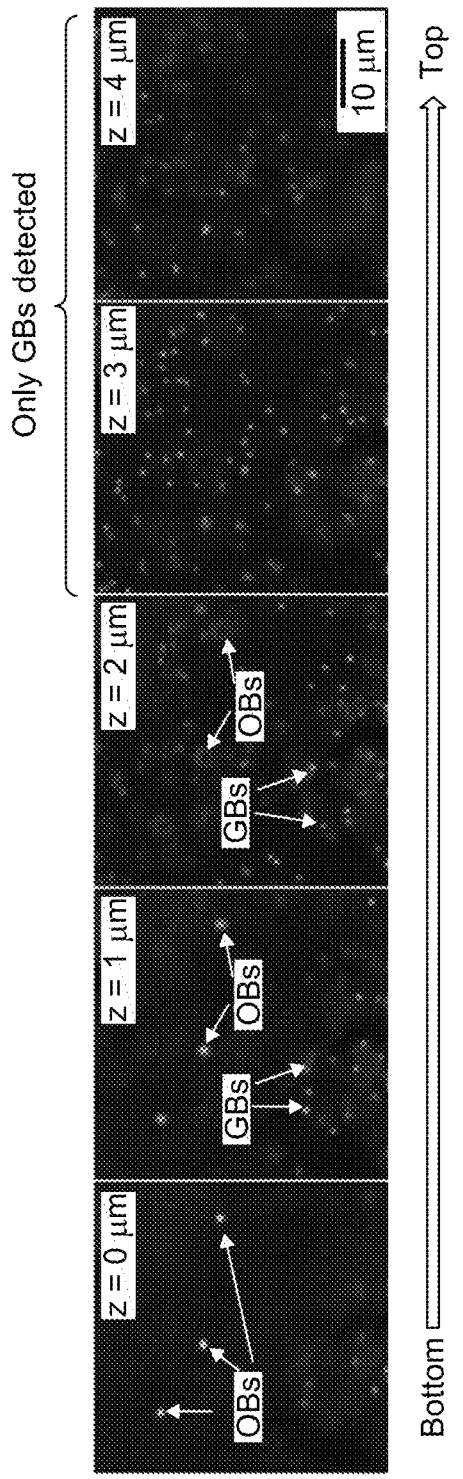

Existing methods for focusing while imaging samples prepared for fluorophore detection (e.g., tissue section samples on a slide) are typically performed with the assistance of fluorescent beads added to the tissue sections prior to imaging. For example, the use of orange fiducial beads on the surface of a coverslip over an in situ sample has been reported for use as a spatial reference to correct for slight misalignments in the microscope stage position over imaging rounds (see, e.g., Zhang M et al. Nature. 2021; 598 (7879): 137-143). Tetraspeck fluorescent microspheres (Invitrogen™) are also commonly used for image alignment under a coverslip (see, e.g., U.S. Pat. Pub. 2010/0047924, which is incorporated herein by reference in its entirety). Described herein are improved methods for image focusing using differentially labelled beads. In embodiments, two or more differentially labelled beads are added to a tissue section, wherein one type of labelled bead is placed under the tissue section, and another type of labelled bead (e.g., labelled with a different fluorophore than the first bead type) is placed across the surface of the tissue, in combination with the tissue transfer methods and embodiments described herein. The combination of differentially colored beads (as illustrated in FIGS. 14A-14C, e.g., wherein "green beads" are located across the surface of the tissue sample, and wherein "orange beads" are located on the bottom plane of the sample) may be used as fiducial markers for a variety of applications. The use of two bead types provides focusing beads (e.g., the green beads) in a plurality of z-axes, while also providing detectable beads (e.g., orange beads, such as Tetraspeck) on the bottom-plane as a reference marker (see, e.g., FIGS. 14B-14C for an example of two-bead detection across a 5 µm tissue section, wherein OBs are detected primarily near the bottom of the tissue, and GBs are detected throughout the sample) for, e.g., camera tip-tilt calculations, channel-to-channel, cycle-to-cycle, and z-stack image registration after sequencing, thereby facilitating improved 3D image alignment.

Section of human kidney FFPE samples were generated and transferred using an agarose polymeric layer onto functionalized glass substrates as described herein. Following immobilization on the receiving substrate, the sample was subjected to pepsin digestion and permeabilization by contacting the sample with an endopeptidase (e.g., 0.01% Pepsin in 0.1N HCl at 37° C.), washing with PBS, and contacting with a surfactant (e.g., 0.5% Triton-X) for 20 to 30 minutes. Two detection modalities were employed: i) padlock probe hybridization and detection and ii) FISH detection of the PLP rolling circle amplification (RCA) products.

Padlock probe detection: To demonstrate the ability of our approach to detect occurrences of transcripts from multiple genes from a transferred kidney tissue section, we probed for the presence of specific genes known to exist in particular regions of the kidney (e.g., the descending limb, the thick descending limb, and collecting duct). For example, in the descending limb the gene targets include SPP1 and VCAM; in the thick ascending limb the gene target is SLC12A1; and within the collecting duct the gene target is AQP2. The transcript for each gene was targeted by 3 padlock probe (PLP) designs, each targeting different regions of the same transcript. Each of the 3 PLPs for the same transcript had different feet (complementary to the target sequence), but the same 10 base barcode in the backbone of the PLP. All PLPs had the same structure from 5' to 3': a first domain (also known as a "foot" or "pad") capable of hybridizing to a first target sequence, a sequencing primer binding sequence, an oligonucleotide barcode from a known set of barcodes, an amplification primer sequence, and a second foot capable of hybridizing to a second target sequence adjacent to the first target sequence.

Hybridization and Probe Ligation: Padlock probes (PLPs) were added at a final concentration of 100 nM each. PLPs were then allowed to hybridize overnight at 37° C. The tissue sections were then washed 1× with a hybridization buffer for 5 min at 37° C. and 2× with 1×PBS for 5 min each at 37° C. Following the washes, SplintR® ligase (New England Biolabs Catalog #M0375S) was added at a final concentration of 2.5 U/uL with 0.2 U/uL SUPERase-In™ RNase inhibitor (Thermo Fisher Catalog #AM2694) in 1× SplintR ligase buffer and incubated for 30-60 min at 37° C. Tissue sections were then washed 1× with 1×PBS and 2× with hybridization buffer.

Rolling Circle Amplification: Phosphorothioated amplification primer was added at a final concentration of 0.5 uM in hybridization buffer and incubated for 1 hr at 37° C. Tissue sections were then washed 1× with hybridization buffer and 2× with 1× PBS. A mutant version of phi29 DNA polymerase was then added with dNTPs (0.5 mM each type, e.g., ddA, ddC, ddG, and ddT), aminoallyl-dUTPs, and 0.2

U/uL SUPERase-In™ RNase inhibitor in DEPC-treated water and incubated for 1 hr at 37° C. Tissue sections were then washed 3× with 1×PBS.

Crosslinking: BS(PEG) 9 was then added at a final concentration of 5 mM in 1×PBS and incubated for 30 min at RT. Tissue sections were then washed 1× with 1× PBS, and 1 M Tris (pH 8.0) added and incubated for 15 min at RT. Tissue sections were then washed 3× with wash buffer (Tris, pH 8.0) and detection was performed.

Detection: TetraSpeck™ microspheres were added to crosslinked tissue sections and allowed to settle for at least 30 min at RT, or centrifuged for 3 min at 2,000 RPM. Prior to the addition of the sequencing primer, tissue sections were incubated with a polymerase, ddNTPs (each type, e.g., ddA, ddC, ddG, and ddT) in flow cell incorporation buffer for 20 min at 55° C. Tissue sections were then washed 3× with a wash buffer (WB), followed by incubation with a second buffer at 55° C. for 20 min and another three washes with WB. Then the sections are incubated with 1U/uL TdT (Thermo Scientific) and ddNTPs (each type, e.g., ddA, ddC, ddG, and ddT), in 1× TdT buffer for 30 min at 37° C. Sequencing primer was then added in hybridization buffer and incubated for 30 min at 37° C. The tissue sections were then washed 3× with flow cell wash buffer, and sequencing-by-synthesis with detectable nucleotides was performed for 5 cycles.

Figure 9:
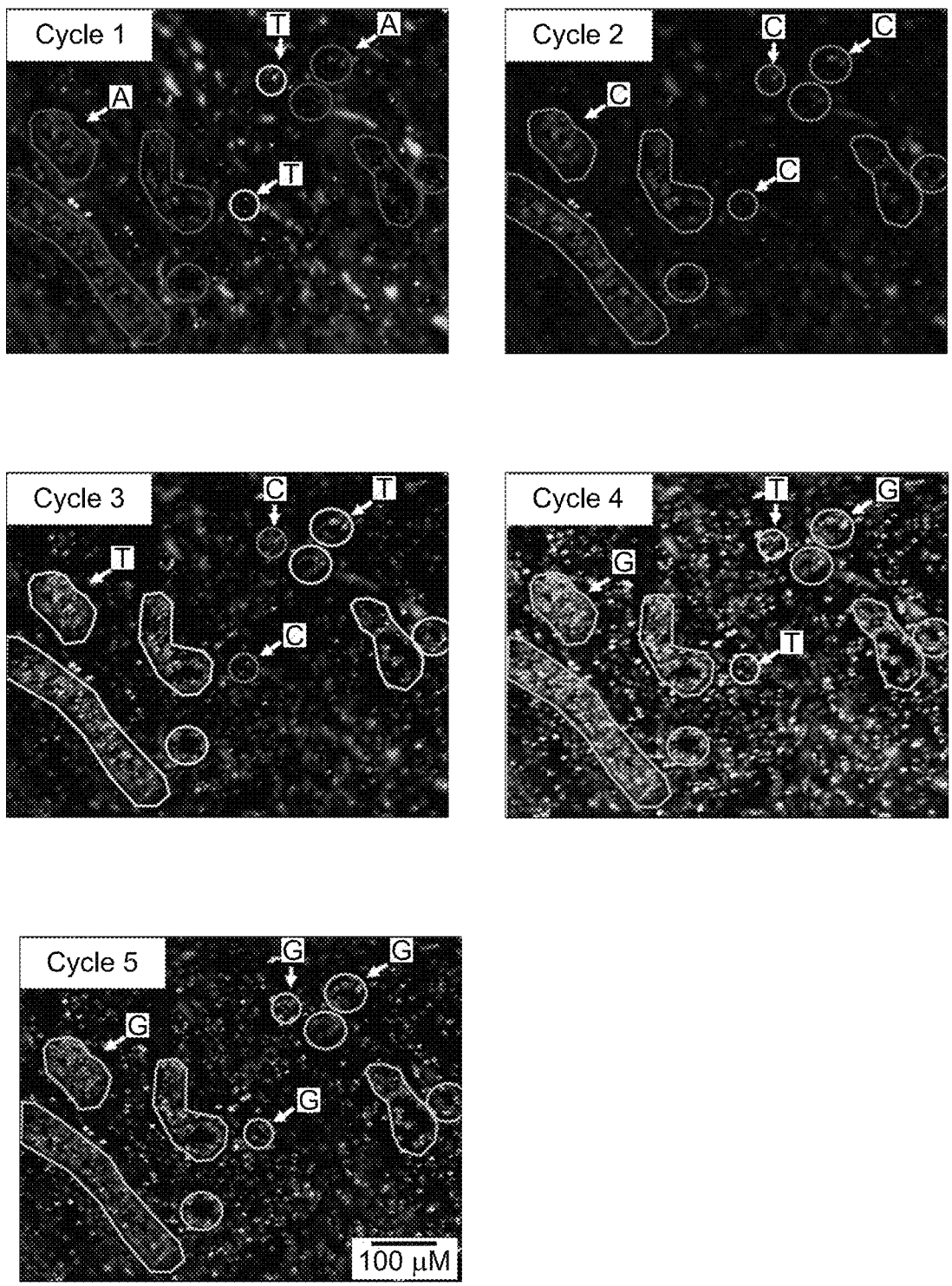
FIG. 9 presents a set of fluorescence microscopy images of cells probed in a multiplex fashion (i.e., simultaneous detection) for 2 genes across 5 in situ sequencing cycles on tissue sections immobilized using the methods described herein. Each tile has two genes highlighted for PLP barcode sequencing: AQP2 and SPP1. The transcript for each gene was targeted by 3 PLP designs, each targeting different regions of the same transcript. Each of the 3 PLPs for the same transcript had different feet (i.e., sequences complementary to the target sequence) but the same 10 base barcode in the backbone of the PLP. The changing color (color not shown) of each dot per cycle is mapped to an appropriate base (A, T, C or G) and the change in color of a dot across the 5 cycles reveals the barcode, which can be used to identify which gene the transcript is a copy of (see, Table 1).

Each nucleotide within a barcode can also be assigned a series of colors (e.g., colors that are visually distinguishable) for the purpose of visualizing the spatial location of the barcode in a cell. Each sequencing cycle produces varying signal intensities in an optically resolved volume of a sample (e.g., a voxel) for each of the 4 channels. The brightness of the representative pixel corresponds to the local concentration of the barcode and is proportional to the product of the signal and barcode matrices (e.g., the product of the signal and barcode matrices results in a value of 4 for barcode). Note, FIG. 9 is in grayscale and therefore the bases called in each cycle are explicitly denoted in each tile with the base corresponding to the detectable signal (e.g., the base corresponding to the pixel denoted by an arrow). The colors can be mapped to an appropriate base (A, T, C or G) and the change in color of a dot across the 5 cycles reveals its barcode sequence, which can be used to identify the gene (see, Table 1).

TABLE 1

In situ gene-specific barcode sequencing across 5 cycles

| Gene | Cycle 1 | Cycle 2 | Cycle 3 | Cycle 4 | Cycle 5 |
|------|---------|---------|---------|---------|---------|
| AQP2 | A | C | T | G | G |
| SPP1 | T | C | C | T | G |

Reading the sequences as described in FIG. 9, our approach can count and determine the spatial location of transcripts for genes targeted simultaneously in tissue sections immobilized using the methods described herein.

Figure 10:
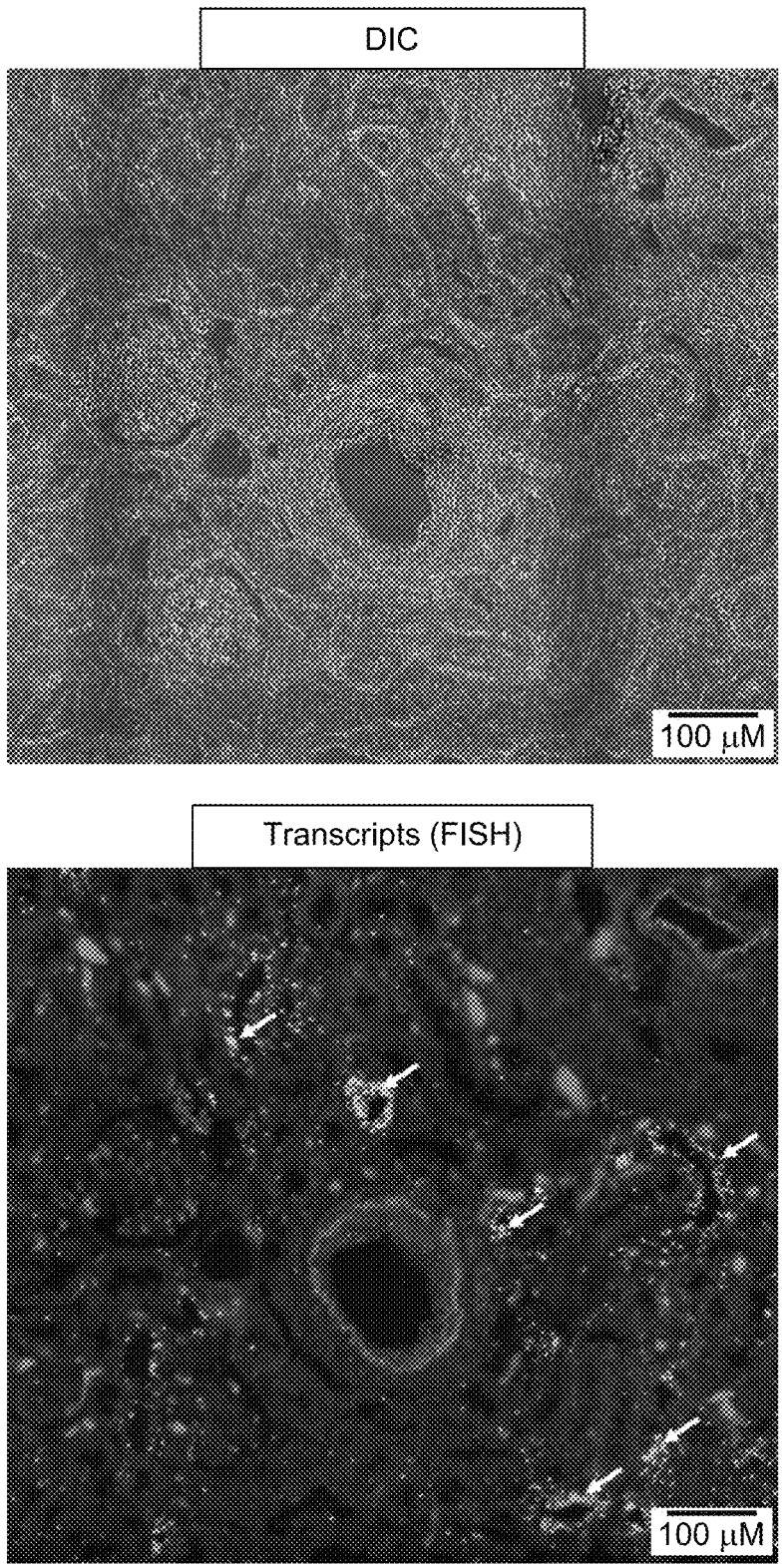
FIG. 10 presents a set of microscopy images of kidney tissue sections immobilized using the methods described herein. The top panel is a differential interference contrast (DIC) image of the immobilized tissue section. The bottom panel is a fluorescence microscopy image of a common FISH probe (e.g., a P5'-Cy5 probe) detecting the amplification products of the PLPs described in FIG. 9. The arrows indicate groups of pixels that were detected with the FISH probe.
Figure 11A:
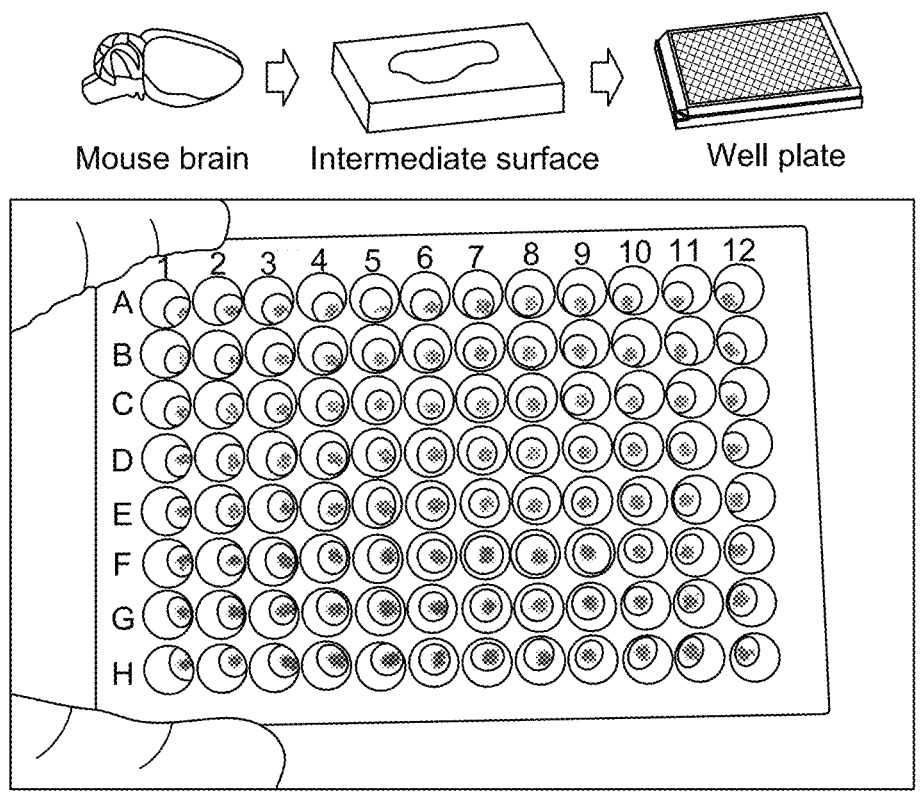
FIGS. 11A-11B.
Figure 11B:
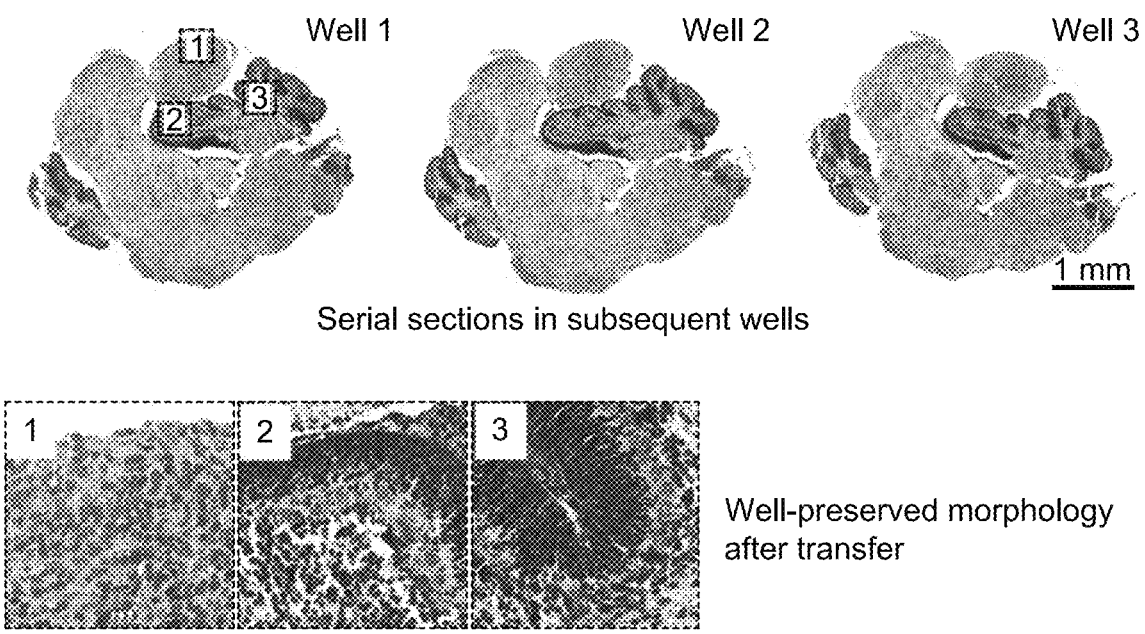

Fluorescence in situ hybridization (FISH) detection. FIG. 10 presents a set of microscopy images of kidney tissue sections immobilized using the methods described herein. The top panel is a differential interference contrast (DIC) image of the immobilized tissue section. The bottom panel is a fluorescence microscopy image of a common FISH probe (e.g., a P5'-Cy5 probe) detecting the amplification products of the PLPs described supra and in FIG. 9. The arrows indicate groups of pixels that were detected with the FISH probe and the relative location of the PLP RCA products within the tissue section. This data demonstrates that detection by FISH of PLP RCA products is successful in kidney tissue sections transferred into a 96-well plate using the methods described herein.

The methods described herein allow for efficient transfer of tissue sections to a receiving substrate without compromising the integrity of the sample. Further, the data presented herein shows subsequent biomolecule detection is possible.

Example 4. Determining a Surgical Margin

For many solid tumors, surgical resection remains the gold standard and tumor-involved margins are associated with poor clinical outcomes. Currently, intraoperative margins evaluation relies on surgeons' sight, palpation, ability to map tumor extension on imaging, and knowledge of anatomy, with some optical imaging technologies aiding the delineation of the mucosal margins of excision, such as intraoperative histopathological assessment of the resection margins by frozen section analysis (FSA) (see, e.g., Giannitto C et al. Front. Oncol. 2021; 11:735002, which is incorporated herein by reference in its entirety). The FSA technique is limited and susceptible to sampling errors. Definitive information on deep resection margins traditionally requires postoperative histopathological analysis.

Surgical margins generally are obtained using two widely-accepted methods: The first is removal of small tissue biopsies from the wound bed by the surgeon. The second is that the entire specimen is examined by the surgeon and/or pathologist after which margins are taken. In addition to determining the presence of tumor in the primary tumor specimen, it is also necessary to determine resection completeness by examining how closely tumor tissue extends to the specimen edges. The presence of tumor tissue within 1 mm of the specimen surface is generally considered a positive margin, while tumor greater than 5 mm away is considered negative. Presence of tumor between 1 and 5 mm from the cut surface is often considered as a close margin (see, e.g., Gao R W et al. Cancer Res. 2018; 78 (17): 5144-5154, which is incorporated herein by reference in its entirety). Near-infrared (NIR) fluorescence imaging using molecular agents has shown promise for in situ imaging during resection. However, for cancers with difficult imaging conditions, surgical value may lie in tumor-mapping of surgical specimens.

Provided herein are methods of determining the size and site of a tissue to be resected from a subject. In embodiments, the method includes immobilizing a tissue sample obtained from the subject onto a hydrogel carrier substrate to generate a sample-carrier construct; contacting the tissue section of the sample-carrier construct with a receiving substrate to generate an immobilized tissue section; removing the hydrogel carrier substrate from the immobilized tissue section; permeabilizing the immobilized tissue section; and contacting a biomolecule (e.g., a tumor-specific biomolecule) from the tissue section with a detection agent thereby detecting the biomolecule in the tissue section, as described herein.

Specific sites in the tissue section are compared, for example, to determine the presence of the tumor-specific biomolecule(s) at different locations in the tissue sample. Based on the comparison, the size and site of a tissue to be resected from the subject is determined. In some embodiments, the biomolecule is a DNA or RNA. In some embodiments, the biomolecule is a messenger RNA (mRNA) molecule. In some embodiments, the biomolecule is a genomic DNA. In some embodiments, the biomolecule includes a full-length sequence of a biomarker described herein. In some embodiments, the biomolecule includes a fragment of the sequence of a biomarker described herein. In some embodiments, the biomolecule is a protein. In some embodiments, the biomolecule is a full-length protein. In some embodiments, the biomolecule is a fragment of a protein. In some embodiments, the biomolecule is a byproduct of a protein. In some embodiments, the protein is any of the exemplary cancer biomarkers described herein.

A non-limiting example of a method for identifying a surgical margin of a tissue to be resected is described herein. Briefly, a biopsy tissue is excised from a subject and imaged for potential tumor tissue cells or other disease related cells (e.g., H&E staining and imaging of the biopsy tissue). After imaging, the tissue is sectioned (in some cases, the tissue is sectioned prior to imaging) and one or more sections of tissue are subjected to the methods described herein for detecting a biomolecule (e.g., one or more tumor-specific biomolecules), as described in Example 3, for example including immobilizing the tissue section onto a hydrogel carrier substrate, generating an immobilized tissue section, removing the hydrogel carrier substrate from the immobilized tissue section, and contacting the biomolecule in the tissue section with a detection agent.

Also provided herein are methods of treating a subject in need thereof that include resecting tissue from the subject using the surgical margin determined by the methods described herein (e.g., the comparison of tumor-specific biomarkers from two or more sites in a tissue section from a subject). For example, when a clinician practices the method, the data obtained can provide the clinician with information on the accurate location of the cancerous or diseased tissue, therefore provide the accurate surgical margin of the tissue to be resected. Using the information of the accurate surgical margin provided by the method described herein, the clinician is able to achieve, e.g., more complete resection, thereby treating the subject.

In some embodiments, the methods described herein are more accurate in determining the surgical margin of a tissue to be resected than the traditional methods, such as medical imaging or scanning methods. In some embodiments, a re-excision includes additional tissue excisions during the initial surgical procedure to obtain the tissue sample. In some embodiments, a re-excision includes additional tissue excisions during a future procedure.

For example, gene expression along the margins of a tissue section indicative of cancer or a disease state and/or the location of receptors along the margins of a tissue section indicative of cancer or a disease state is determined via detecting one or more biomolecules in the tissue section (e.g., detection by sequencing, imaging, and/or immunohistochemical reagent staining and detection). Additionally, known mutations associated with a cancer or disease state can be spatially identified along the margins of a tissue section. Gene expression analysis and/or receptor presence and/or mutational state of cells within the tissue margins can be used to determine whether a surgeon has sufficiently resected the tissue. For example, the presence of one or more genes, receptors and/or mutations indicative of a cancer or disease state in a spatially analyzed tissue margin section would indicate that the resection of the cancerous or diseased tissue was not complete as such a more expanded resection might be necessary. When the tissue section margins are absent of those biomarkers that were used to indicate a cancer or disease state, then a resection could be considered successful for that location.

Example 5. Switchable Skin Specimen Tape Transfer

Skin sample collection via tape stripping is a minimally invasive procedure that is actively used for a number of clinical and research applications. For example, collection of stratum corneum via tape stripping is used in the identification of epidermal biomarkers in skin cancers and inflammatory disorders. Sequential application allows deeper levels of the stratum corneum to be accessed with each strip. Examples of commercial tape stripping solutions include the D-squame skin sample disc (CuDerm) and the Smart Sticker™ (DermTech). Cells captured via tape stripping are then typically contacted with an enzymatic digestion solution to extract genomic material and perform gene expression analysis, for example, as described for RNA profiling of nonlesional psoriatic skin in Tsoi L C et al. J. Invest. Dermatol. 2022; 142 (6): 1587-1596. Skin tape stripping has also been used for profiling gene expression signatures associated with allergic contact dermatitis (see, e.g., Tam I et al. Contact Dermatitis. 2021; 84 (5): 308-316) and in skin cancer screening (see, e.g., Hughes A J et al. Br. J. Dermatol. 2021; 185 (1): 26-35), each of which is incorporated herein by reference in its entirety.

While existing tape stripping solutions capture cells for subsequent lysis and nucleic acid profiling, they are destructive to the cellular neighborhoods captured on the tape, and do not preserve in situ spatial information. For example, most tape stripping protocols require multiple tape strips to be applied to collect sufficient nucleic acid for downstream analysis, while losing information on the cellular composition and heterogeneity of the individual skin layers being extracted during each tape application. Combining a minimally invasive procedure such as tape stripping for skin sample collection and analysis, while preserving the spatial information of the skin collection area, would therefore provide useful information as to the localization and presence of any biomolecules in the collection area.

Figure 13:
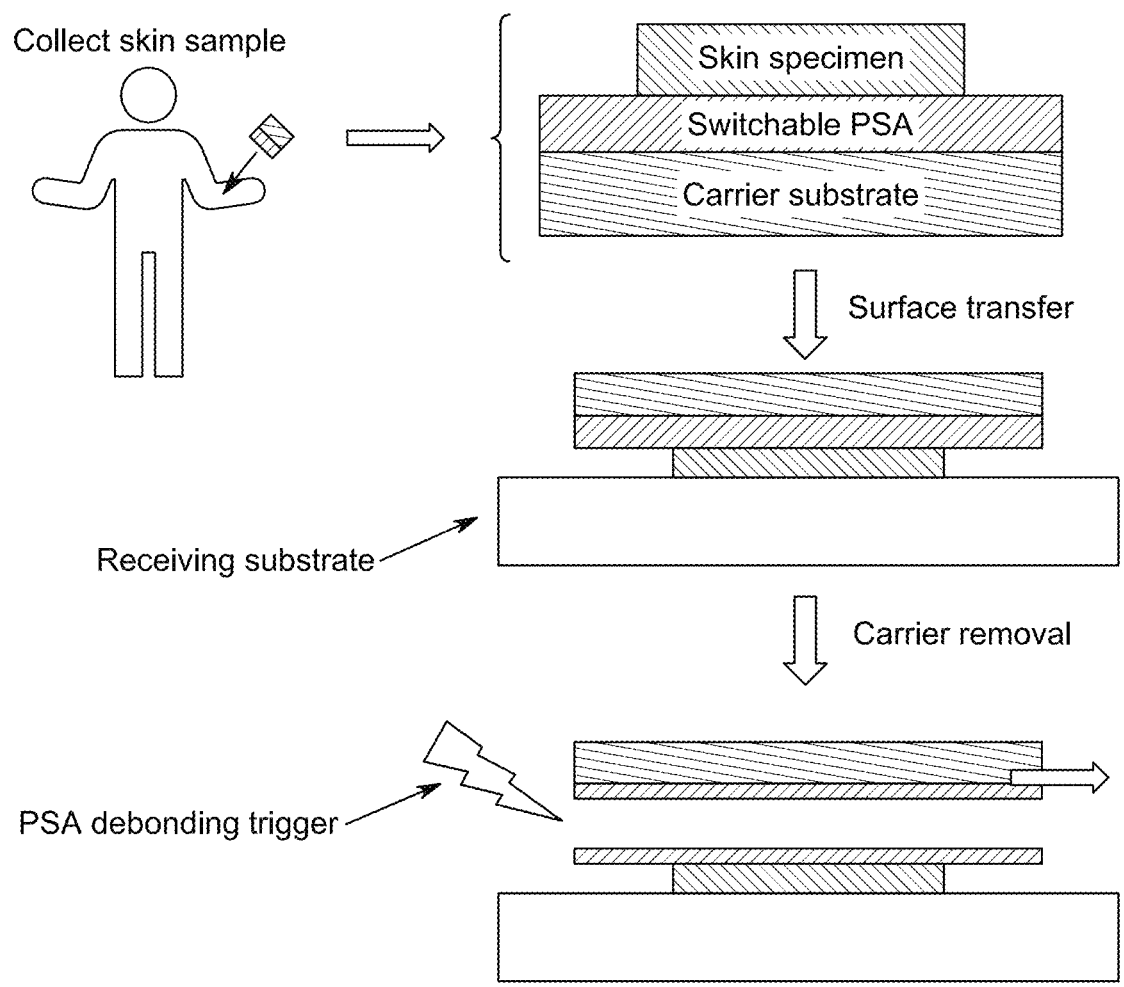
FIG. 13 illustrates an embodiment described herein using a carrier substrate including a switchable adhesive (e.g., a pressure-sensitive adhesive (PSA)) for skin sample collection and transfer to a receiving substrate (e.g., a glass slide), wherein the adhesive debonds or degrades in response to a specific stimulus). A skin sample is collected from a subject by contacting the switchable PSA to the skin of the subject and applying constant pressure. The collected skin specimen (e.g., the skin specimen adhered to the carrier substrate including the switchable PSA) is transferred to a receiving substrate using the methods described herein. A PSA debonding trigger (e.g., a chemical or UV stimulus) is applied, degrading the adhesive, and the carrier substrate layer is removed, leaving behind the skin specimen adsorbed to the receiving substrate. Additional processing may be performed to remove residual adhesive from the adsorbed skin specimen.

The tissue transfer and biomolecule detection methods described herein are useful in preserving the spatial information of a non-invasively collected skin sample (e.g., a skin sample collected via tape stripping). FIG. 13 illustrates an embodiment described herein using a carrier substrate including a switchable adhesive (e.g., a pressure-sensitive adhesive (PSA)) for skin sample collection and transfer to a receiving substrate (e.g., a glass slide), wherein the adhesive de-bonds and/or degrades in response to a specific stimulus). Exemplary switchable adhesives include, for example, graphene/shape memory polymers (GSMP), azopolymers, optically switchable adhesives, and thermal-responsive hydrogels, as described in Hohl D K and Weder C. Adv. Optical Mater. 2019; 1900230, Lee T H et al. RSC Adv. 2021; 11:37392-37402, Tseng Y M et al. ACS Appl. Mater. Interfaces. 2021; 13 (24): 29048-29057, and Liu Z and Yan F. Adv. Sci. 2022; 9 (12): 2200264, each of which is incorporated herein by reference in its entirety. For example, the skin sample is collected from a subject by contacting the switchable PSA to the skin of the subject and applying constant pressure. The carrier substrate including the switchable PSA may be in the form of, for example, a multi-layer tape. The carrier substrate is made of an inert material as described herein, for example, Kapton™, glass, PMMA, or COC. In some embodiments, multiple skin samples are collected from the same sample area of the subject by using multiple carrier substrates (e.g., multiple pieces of switchable PSA-containing tape) including the switchable PSA. Additional non-invasive tape stripping methods for the collection of a skin sample are described in U.S. Pat. Pub. Nos. 2018/0110500 and 2020/0149115, each of which is incorporated herein by reference in its entirety.

The collected skin specimen (e.g., the skin specimen adhered to the carrier substrate including the switchable PSA) is transferred to a receiving substrate using the methods described herein (e.g., the receiving substrate is functionalized with cell-adsorbing chemical groups, such as amines). A PSA debonding trigger (e.g., a chemical or UV stimulus) is applied, degrading the adhesive, and the carrier substrate layer is removed, leaving behind the skin specimen adsorbed to the receiving substrate. Debonding, for example, include the cleavage of polymers in the PSA by any of the means described herein. Additional processing may be performed to remove residual adhesive from the adsorbed skin specimen. Additional examples of debonding triggers include a change in pH, ionic strength change, temperature change, exposure to specific wavelengths of light, and/or exposure to electric or magnetic fields.

Effective PSA debonding triggers will not damage the skin specimen, or release the skin specimen from the receiving substrate. In some embodiments, the carrier substrate is porous (e.g., semi-porous) such that the PSA debonding trigger (e.g., a debonding chemical) is able to pass through the carrier substrate and contact the PSA. The carrier substrate may include perforations to allow for the PSA debonding trigger to reach the adhesive. In embodiments, the receiving substrate includes a switchable adhesive (e.g., a switchable PSA) as described herein. In embodiments, the receiving substrate includes an optically switchable adhesive.

P-EMBODIMENTS

The present disclosure provides the following illustrative embodiments:

Embodiment P1. A method of detecting a biomolecule in a tissue section, said method comprising: immobilizing the tissue section onto a hydrogel carrier substrate to generate a sample-carrier construct; contacting the tissue section of the sample-carrier construct with a receiving substrate to generate an immobilized tissue section; removing the hydrogel carrier substrate from the immobilized tissue section; permeabilizing the immobilized tissue section; and contacting said biomolecule from said tissue section with a detection agent thereby detecting the biomolecule in the tissue section.

Embodiment P2. The method of Embodiment P1, further comprising permeabilizing the tissue section of the sample-carrier construct prior to binding the immobilized specific binding agent to the biomolecule.

Embodiment P3. The method of Embodiment P1 or Embodiment P2, wherein the biomolecule is a nucleic acid sequence, carbohydrate, or protein.

Embodiment P4. The method of Embodiment P1 or Embodiment P2, wherein the biomolecule is a nucleic acid sequence.

Embodiment P5. The method of any one of Embodiment P1 to Embodiment P4, further comprising amplifying the nucleic acid sequence to generate amplification products.

Embodiment P6. The method of Embodiment P5, further comprising detecting the amplification products.

Embodiment P7. The method of any one of Embodiment P1 to Embodiment P6, wherein the detection agent comprises a label.

Embodiment P8. The method of any one of Embodiment P1 to Embodiment P6, wherein the detection agent comprises a fluorescent label.

Embodiment P9. The method of any one of Embodiment P1 to Embodiment P6, wherein the detection agent comprises a protein-specific binding agent.

Embodiment P10. The method of any one of Embodiment P1 to Embodiment P6, wherein said detection agent comprises a protein-specific binding agent bound to a nucleic acid sequence, bioconjugate reactive moiety, an enzyme, or a label.

Embodiment P11. The method of Embodiment P10, wherein the protein-specific binding agent is an antibody, single-chain Fv fragment (scFv), antibody fragment-antigen binding (Fab), affimer, or an aptamer.

Embodiment P12. The method of any one of Embodiment P1 to Embodiment P11, further comprising digesting the tissue section by contacting the sample-carrier construct with an endopeptidase.

Embodiment P13. The method of any one of Embodiment P1 to Embodiment P12, where contacting said biomolecule comprises hybridizing a sequencing primer to the biomolecule and sequencing the biomolecule.

Embodiment P14. The method of Embodiment P13, wherein sequencing comprises (a) extending a sequencing primer by incorporating a labeled nucleotide, or labeled nucleotide analogue and (b) detecting the label to generate a signal for each incorporated nucleotide or nucleotide analogue.

Embodiment P15. The method of any one of Embodiment P1 to Embodiment P12, where contacting said biomolecule comprises hybridizing a padlock probe to two adjacent nucleic acid sequences of the biomolecule, wherein the padlock probe is a single-stranded polynucleotide having a 5' and a 3' end, the padlock probe comprises at least one oligonucleotide barcode, and wherein the padlock probe comprises a primer binding sequence.

Embodiment P16. The method of Embodiment P15, further comprising ligating the 5' and 3' ends of the padlock probe to form a circular polynucleotide.

Embodiment P17. The method of any one of Embodiment P1 to Embodiment P16, further comprising imaging the immobilized tissue section.

Embodiment P18. A method of capturing a biomolecule from a tissue section, said method comprising: immobilizing the tissue section onto a hydrogel carrier substrate to generate a sample-carrier construct; contacting the tissue section of the sample-carrier construct with a receiving substrate, wherein said receiving substrate comprises an immobilized specific-binding agent; and binding the immobilized specific-binding agent to the biomolecule from said tissue section thereby capturing a biomolecule from the tissue section.

Embodiment P19. The method of Embodiment P18, wherein the receiving substrate comprises a plurality of immobilized specific binding agents.

Embodiment P20. The method of Embodiment P18 or Embodiment P19, wherein the biomolecule is a target nucleic acid sequence.

Embodiment P21. The method of Embodiment P20, wherein the immobilized specific-binding agent comprises an oligonucleotide complementary to the target nucleic acid sequence.

Embodiment P22. The method of Embodiment P19 or Embodiment P20, wherein the immobilized specific-binding agent comprises a poly(T) sequence.

Embodiment P23. The method of Embodiment P20, wherein the immobilized specific-binding agent comprises a spatial barcode, unique molecule identifying sequence, cleavable site, an amplification primer binding sequence, or a combination thereof.

Embodiment P24. The method of any one of Embodiment P20 to Embodiment P23, further comprising extending with a polymerase the target nucleic acid sequence bound to the immobilized specific binding agent.

Embodiment P25. A method of immobilizing a tissue section to a receiving substrate, wherein the tissue section comprises a thickness of about 1 µm to about 50 µm, said method comprising: contacting the tissue section with a hydrogel carrier substrate to generate a sample-carrier construct comprising the carrier substrate and the tissue section; contacting the tissue section of the sample-carrier construct with the receiving substrate; and removing the carrier substrate from the sample-carrier construct, thereby immobilizing the tissue section to the receiving substrate.

Embodiment P26. The method of Embodiment P1, wherein substantially all of the tissue section is immobilized to the receiving substrate.

Embodiment P27. A method of immobilizing a portion of a tissue section to a receiving substrate, wherein the tissue section comprises a thickness of about 1 µm to about 50 µm, said method comprising: contacting the tissue section with a hydrogel carrier substrate to generate a sample-carrier construct comprising the carrier substrate and the tissue section; removing a portion of the sample-carrier construct, wherein the portion comprises a portion of the carrier substrate and a portion of the tissue section; contacting the tissue section of the portion of the sample-carrier construct with the receiving substrate thereby immobilizing the tissue section to the receiving substrate.

Embodiment P28. The method of any one of Embodiment P1 to Embodiment P27, wherein the thickness of the tissue section is about 1 µm to about 20 µm.

Embodiment P29. The method of any one of Embodiment P1 to Embodiment P27, wherein the thickness of the tissue section is about 5 µm to about 12 µm.

Embodiment P30. The method of any one of Embodiment P1 to Embodiment P29, wherein the tissue section comprises a tissue or a cell.

Embodiment P31. The method of any one of Embodiment P1 to Embodiment P30, wherein the tissue section is embedded in an embedding material comprising paraffin wax, polyepoxide polymer, polyacrylic polymer, agar, gelatin, celloidin, cryogel, optimal cutting temperature (OCT) compositions, glycols, or a combination thereof.

Embodiment P32. The method of Embodiment P31, further comprising removing the embedding material.

Embodiment P33. The method of Embodiment P31, further comprising removing the embedding material prior to contacting the tissue section of the sample-carrier construct with the receiving substrate.

Embodiment P34. The method of any one of Embodiment P21 to Embodiment P33, wherein the hydrogel carrier substrate comprises agarose, amylose, amylopectin, alginate, gelatin, cellulose, polyolefin, and/or acrylate polymers.

Embodiment P35. The method of any one of Embodiment P1 to Embodiment P33, wherein the hydrogel carrier substrate comprises agarose, amylose, or amylopectin.

Embodiment P36. The method of any one of Embodiment P1 to Embodiment P33, wherein the hydrogel carrier substrate comprises less than about 5% agarose.

Embodiment P37. The method of any one of Embodiment P1 to Embodiment P33, wherein the hydrogel carrier substrate further comprises a support scaffold.

Embodiment P38. The method of Embodiment P37, wherein the support scaffold comprises a thermoplastic elastomer.

Embodiment P39. The method of Embodiment P37, wherein the support scaffold comprises polyethylene terephthalate.

Embodiment P40. The method of any one of Embodiment P1 to Embodiment P33, wherein the hydrogel carrier substrate comprises a Young's modulus of about 5 kPa to about 30 kPa.

Embodiment P41. The method of any one of Embodiment P1 to Embodiment P33, wherein the hydrogel carrier substrate comprises interfacial water, wherein the interfacial water is between the carrier substrate and the tissue section.

Embodiment P42. The method of any one of Embodiment P1 to Embodiment P33, wherein the hydrogel carrier substrate comprises about 80% to about 99% water.

Embodiment P43. The method of any one of Embodiment P1 to Embodiment P42, wherein the receiving substrate comprises a functionalized glass surface or a functionalized plastic surface.

Embodiment P44. The method of Embodiment P43, wherein the functionalized glass surface comprises (3-aminopropyl)triethoxysilane (APTES), (3-Aminopropyl)trimethoxysilane (APTMS), γ-Aminopropylsilatrane (APS), or N-(6-aminohexyl)aminomethyltriethoxysilane (AHAMTES).

Embodiment P45. The method of any one of Embodiment P1 to Embodiment P44, wherein prior to contacting the tissue section with the receiving substrate, the sample-carrier construct is stored for one or more days.

Embodiment P46. The method of Embodiment P45, wherein the sample-carrier construct is stored for 1 to 90 days.

Embodiment P47. The method of Embodiment P45, wherein the sample-carrier construct is stored for 1 to 30 days.

Embodiment P48. The method of any one of Embodiment P45 to Embodiment P47, wherein the sample-carrier construct is stored at less than about 25° C.

Embodiment P49. The method of any one of Embodiment P45 to Embodiment P47, wherein the sample-carrier construct is stored at less than about 5° C.

Embodiment P50. The method of any one of Embodiment P45 to Embodiment P47, wherein the sample-carrier construct is stored at about 4° C.

Embodiment P51. The method of any one of Embodiment P1 to Embodiment P50, wherein removing the carrier substrate comprises physically removing, thermally removing, chemically removing, or enzymatically removing.

Embodiment P52. A microplate, comprising: a substrate comprising a surface, the surface comprising a plurality of wells separated from each other by interstitial regions on the surface, wherein one or more wells comprises a tissue section and a carrier substrate, wherein the tissue section comprises a thickness of about 1 µm to about 50 µm and the carrier substrate comprises a hydrogel.

Embodiment P53. A method of detecting a biomolecule in a tissue section, said method comprising: immobilizing the tissue section onto a hydrogel carrier substrate to generate a sample-carrier construct; contacting the tissue section of the sample-carrier construct with a receiving substrate to generate an immobilized tissue section; removing the hydrogel carrier substrate from the immobilized tissue section; permeabilizing the immobilized tissue section; and contacting said biomolecule from said tissue section with a detection agent thereby detecting the biomolecule in the tissue section.

Embodiment P54. The method of Embodiment P53, wherein the biomolecule is a nucleic acid sequence, carbohydrate, or protein.

Embodiment P55. The method of Embodiment P53, wherein the biomolecule is a nucleic acid sequence.

Embodiment P56. The method of any one of Embodiment P53 to P55, further comprising amplifying the nucleic acid sequence to generate amplification products.

Embodiment P57. The method of Embodiment P56, further comprising detecting the amplification products.

Embodiment P58. The method of any one of Embodiment P53 to Embodiment P57, wherein the detection agent comprises a label.

Embodiment P59. The method of any one of Embodiment P53 to Embodiment P57, wherein the detection agent comprises a fluorescent label.

Embodiment P60. The method of any one of Embodiment P53 to Embodiment P57, wherein the detection agent comprises a protein-specific binding agent.

Embodiment P61. The method of any one of Embodiment P53 to Embodiment P57, wherein said detection agent comprises a protein-specific binding agent bound to a nucleic acid sequence, bioconjugate reactive moiety, an enzyme, or a label.

Embodiment P62. The method of Embodiment P61, wherein the protein-specific binding agent is an antibody, single domain antibody, single-chain Fv fragment (scFv), antibody fragment-antigen binding (Fab), affimer, or an aptamer.

Embodiment P63. The method of any one of Embodiment P53 to Embodiment P62, further comprising digesting the tissue section by contacting the sample-carrier construct with an endopeptidase.

Embodiment P64. The method of any one of Embodiment P53 to Embodiment P63, where contacting said biomolecule comprises hybridizing a sequencing primer to the biomolecule and sequencing the biomolecule.

Embodiment P65. The method of Embodiment P64, wherein sequencing comprises (a) extending a sequencing primer by incorporating a labeled nucleotide, or labeled nucleotide analogue and (b) detecting the label to generate a signal for each incorporated nucleotide or nucleotide analogue.

Embodiment P66. The method of any one of Embodiment P53 to Embodiment P63, where contacting said biomolecule comprises hybridizing a padlock probe to two adjacent nucleic acid sequences of the biomolecule, wherein the padlock probe is a single-stranded polynucleotide having a 5' and a 3' end, the padlock probe comprises at least one oligonucleotide barcode, and wherein the padlock probe comprises a primer binding sequence.

Embodiment P67. The method of Embodiment P66, further comprising ligating the 5' and 3' ends of the padlock probe to form a circular polynucleotide.

Embodiment P68. The method of any one of Embodiment P53 to P67, further comprising imaging the immobilized tissue section.

Embodiment P69. A method of capturing a biomolecule from a tissue section, said method comprising: immobilizing the tissue section onto a hydrogel carrier substrate to generate a sample-carrier construct; contacting the tissue section of the sample-carrier construct with a receiving substrate, wherein said receiving substrate comprises an immobilized specific-binding agent; and binding the immobilized specific-binding agent to the biomolecule from said tissue section thereby capturing a biomolecule from the tissue section.

Embodiment P70. The method of Embodiment P68, wherein the receiving substrate comprises a plurality of immobilized specific binding agents.

Embodiment P71. The method of Embodiment P69 or Embodiment P70, wherein the biomolecule is a target nucleic acid sequence.

Embodiment P72. The method of Embodiment P71, wherein the immobilized specific-binding agent comprises an oligonucleotide complementary to the target nucleic acid sequence.

Embodiment P73. The method of Embodiment P71 or Embodiment P72, wherein the immobilized specific-binding agent comprises a poly(T) sequence.

Embodiment P74. The method of Embodiment P71, wherein the immobilized specific-binding agent comprises a spatial barcode, unique molecule identifying sequence, cleavable site, an amplification primer binding sequence, or a combination thereof.

Embodiment P75. The method of any one of Embodiment P71 to Embodiment P74, further comprising extending with a polymerase the target nucleic acid sequence bound to the immobilized specific binding agent.

Embodiment P76. A method of immobilizing a tissue section to a receiving substrate, wherein the tissue section comprises a thickness of about 1 µm to about 50 µm, said method comprising: contacting the tissue section with a hydrogel carrier substrate to generate a sample-carrier construct comprising the carrier substrate and the tissue section; contacting the tissue section of the sample-carrier construct with the receiving substrate; and removing the carrier substrate from the sample-carrier construct, thereby immobilizing the tissue section to the receiving substrate.

Embodiment P77. The method of Embodiment P53, wherein substantially all of the tissue section is immobilized to the receiving substrate.

Embodiment P78. A method of immobilizing a portion of a tissue section to a receiving substrate, wherein the tissue section comprises a thickness of about 1 µm to about 50 µm, said method comprising: contacting the tissue section with a hydrogel carrier substrate to generate a sample-carrier construct comprising the carrier substrate and the tissue section; removing a portion of the sample-carrier construct, wherein the portion comprises a portion of the carrier substrate and a portion of the tissue section; contacting the tissue section of the portion of the sample-carrier construct with the receiving substrate thereby immobilizing the tissue section to the receiving substrate.

Embodiment P79. A method of obtaining an image of a tissue section, said method comprising: immobilizing the tissue section onto a hydrogel carrier substrate to generate a sample-carrier construct comprising the carrier substrate and the tissue section; contacting the tissue section of the sample-carrier construct with a receiving substrate to generate an immobilized tissue section; removing the hydrogel carrier substrate from the immobilized tissue section; and imaging the tissue section, thereby obtaining an image of the tissue section.

Embodiment P80. A method of obtaining an image of a portion of a tissue section, said method comprising: immobilizing the tissue section onto a hydrogel carrier substrate to generate a sample-carrier construct comprising the carrier substrate and the tissue section; removing a portion of the sample-carrier construct, wherein the portion comprises a portion of the carrier substrate and a portion of the tissue section; contacting the tissue section of the portion of the sample-carrier construct with a receiving substrate to generate an immobilized tissue section; removing the hydrogel carrier substrate from the immobilized tissue section; and imaging the tissue section, thereby obtaining an image of a portion of the tissue section.

Embodiment P81. The method of Embodiment P79 or Embodiment P80, wherein prior to imaging, the method further comprises permeabilizing the immobilized tissue section.

Embodiment P82. The method of Embodiment P79 or Embodiment P80, wherein prior to imaging, the method does not comprise permeabilizing the immobilized tissue section.

Embodiment P83. The method of any one of Embodiment P79 to Embodiment P82, wherein the imaging comprises phase-contrast microscopy, bright-field microscopy, Nomarski differential-interference-contrast microscopy, dark field microscopy, electron microscopy, or cryo-electron microscopy.

Embodiment P84. The method of any one of Embodiment P79 to Embodiment P83, wherein prior to imaging, the method further comprises contacting the immobilized tissue section with one or more imaging reagents or stains.

Embodiment P85. The method of Embodiment P84, wherein the one or more imaging reagents or stains comprise hematoxylin and eosin (H&E) staining reagents.

Embodiment P86. The method of Embodiment P84, wherein the one or more imaging reagents or stains comprise phase-contrast microscopy, bright-field microscopy, Nomarski differential-interference-contrast microscopy, or dark field microscopy imaging reagents.

Embodiment P87. The method of Embodiment P84, wherein the one or more imaging reagents or stains comprise electron microscopy or cryo-electron microscopy imaging reagents.

Embodiment P88. The method of any one of Embodiment P53 to Embodiment P78, wherein the thickness of the tissue section is about 1 µm to about 20 µm.

Embodiment P89. The method of any one of Embodiment P53 to Embodiment P78, wherein the thickness of the tissue section is about 5 µm to about 12 µm.

Embodiment P90. The method of any one of Embodiment P53 to Embodiment P89, wherein the tissue section comprises a tissue or a cell.

Embodiment P91. The method of any one of Embodiment P53 to Embodiment P90, wherein the tissue section is embedded in an embedding material comprising paraffin wax, polyepoxide polymer, polyacrylic polymer, agar, gelatin, celloidin, cryogel, optimal cutting temperature (OCT) compositions, glycols, or a combination thereof.

Embodiment P92. The method of Embodiment P91, further comprising removing the embedding material.

Embodiment P93. The method of Embodiment P91, further comprising removing the embedding material prior to contacting the tissue section of the sample-carrier construct with the receiving substrate.

Embodiment P94. The method of any one of Embodiment P73 to Embodiment P93, wherein the hydrogel carrier substrate comprises agarose, amylose, amylopectin, alginate, gelatin, cellulose, polyolefin, polyethylene glycol, polyvinyl alcohol, and/or acrylate polymers and copolymers thereof.

Embodiment P95. The method of any one of Embodiment P53 to Embodiment P93, wherein the hydrogel carrier substrate comprises agarose, amylose, or amylopectin.

Embodiment P96. The method of any one of Embodiment P53 to Embodiment P93, wherein the hydrogel carrier substrate comprises less than about 5% agarose.

Embodiment P97. The method of any one of Embodiment P53 to Embodiment P93, wherein the hydrogel carrier substrate further comprises a support scaffold.

Embodiment P98. The method of Embodiment P97, wherein the support scaffold comprises a thermoplastic elastomer.

Embodiment P99. The method of Embodiment P97, wherein the support scaffold comprises polyethylene terephthalate.

Embodiment P100. The method of any one of Embodiment P53 to Embodiment P93, wherein the hydrogel carrier substrate comprises a Young's modulus of about 5 kPa to about 30 kPa.

Embodiment P101. The method of any one of Embodiment P53 to Embodiment P93, wherein the hydrogel carrier substrate comprises interfacial water, wherein the interfacial water is between the carrier substrate and the tissue section.

Embodiment P102. The method of any one of Embodiment P53 to Embodiment P93, wherein the hydrogel carrier substrate comprises about 80% to about 99% water.

Embodiment P103. The method of any one of Embodiment P53 to Embodiment P102, wherein the receiving substrate comprises a functionalized glass surface or a functionalized plastic surface.

Embodiment P104. The method of Embodiment P103, wherein the functionalized glass surface comprises (3-aminopropyl)triethoxysilane (APTES), (3-Aminopropyl)trimethoxysilane (APTMS), γ-Aminopropylsilatrane (APS), N-(6-aminohexyl)aminomethyltriethoxysilane (AHAMTES), polyethylenimine (PEI), 5,6-epoxyhexyltriethoxysilane, or triethoxysilylbutyraldehyde, or a combination thereof.

Embodiment P105. The method of any one of Embodiment P53 to Embodiment P104, wherein prior to contacting the tissue section with the receiving substrate, the sample-carrier construct is stored for one or more days.

Embodiment P106. The method of Embodiment P105, wherein the sample-carrier construct is stored for 1 to 90 days.

Embodiment P107. The method of Embodiment P105, wherein the sample-carrier construct is stored for 1 to 30 days.

Embodiment P108. The method of any one of Embodiment P105 to Embodiment P107, wherein the sample-carrier construct is stored at less than about 25° C.

Embodiment P109. The method of any one of Embodiment P105 to Embodiment P107, wherein the sample-carrier construct is stored at less than about 5° C.

Embodiment P110. The method of any one of Embodiment P105 to Embodiment P107, wherein the sample-carrier construct is stored at about 4° C.

Embodiment P111. The method of any one of Embodiment P53 to Embodiment P110, wherein removing the carrier substrate comprises physically removing, thermally removing, chemically removing, or enzymatically removing.

Embodiment P112. A microplate, comprising: a substrate comprising a surface, the surface comprising a plurality of wells separated from each other by interstitial regions on the surface, wherein one or more wells comprises a tissue section and a carrier substrate, wherein the tissue section comprises a thickness of about 1 µm to about 50 µm and the carrier substrate comprises a hydrogel.

Additional Embodiments

The present disclosure provides the following additional illustrative embodiments:

Embodiment 1. A method of detecting a biomolecule in a tissue section, said method comprising: a) immobilizing the tissue section onto a carrier substrate to generate a sample-carrier construct, wherein said carrier substrate comprises a first adhesion strength; b) contacting the tissue section of the sample-carrier construct with a receiving substrate to generate an immobilized tissue section, wherein said receiving substrate comprises a second adhesion strength, wherein the second adhesion strength is greater than the first adhesion strength; c) removing the carrier substrate from the immobilized tissue section; d) permeabilizing the immobilized tissue section; and e) contacting said biomolecule in said tissue section with a detection agent thereby detecting the biomolecule in the tissue section, wherein the detection agent comprises a fluorophore.

Embodiment 2. The method of Embodiment 1, wherein step c) occurs prior to step e).

Embodiment 3. The method of Embodiment 1, wherein step c) occurs prior to step d).

Embodiment 4. The method of any one of Embodiments 1 to 3, wherein generating a sample-carrier construct comprises forming a plurality of non-covalent bonds between the tissue section and the carrier substrate.

Embodiment 5. The method of any one of Embodiments 1 to 4, wherein the carrier substrate comprises water molecules attached to the surface of said carrier substrate.

Embodiment 6. The method of any one of Embodiments 1 to 5, wherein the carrier substrate comprises a compression modulus greater than about 100 kPa.

Embodiment 7. The method of any one of Embodiments 1 to 6, wherein generating an immobilized tissue section comprises forming a plurality of covalent bonds between the tissue section and the receiving substrate.

Embodiment 8. The method of any one of Embodiments 1 to 7, wherein the receiving substrate comprises (3-aminopropyl)triethoxysilane (APTES), (3-Aminopropyl)trimethoxysilane (APTMS), γ-Aminopropylsilatrane (APS), N-(6-aminohexyl)aminomethyltriethoxysilane (AHAMTES), polyethylenimine (PEI), 5,6-epoxyhexyltriethoxysilane, or triethoxysilylbutyraldehyde, or a combination thereof.

Embodiment 9. The method of any one of Embodiments 1 to 8, wherein the biomolecule is a nucleic acid sequence, carbohydrate, or protein.

Embodiment 10. The method of any one of Embodiments 1 to 9, wherein the biomolecule is a nucleic acid sequence.

Embodiment 11. The method of Embodiment 10, further comprising amplifying the nucleic acid sequence to generate amplification products.

Embodiment 12. The method of Embodiment 11, further comprising detecting the amplification products.

Embodiment 13. The method of any one of Embodiments 1 to 9, wherein the detection agent comprises a protein-specific binding agent.

Embodiment 14. The method of any one of Embodiments 1 to 9, wherein said detection agent comprises a protein-specific binding agent bound to a nucleic acid sequence, bioconjugate reactive moiety, an enzyme, or a label.

Embodiment 15. The method of Embodiment 13 or 14, wherein the protein-specific binding agent is an antibody, single domain antibody, single-chain Fv fragment (scFv), antibody fragment-antigen binding (Fab), affimer, or an aptamer.

Embodiment 16. The method of any one of Embodiments 1 to 15, further comprising digesting the tissue section by contacting the sample-carrier construct with an endopeptidase.

Embodiment 17. The method of any one of Embodiments 1 to 16, wherein step e) comprises hybridizing a sequencing primer to the biomolecule and sequencing the biomolecule.

Embodiment 18. The method of Embodiment 17, wherein sequencing comprises (a) extending a sequencing primer by incorporating a labeled nucleotide, or labeled nucleotide analogue and (b) detecting the label to generate a signal for each incorporated nucleotide or nucleotide analogue.

Embodiment 19. The method of any one of Embodiments 1 to 18, wherein step e) comprises hybridizing a padlock probe to two adjacent nucleic acid sequences of the biomolecule, wherein the padlock probe is a single-stranded polynucleotide having a 5' and a 3' end, the padlock probe comprises at least one oligonucleotide barcode and a primer binding sequence.

Embodiment 20. The method of Embodiment 19, further comprising ligating the 5' and 3' ends of the padlock probe to form a circular polynucleotide.

Embodiment 21. The method of any one of Embodiments 1 to 18, wherein step e) comprises hybridizing a padlock probe to a nucleic acid sequence of the biomolecule, wherein the padlock probe is a single-stranded polynucleotide having a 5' and a 3' end, wherein the 3' end hybridizes to a first complementary region of the biomolecule and the 5' end hybridizes to a second complementary region of the biomolecule, and wherein the padlock probe comprises a primer binding sequence.

Embodiment 22. The method of Embodiment 21, further comprising extending the 3' end of the padlock probe along the nucleic acid sequence of the biomolecule to generate a complementary sequence and ligating the complementary sequence to the 5' end of the padlock probe thereby forming a circular oligonucleotide.

Embodiment 23. The method of Embodiment 21 or 22, wherein the second complementary region is about 5 to about 75 nucleotides in the 5' direction with respect to the first complementary region.

Embodiment 24. The method of any one of Embodiments 1 to 23, further comprising imaging the immobilized tissue section.

Embodiment 25. The method of any one of Embodiments 1 to 24, wherein the thickness of the tissue section is about 1 μm to about 20 μm.

Embodiment 26. The method of any one of Embodiments 1 to 25, wherein the carrier substrate comprises agarose, amylose, amylopectin, alginate, gelatin, cellulose, polyolefin, polyethylene glycol, polyvinyl alcohol, and/or acrylate polymers and copolymers thereof.

Embodiment 27. The method of any one of Embodiments 1 to 25, wherein the carrier substrate comprises agarose, amylose, or amylopectin.

Embodiment 28. The method of any one of Embodiments 1 to 27, wherein the carrier substrate comprises about 2% to about 10% agarose.

Embodiment 29. The method of any one of Embodiments 1 to 28, wherein the hydrogel carrier substrate further comprises a support scaffold.

Embodiment 30. The method of any one of Embodiments 1 to 29, wherein the hydrogel carrier substrate comprises a Young's modulus of about 5 kPa to about 30 kPa.

Embodiment 31. The method of any one of Embodiments 1 to 30, wherein the sample-carrier construct comprises interfacial water, wherein the interfacial water is between the carrier substrate and the tissue section.

Embodiment 32. The method of any one of Embodiments 1 to 31, wherein the carrier substrate comprises about 80% to about 99% water.

Embodiment 33. The method of any one of Embodiments 1 to 32, wherein the receiving substrate comprises a functionalized glass surface or a functionalized plastic surface.

Embodiment 34. The method of any one of Embodiments 1 to 33, wherein prior to contacting the tissue section with the receiving substrate, the sample-carrier construct is stored for one or more days.

Embodiment 35. The method of Embodiment 34, wherein the sample-carrier construct is stored for 1 to 90 days.

Embodiment 36. The method of Embodiment 34, wherein the sample-carrier construct is stored for 1 to 30 days.

Embodiment 37. The method of any one of Embodiments 34 to 36, wherein the sample-carrier construct is stored at less than about 25° C.

Embodiment 38. The method of any one of Embodiments 34 to 36, wherein the sample-carrier construct is stored at less than about 5° C.

Embodiment 39. The method of any one of Embodiments 34 to 36, wherein the sample-carrier construct is stored at about 4° C.

Embodiment 40. The method of any one of Embodiments 1 to 39, wherein removing the carrier substrate comprises physically removing, thermally removing, chemically removing, or enzymatically removing.

Embodiment 41. A method of detecting a biomolecule in a tissue section, said method comprising: a) immobilizing the tissue section onto a hydrogel carrier substrate to generate a sample-carrier construct; b) contacting the tissue section of the sample-carrier construct with a receiving substrate to generate an immobilized tissue section; c) removing the hydrogel carrier substrate from the immobilized tissue section; d) permeabilizing the immobilized tissue section; and e) contacting said biomolecule in said tissue section with a detection agent thereby detecting the biomolecule in the tissue section, wherein the detection agent comprises a fluorophore.

Embodiment 42. The method of Embodiment 41, wherein the biomolecule is a nucleic acid sequence, carbohydrate, or protein.

Embodiment 43. The method of Embodiment 41 or 42, wherein the biomolecule is a nucleic acid sequence.

Embodiment 44. The method of Embodiment 42 or 43, further comprising amplifying the nucleic acid sequence to generate amplification products.

Embodiment 45. The method of Embodiment 44, further comprising detecting the amplification products.

Embodiment 46. The method of any one of Embodiments 41 to 45, wherein the detection agent comprises a protein-specific binding agent.

Embodiment 47. The method of any one of Embodiments 41 to 45, wherein said detection agent comprises a protein-specific binding agent bound to a nucleic acid sequence, bioconjugate reactive moiety, an enzyme, or a label.

Embodiment 48. The method of Embodiment 46 or 47, wherein the protein-specific binding agent is an antibody, single domain antibody, single-chain Fv fragment (scFv), antibody fragment-antigen binding (Fab), affimer, or an aptamer.

Embodiment 49. The method of any one of Embodiment 41 to 48, further comprising digesting the tissue section by contacting the sample-carrier construct with an endopeptidase.

Embodiment 50. The method of any one of Embodiments 41 to 49, wherein step e) comprises hybridizing a sequencing primer to the biomolecule and sequencing the biomolecule.

Embodiment 51. The method of Embodiment 50, wherein sequencing comprises (a) extending a sequencing primer by incorporating a labeled nucleotide, or labeled nucleotide analogue and (b) detecting the label to generate a signal for each incorporated nucleotide or nucleotide analogue.

Embodiment 52. The method of any one of Embodiments 41 to 49, wherein step e) comprises hybridizing a padlock probe to two adjacent nucleic acid sequences of the biomolecule, wherein the padlock probe is a single-stranded polynucleotide having a 5' and a 3' end, the padlock probe comprises at least one oligonucleotide barcode, and wherein the padlock probe comprises a primer binding sequence.

Embodiment 53. The method of Embodiment 52, further comprising ligating the 5' and 3' ends of the padlock probe to form a circular polynucleotide.

Embodiment 54. The method of any one of Embodiments 41 to 49, wherein step e) comprises hybridizing a padlock probe to a nucleic acid sequence of the biomolecule, wherein the padlock probe is a single-stranded polynucleotide having a 5' and a 3' end, wherein the 3' end hybridizes to a first complementary region of the biomolecule and the 5' end hybridizes to a second complementary region of the biomolecule, and wherein the padlock probe comprises a primer binding sequence.

Embodiment 55. The method of Embodiment 54, further comprising extending the 3' end of the padlock probe along the nucleic acid sequence of the biomolecule to generate a complementary sequence and ligating the complementary sequence to the 5' end of the padlock probe thereby forming a circular oligonucleotide.

Embodiment 56. The method of Embodiment 54 or 55, wherein the second complementary region is about 5 to about 75 nucleotides in the 5' direction with respect to the first complementary region.

Embodiment 57. The method of any one of Embodiments 41 to 56, further comprising imaging the immobilized tissue section.

Embodiment 58. A method of capturing a biomolecule from a tissue section, said method comprising: i) immobilizing the tissue section onto a hydrogel carrier substrate to generate a sample-carrier construct; ii) contacting the tissue section of the sample-carrier construct with a receiving substrate, wherein said receiving substrate comprises an immobilized specific-binding agent; and iii) binding the immobilized specific-binding agent to the biomolecule from said tissue section thereby capturing a biomolecule from the tissue section.

Embodiment 59. The method of Embodiment 58, wherein the receiving substrate comprises a plurality of immobilized specific binding agents.

Embodiment 60. The method of Embodiment 58 or 59, wherein the biomolecule is a target nucleic acid sequence.

Embodiment 61. The method of Embodiment 60, wherein the immobilized specific-binding agent comprises an oligonucleotide complementary to the target nucleic acid sequence.

Embodiment 62. The method of Embodiment 60 or 61, wherein the immobilized specific-binding agent comprises a poly(T) sequence.

Embodiment 63. The method of Embodiment 60, wherein the immobilized specific-binding agent comprises a spatial barcode, unique molecule identifying sequence, cleavable site, an amplification primer binding sequence, or a combination thereof.

Embodiment 64. The method of any one of Embodiments 60 to 63, further comprising extending with a polymerase the target nucleic acid sequence bound to the immobilized specific binding agent.

Embodiment 65. A method of immobilizing a tissue section to a receiving substrate, wherein the tissue section comprises a thickness of about 1 µm to about 50 µm, said method comprising: contacting the tissue section with a hydrogel carrier substrate to generate a sample-carrier construct comprising the carrier substrate and the tissue section; contacting the tissue section of the sample-carrier construct with the receiving substrate; and removing the carrier substrate from the sample-carrier construct, thereby immobilizing the tissue section to the receiving substrate.

Embodiment 66. The method of any one of Embodiments 1 to 25, wherein substantially all of the tissue section is immobilized to the receiving substrate.

Embodiment 67. A method of immobilizing a portion of a tissue section to a receiving substrate, wherein the tissue section comprises a thickness of about 1 µm to about 50 µm, said method comprising: contacting the tissue section with a hydrogel carrier substrate to generate a sample-carrier construct comprising the carrier substrate and the tissue section; removing a portion of the sample-carrier construct, wherein the portion comprises a portion of the carrier substrate and a portion of the tissue section; contacting the tissue section of the portion of the sample-carrier construct with the receiving substrate thereby immobilizing the tissue section to the receiving substrate.

Embodiment 68. A method of obtaining an image of a tissue section, said method comprising: immobilizing the tissue section onto a hydrogel carrier substrate to generate a sample-carrier construct comprising the carrier substrate and the tissue section; contacting the tissue section of the sample-carrier construct with a receiving substrate to generate an immobilized tissue section; removing the hydrogel carrier substrate from the immobilized tissue section; and imaging the tissue section, thereby obtaining an image of the tissue section.

Embodiment 69. A method of obtaining an image of a portion of a tissue section, said method comprising: A) immobilizing the tissue section onto a hydrogel carrier substrate to generate a sample-carrier construct comprising the carrier substrate and the tissue section; B) removing a portion of the sample-carrier construct, wherein the portion comprises a portion of the carrier substrate and a portion of the tissue section; C) contacting the tissue section of the portion of the sample-carrier construct with a receiving substrate to generate an immobilized tissue section; D) removing the hydrogel carrier substrate from the immobilized tissue section; and E) imaging the tissue section, thereby obtaining an image of a portion of the tissue section.

Embodiment 70. The method of Embodiment 68 or 69, wherein prior to imaging, the method further comprises permeabilizing the immobilized tissue section.

Embodiment 71. The method of Embodiment 68 or 69, wherein prior to imaging, the method does not comprise permeabilizing the immobilized tissue section.

Embodiment 72. The method of any one of Embodiments 68 to 71, wherein the imaging comprises phase-contrast microscopy, bright-field microscopy, Nomarski differential-interference-contrast microscopy, dark field microscopy, electron microscopy, or cryo-electron microscopy.

Embodiment 73. The method of any one of Embodiments 68 to 72, wherein prior to imaging, the method further comprises contacting the immobilized tissue section with one or more imaging reagents or stains.

Embodiment 74. The method of Embodiment 73, wherein the one or more imaging reagents or stains comprise hematoxylin and eosin (H&E) staining reagents.

Embodiment 75. The method of Embodiment 73, wherein the one or more imaging reagents or stains comprise phase-contrast microscopy, bright-field microscopy, Nomarski differential-interference-contrast microscopy, or dark field microscopy imaging reagents.

Embodiment 76. The method of Embodiment 73, wherein the one or more imaging reagents or stains comprise electron microscopy or cryo-electron microscopy imaging reagents.

Embodiment 77. The method of any one of Embodiments 41 to 76, wherein the thickness of the tissue section is about 1 µm to about 20 µm.

Embodiment 78. The method of any one of Embodiments 41 to 76, wherein the thickness of the tissue section is about 5 µm to about 12 µm.

Embodiment 79. The method of any one of Embodiments 41 to 78, wherein the tissue section comprises a tissue or a cell.

Embodiment 80. The method of any one of Embodiments 41 to 79, wherein the tissue section is embedded in an embedding material comprising paraffin wax, polyepoxide polymer, polyacrylic polymer, agar, gelatin, celloidin, cryogel, optimal cutting temperature (OCT) compositions, glycols, or a combination thereof.

Embodiment 81. The method of Embodiment 80, further comprising removing the embedding material.

Embodiment 82. The method of Embodiment 80, further comprising removing the embedding material prior to contacting the tissue section of the sample-carrier construct with the receiving substrate.

Embodiment 83. The method of any one of Embodiments 41 to 82, wherein the hydrogel carrier substrate comprises agarose, amylose, amylopectin, alginate, gelatin, cellulose, polyolefin, polyethylene glycol, polyvinyl alcohol, and/or acrylate polymers and copolymers thereof.

Embodiment 84. The method of any one of Embodiments 41 to 82, wherein the hydrogel carrier substrate comprises agarose, amylose, or amylopectin.

Embodiment 85. The method of any one of Embodiments 41 to 82, wherein the hydrogel carrier substrate comprises less than about 5% agarose.

Embodiment 86. The method of any one of Embodiments 41 to 85, wherein the hydrogel carrier substrate further comprises a support scaffold.

Embodiment 87. The method of Embodiment 86, wherein the support scaffold comprises a thermoplastic elastomer.

Embodiment 88. The method of Embodiment 86, wherein the support scaffold comprises polyethylene terephthalate.

Embodiment 89. The method of any one of Embodiments 41 to 88, wherein the hydrogel carrier substrate comprises a Young's modulus of about 5 kPa to about 30 kPa.

Embodiment 90. The method of any one of Embodiments 41 to 89, wherein the sample-carrier construct comprises interfacial water, wherein the interfacial water is between the carrier substrate and the tissue section.

Embodiment 91. The method of any one of Embodiments 41 to 90, wherein the hydrogel carrier substrate comprises about 80% to about 99% water.

Embodiment 92. The method of any one of Embodiments 41 to 91, wherein the receiving substrate comprises a functionalized glass surface or a functionalized plastic surface.

Embodiment 93. The method of Embodiment 92, wherein the functionalized glass surface comprises (3-aminopropyl) triethoxysilane (APTES), (3-Aminopropyl) trimethoxysilane (APTMS), γ-Aminopropylsilatrane (APS), N-(6-aminohexyl)aminomethyltriethoxysilane (AHAMTES), polyethylenimine (PEI), 5,6-epoxyhexyltriethoxysilane, or triethoxysilylbutyraldehyde, or a combination thereof.

Embodiment 94. The method of any one of Embodiments 41 to 93, wherein prior to contacting the tissue section with the receiving substrate, the sample-carrier construct is stored for one or more days.

Embodiment 95. The method of Embodiment 94, wherein the sample-carrier construct is stored for 1 to 90 days.

Embodiment 96. The method of Embodiment 94, wherein the sample-carrier construct is stored for 1 to 30 days.

Embodiment 97. The method of any one of Embodiments 94 to 96, wherein the sample-carrier construct is stored at less than about 25° C.

Embodiment 98. The method of any one of Embodiments 94 to 96, wherein the sample-carrier construct is stored at less than about 5° C.

Embodiment 99. The method of any one of Embodiments 94 to 96, wherein the sample-carrier construct is stored at about 4° C.

Embodiment 100. The method of any one of Embodiments 41 to 99, wherein removing the carrier substrate comprises physically removing, thermally removing, chemically removing, or enzymatically removing.

Embodiment 101. A method of determining a surgical margin of a tissue to be resected in a subject, said method comprising: immobilizing a tissue section obtained from said subject onto a hydrogel carrier substrate to generate a sample-carrier construct; contacting the tissue section of the sample-carrier construct with a receiving substrate to generate an immobilized tissue section; removing the hydrogel carrier substrate from the immobilized tissue section; permeabilizing the immobilized tissue section; contacting a biomolecule at a first location in the tissue section with a detection agent thereby detecting the presence of said biomolecule in the first location in the tissue section, wherein the detection agent comprises a fluorophore; determining the presence of said biomolecule at one or more different locations in the tissue section by contacting said detection agent at one or more different locations in the tissue section; comparing the presence of said biomolecule in the first location to the presence of said biomolecule in the one or more different locations, and determining the surgical margin of the tissue to be resected from the subject based on the comparison.

Embodiment 102. A microplate, comprising: a substrate comprising a surface, the surface comprising a plurality of wells separated from each other by interstitial regions on the surface, wherein one or more wells comprises a tissue section and a carrier substrate, wherein the tissue section comprises a thickness of about 1 μm to about 50 μm and the carrier substrate comprises a hydrogel.

What is claimed is:

1. A method of detecting nucleic acids in a tissue section, comprising:
    contacting a plurality of discrete tissue samples attached to a solid support with a plurality of circularizable probes, wherein a circularizable probe binds to a nucleic acid molecule in a discrete tissue sample, and wherein each discrete tissue sample comprises a tissue section comprising a width of about 4 mm to about 10 mm and a thickness of about 5 μm to about 12 μm;
    forming a circular oligonucleotide in the tissue section, and amplifying the circular oligonucleotide to form amplification products; and
    detecting the amplification products by binding a fluorescently labeled probe to the amplification product and detecting the fluorescent label.

2. The method of claim 1, wherein the nucleic acid molecule is attached to a specific binding agent.

3. The method of claim 1, wherein the nucleic acid molecule is an RNA molecule.

4. The method of claim 1, wherein the nucleic acid molecule is a cDNA molecule.

5. The method of claim 1, where the tissue section comprises liver tissue, kidney tissue, lung tissue, thymus tissue, adrenal tissue, skin tissue, bladder tissue, colon tissue, spleen tissue, or brain tissue.

6. The method of claim 1, wherein the fluorescently labeled probe is a fluorescently labeled nucleotide.

7. The method of claim 1, wherein the fluorescently labeled probe is a fluorescently labeled oligonucleotide.

8. The method of claim 1, wherein each tissue section is a formalin-fixed and paraffin embedded (FFPE) tissue section.

9. The method of claim 1, wherein each tissue section is a frozen tissue section.

10. The method of claim 1, wherein a length and/or diameter of each tissue section is about 4 mm to about 10 mm.

11. The method of claim 1, wherein a thickness of each tissue section is less than 6 μm, 7 μm, 8 μm, 9 μm or 10 μm.

12. The method of claim 1, wherein each tissue section comprises breast tissue, lung tissue, colon tissue, lymph tissue, kidney tissue, bone tissue, tonsil tissue, or brain tissue.

13. The method of claim 1, wherein the solid support is glass.

14. The method of claim 1, wherein the nucleic acid molecule comprises a barcode sequence.

15. The method of claim 1, wherein the circularizable probe comprises a barcode sequence.

16. The method of claim 1, wherein the circularizable probe is a single stranded polynucleotide comprising a 5'-end and a 3'end, and forming the circular oligonucleotide comprises ligating the 5'-end and a 3'end together to form the circular oligonucleotide.

17. The method of claim 1, wherein the circularizable probe is a single stranded polynucleotide comprising a 5'-end and a 3'end, and forming the circular oligonucleotide comprises extending the 3'end to form a complementary sequence of the nucleic acid molecule, and ligating the complementary sequence to the 5'-end to form the circular oligonucleotide.

18. The method of claim 1, wherein each discrete tissue sample is separated from each other by about 1 mm or greater.

19. The method of claim 1, wherein each discrete tissue sample is separated from each other by about 1 mm.

* * * * *